United States Patent
Finke et al.

(10) Patent No.: US 6,538,002 B1
(45) Date of Patent: Mar. 25, 2003

(54) CYCLOPENTYL MODULATORS OF CHEMOKINE RECEPTOR ACTIVITY

(75) Inventors: Paul E. Finke, Milltown, NJ (US); Malcolm Maccoss, Freehold, NJ (US); Sander G. Mills, Scotch Plains, NJ (US); Bryan Oates, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/591,631

(22) Filed: Jun. 8, 2000

Related U.S. Application Data

(60) Provisional application No. 60/138,763, filed on Jun. 11, 1999.

(51) Int. Cl.$^7$ ..................... A01N 43/40; C07D 401/00; C07D 211/20; C07D 211/24; C07D 403/00

(52) U.S. Cl. ..................... 514/278; 514/318; 514/317; 514/319; 514/322; 514/323; 514/324; 514/824; 514/826; 514/918; 546/17; 546/196; 546/198; 546/200; 546/201; 546/213; 546/217; 546/234; 546/236; 546/237; 546/239

(58) Field of Search .................. 546/17, 206, 213, 546/217, 234, 236, 237, 239, 196, 198, 200; 514/317, 318, 319, 322, 323, 324, 824, 826, 918, 278

(56) References Cited

U.S. PATENT DOCUMENTS

| | | |
|---|---|---|
| 3,647,804 A | 3/1972 | Rynbrandt et al. |
| 4,105,666 A | 8/1978 | Ward |
| 4,281,132 A | 7/1981 | Ward |
| 5,169,844 A | 12/1992 | Commons et al. |
| 5,424,319 A | 6/1995 | Hanson et al. |
| 5,712,279 A | 1/1998 | Biller et al. |
| 5,750,549 A | 5/1998 | Caldwell et al. |
| 5,935,974 A | 8/1999 | Rae et al. |
| 6,054,468 A | 4/2000 | Geerts et al. |

FOREIGN PATENT DOCUMENTS

| | | |
|---|---|---|
| WO | WO 98/25617 | 6/1998 |
| WO | WO 98/31364 | 7/1998 |
| WO | WO 99/04794 | 2/1999 |
| WO | WO 99/09984 | 3/1999 |

OTHER PUBLICATIONS

Y. Huang et al., "The role of a mutant CCR5 allele in HIV–1 transmission and disease progression", Nature Medicine, vol. 2, No. 11, pp. 1240–1243 (Nov. 1996).

H. Choe et al., "The Beat–Chemokine Receptors CCR3 and CCR5 Facilitate Infection by Primary HIV–1 Isolates", Cell, vol. 85, pp. 1135–1148 (Jun. 1996).

C. Mark Hill et al., "Natural resistance to HIV?", Nature, vol. 383, pp. 668–669 (Aug. 1996).

M. Devalaraja et al., "Multiple chemotactic factors: fine control or redundancy?", Trends in Pharm. Sci., vol. 20, pp. 151–156 (1999).

A. Fauci et al., "Acquired Immunodeficiency Syndrome: Epidemiologic, Clinical Immunologic, and Therapeutic Considerations", Annals of Internal Medicine, vol. 100, pp. 92–106 (1984).

M. Dean et al., "Genetic Restriction of HIV–1 Infection and Progression to AIDS by a Deletion Allele of the CKR5 Structural Gene", Science, vol. 273, pp. 1856–1862 (Sep. 1996).

N. Suzuki et al., "Selective accumulation of CCR5+ T lymphocytes into inflamned joints of rheumatoid arthritis", Int'l Immunology, vol. 11, No. 4, pp. 553–559 (Apr. 1999).

Cooke et al., "The deletion of CCR5 receptor in rheumatoid arthritis", Arthritis & Rheumatism, vol. 41, No. 6, pp. 1135–6 (1998).

C. Plater–Zyberk et al., "Effect of a CC chemokine receptor antagonist on collagen induced arthritis in DBA/1 mice", Immunology Letters, vol. 57, pp. 117–120 (1997).

C. Plater–Zyberk et al., "A chemokine receptor antagonist reduces the incidence of collagen induced arthritis", Arthritis & Rheumatism, vol. 41, Supp. 9, p. S99, (1998).

J. L. Pablos et al., "The Homozygous D32 deletion of the CC Chemokine Rceptor CCR5 Gene Protects Against Rheumatoid Arthritis", Arthritis & Rheumatism, vol. 40, Supp. 9, p. S157, (Sep. 1997).

(List continued on next page.)

Primary Examiner—Alan L. Rotman
Assistant Examiner—Raymond Covington
(74) Attorney, Agent, or Firm—Kenneth R. Walton; Melvin Winokur

(57) ABSTRACT

The present in to s directed to compounds of the formula I:

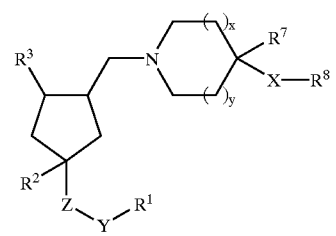

(wherein $R^1$, $R^2$, $R^3$, $R^7$, $R^8$, X, Y, Z, x and y are defined herein) which are useful as modulators of chemokine receptor activity. In particular, these compounds are useful as modulators of the chemokine receptors CCR-5 and/or CCR-3.

20 Claims, No Drawings

OTHER PUBLICATIONS

A. H. Hajeer et al., "The CCR5 Delta 32 Polymorphism is not Protective in RA", Arthritis & Rheumatism, vol. 42, Supp. 0, p. S194 (Sep. 1999).

M. Mack et al., "Predominance of Mononuclear Cells Expressing the Chemokine Receptor CCR5 in Synovial Effusions of Patients with Different Forms of Arthritis", Arthritis & Rheumatism, vol. 42, No. 5, pp. 981–988 (May 1999).

A.D. Luster et al., "Role of the monocyte chemoattractant protein and eotaxin subfamily of chemokines in allergic inflammation", Journal of Leukocyte Biology, vol. 62, pp. 620–633 (Nov. 1997).

A. B. Kay, "Asthma and Inflammation", Journal of Allergy and Clinical Immunology, vol. 87, No. 5, pp. 893–910 (May 1991).

S. Ying et al., "Enhanced expression of eotaxin and CCR3 mRNA and protein in atopic asthma Association with airway hyperresponsiveness and predominant colocalization of eotaxin mRNA to bronchial epithelial and endothelial cells", Eur. J. Immunology, vol. 27, No. 12, pp. 3507–3516 (1997).

C. Mackay et al., "Identification of Eosinophilic Chemokines and Chemokine Receptors, and Prospects for Therapeutic Intervention for Allergic Disease", Prog. Allergy Clin. Immunology, 16th Proc. Int. Congr. Allergol. Clin. Immunol., pp. 27–32 (1997).

S. Ying et al., Eosinophil Chemotacatic Chemokines (Eotaxin, Eotaxin–2 RANTES, Monocyte Chemoattractant Protein–3 (MCP–3), and MCP–4), and C–C Chemokine Receptor 3 Expression in Bronchial Biopsies from Atopic and Nonatopic (Intrinsic) Asthmatics, J. Immunology, vol. 163, No. 11 pp. 6321–9 (Dec. 1999).

J. A. Gonzalo et al., "The Coordinated Action of CC Chemokines in the Lung Orchestrates Allergic Inflammation and Airway Hyperresponsiveness", J. Exp. Med., vol. 188, No. 1, pp. 157–167 (Jul. 1998).

J. C. Grimaldi et al., "Depletion of eosinophils in mice through the use of antibodies specific for C–C chemokine receptor 3 (CCR3)", J. of Leukocyte Biology, vol. 65, pp. 846–853 (Jun. 1999).

H. Heath et al., "Chemokine Receptor Usage by Human Eosinophils", J. Clin. Invest., vol. 99, No. 2, pp. 178–184 (Jan. 1997).

M. Samson et al., "Resistance to HIV–1 infection in caucasian individuals bearing mutant alleles of the CCR–5 chemokine receptor gene", Nature, vol. 382, pp. 722–725 (Aug. 1996).

J. J. Gomez–Reino et al., "Association of Rheumatoid Arthritis with a Functional Chemokine Receptor, CCR5", Arthritis & Rheumatism, vol. 42, No. 5, May 1999, pp. 989–992.

T. J. Schall, "Biology of the Rantes/sis Cytokine Family", Cytokine, vol. 3, No. 3, May 1991, pp. 165–183.

P. M. Murphy, "The Molecular Biology of Leukocyte Chenoattractant Receptors", Annual Review of Immunology, vol. 12, 1994, pp. 593–633.

H. Deng et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of C–C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

A. Chaudhuri et al., "Expression of the Duffy Antigen in K562 Cells," J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2422–2426.

D. Smith et al., "Blocking of HIV–1 Infectivity by a Soluble, Secreted Form of the CD4 Antigen", Science, vol. 238, 1987, pp. 1704–1707.

J. A. Levy, "Infection by Human Immunodeficiency Virus—CD4 is not Enough", N. Eng. J. Med., vol. 335, No. 20, Nov. 1996, pp. 1528–1530.

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistance to HIV–1 infection in caucasian individuals bearing mutant alleles of the CCR–5 cehmokine receptor gene", Nature, vol. 382, Aug. 1996, pp. 722–725.

C. M. Hill et al., "Natural resistance to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

Ko et al., "Preparation of N–ureidoalkyl–piperidines as modulators of chemokine receptor activity", Chemical Abstracts No. 133:43441, Absract of WO 00/35449.

CYCLOPENTYL MODULATORS OF CHEMOKINE RECEPTOR ACTIVITY

This application claims the benefit of U.S. Provisional Application No. 60/138,763, filed Jun. 11, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C—X—C ($\alpha$) and C—C ($\beta$), depending on whether the first two cysteines are separated by a single amino acid (C—X—C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72,415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270,16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR3, CXCR-4, have been implicated as being important mediators of inflammatory and immunoregulatory disorders and diseases, including, asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of a topic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-II, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4(Levy, *N. Engl. J. Med.*, 335(20), 1528–1530 (Nov. 14 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, a topic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

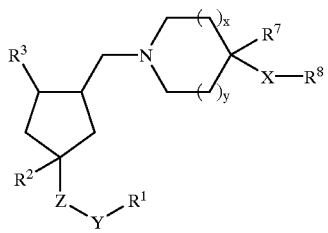

I wherein:
X is selected from: —($C_{0-6}$ alkyl)—Q—($C_{0-6}$ alkyl)—, —($C_{0-6}$ alkyl)-$C_{3-8}$ cycloalkyl-($C_{0-6}$ alkyl)—, $C_{2-10}$ alkenyl, and $C_{2-10}$ alkynyl,
where the alkyl is unsubstituted or substituted with 1–7 substituents
where the substituents are independently selected from:
(a) halo,
(b) hydroxy,
(c) —O—$C_{1-3}$ alkyl, and
(d) trifluoromethyl,
and where Q is selected from:
a single bond, —O—, —$SO_2$—, —$NR^{10}$—, —$NR^{10}$—$SO_2$—, —$SO_2$—$NR^{10}$—, —S—, and —SO—,
and where $R^{10}$ is independently selected from: hydrogen, $C_{1-6}$ alkyl, benzyl, phenyl, (CO)$C_{1-6}$ alkyl, —$SO_2$—$C_{1-6}$ alkyl, and $C_{1-6}$ alkyl-$C_{3-6}$ cycloalkyl,
which is unsubstituted or substituted with 1–3 substituents where the substituents are independently selected from: halo, $C_{1-3}$ alkyl, $C_{1-3}$ alkoxy and trifluoromethyl;
is selected from:
a single bond, —(CO)—, —(CO)O—, —O(CO)—, —$SO_2$—, —$C_{1-10}$ alkyl—, —(CO)$NR^9$—, —$NR^9$(CO)—, —(CS)$NR^9$—, and —$NR^9$(CS)—;
where $R^9$ is independently selected from hydrogen, $C_{1-6}$ alkyl, $C_{3-8}$ cycloalkyl, phenyl, and $C_{1-6}$ alkyl-phenyl, which is unsubstituted or substituted with 1–3 substituents where the substituents are independently selected from: halo, $C_{1-3}$ alkyl, $C_{1-3}$ alkoxy, $C_{3-8}$ cycloalkyl, phenyl and trifluoromethyl;
Z is selected from:
a single bond, —$NR^9$—, —O—, and —$C_{1-10}$ alkyl—;
$R^1$ is selected from:
phenyl, naphthyl, heterocycle, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, $C_{1-4}$ alkyl-phenyl or $C_{1-4}$ alkyl-heterocycle, which is unsubstituted or substituted with 1–3 substituents where the substituents are independently selected from: halo, $C_{1-3}$ alkyl, $C_{1-3}$ alkoxy, trifluoromethoxy and trifluoromethyl,
or when Z is —$NR^9$—, then $R^9$ and $R^1$ may be joined together to form a 5–8 membered alkyl or heterocycle ring which may be unsubstituted or substituted with halo, $C_{1-3}$ alkyl, and $C_{1-3}$ alkoxy;
$R^2$ is selected from:
(1) hydrogen, and
(2) hydroxy,
or $R^2$ and Z may be joined together to form a double bond;
$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;
$R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy,
(4) halo, and
(5) phenyl,
or $R^7$ and $R^8$ may be linked together through X and the carbon atom to which they are attached to form a 5-membered ring selected from the group consisting of:

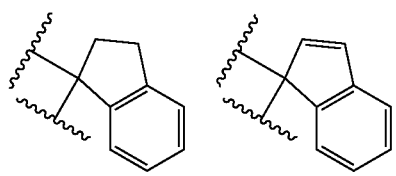

-continued

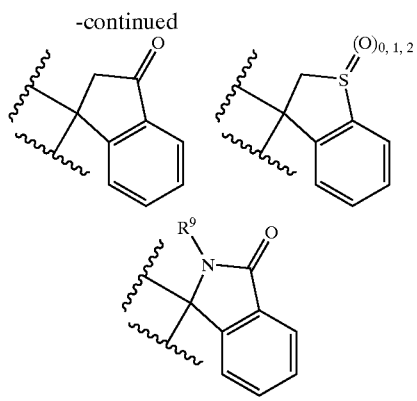

$R^8$ is selected from:
  hydrogen, $C_{3-8}$ cycloalkyl, phenyl, naphthyl, biphenyl, and heterocycle,
  which is unsubstituted or substituted with 1–7 of $R^{12}$ where $R^{12}$ is independently selected from:
  (a) halo,
  (b) cyano,
  (c) hydroxy,
  (d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), trifluoromethyl, and —$NR^9R^{10}$,
  (e) —O—$C_{1-6}$ alkyl, which is unsubstituted or substituted with 1–5 of $R^{13}$,
  (f) —$CF_3$,
  (g) —$CHF_2$,
  (h) —$CH_2F$,
  (i) —$NO_2$,
  (j) $C_{0-6}$ alkyl-phenyl or $C_{0-6}$ alkyl-heterocycle, which is unsubstituted or substituted with 1–7 substituents where the substituents are independently selected from:
    (i) halo,
    (ii) hydroxy,
    (iii) $C_{1-6}$ alkyl,
    (iv) —O—$C_{1-6}$ alkyl,
    (v) —$CF_3$,
    (vi) —$OCF_3$,
    (vii) —$NO_2$,
    (viii) —CN,
    (ix) —$SO_2$—$C_{1-6}$ alkyl,
    (x) —$CO_2R^9$,
    (xi) —$NR^9R^{10}$,
    (xii) —$CONR^9R^{10}$,
    (xiii) —$SO_2$—$NR^9R^{10}$, and
    (xiv) —$NR^9$—$SO_2$—$R^{10}$;
  (k) —$CO_2R^9$,
  (l) tetrazolyl,
  (m) —$NR^9R^{10}$,
  (n) —$NR^9$—$COR^{10}$,
  (o) —$NR^9$—$CO_2R^{10}$,
  (p) —CO—$NR^9R^{10}$,
  (q) —OCO—$NR^9R^{10}$,
  (r) —$NR^9CO$—$NR^9R^{10}$,
  (s) —$S(O)_m$—$R^9$, wherein m is an integer selected from 0, 1 and 2,
  (t) —$S(O)_2$—$NR^9R^{10}$,
  (u) —$NR^9S(O)_2$—$R^{10}$, and
  (v) —$NR^9S(O)_2$—$NR^9R^{10}$;
x is an integer selected from 0, 1 and 2, and y is an integer selected from 0, 1 and 2, with the proviso that the sum of x and y is 2;

and pharmaceutically acceptable salts thereof and individual diastereomers thereof.

One embodiment of the present invention is a compound of formula I, wherein Y is selected from a single bond, —(CO)—, —(CS)NR$^9$—, —(CO)O—, —$SO_2$—, and —(CO)NR$^9$—, where $R^9$ is independently selected from hydrogen and $C_{1-6}$ alkyl;

Z is selected from a single bond, —O—, and —NR$^9$—;

$R^1$ is selected from:
  phenyl, heterocycle, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, $C_{1-4}$ alkyl-phenyl or $C_{1-4}$ alkyl-heterocycle, which is unsubstituted or substituted with 1–3 substituents where the substituents are independently selected from: halo, $C_{1-3}$ alkyl, $C_{1-3}$ alkoxy, trifluoromethoxy and trifluoromethyl, or when Z is —NR$^9$—, then $R^9$ and $R^1$ may be joined together to form a 5–8 membered alkyl or heterocycle ring which may be unsubstituted or substituted with halo, $C_{1-3}$ alkyl, and $C_{1-3}$ alkoxy;
and all other variables are as previously defined;

and pharmaceutically acceptable salts thereof and individual diastereomers thereof.

Preferred compounds of the present invention include those of formula Ia:

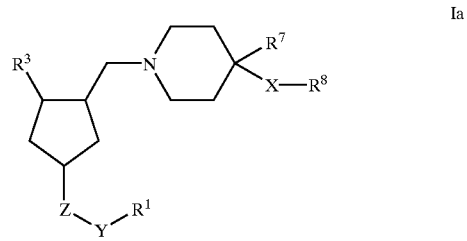

Ia wherein $R^1$, $R^3$, $R^7$, $R^8$, X, Y and Z are defined herein; and pharmaceutically acceptable salts and individual diastereomers thereof.

More preferred compounds of the present invention include those of formula Ic:

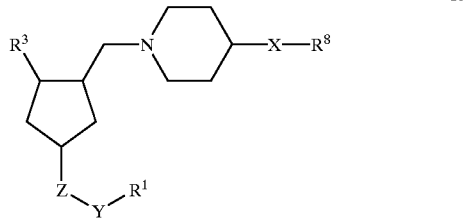

Ic wherein $R^1$, $R^3$, $R^8$, X, Y and Z are defined herein; and pharmaceutically acceptable salts and individual diastereomers thereof.

Highly preferred compounds of the present invention include those of formula Id:

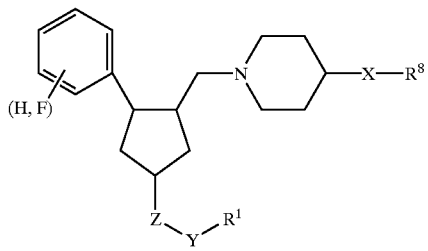

wherein $R^1$, $R^8$, X, Y and Z are defined herein; and pharmaceutically acceptable salts and individual diastereomers thereof.

In the present invention it is preferred that X is:
—($C_{0-4}$ alkyl)—Q—($C_{0-4}$ alkyl)—,
where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl,
and where Q is selected from:
a single bond, —O—, —$SO_2$—, —$NR^{10}$—, —S—, and —SO—,
and where $R^{10}$ is independently selected from: hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cycloalkyl, which is unsubstituted or substituted with 1–3 substituents where the substituents are independently selected from: halo, $C_{1-3}$ alkyl, $C_{1-3}$ alkoxy and trifluoromethyl.

In the present invention it is more preferred that X is:
—($C_{0-2}$ alkyl)—Q—($C_{0-2}$ alkyl)—,
where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl,
and where Q is selected from:
a single bond, —O—, —$SO_2$—, —$NR^{10}$—, —S—, and —SO—,
where $R^{10}$ is independently selected from: hydrogen, $C_{1-6}$ alkyl, $C_{2-6}$ alkenyl, $C_{26}$ alkynyl, benzyl, phenyl, and $C_{1-6}$ alkyl-$C_{3-6}$ cycloalkyl, which is unsubstituted or substituted with 1–3 substituents where the substituents are independently selected from: halo, $C_{1-3}$ alkyl, $C_{1-3}$ alkoxy and trifluoromethyl.

In the present invention it is even more preferred that X is selected from:
—($C_{0-2}$ alkyl)—Q—($C_{0-2}$ alkyl)—, where the alkyl is unsubstituted or substituted with fluoro,
and where Q is selected from:
a single bond, —$SO_2$—, —SO—, and —$NR^{10}$—,
where $R^{10}$ is independently selected from: hydrogen, $C_{1-3}$ alkyl, $C_{2-3}$ alkenyl, and $C_{2-3}$ alkynyl.

In the present invention it is still more preferred that X is selected from:
(1) a single bond,
(2) —$CH_2CH_2$—,
(3) —$CH_2CH_2CH_2$—,
(4) —$CH_2CH_2$—$CF_2$—,
(5) —$CH_2CH_2$—$SO_2$—, and
(6) —$CH_2CH_2$—SO—.

In the present invention it is preferred that Y is selected from:
a single bond, —(CO)—, —(CS)$NR^9$—, —(CO)O—, —$SO_2$—, and —(CO)$NR^9$—,
where $R^9$ is independently selected from hydrogen and $C_{1-6}$ alkyl.

In the present invention it is more preferred that Y is selected from:
a single bond, —(CO)—, —(CS)$NR^9$—, —(CO)O—, —$SO_2$—, and —(CO)$NR^9$—,
where $R^9$ is independently selected from hydrogen and methyl.

In the present invention it is preferred that Z is selected from:
a single bond, —O—, and —$NR^9$—,
where $R^9$ is independently selected from hydrogen, $C_{1-6}$ alkyl, $C_{3-8}$ cycloalkyl, phenyl, and $C_{1-6}$ alkyl-phenyl, which is unsubstituted or substituted with 1–3 substituents where the substituents are independently selected from: halo, $C_{1-3}$ alkyl, $C_{1-3}$ alkoxy, phenyl and trifluoromethyl;

In the present invention it is more preferred that Z is selected from:
a single bond, —O—, and —$NR^9$—,
where $R^9$ is independently selected from hydrogen, $C_{1-6}$ alkyl, $C_{3-8}$ cycloalkyl, phenyl, and $C_{1-6}$ alkyl-phenyl, which is unsubstituted or substituted with 1–3 substituents where the substituents are independently selected from: $C_{1-3}$ alkyl, phenyl and $C_{1-3}$ alkoxy;

In the present invention it is preferred that $R^1$ is selected from: $C_{1-10}$ alkyl, cyclohexyl, $C_{0-2}$ alkyl-phenyl, tetrazolyl, and $CH_2$-cyclohexyl, which is unsubstituted or substituted with 1–3 substituents where the substituents are independently selected from: halo, $C_{1-3}$ alkyl, $C_{1-3}$ alkoxy, trifluoromethoxy and trifluoromethyl.

In the present invention it is more preferred that $R^1$ is selected from: methyl, iso-butyl, tert-butyl, hexyl, cyclohexyl, $CH_2$-cyclohexyl, tetrazolyl, and $C_{0-2}$ alkyl-phenyl wherein the phenyl is unsubstituted or substituted with 1–3 substituents where the substituents are independently selected from: chloro, fluoro, methyl, tert-butyl, trifluoromethoxy and trifluoromethyl.

In the present invention it is preferred that $R^2$ is hydrogen.

In the present invention it is preferred that $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:

phenyl, which may be unsubstituted or substituted with 1–5 substituents where the substituents are independently selected from:
(a) fluoro, and
(b) chloro; and
unsubstituted thienyl.

In the present invention it is still more preferred that $R^3$ is unsubstituted phenyl, (3-fluoro)phenyl or 3-thienyl.

In the present invention it is preferred that $R^7$ is hydrogen, fluoro, hydroxy or $C_{1-6}$ alkyl.

In the present invention it is more preferred that $R^7$ is hydrogen or fluoro.

In the present invention it is even more preferred that $R^7$ is hydrogen.

In the present invention it is preferred that $R^8$ is selected from: phenyl, naphthyl, cyclohexyl, benzoimidazolyl, benzofurazanyl, imidazopyridyl, imidazolyl, isoxazolyl, oxazolyl, pyrazinyl, pyridazinyl, pyridyl, pyrimidyl, thiazolyl, tetrazolopyridyl, pyrazolyl, tetrahydroindazolyl, tetrahydroimidazopyridyl, and tetrahydropyrazolopyridyl;
which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) $C_{0-6}$ alkyl-phenyl or $C_{0-6}$ alkyl-heterocycle, which is unsubstituted or substituted with 1–7 substituents where the substituents are independently selected from:
(i) halo,
(ii) hydroxy,
(iii) $C_{1-6}$ alkyl,
(iv) —O—$C_{1-6}$ alkyl,
(v) —$CF_3$,
(vi) —$OCF_3$,
(vii) —$NO_2$,
(viii) —CN,
(ix) —$SO_2$—$C_{1-6}$ alkyl,
(x) —$CO_2R^9$,
(xi) —$NR^9R^{10}$,
(xii) —$CONR^9R^{10}$,
(xiii) —$SO_2$—$NR^9R^{10}$, and
(xiv) —$NR^5$—$SO_2$—$R^{10}$;
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

In an aspect of the preceding embodiment, in the present invention it is preferred that $R^8$ is selected from: phenyl, naphthyl, cyclohexyl, benzoimidazolyl, benzofurazanyl, imidazopyridyl, imidazolyl, isoxazolyl, oxazolyl, pyrazinyl, pyridazinyl, pyridyl, pyrimidyl, thiazolyl, and tetrazolopyridyl; which is unsubstituted or substituted with 1–7 substituents as set forth in the preceding paragraph.

In the present invention it is more preferred that $R^8$ is selected from: phenyl, imidazopyridyl, imidazolyl, oxazolyl, pyrazolyl, pyridyl, thiazolyl, tetrahydroindazolyl, tetrahydroimidazopyridyl, and tetrahydropyrazolopyridyl;
which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(h) $C_{1-6}$ alkyl,
(i) $C_{1-3}$ alkyl-phenyl or $C_{1-3}$ alkyl-pyridyl, which is unsubstituted or substituted with 1–4 substituents where the substituents are independently selected from:
(i) halo,
(ii) $C_{1-6}$ alkyl,
(iii) —O—$C_{1-6}$ alkyl,
(iv) —$CF_3$,
(vi) —$OCF_3$,
(vii) —CN, and
(j) —O—$C_{1-6}$ alkyl.

In an aspect of the preceding embodiment, in the present invention it is preferred that $R^8$ is selected from: phenyl, imidazopyridyl, imidazolyl, oxazolyl, pyrazolyl, pyridyl, and thiazolyl; which is unsubstituted or substituted with 1–5 substituents as set forth in the preceding paragraph.

In the present invention it is even more preferred that $R^8$ is selected from: imidazolyl, oxazolyl, pyrazolyl, thiazolyl, tetrahydroindazolyl, tetrahydroimidazopyridyl, and tetrahydropyrazolopyridyl;
which is unsubstituted or substituted with 1–3 substituents where the substituents are independently selected from:
(a) fluoro,
(b) cyano,
(c) $C_{1-3}$ alkyl,
(d) —$CH_2$-phenyl, which is unsubstituted or substituted with 1–4 substituents where the substituents are independently selected from:
(i) fluoro,
(ii) chloro,
(iii) —O—$CH_3$,
(i v) —$CF_3$,
(v) —CN, and
(e) —$CF_3$.

In an aspect of the preceding embodiment, in the present invention it is preferred that $R^8$ is selected from: imidazolyl, oxazolyl, pyrazolyl, and thiazolyl; which is unsubstituted or substituted with 1–3 substituents as set forth in the preceding paragraph.

In the present invention it is still more preferred that $R^8$ is selected from: 5-(3-benzyl)pyrazolyl, 5-(1-methyl-3-benzyl)pyrazolyl, 5-(1-ethyl-3-benzyl)-pyrazolyl, 5-(2-benzyl)thiazolyl, 5-(2-benzyl-4-methyl)thiazolyl, and 5-(2-benzyl-4-ethyl)thiazolyl).

In the present invention it is preferred that x is an integer which is 1 and y is an integer which is 1.

It is to be understood that embodiments of the present invention include, but are not limited to, compounds of formula I wherein $R^1$, $R^2$, $R^3$, $R^7$, $R^8$, X, Y, Z, x and y n are defined in accordance with one of the embodiments or aspects thereof as set forth above. Any and all possible combinations of preferred, more preferred, even more preferred, highly preferred, more highly preferred, and most preferred definitions of these variables in formulas I are within the scope of the present invention.

The compounds of the instant invention have at least two asymmetric centers at the ring junction of the substitutents bearing the piperidine and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

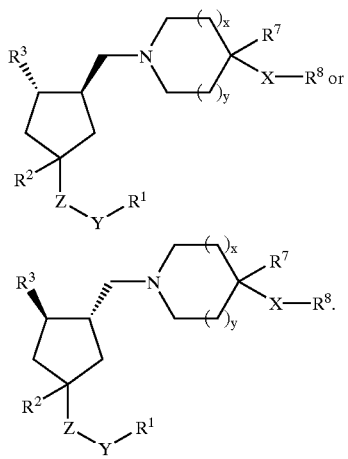

The relative configurations of the even more preferred compounds of this invention with respect to the configuration at the 1-position of the cyclopentane ring is cis with respect to the orientation of $R^3$ as depicted:

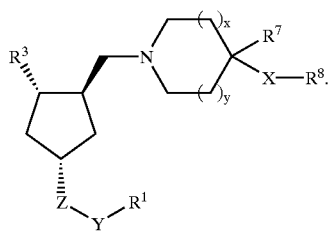

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression ". . . which is unsubstituted or substituted with . . . " "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

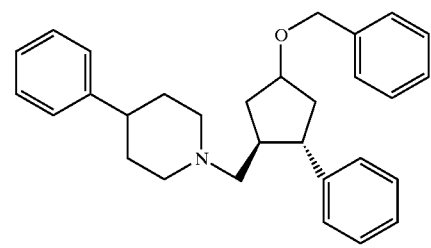

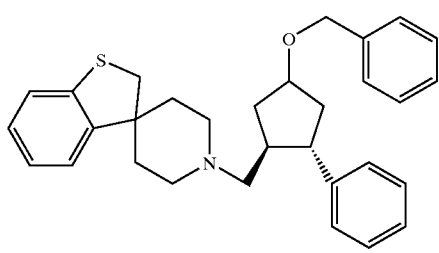

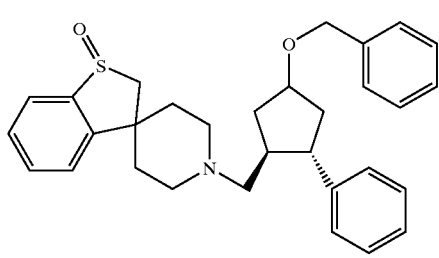

-continued

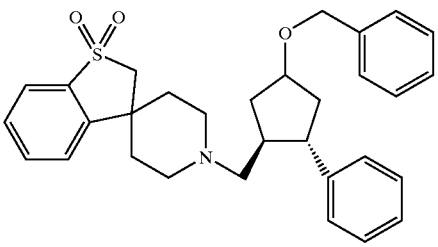

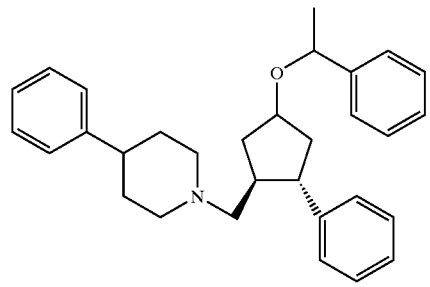

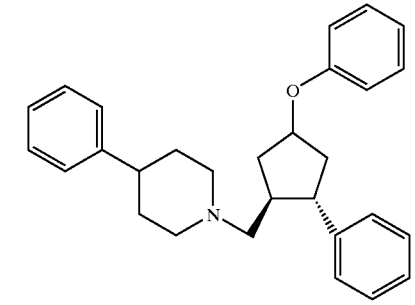

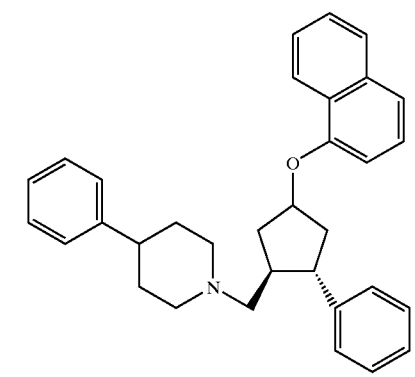

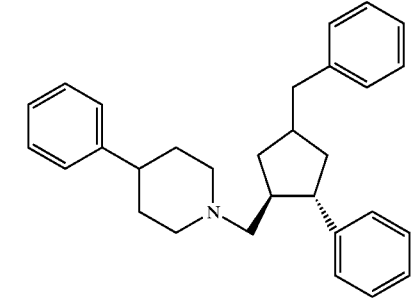

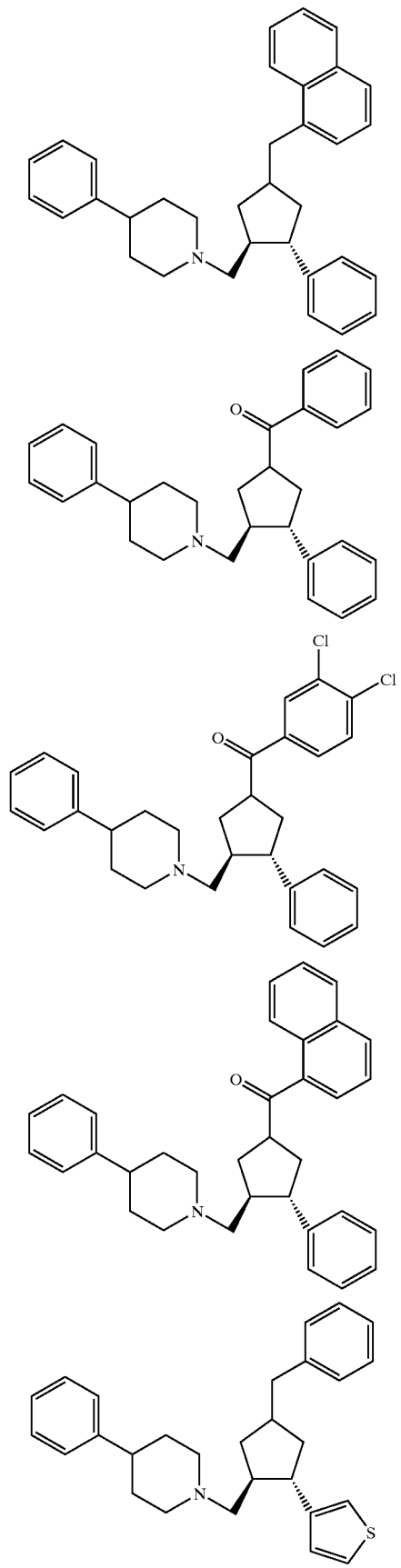
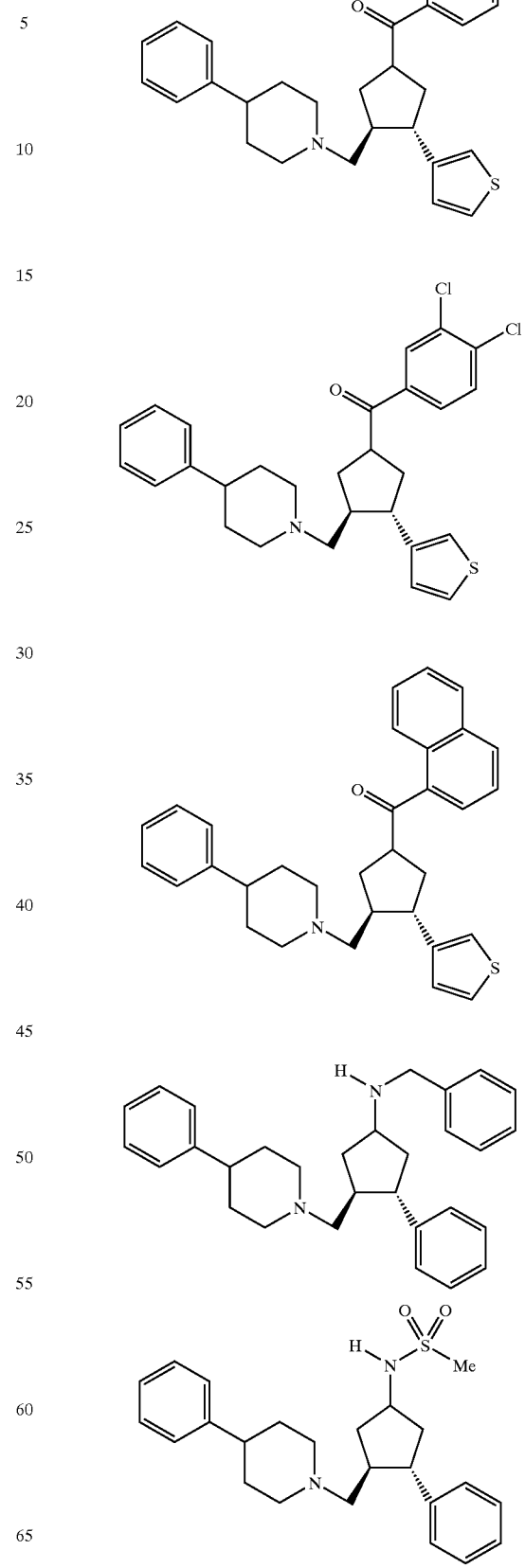

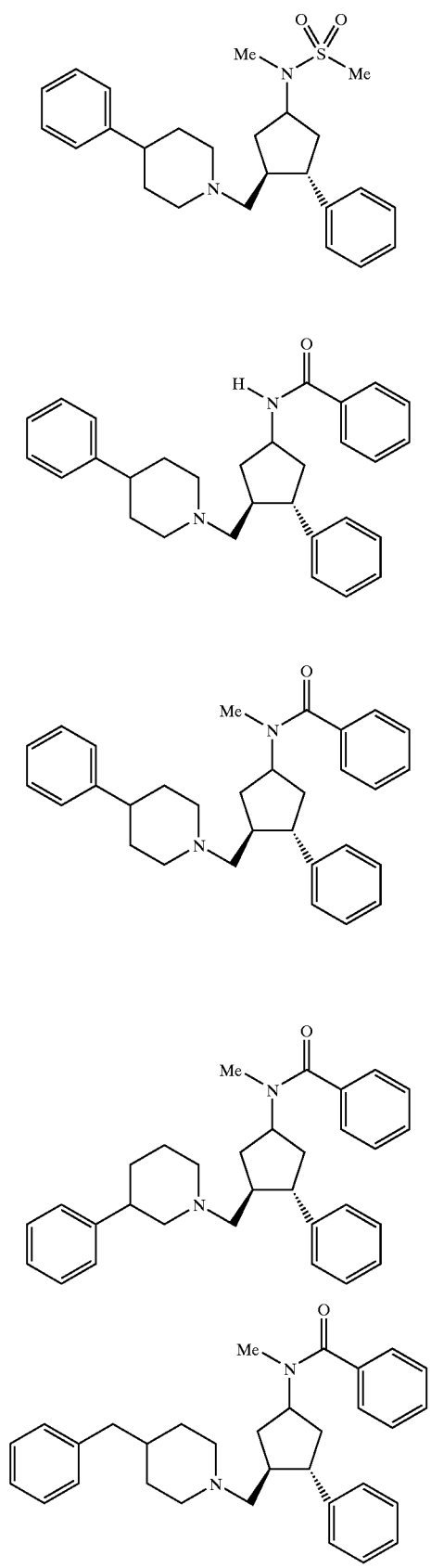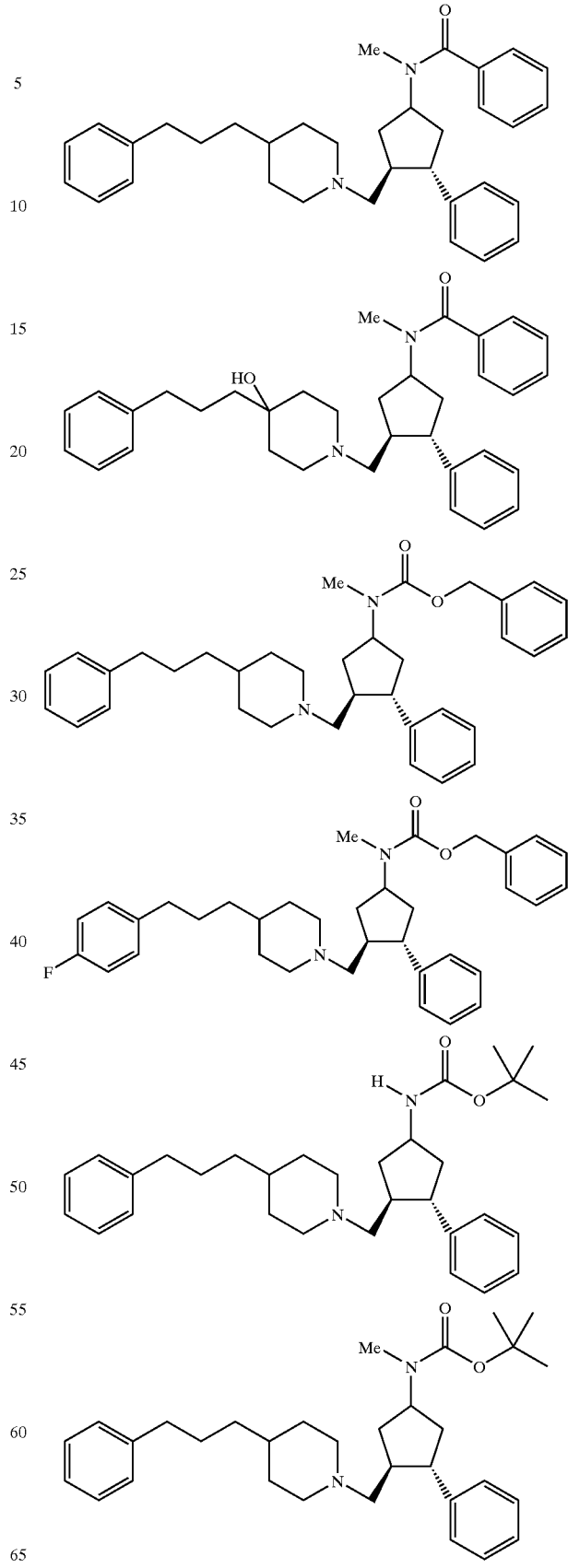

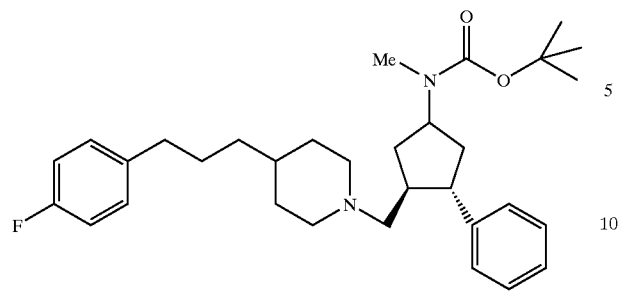
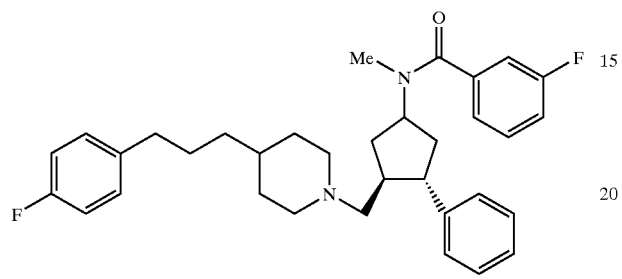
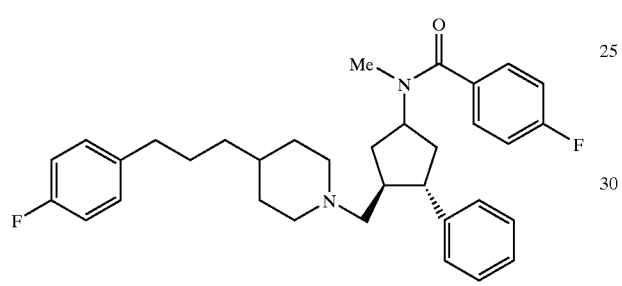
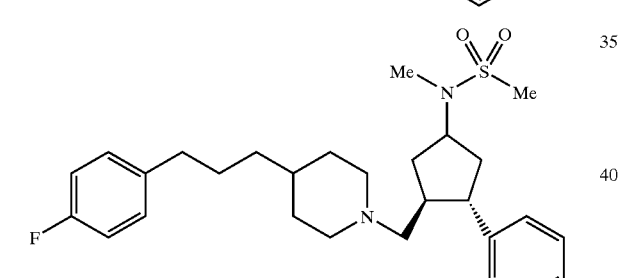
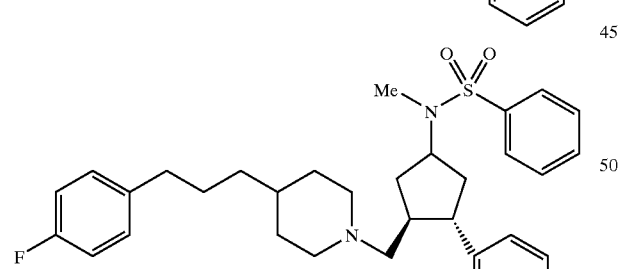
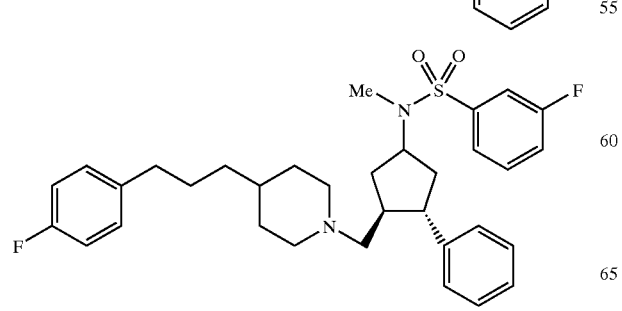
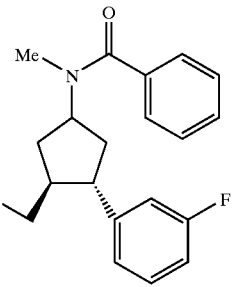
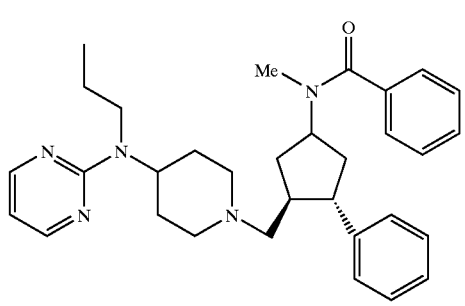
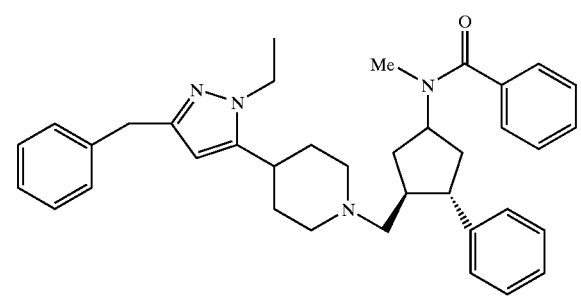
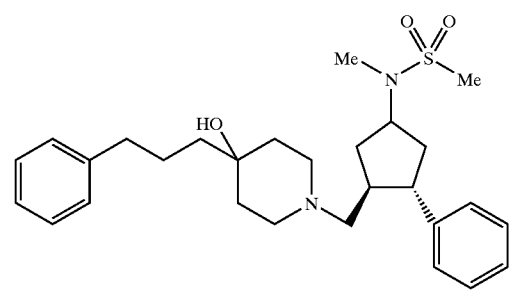
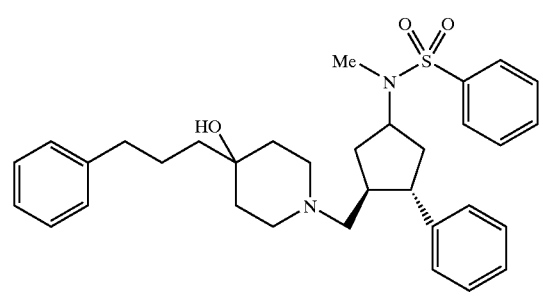

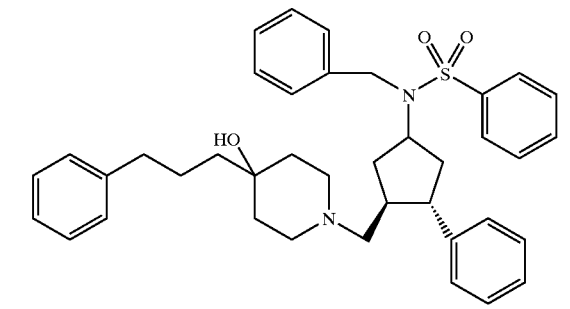
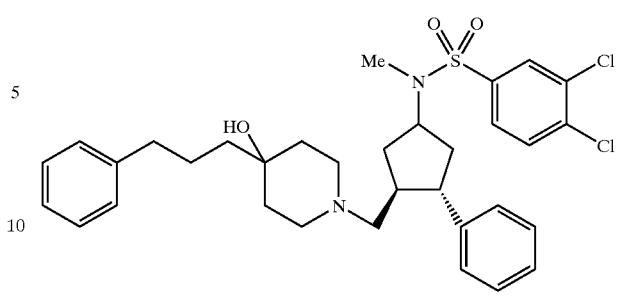
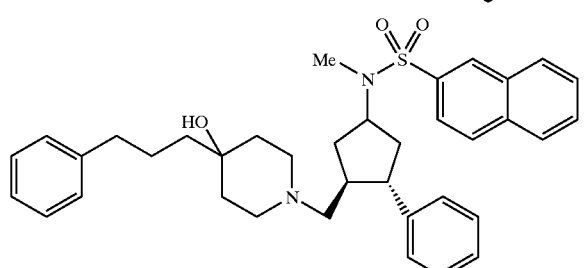
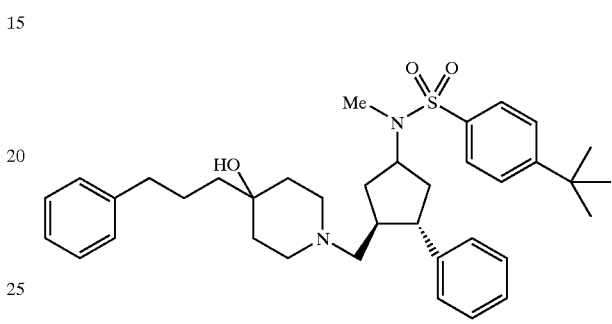
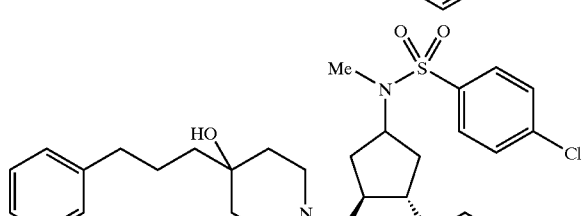
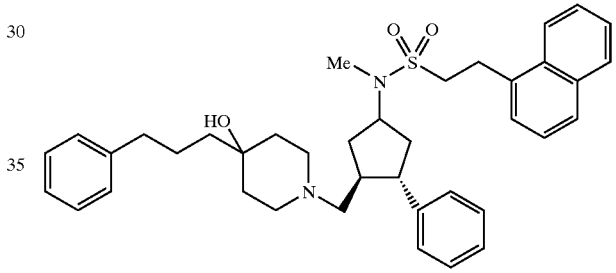
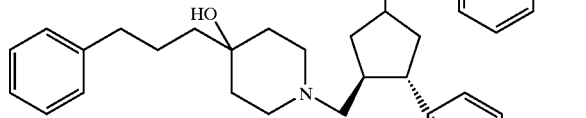
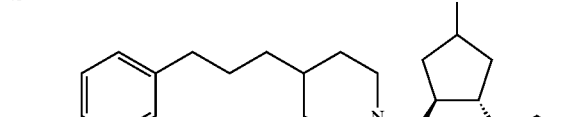
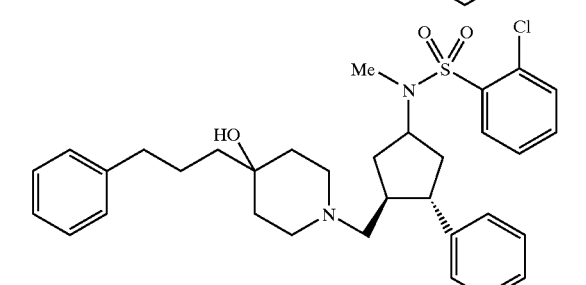
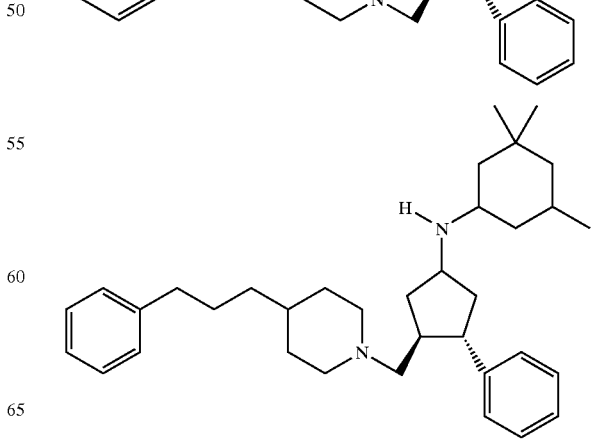
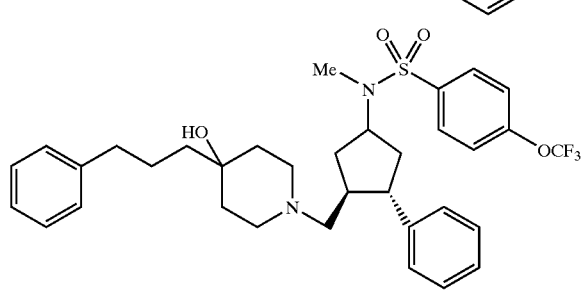

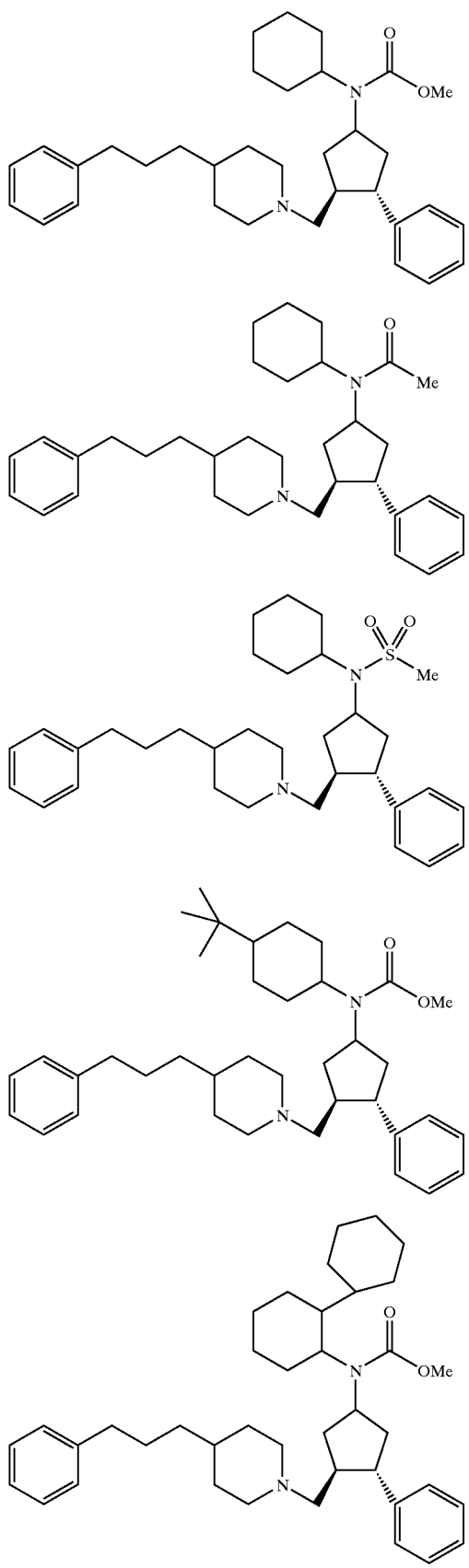
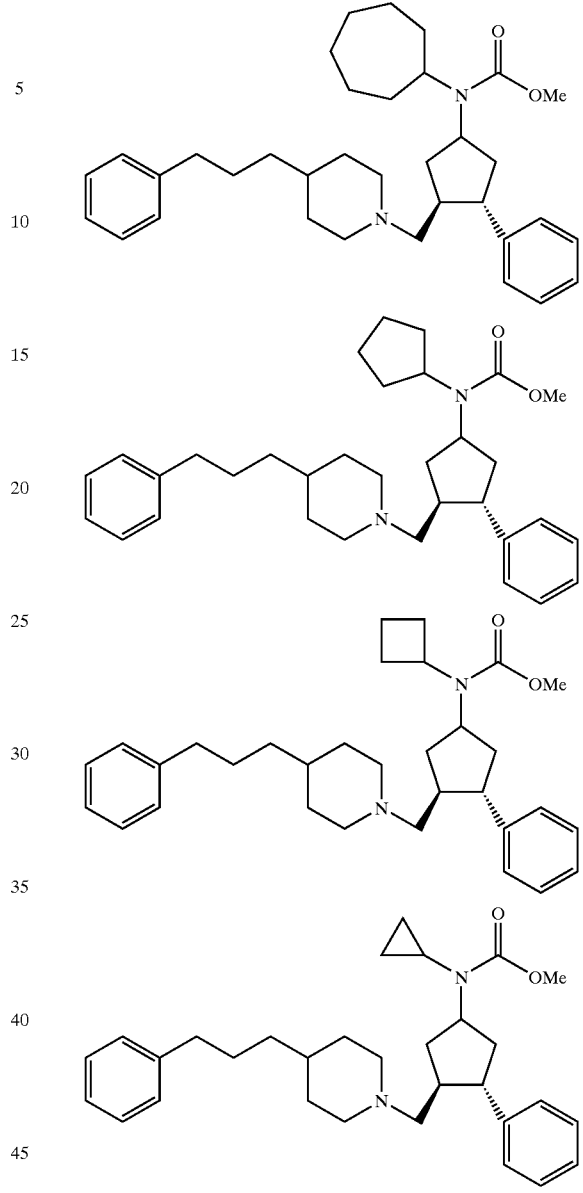

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, a topic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (LLD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, a topic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, a topic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antuinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antuitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β-2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG—CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-lox, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
|---|---|---|
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (−)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |

ANTIVIRALS -continued

| Drug Name | Manufacturer | Indication |
|---|---|---|
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TM Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |

-continued

IMMUNO-MODULATORS

| Drug Name | Manufacturer | Indication |
|---|---|---|
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrel Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral | Norwich Eaton | diarrhea and |

-continued

OTHER

| Drug Name | Manufacturer | Indication |
|---|---|---|
| Nutrition | Pharmaceuticals | malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of FHV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5646148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy- propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available, are made from known procedures or are prepared as illustrated.

SCHEME 1

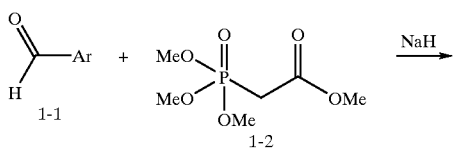

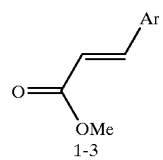

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

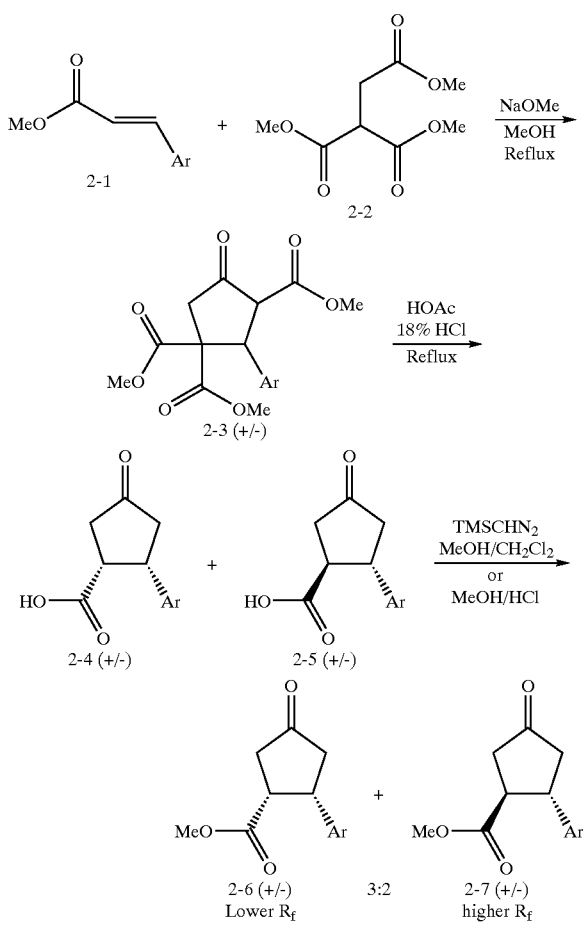

The preparation cyclopentane intermediates having a C-4-aryl substituent within the scope of the instant invention is detailed in Scheme 2 and as described by von A. W. Frahm, Liebigs Ann. Chem., 1969, 728, 21. Treatment of a trans-cinnamic ester such as 2-1 (from Scheme 1) with trimethyl 1,1,2-ethanetricarboxylate (2-2) in the presence of an equivalent of an alkoxide base such as sodium methoxide in refluxing methanol gives the racemic cyclopentane ketotriester 2-3. Hydrolysis of the esters with HCl in acetic acid at reflux with concurrent double decarboxylation affords a mixture of the cis and trans keto-acids 2-4 and 2-5. The predominant initial product is the cis isomer 2-4, however, a better cis:trans ratio of products can be obtained with longer refluxing times. Thus, for example, after 72 h a 3:2 cis:trans ratio is achieved. Esterification of the mixture of acids can be done in a variety of ways, such as with trimethylsilyldiazomethane or acid catalyzed esterification in methanol. The isomers can readily be separated by chromatography and the cis I trans assignment for each is based on literatrure NMR data for 2-6 and 2-7.

SCHEME 3

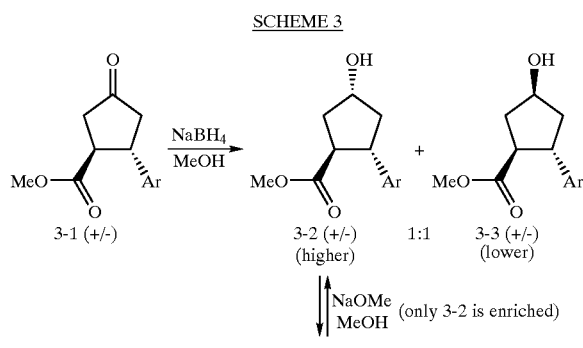

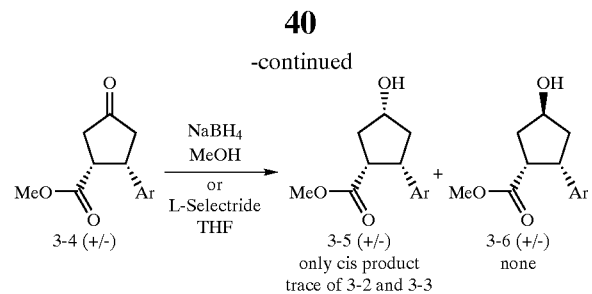

The preparation of further cyclopentane intermediates having a C4 aryl substituent within the scope of the instant invention is detailed in Scheme 3. The trans ketone 3-1 (from Scheme 2) is reduced with sodium borohydride to a near 1:1 mixture of alcohols 3-2 and 3-3, while the cis ketone 3-4 (from Scheme 2) afforded a single cis product after reduction by either sodium borohydride or L-Selectride in THF. The structure 3-5 for the cis reduction product is based on the well established reduction of the cyclopentanones from the least hindered face. The assignment of the trans reduction products was then established by equilibration of 3-5 in methanolic sodium methoxide which only gives enhancement of 3-2 by TLC and NMR.

SCHEME 4

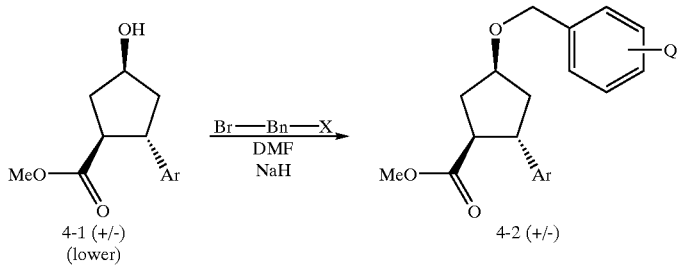

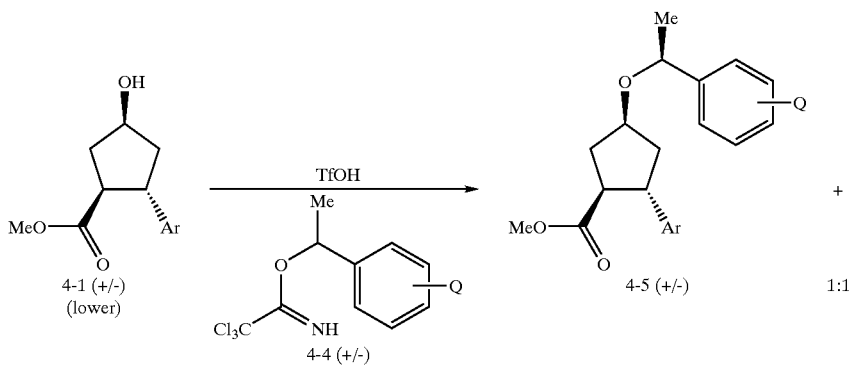

-continued

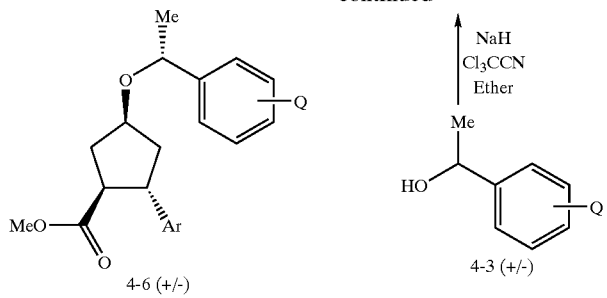

The preparation cyclopentane intermediates having a C-4 aryl and C-1 ether substituents within the scope of the instant invention is detailed in Scheme 4. Alkylation of either separated alcohol from Scheme 3, such as the lower $R_f$ alcohol 4-1, with a benzyl halide, such as benzyl bromide, can be done in DMF using a strong base such as NaH. Alternatively, alkylation with an (x-substituted benzylic alcohol such as 4-3 can be achieved through conversion to its trichloroacetimidate 4-4 and reaction with 4-1 in the presence of a strong acid catalyst such as triflic acid. The latter case results in two racemic diastereomeric products which may be separated by chromatography, but their respective stereochemistries were not assigned.

Use of the higher $R_f$ diastereomer from Scheme 3 results in its respective racemic diastereomers.

Preparation of some 1,3,4-trisubstituted cyclopentanes within the scope of the instant invention is given in Scheme 5. Reduction of ester 5-1 (from Scheme 4), for example, with lithium borohydride, diisobutylaluminum hydride, lithium aluminum hydride, or sodium bis(2-methoxyethoxy) aluminum hydride provides the primary alcohol 5-2. Oxidation to the aldehyde 5-3 can be carried out under numerous conditions, such with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 5-4 (see Schemes 12 to 30), using for example sodium triacetoxyborohydride or sodium cyanoborohydride in a suitable solvent, such as methylene chloride, 1,2-dichloroethane, THF, acetonitrile or methanol, then provides a 3-((4-substitutedpiperidin-1-yl)methyl) cyclopentane derivative 5-5 which can itself be a chemokine receptor modulator or can be further modified as detailed below in Scheme 14.

SCHEME 5

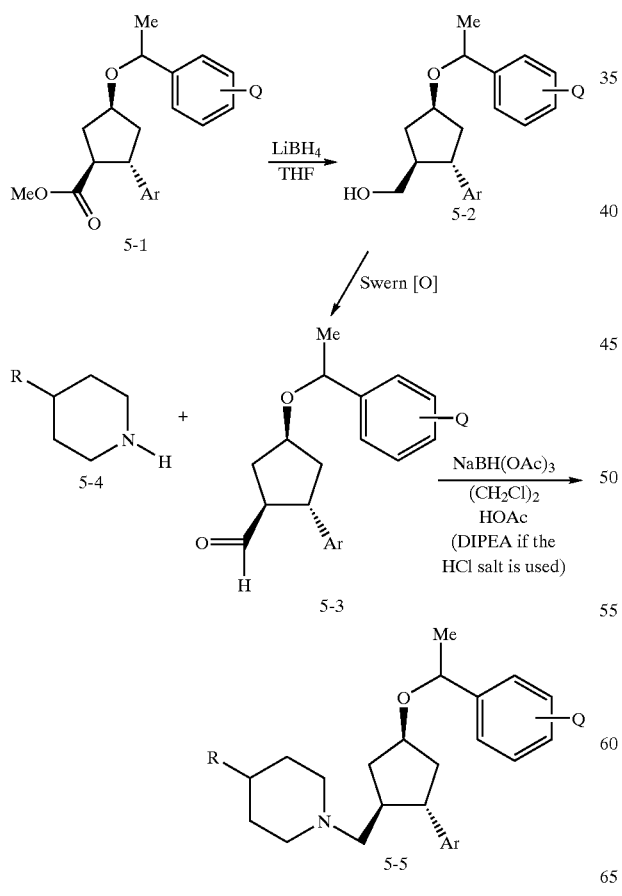

SCHEME 6A

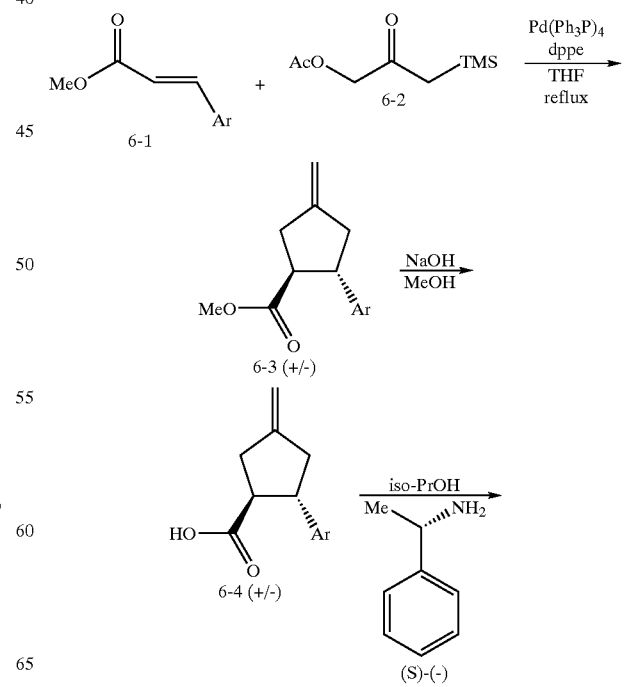

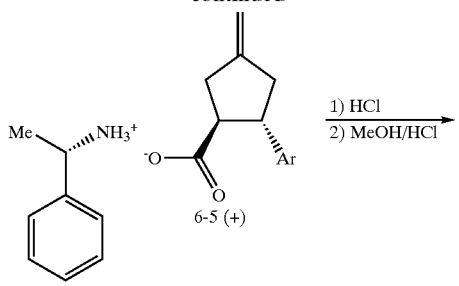
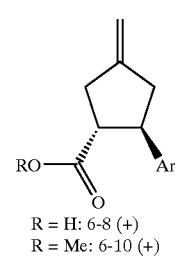
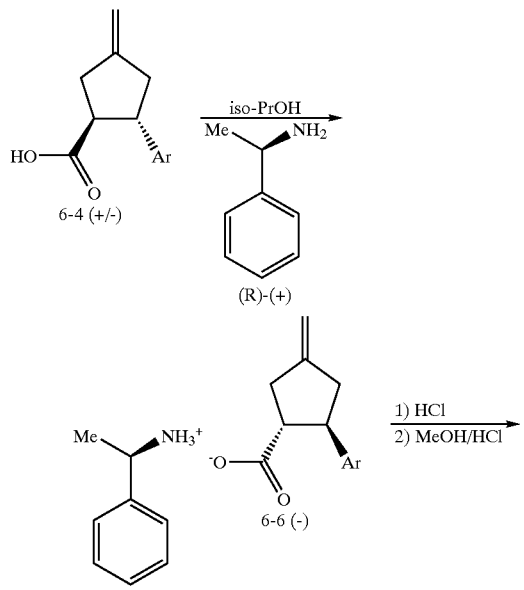

An alternative preparation of cyclopentane intermediates having a C-4 aryl substituent within the scope of the instant invention is detailed in Scheme 6A and was used to prepare non-racemic cyclopentane derivatives. Treatment of a trans-cinnamic ester such as 6-1 (see Scheme 1) with 2-((trimethylsilyl)methyl)-2-propen-1-yl acetate (6-2) in the presence of a catalytic amount of tetrakis (triphenylphosphine) palladium (0) and 1,2-bis (diphenylphosphino)ethane in THF at reflux afforded the exo-methylene cyclopentane 6-3. Hydrolysis of the ester can be done several ways, such as with aqueous sodium or lithium hydroxide in methanol or THF, to obtain the racemic acid 6-4. Resolution of the enantiomers can be accomplished by fractional crystallization from isopropanol, or other suitable solvents, of the salts with either (R)-(+)- or (S)-(−)-(α-methylbenzyl amine to give the salts 6-5 and 6-6. The non-racemic acids 6-7 and 6-8 are recovered by acidification and extraction. Reesterification to non-racemic 6-9 and 6-10 can be done in a variety of ways, such as with trimethylsilyldiazomethane or acid catalyzed esterification in methanol.

SCHEME 6B

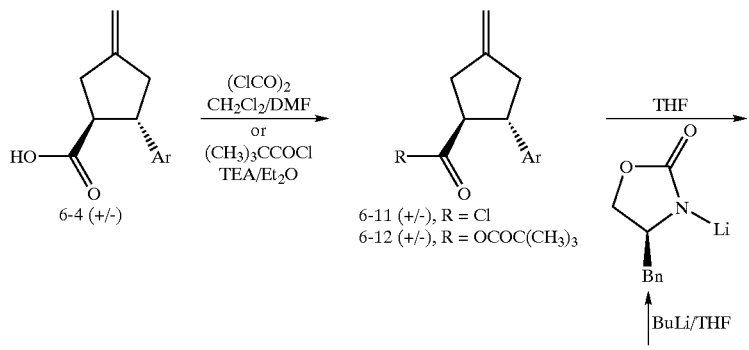

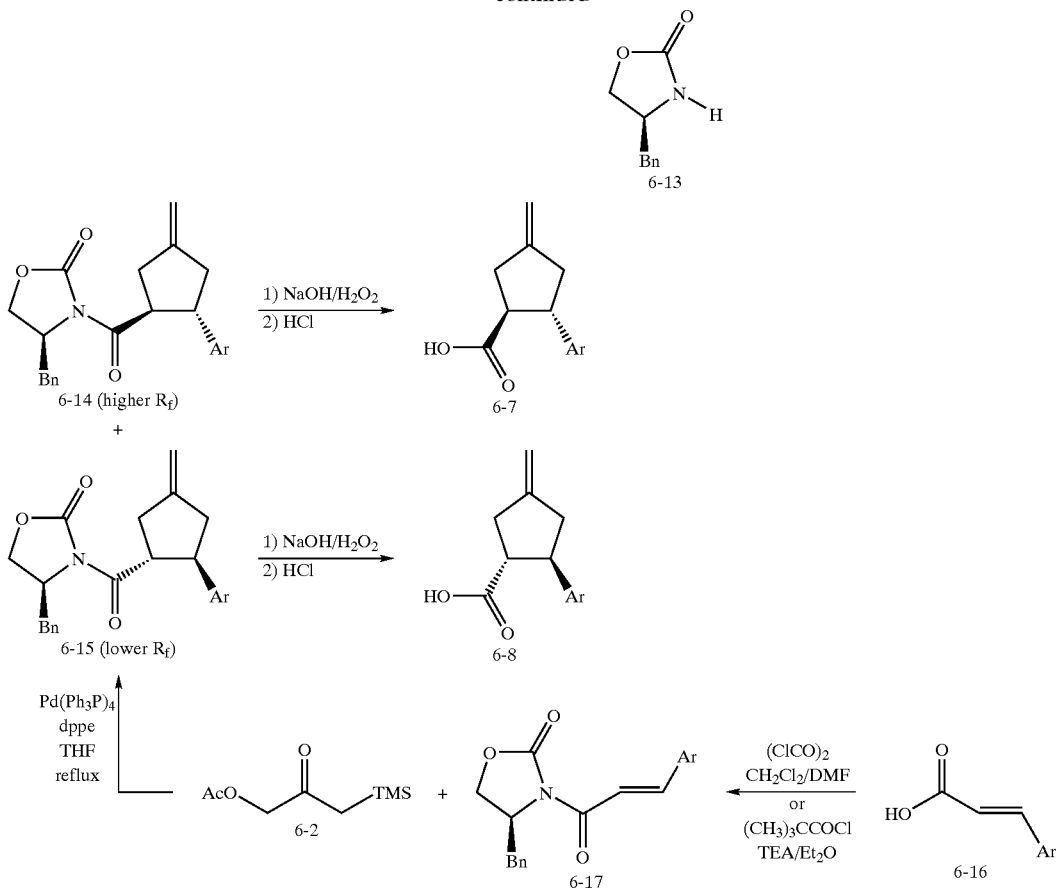

An alternative preparation of non-racemic cyclopentane intermediates having a C-4 aryl substituent within the scope of the instant invention is detailed in Scheme 6B. Conversion of the cyclopentane acid 6-4 (from Scheme 6A) to the acid chloride 6-11 under standard conditions, such as with oxalyl chloride in methylene chloride with a catalytic amount of DMF, or to the mixed anhydride 6-12, prepared in situ with trimethylacetyl chloride in ether with TEA as base, followed by reaction with the preformed lithium salt of (S)-(−)-4-benzyl-2-oxazolidinone 6-13, afforded the two non-racemic diastereomeric products 6-14 and 6-15, which are then separable by chromatography. Hydrolysis of each diastereomer under standard conditions, such as with lithium hydroxide and hydrogen peroxide, affords the two non-racemic acids 6-7 and 6-8. Alternatively, in order to obtain an enhanced amount of the desired diastereomer 6-14 before separation, similar conversion of the starting trans-cinnamic acid 6-16 (Scheme 1) to the chiral trans-cinnamate 6-17 followed by the ring formation reaction with 2-((trimethylsilyl)methyl)-2-propen-1-yl acetate (6-2) as detailed in Scheme 6A affords a 60:40 product mixture of 6-14: 6-15.

SCHEME 7

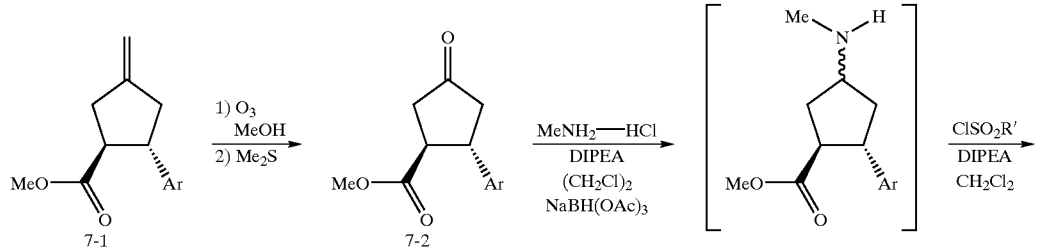

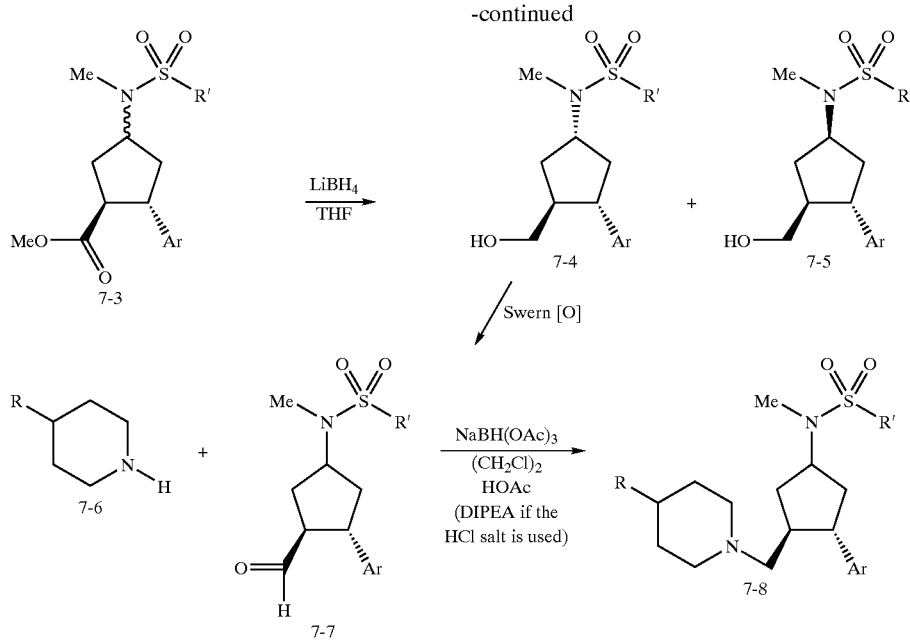

An alternative route for the preparation of some 1,3,4-trisubstituted cyclopentanes within the scope of the instant invention is given in Scheme 7. Oxidation of 7-1 (from Scheme 6, either racemic or non-racemic) with ozone at −73° C. in an alcoholic solvent, such as methanol, followed by treatment with dimethyl sulfide affords the ketone 7-2 (same as racemic 2-7 in Scheme 2). Reductive alkylation of methylamine with 7-2, using for example sodium triacetoxyborohydride or sodium cyanoborohydride, followed by acylation with a sulfonyl chloride (or other acylation or sulfonylation reagent as detailed in Scheme 10) gives the sulfonamide 7-3 as a mixture of isomers. Reduction of the ester mixture, for example with lithium borohydride at rt to 65° C., provides the primary alcohol which are separated by chromatography into the two diastereomers at C-1, 7-4 and 7-5. Oxidation to the aldehyde(s) 7-7 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive alkylation of a cyclic amine, such as piperidine 7-6 (see Schemes 12 to 30) with 7-7, using for example sodium triacetoxyborohydride or sodium cyanoborohydride, then provides a 3-((4-substitutedpiperidin-1-yl)methyl) cyclopentane derivative 7-8 which can itself be a chemokine receptor modulator or can be further modified as detailed below in Scheme 14.

SCHEME 8

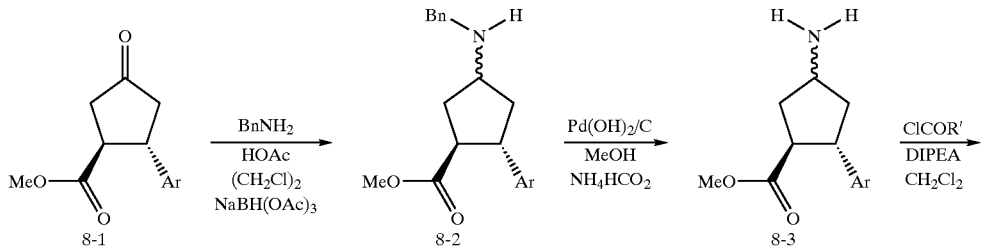

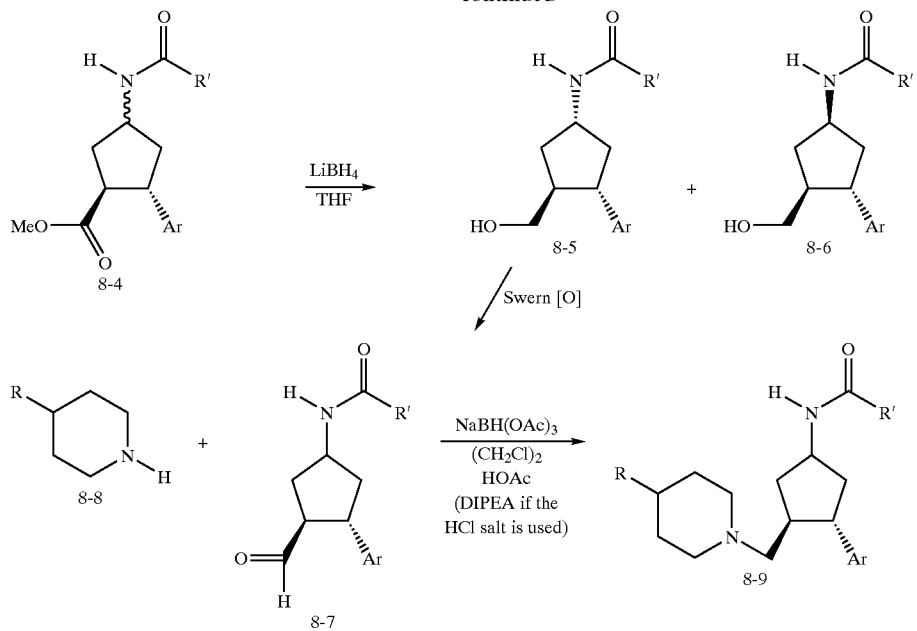

An alternative route for the preparation of some 1,3,4-trisubstituted cyclopentanes within the scope of the instant invention is given in Scheme 8. Reductive alkylation of benzylamine with 8-1 (from Scheme 2 or 6), using for example sodium triacetoxyborohydride or sodium cyanoborohydride, gives 8-2 which can be hydrogenated under standard conditions, such as in methanol in the presence of a palladium catalyst, for example Pd/C or Pearlman's catalyst, and using either hydrogen under pressure or ammonium formate at reflux, to afford the primary amine 8-3. Acylation with an acyl chloride (or other acylation or sulfonylation reagent as detailed in Scheme 10) gives the amide 8-4 as a mixture of isomers. Reduction of the ester mixture, for example with lithium borohydride at rt to 65° C., provides the primary alcohol which may be separated into the two diastereomers at C-1, 8-5 and 8-6. Oxidation to the aldehyde(s) 8-7 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 8-8 (see Schemes 12 to 30), using for example sodium triacetoxyborohydride or sodium cyanoborohydride, then provides a 3-((4-substitutedpiperidin-1-yl)methyl) cyclopentane derivative 8-9 which can itself be a chemokine receptor modulator or can be further modified as detailed below in Scheme 14.

SCHEME 9

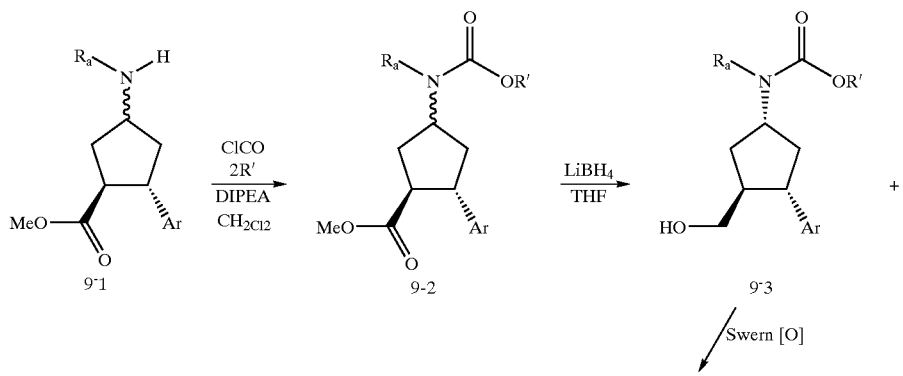

-continued

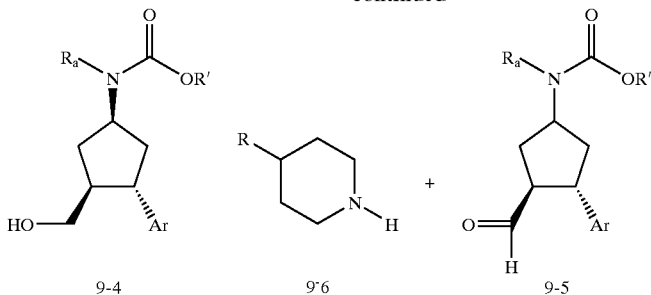

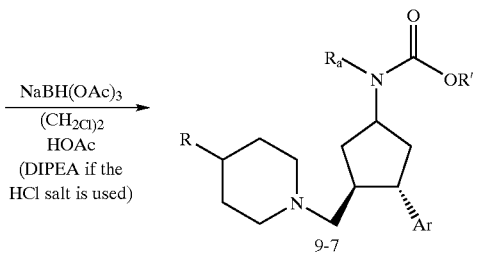

An alternative route for the preparation of some 1,3,4-trisubstituted cyclopentanes within the scope of the instant invention is given in Scheme 9. Acylation of the amine 9-1, usually as a mixture of isomers from Scheme 7 or 8, with a chloroformate gives the carbamate 9-2. Reduction of the ester mixture, for example with lithium borohydride at rt to 65° C., provides the primary alcohol which may be separated into the two diastereomers at C-1, 9-3 and 9-4, if 9-1 started as a mixture. Oxidation to the aldehyde 9-5 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 3-6 (see Schemes 12 to 30), using for example sodium triacetoxyborohydride or sodium cyanoborohydride, then provides a 3-((4-substitutedpiperidin-1-yl)methyl) cyclopentane derivative 9-7 which may itself be a chemokine receptor modulator or may be further modified as detailed below in Scheme 14.

SCHEME 10

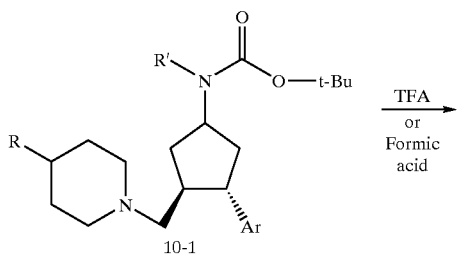

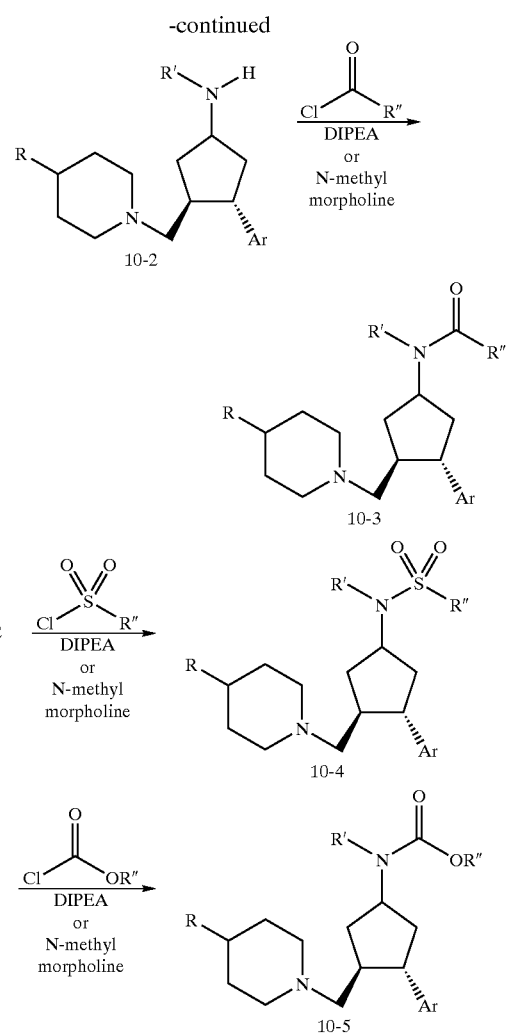

-continued

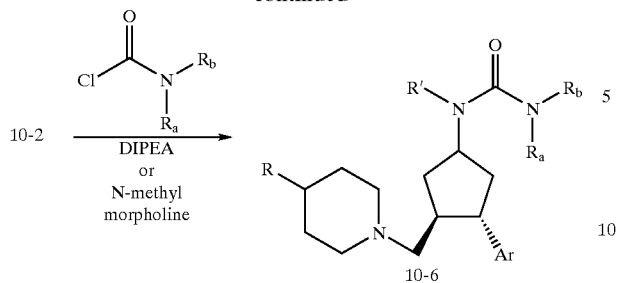

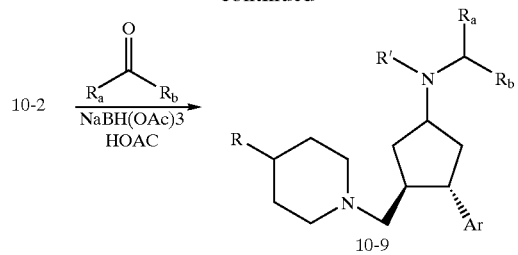

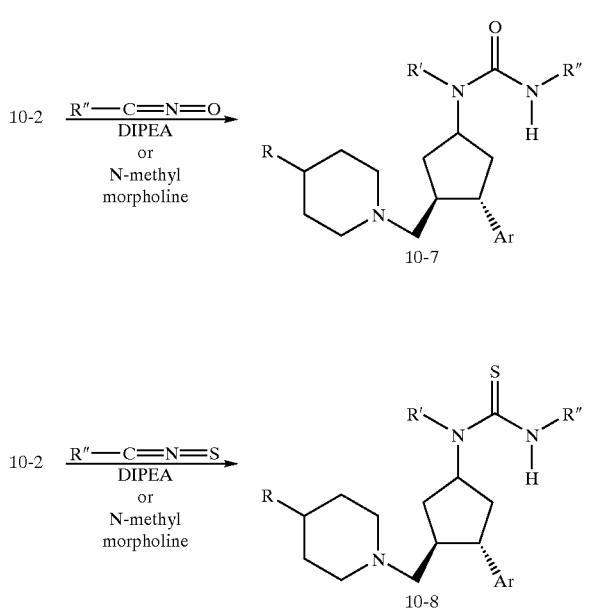

Another method of preparing compounds within the scope of the instant invention is given in Scheme 10. In the case where R' in Scheme 9 is t-butyl (or PMB), such as shown in 10-1, the Boc (or PMB ester) group can be removed with strong acid, such as trifluoroacetic acid at rt or formic acid at rt to 60° C., to generate the amine 10-2 which already has the C-3 position fully functionalized. Alternatively, if R' in Scheme 9 is PMB or benzyl, amine 10-2 can be generated by standard hydrogenation, the choice of carbamate depends on the compatability with R. The amine of 10-2 can then be converted to a variety of nitrogen based derivatives at the C-1 position. For example, acylation with an alkyl or aryl acid chloride, or a carboxylic acid plus an activating agent, such as EDC, DCC, DIC or BOP-Cl, affords amide 10-3. Use of an alkyl or aryl sulfonyl chloride gives sulfonamides 10-4, use of an alkyl or aryl chloroformate gives carbamates 10-5, use of an alkyl or aryl carbamoyl chloride or isocyanate gives ureas 10-6 and 10-7, and use of an alkyl or aryl isothiocyanate gives thioureas 10-8. These reaction can be done in a variety of suitable solvents, such as methylene chloride, dichloroethane, THF or methanol. For each of these reactions, an amine base is employed, such as TEA, DIPEA, n-methyl morpholine, pyridine or 2,6-lutidine. Alternatively, reductive alkylation with an aldehyde or ketone with a suitable reducing agent, such as sodium cyanoborohydride or sodium triacetoxyborohydride, in a suitable solvent, such as methylene chloride or dichloroethane, can afford the di-basic amine derivative 10-9.

SCHEME 11

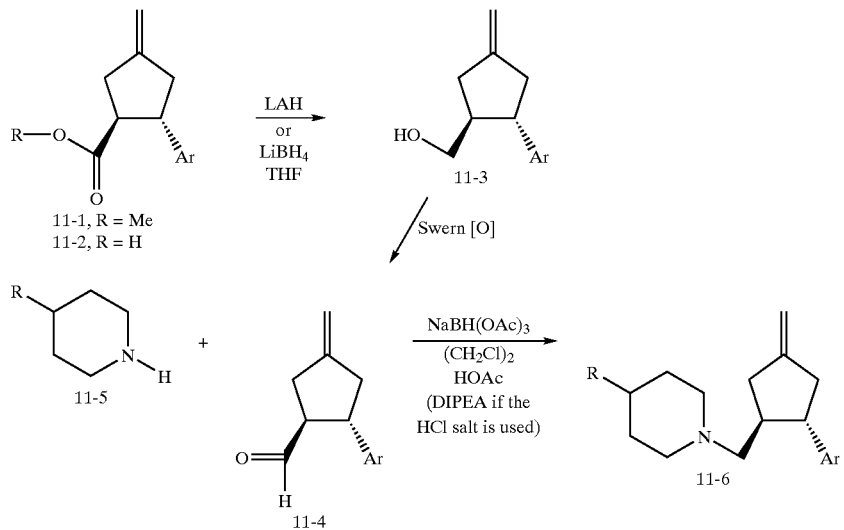

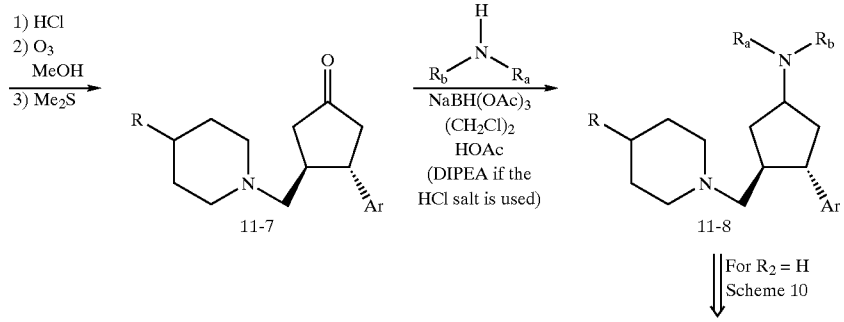

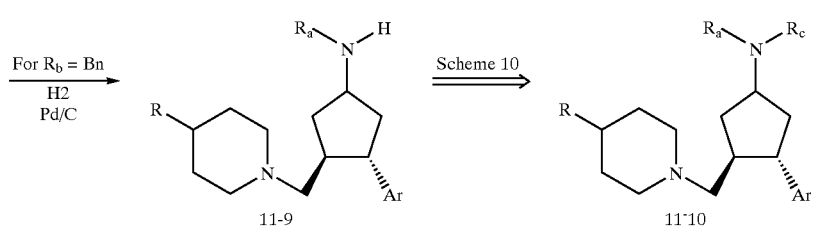

Another method of preparing compounds within the scope of the instant invention is given in Scheme 11. Reduction of either ester 11-1 with lithium aluminum hydride or lithium borohydride or acid 11-2 with lithium aluminum hydride affords the exo-methylene alcohol 11-3. Oxidation to the aldehyde 11-4 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic-Chemistry". 4th ed., John Wiley & Sons, New York, pp. 1167–1171 (1992)). Reductive alkylation of a cyclic amine, such as piperidine 11-5 (see Schemes 12 to 30) with 11-4, using for example sodium triacetoxyborohydride or sodium cyanoborohydride, then provides a 3-((4-substitutedpiperidin-1-yl)methyl) cyclopentane derivative 11-6. Oxidation of the exo-methylene of 11-6 to a ketone 11-7 can be done on the hydrochloride salt of 11-6 in methanol with ozone at −73° C. followed by dimethyl sulfide work-up. Reductive alkylation of a primary or secondary amine with 11-7 using for example sodium triacetoxyborohydride or sodium cyanoborohydride affords the amine 11-8 which itself be a chemokine receptor modulator or can be further modified as already detailed in Schemes 7-10. Thus, if $R_b$ of 11-8 is H, further functionalization of 11-8 as detailed in Scheme 10 can afford 11-10 as other examples of chemokine receptor modulators. Alternatively, if $R_2$ is benzyl or some other amine protecting group, and the piperidine substituent R is stable to hydrogenation or other means for removing the $R_2$ group to give 11-9, then further functionalization to 11-10 is also possible.

SCHEME 12

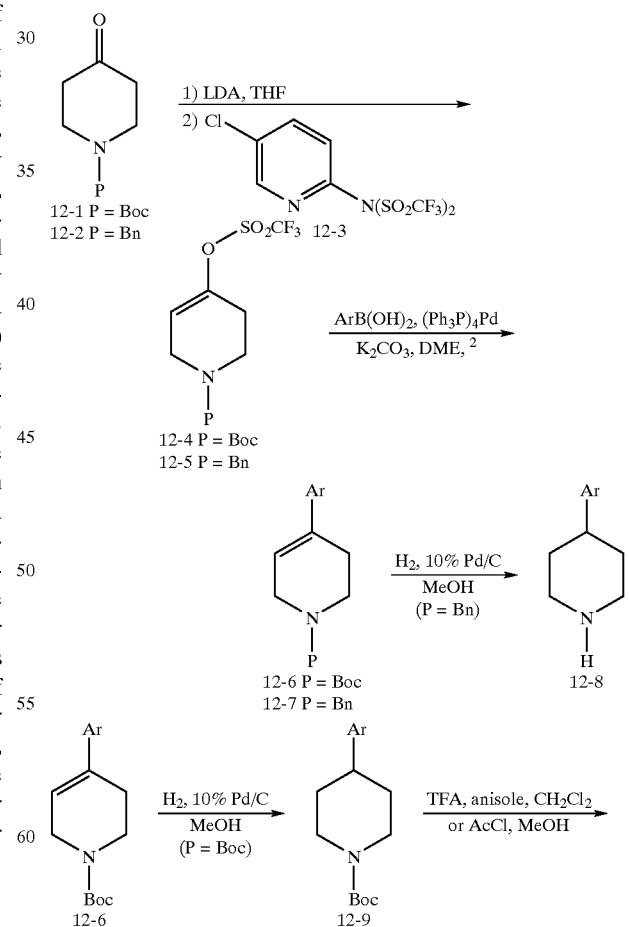

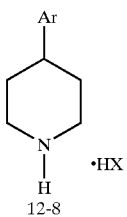
12-8

One method of generating 4-aryl piperidines as intermediates is given in Scheme 12. Reaction of commercially available 12-1 or 12-2 with a strong base, such as LDA, LiHDMS, NaHMDS, KHMDS, or NaH followed by treating with a suitable triflating agent, such as 5-chloropyrid-2-yl triflimide (12-3), N-phenyl triflimide or triflic anhydride, provides enol triflates 12-4 or 12-5. Heating with commercially available aryl boronic acids in the presence of a suitable palladium(0) catalyst such as tetrakis triphenylphosphine palladium, a base (such as potassium carbonate or sodium carbonate), in a solvent such as DME, THF, dioxane or toluene/ethanol, effects coupling to provide the unsaturated products 12-6 or 12-7. In the case of 12-7, treatment with a heterogeneous palladium catalyst in methanol or ethanol in an atmosphere of hydrogen provides the desired intermediate 12-8. Alternatively, the Boc protected derivative 12-6 is hydrogenated under standard conditions to provided the saturated piperidine 12-9, which is then deprotected under acidic conditions (such as trifluoroacetic acid and anisole in methylene chloride), to provide 12-8 as a salt, which is then utilized as the cyclic secondary amine component as shown above in Schemes 5, 7, 8, 9 and 11.

hydrogenolytic conditions, for example with triethylsilane and trifluoroacetic acid or under dissolving metal conditions (for example, sodium or lithium metal in ammonia or a lower alkyl amine). If the N-benzyl group is not removed under these conditions, it may be cleaved by treatment with either vinyl chloroformate and then hydrogen chloride or by treatment with 2-chloroethyl chloroformate followed by heating in methanol. The product 13-4 is then utilized as the cyclic secondary amine component as shown above in Schemes 5, 7, 8, 9 and 11.

SCHEME 13

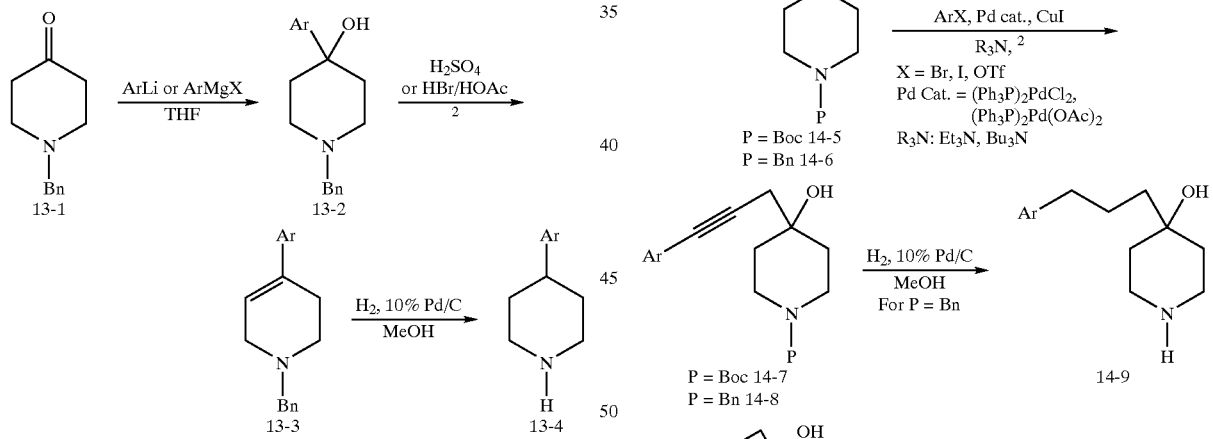

An alternative method of generating 4-aryl piperidines as intermediates is given in Scheme 13. Reaction of commercially available 13-1 with an aryl magnesium halide or with an aryllithium (in the presence or absence of anhydrous cerium trichloride) provides tertiary alcohol 13-2, which upon treatment under acidic conditions (such as sulfuric acid, HBr in acetic acid, HCl in acetic acid) or under dehydrating conditions (such as with thionyl chloride in pyridine or with phosphorus oxychloride) provides olefin 13-3. Hydrogenation under standard conditions using either hydrogen gas; or a hydrogen donor (such as ammonium formate or cyclohexene) effects reduction of the double bond and cleavage of the N-benzyl group to provide the desired intermediate 13-4. Under some circumstances it may be preferable to reduce the double bond under non-

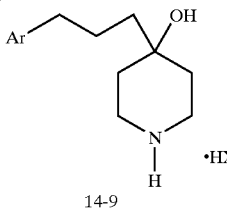

14-9

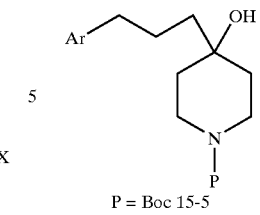

P = Boc 15-5
P = Bn 15-6

H₂, 10% Pd/C
————————→
MeOH
For P = Bn

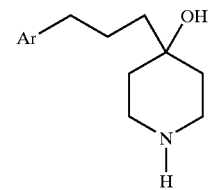

15-7

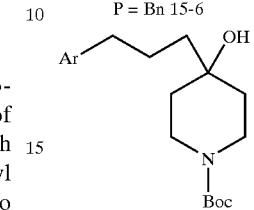

15-5

TFA, anisole, CH₂Cl₂
————————→
or AcCl, MeOH

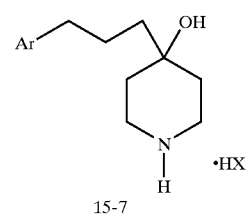

15-7

Once route for the preparation of 4-hydroxy-4-(3-arylpropyl)piperidines is given in Scheme 14. Treatment of commercially available 4-piperidones 14-1 or 14-2 with trimethylsulfonium iodide and sodium hydride in dimethyl sulfoxide at or above room temperature provides spiro epoxides 14-3 or 14-4. Addition of the lithium salt of trimathylsilylacetylene to these epoxides in the presence of lithium perchlorate in THF at 0 degrees C., followed by treatment of the crude intermediate with potassium carbonate in methanol, affords the acetylenic alcohols 14-5 or 14-6. Heating of these alkynes with an aromatic halide or triflate in the presence of copper(I) iodide, a palladium catalyst such as bis(triphenylphosphine)palladium dichloride or bis(triphenylphosphine)palladium diacetate in the presence of a tertiary amine base such as triethylamine or tributylamine, then provides coupling products 14-7 or 14-8. In the case of the N-benzyl protected intermediate 14-8, hydrogenation/hydrogenolysis under standard conditions (for example 10% Pd/C in an atmosphere of hydrogen) provides desired intermediate 14-9. For the Boc protected species 14-7, hydrogenation as above provides the saturated piperidine 14-10, and treatment of this compound under anhydrous acidic conditions (for example, trifluoroacetic acid and anisole in methylene chloride, or acetyl chloride in methanol) then yields the salt of intermediate 14-9. This compound is then utilized as the cyclic secondary amine component as shown above in Schemes 5, 7, 8, 9 and 11. Alternatively, if 4-piperidone is attached directly to the functionalized alkylcyclopentane framework described above, then the chemistry described herein can be carried out treating the aforementioned alkylcyclopentane segment as 'P' given in Scheme 14.

SCHEME 15

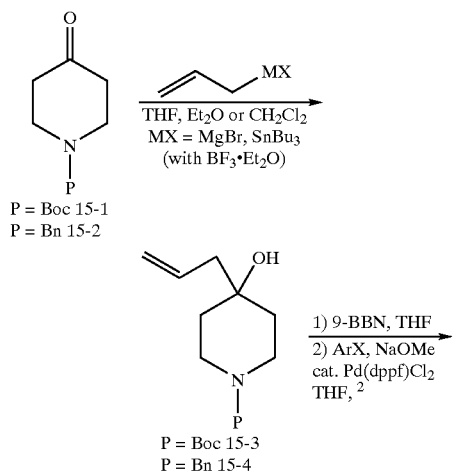

An alternative route for the preparation of 4-hydroxy-4-(3-arylpropyl)piperidines is given in Scheme 15. Treatment of commercially available 4-piperidones 15-1 or 15-2 with a suitable allyl metal compound (such as allylmagnesium bromide or allyltributylstannane (in the presence of boron trifluoride etherate) in THF, ether or dichloromethane, provides adducts 15-3 or 154. Hydroboration with a dialkylborane, such as 9-borabicyclo[3.3. 1 ]nonane (9-BBN), followed by treatment with an aryl halide (the halides preferably being bromide or iodide) or aryl triflate and sodium methoxide in the presence of a suitable soluble palladium catalyst, for example Pd(dppf)Cl₂, in warm to refluxing THF, provides the 3-arylpropyl derivalives 15-5 and 15-6. For benzylamine 15-6, hydrogenolysis under standard conditions provides the desired intermediate 15-7. For Boc substituted piperidine 15-5, exposure to suitable anhydrous acidic conditions (for example trifluoroacetic acid and anisole in methylene chloride at temperatures from 0–25 degrees C.) affords the salt of 15-7. This compound is then utilized as the cyclic secondary amine component as shown above in Schemes 5, 7, 8, 9 and 11. Alternatively, if no functionality are present in the alkyl pyrrolidine framework that would be adversely effected by the above mentioned chemistry, then 4-piperidone may be attached directly to the alkylcyclopentane framework described above, and the chemistry described in this paragraph can be carried out equating the alkylcyclopentane segment to the group 'P' given in Scheme 15, structures 1 through 6.

SCHEME 16

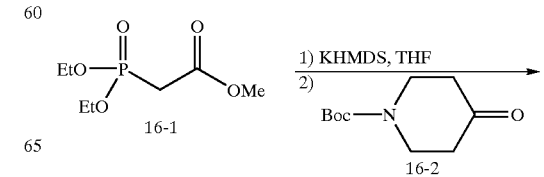

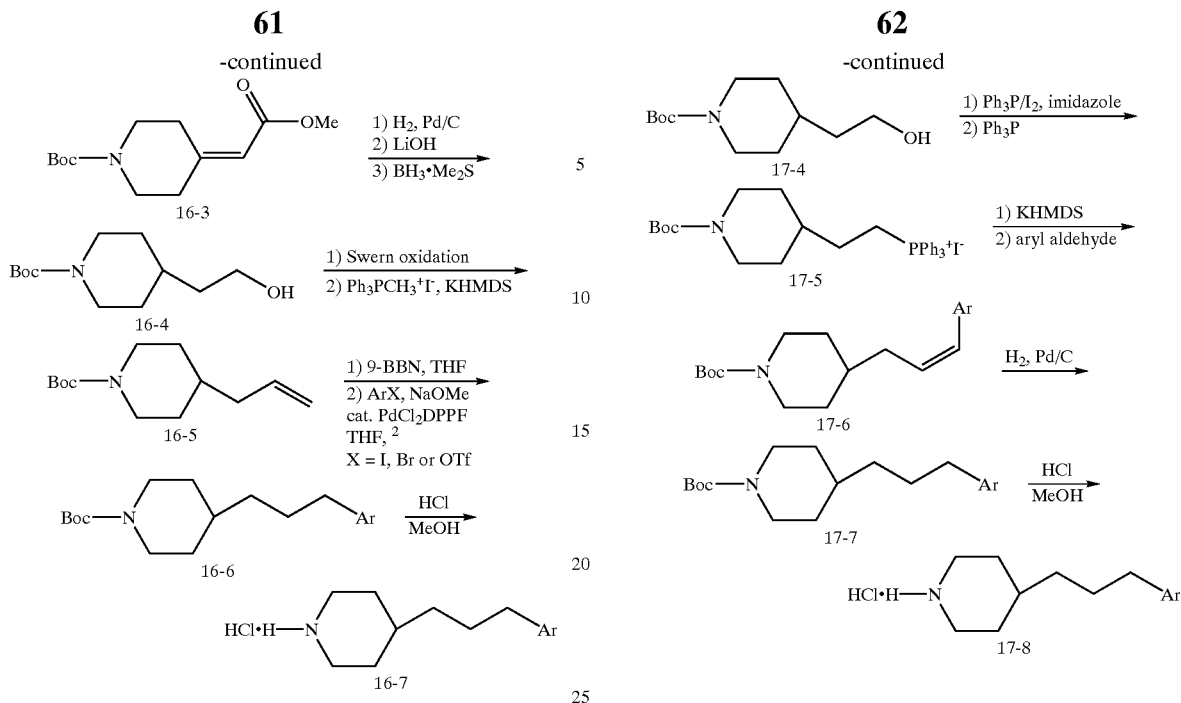

A route for the preparation of 4-(3-arylpropyl)piperidines is given in Scheme 16. Treatment of phosphonoacetate 16-1 with KHMDS followed by addition of commercially available N-Boc -4-piperidone 16-2 provides unsaturated ester 16-3. Hydrogenation of 16-3 followed by hydrolysis to the acid and then reduction with borane·methyl sulfide then affords primary alcohol 16-4. Mild oxidation of 16-4 under Swern conditions provides the corresponding aldehyde, which upon treatment with the Wittig reagent prepared from methyltriphenylphosphonium iodide and KHMDS yields olefin 16-5. Hydroboration with a dialkylborane, such as 9-borabicyclo[3.3.1]nonane (9-BBN), followed by treatment with an aryl halide (the halides preferably being bromide or iodide) or aryl triflate in the presence of a suitable soluble palladium catalyst, for example PdCl$_2$DPPF, in warm to refluxing THF, provides the 3-arylpropyl derivative 16-6. Removal of the Boc group under acidic conditions, for example with HCl in methanol or with trifluoroacetic acid in methylene chloride, then affords the 1-unsubstituted piperidine 16-7, which can then be employed as the secondary amine component in the syntheses described above in Schemes 5, 7, 8, 9 and 11.

SCHEME 17

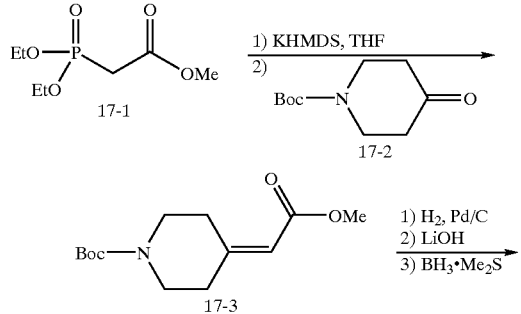

Another route for the preparation of 4-(3-arylpropyl) piperidines is given in Scheme 17. Treatment of phosphonoacetate 17-1 with KHMDS followed by addition of commercially available N-Boc -4-piperidone 17-2 provides unsaturated ester 17-3. Hydrogenation of 17-3 followed by hydrolysis to the acid and then reduction with borane-methyl sulfide then affords primary alcohol 17-4. Formation of the alkyl iodide with triphenylphosphine and iodine in the presence of imidazole followed by treatment with triphenylphosphine provides phosphonium salt 17-5. Deprotonation with a suitable base, for example, KHMDS, LiHMDS, NaHMDS, NaH, LDA, or KH affords the Wittig agent in situ, which upon treatment with a suitable aromatic aldehyde yields the unsaturated derivative 17-6. Hydrogenation under standard conditions provides 17-7, and removal of the Boc group with HCl in methanol or with other acidic conditions then provides the 1-unsubstituted piperidine 17-8, which can then be employed as the secondary amine component in the syntheses described above in Schemes 5, 7, 8, 9 and 11.

SCHEME 18

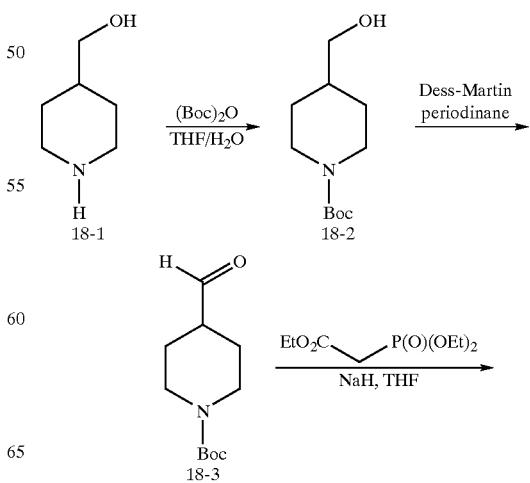

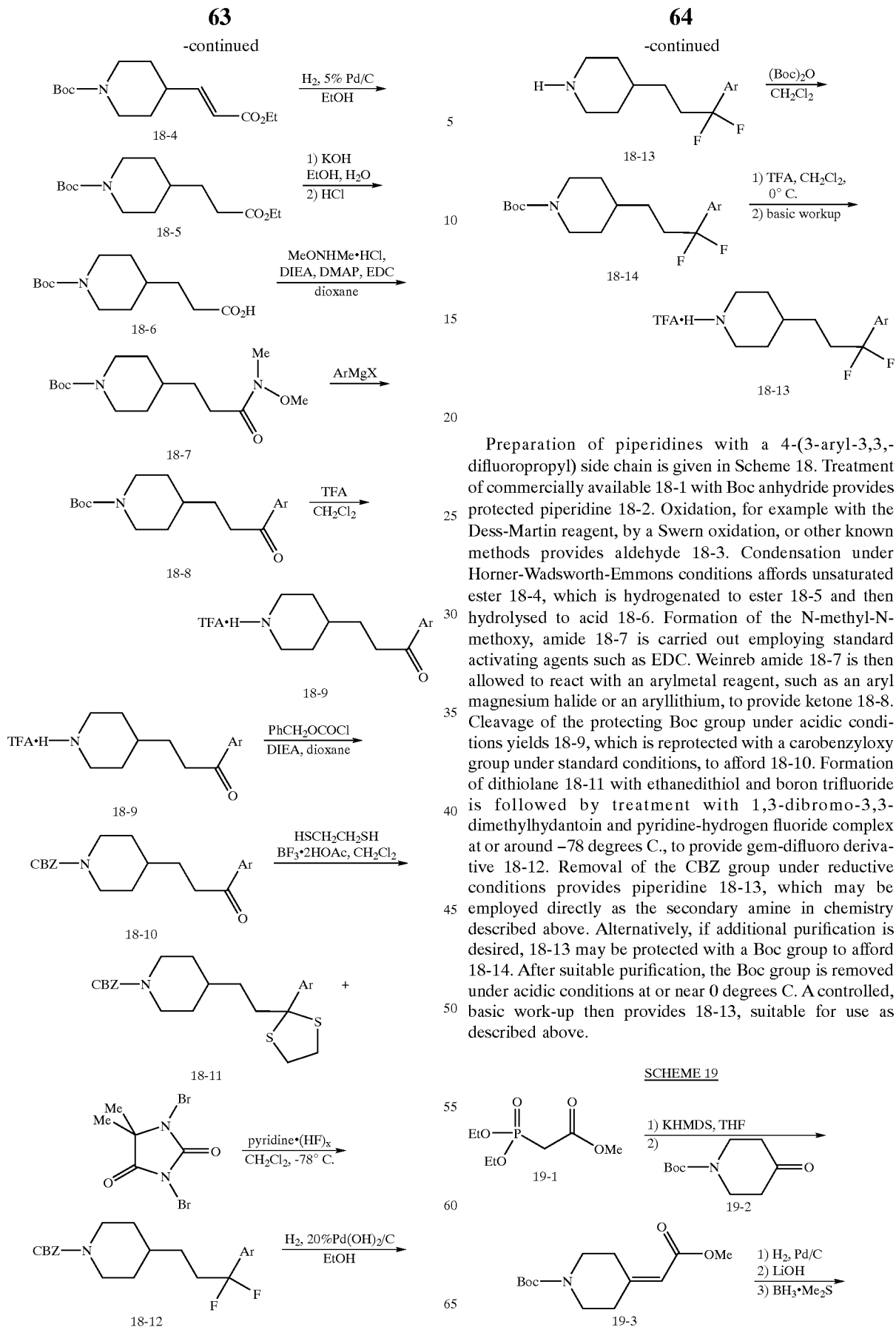

Preparation of piperidines with a 4-(3-aryl-3,3,-difluoropropyl) side chain is given in Scheme 18. Treatment of commercially available 18-1 with Boc anhydride provides protected piperidine 18-2. Oxidation, for example with the Dess-Martin reagent, by a Swern oxidation, or other known methods provides aldehyde 18-3. Condensation under Horner-Wadsworth-Emmons conditions affords unsaturated ester 18-4, which is hydrogenated to ester 18-5 and then hydrolysed to acid 18-6. Formation of the N-methyl-N-methoxy, amide 18-7 is carried out employing standard activating agents such as EDC. Weinreb amide 18-7 is then allowed to react with an arylmetal reagent, such as an aryl magnesium halide or an aryllithium, to provide ketone 18-8. Cleavage of the protecting Boc group under acidic conditions yields 18-9, which is reprotected with a carobenzyloxy group under standard conditions, to afford 18-10. Formation of dithiolane 18-11 with ethanedithiol and boron trifluoride is followed by treatment with 1,3-dibromo-3,3-dimethylhydantoin and pyridine-hydrogen fluoride complex at or around −78 degrees C., to provide gem-difluoro derivative 18-12. Removal of the CBZ group under reductive conditions provides piperidine 18-13, which may be employed directly as the secondary amine in chemistry described above. Alternatively, if additional purification is desired, 18-13 may be protected with a Boc group to afford 18-14. After suitable purification, the Boc group is removed under acidic conditions at or near 0 degrees C. A controlled, basic work-up then provides 18-13, suitable for use as described above.

SCHEME 19

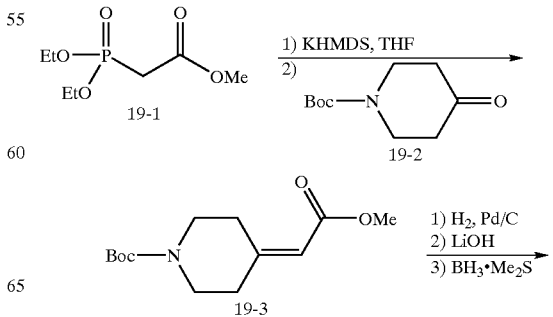

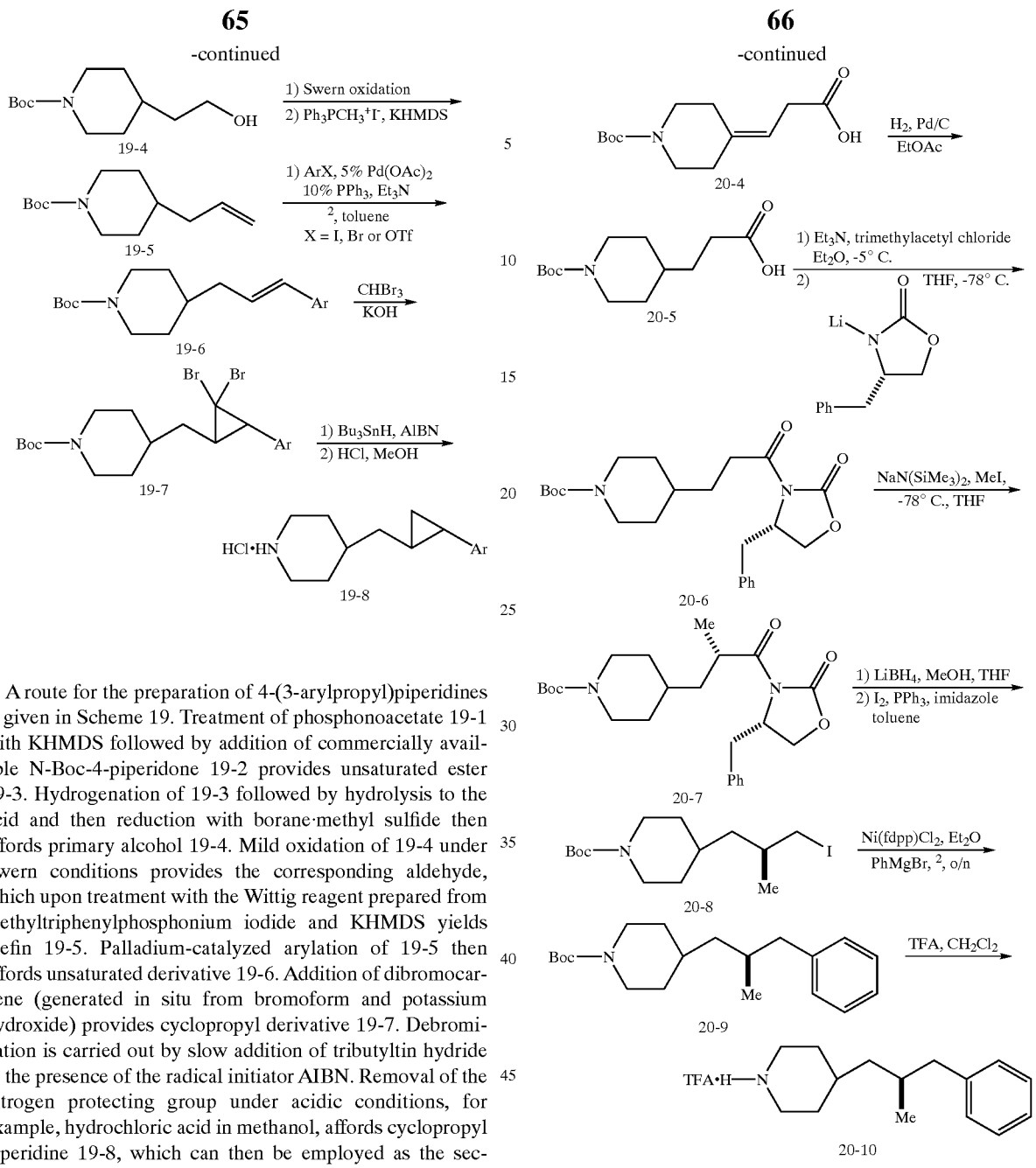

A route for the preparation of 4-(3-arylpropyl)piperidines is given in Scheme 19. Treatment of phosphonoacetate 19-1 with KHMDS followed by addition of commercially available N-Boc-4-piperidone 19-2 provides unsaturated ester 19-3. Hydrogenation of 19-3 followed by hydrolysis to the acid and then reduction with borane·methyl sulfide then affords primary alcohol 19-4. Mild oxidation of 19-4 under Swern conditions provides the corresponding aldehyde, which upon treatment with the Wittig reagent prepared from methyltriphenylphosphonium iodide and KHMDS yields olefin 19-5. Palladium-catalyzed arylation of 19-5 then affords unsaturated derivative 19-6. Addition of dibromocarbene (generated in situ from bromoform and potassium hydroxide) provides cyclopropyl derivative 19-7. Debromination is carried out by slow addition of tributyltin hydride in the presence of the radical initiator AIBN. Removal of the nitrogen protecting group under acidic conditions, for example, hydrochloric acid in methanol, affords cyclopropyl piperidine 19-8, which can then be employed as the secondary amine component in the syntheses described above in Schemes 5, 7, 8, 9 and 11.

SCHEME 20

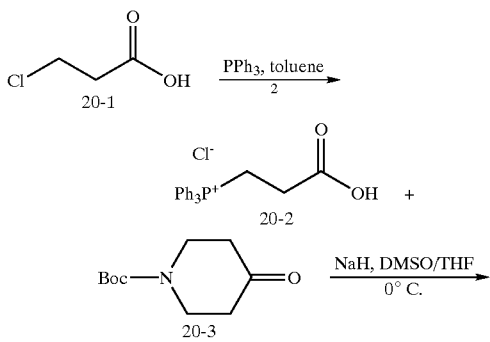

A route for the preparation of 4-(3-aryl-2-methylpropyl) piperidines is given in Scheme 20. Treatment of commercially available 3-chloropropionic acid (20-1) with triphenylphosphine In refluxing toluene provides phosphonium salt 20-2. Treatment with sodium hydride in DMSO/THF provides the ylide in situ, which upon addition of piperidone 20-3 affords the adduct 20-4. Reduction of the double bond, for example with hydrogen gas in the presence of a palladium catalyst, gives acid 20-5. Treatment of 20-5 with trimethylacetyl chloride and triethyl amine generates the mixed anhydride in situ, which upon treatment with the lithium salt of 4-(S)-benzyl-2-oxazolidone yields 20-6. Deprotonation of 20-6 with sodium hexamethyldisilazide, followed by addition of methyl iodide, provides alpha-methyl derivative 20-7. Reduction of acyl-oxazolidone 20-7 with lithium borohydride produces the corresponding primary alcohol, which is converted to primary iodide 20-8 with iodine, triphenylphiosphine and imidazole in toluene.

Coupling with phenyl magnesium bromide in the presence of Ni(fdpp)Cl$_2$ affords aralkyl derivative 20-9, which is then deprotected under acidic conditions to provide piperidine 20-10. Piperidine 20-10 can then be employed as the secondary amine component in the syntheses described above in Schemes 5, 7, 8, 9 and 11.

SCHEME 21

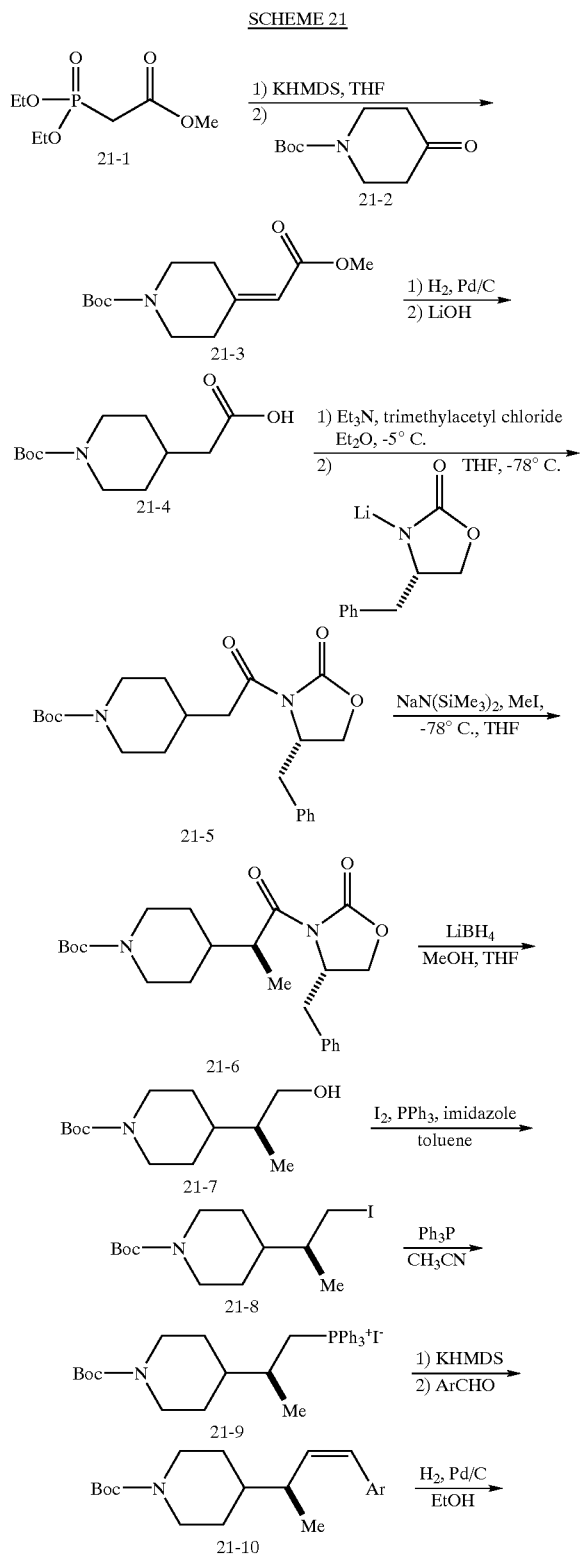

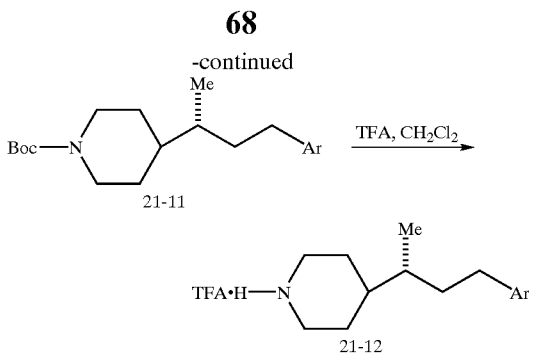

A route for the preparation of 4-(3-aryl-1-methylpropyl) piperidines is given in Scheme 21. Addition of the anion of phosphonoester 21-1 to piperidone 21-2 provides unsaturated ester 21-3. Reduction of the double bond and hydrolysis of the ester affords acid 21-4. Treatment of 21-4 with triethylamine and trimethylacetyl chloride provides the mixed anhydride in situ, which is then coupled with the lithium salt of 4-(S)-benzyl-2-oxazolidone, to yield acyl oxazolidone 21-5. Deprotonation with sodium hexamethyldisilazide followed by addition of methyl iodide provides 21-6. Reduction of 21-6 with lithium borohydride affords alcohol 21-7, which upon treatment with iodine, triphenylphosphine and imidazole in toluene is converted to iodide 21-8. Treatment with triphenylphosphine gives phosphonium salt 21-9, which is converted to th ylide with potassium hexamethyldisilazide. Addition of an aryl aldehyde generates unsaturated aryl derivative 21-10. Hydrogenation provides saturated piperidine 21-11, which is then deprotected under acidic conditions to afford 21-12, which can then be employed as the secondary amine component in the syntheses described above in Schemes 5, 7, 8, 9 and 11.

SCHEME 22

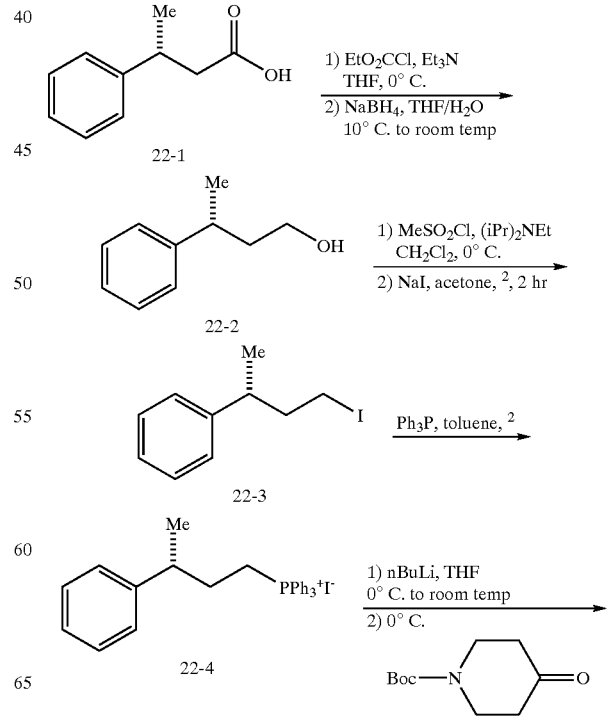

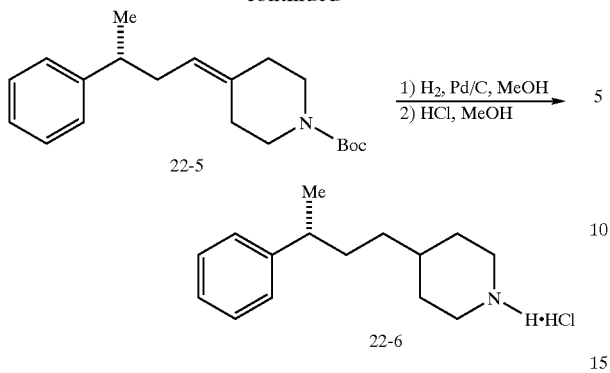

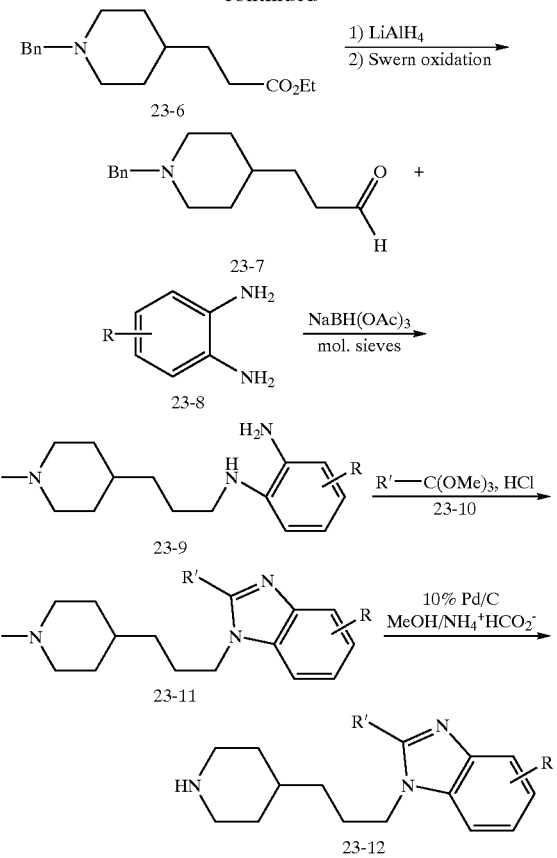

A route for the preparation of 4-(3-aryl-3-methylpropyl)piperidines is given in Scheme 22. Treatment of commercially available 4-(R)-phenylbutyric acid (22-1) with ethyl chloroformate and triethylamine forms the asymmetric anhydride in situ, which upon treatment with sodium borohydride provides primary alcohol 22-1. Alternatively, this,; conversion can be carried out by treatment of 22-1 with borane-THF. Activation of the hydroxy group of 22-2 with methanesulfonyl chloride in the presence of a hindered base such as N,N-(diisopropyl)ethylamine, followed by displacement with sodium iodide in refluxing acetone affords iodide 22-3. Heating with triphenylphosphine in toluene provides the phosphonium salt 22-4.

Deprotonation of this salt with a strong base, for example n-butyl lithium generates the Wittig reagent in situ, which is then allowed to react with N-Boc-4-piperidone, to yield olefin 22-5. Hydrogenation of the double bond followed by treatment with acid, for example HCl in methanol, then provides the secondary amine salt 22-6, which can then be employed as the secondary amine component in the syntheses described above in Schemes 5, 7, 8, 9 and 11.

SCHEME 23

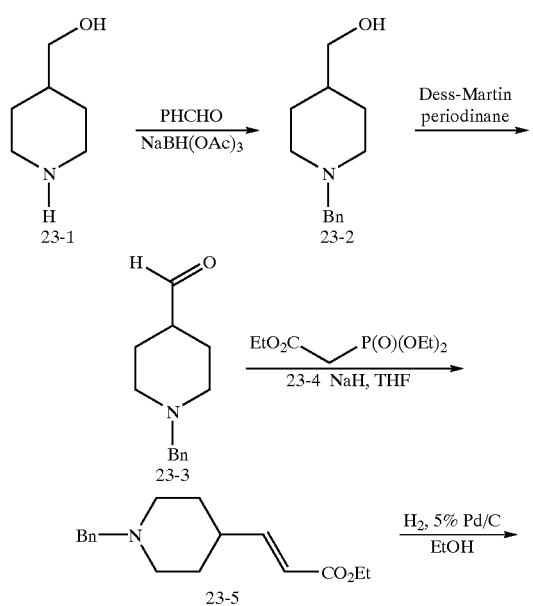

A route for the preparation of 4-(3-(benzimidazol-2-5 yl)propyl)piperidines is given in Scheme 23. Protection of piperidine 23-1 under reductive amination conditions provides benzylamine 23-2. Oxidation to aldehyde 23-3 is carried out under standard conditions, for example with the Dess-Martin periodinane. Addition of ester 23-4 provides unsaturated olefin 23-5, which upon reduction affords ester 23-6. Reduction with lithium aluminum hydride or other strong hydride reducing agents followed by mild oxidation provides aldehyde 23-7. Upon combination with diamine 23-8 under reductive alkylation conditions affords the N-alkylated derivative 23-9. Treatment with orthoformate derivative 23-10 in the presence of acid Fields benzimidazole 23-11, which upon hydrogenation with palladium on carbon under transfer hydrogenation conditions generates piperidine 23-12, which can then be employed as the secondary amine component in the syntheses described above in Schemes 5, 7, 8, 9 and 11.

SCHEME 24

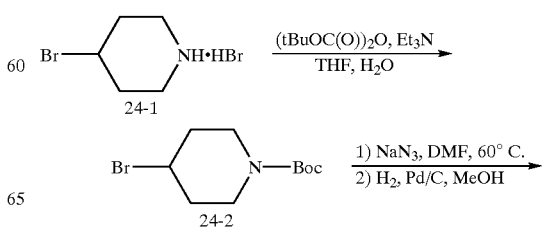

-continued

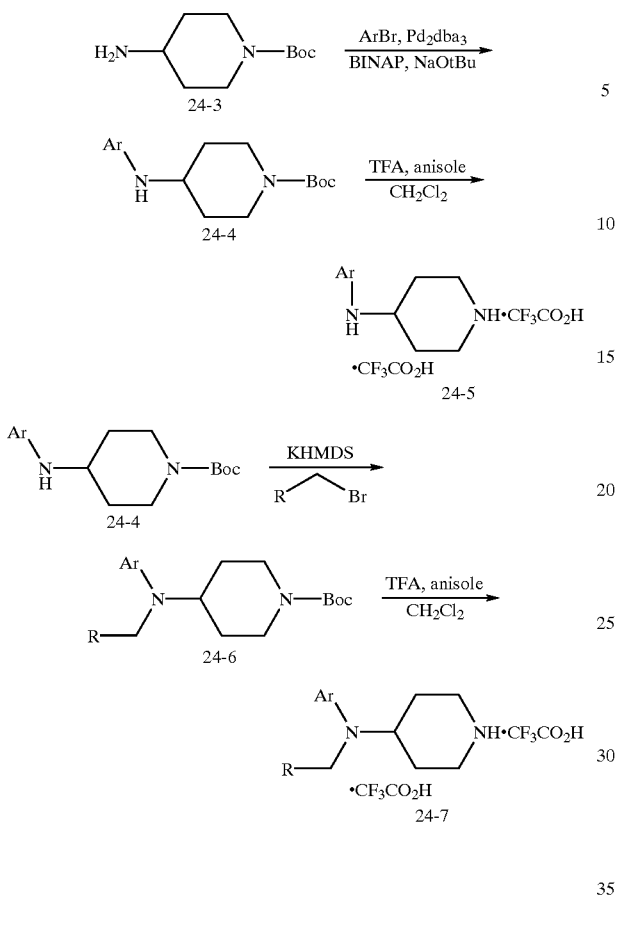

SCHEME 25

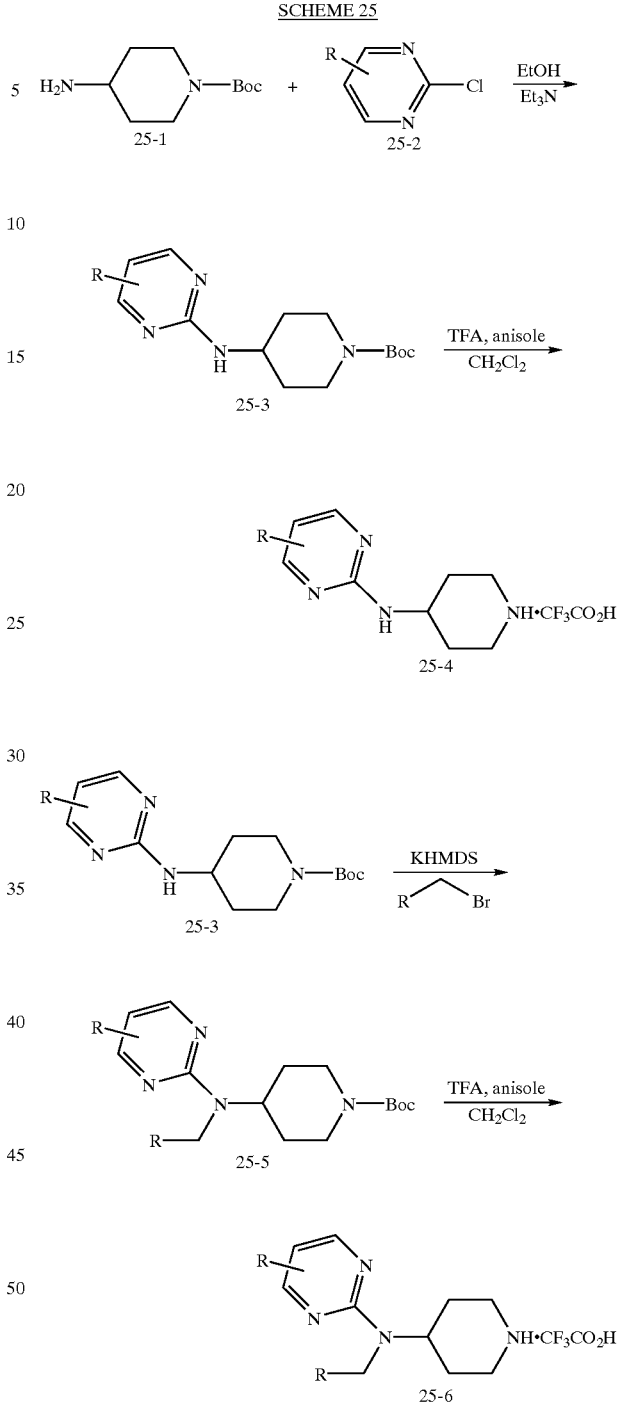

Procedures for synthesizing certain CCR5 receptor modulators containing 4-(heteroarylamino)piperidine functionality are shown in Scheme 24. After protecting commercially available 4-bromopiperidine, the bromide is displaced with sodium azide, and the azide is reduced, for example by catalytic reduction, to provide aminopiperidine 24-3. Treatment of 24-3 with an aryl or heteroaryl halide (the halide preferably being bromide) in the presence of a palladium catalyst, sodium t-butoxide and a suitable bidentate ligand (such as BINAP), according to the conditions of Buchwald et al, provides arylamine 24-4. Direct acidic deprotection of 24-4 may be carried out to provide secondary amine 24-5. Alternatively, amine 24-4 may be alkylated with a suitable alkyl, alkenyl or alkynyl halide (wherein the halide is bromo or iodo in the case of an alkyl group and chloro or bromo in the case of allylic or propargylic functionality) in the presence of a strong base, such as potassium hexamethyldisilazide, to provide trisubstituted amine 24-6. Acidic deprotection, for example, trifluoroacetic acid and anisole in dichloromethane, or methanolic hydrochloric acid, then provides the bis ammonium salt, which in the case of trifluoroacetic acid deprotection, is compound 24-7. The secondary piperidines 24-5 and 24-7 are then utilized as the cyclic secondary amine component as shown above in Schemes 5, 7, 3, 9 and 11.

For certain aminoheterocycles, direct displacement of a halogen may provide improved access to the desired intermediates. For example, as shown in Scheme 25, unsubstituted and substituted 2-chloropyrimidines 25-2 may be coupled directly to amine 25-1 in the presence of a suitable base, such as triethylamine, to provide aminopyrimidine 25-3. Acidic deprotection then affords 25-4. Alternatively, 25-3 may be alkylated in the presence of a strong base to provide 25-5, which upon deprotection gives intermediate 25-6. The secondary piperidines 25-4 and 25-6 are then utilized as the cyclic secondary amine component as shown in Schemes 5, 7, 8, 9 and 11.

SCHEME 26

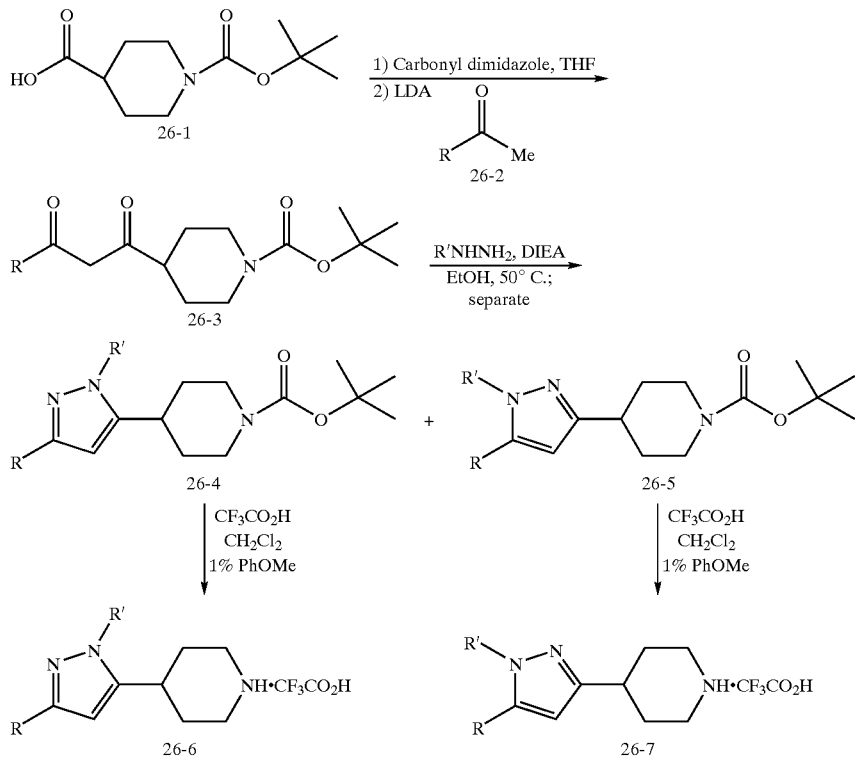

One preparation of piperidine subunits containing functionalized pyrazoles at C4 of the piperidine is given in Scheme 26. Treatment of piperidine 26-1 with carbonyldiimidazole to form the acyl imidazole, followed by addition of a dialkyl or alkyl-aryl ketone (26-2) in the presence of lithium diisopropylamide (LDA) gives the diketone 26-3. Treatment with a monoalkyhydrazine in an alcohol solvent at temperatures between 0 to 100 degrees C. (preferably about 50 degrees C.) in the presence of a hindered base such as DEA then provides a mixture of the isomeric pyrazoles 26-4 and 26-5. After separation of these compounds by chromatography or crystallization, the individual products are deblocked under acidic conditions (for example trifluoroacetic acid and anisole with or without methylene chloride as a co-solvent) to provide the piperidine salts 26-6 and 26-7, which are then used as the cyclic secondary amine component as shown above in Scheme 2 and in Schemes 5, 7, 8, 9 and 11.

SCHEME 27

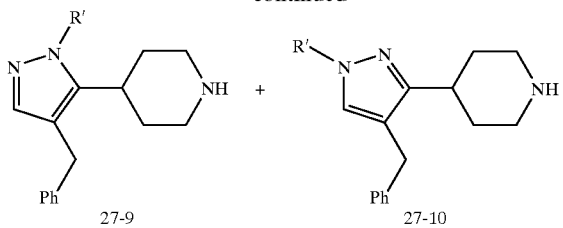

Another preparation of piperidine subunits containing functionalized pyrazoles at C4 of the piperidine is given in Scheme 27. Treatment of commercially available bromide 27-1 with triphenylphosphine in refluxing toluene provides phosphonium salt 27-2, which after treatment with a strong anhydrous base such as potassium hexamethyldisilazide in toluene and the piperidine ketone 27-3 provides the olefin 27-4. Hydroboration followed by an oxidative work-up with chromic acid then affords ketone 27-5. Selective formylation of 27-5 with methyl formate in the presence of potassium t-butoxide selectively affords ketoaldehyde 27-6. Heating of 27-6 with a monoalkylhydrazine in methanol in the presence of a hindered (or insoluble) base such as DEA then provides a mixture of the 1,4-disubstituted pyrazoles 27-7 and 27-8. After separation by chromatography, crystallization or fractional distillation, the purified isomers are deprotected under transfer hydrogenation conditions to provide the piperidines 27-9 and 27-10, which are then utilized as the cyclic secondary amine component as shown above in Schemes 5, 7, 8, 9 and 11.

SCHEME 28

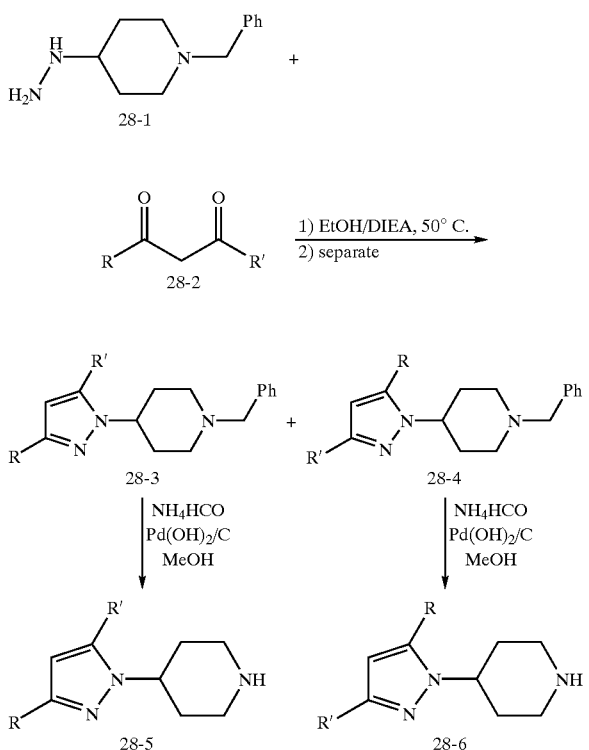

A preparation of piperidine subunits containing 3,5-difunctionalized pyrazoles linked through N-1 to C-4 of the piperidine is given in Scheme 28. Treatment of commercially available hydrazine 28-1 with diketone 28-2 in ethanol at 0 to 90 degrees C. (preferably 50 degrees C.) in the presence of DEEA provides a mixture of pyrazoles 28-3 and 28-4, which are separated under standard conditions, for example HPLC. Removal of the benzyl groups by transfer hydrogenation provides the secondary piperidines 28-5 and 28-6, which are then utilized as the cyclic secondary amine component as shown above in Schemes 5, 7, 8, 9 and 11.

SCHEME 29

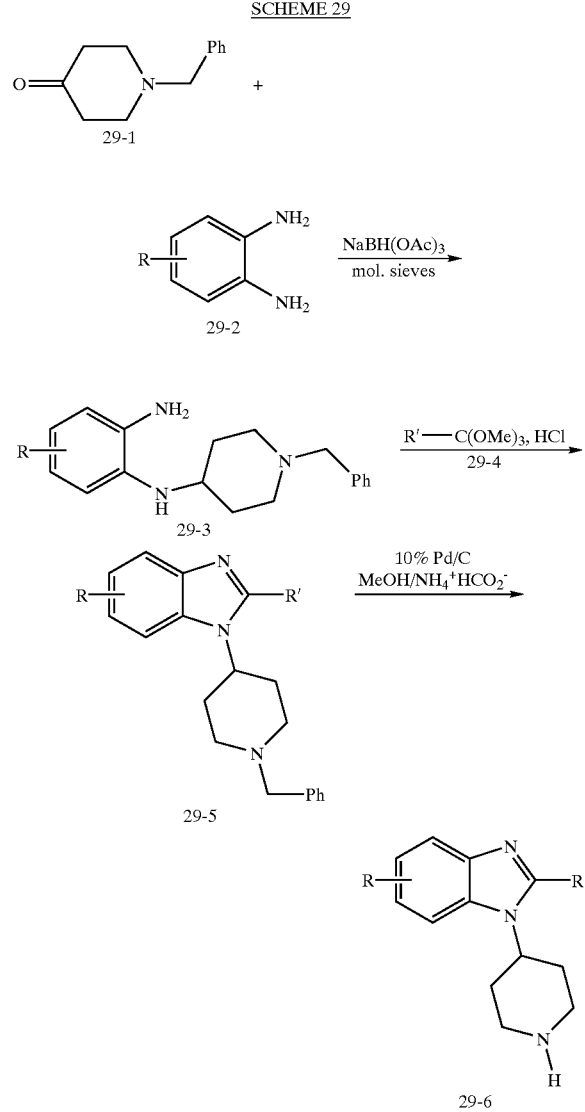

A preparation of 4-(benzimidazol-1-yl)piperidine subunits is given in Scheme 29. Combining piperidone 29-1 and diamine 29-2 in the presence of sodium triacetoxyborohydride under dehydrating conditions provides reductive amination product 29-3. Addition of a suitably substituted ortho ester 29-4 in the presence of a acid catalyst, for example concentrated hydrochloric acid, provides benzimidazole intermediate 29-5. Deprotection under reductive conditions, for example with palladium on carbon under transfer hydrogenation conditions, then provides secondary amine 29-6, which is then utilized as the cyclic secondary amine component as shown above in Schemes 5, 7, 8, 9 and 11.

SCHEME 30

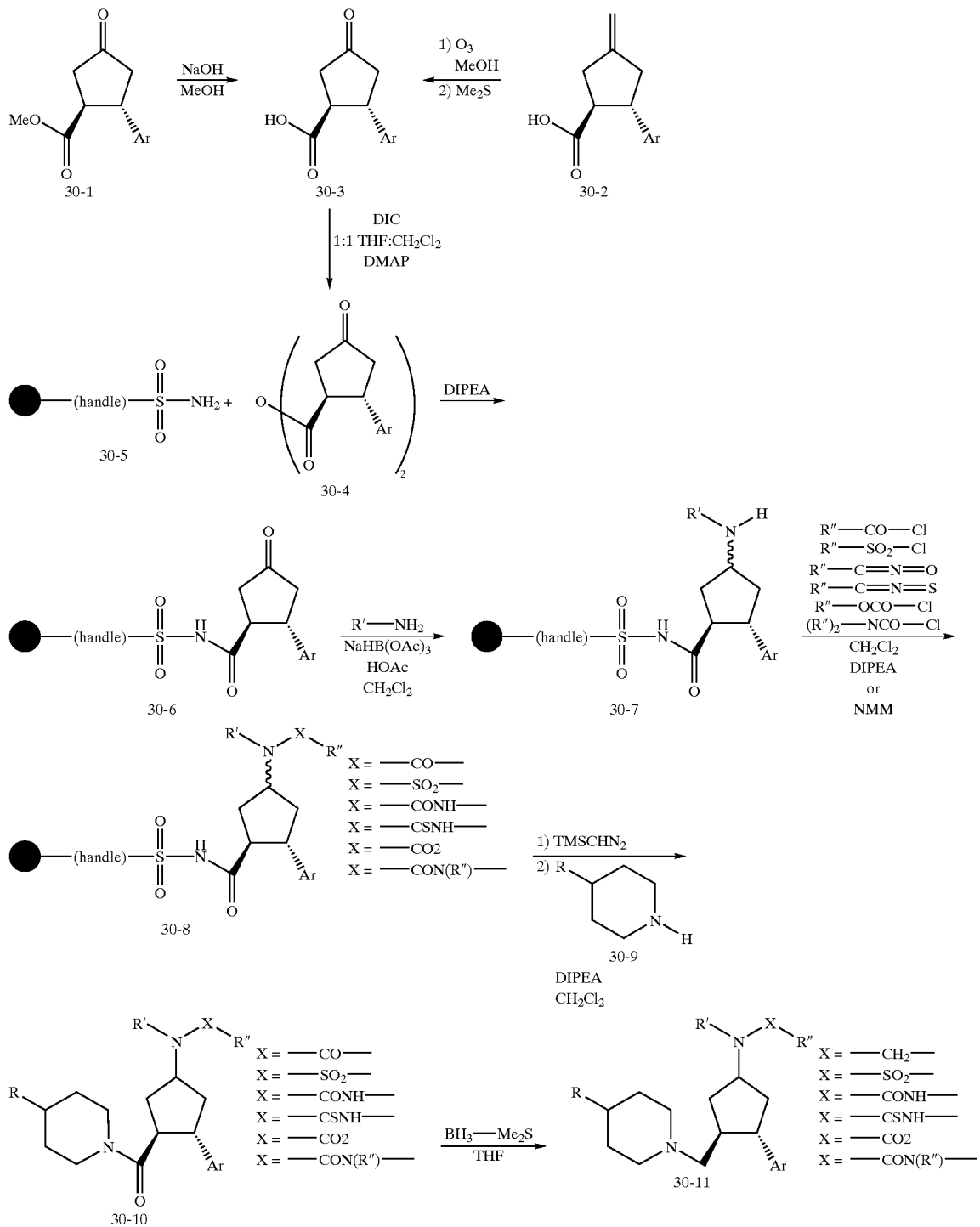

Another method of preparing compounds within the scope of the instant invention is given in Scheme 30 in which most of the chemistry is done on a resin and thus simplifies the isolations. Thus, the keto-acid 30-3, prepared either by standard hydrolysis of the ester 30-1 or oxidation of the exo-methylene of 30-2 with ozone in methanol at −70° C. followed by treatment with dimethyl sulfide, is first activated as its anhydride 30-4 by treatment with a dehydrating agent, such as dicyclohexylcarbodiimide or diisopropylcarbodiimde, in a suitable solvent, such as THF or methylene chloride or a mixture of these, with a catalytic amount of DMAP. Reaction of 30-4 with a suitable sulfonamide linker 30-5, such as a linker described by G. W. Kenner, *J. Chem. Soc., Chem. Comm.*, 1971, 636 or any other suitable sulfonamide linker known in the art, affords the resin-bound cyclopentanone 30-6. Reductive amination of various amines with 30-6 affords the resin-bound amino derivative 30-7. Acylation or sulfonylation can be done under standard conditions, such as with alkyl or aryl acid chlorides, sulfonyl chlorides, isocyanates, isothiocyanates, chloroformates, carbamoyl chlorides or other standard acylating agent, usually in the presence of an amine base, such as triethylamine, diisopropylethylamine, N-methylmorpholine, or pyridine, to afford the resin-bound amine derivative 30-8. Activation of the resin sulfonamide linker with trimethylsilyldiazomethane and displacement with an amine, such as the piperidine 30-9 (see Schemes 12-29) in which R must be stable to borane-dimethyl sulfide reduction, gives the corresponding amide 30-10. Subsequent reduction of the amide 30-10 with borane-dimethyl sulfide can then afford a variety of examples of chemokine receptor modulators. If the amine derivative in 30-10 (—N—X—) is also reducable, then a (corresponding diamine will be obtained which can also be a chemokine receptor modulator. Alternatively, for the preparation of amine derivatives which are not stable to the diborane-methyl sulfide conditions, such as for the amide moiety (30-10, X=—CO—), the acylation step can be done after the cleavage/reduction sequence as detailed in Scheme 10. When either R or R' are suitable for further elaboration as detailed in Scheme 10, additional derivatives can also be prepared.

SCHEME 31

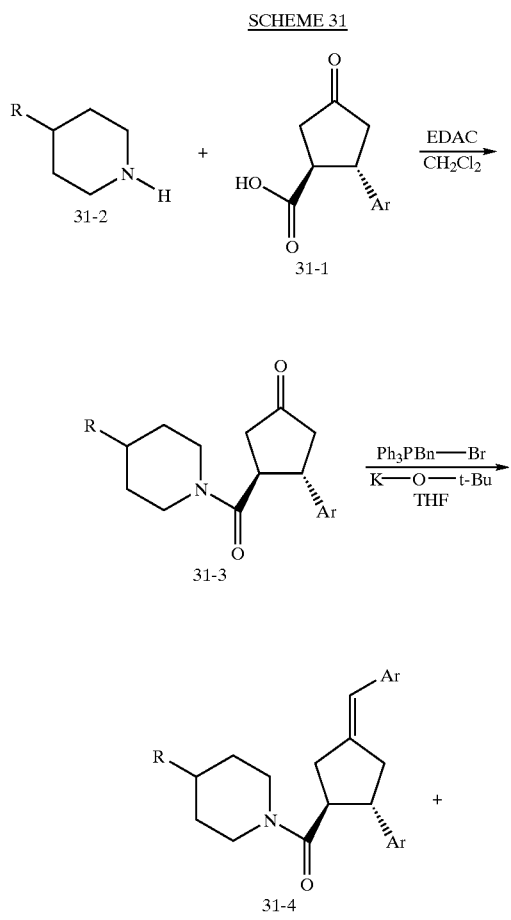

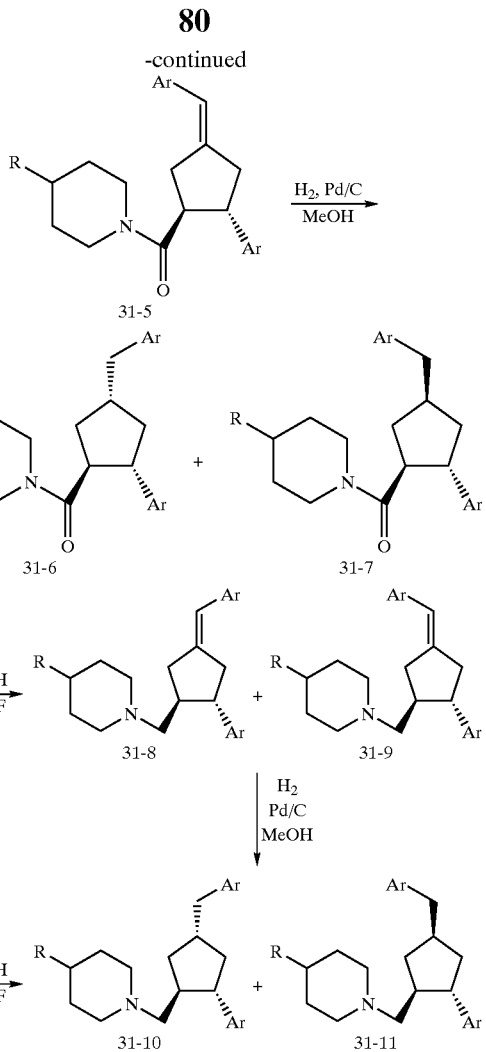

Another method of preparing compounds within the scope of the instant invention is given in Scheme 31. Condensation of the acid 31-1 (see Scheme 30) with a 4-substituted piperidine 31-2 (see Scheme 12-29) in the presence of a dehydrating agent, such as DIC, DCC or EDAC, in a suitable solvent, such as methylene chloride, gives the ketone/amide 31-3. Reaction of the ketone of 31-3 with benzyltriphenylphophonium bromide in the presence of a base such as potassium t-butoxide gives a mixture of the benzylidene isomers 31-4 and 31-5 which may be separable by chromatographic methods and which may be themselves chemokine receptor modulators. Hydrogenation under standard conditions with Pd/C or Pearlman's catalyst in methanol affords the benzyl derivatives 31-6 and 31-7 which may be separable by chromatographic methods. Alternatively, reduction of the amide, either before or after the hydrogenation, affords the piperidinylmethyl compounds 31-8 and 31-9 and 31-10 and 31-11, either of which may be separable by chromatographic methods.

SCHEME 32

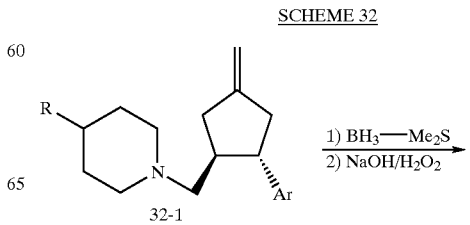

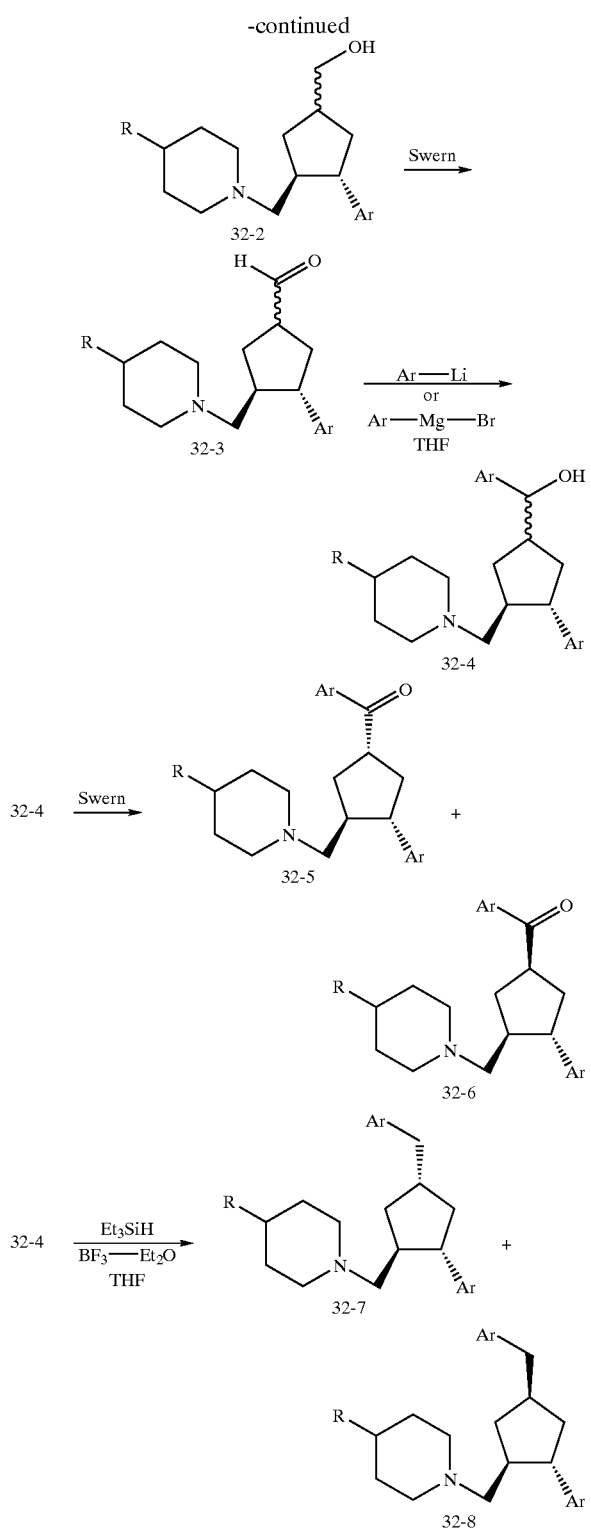

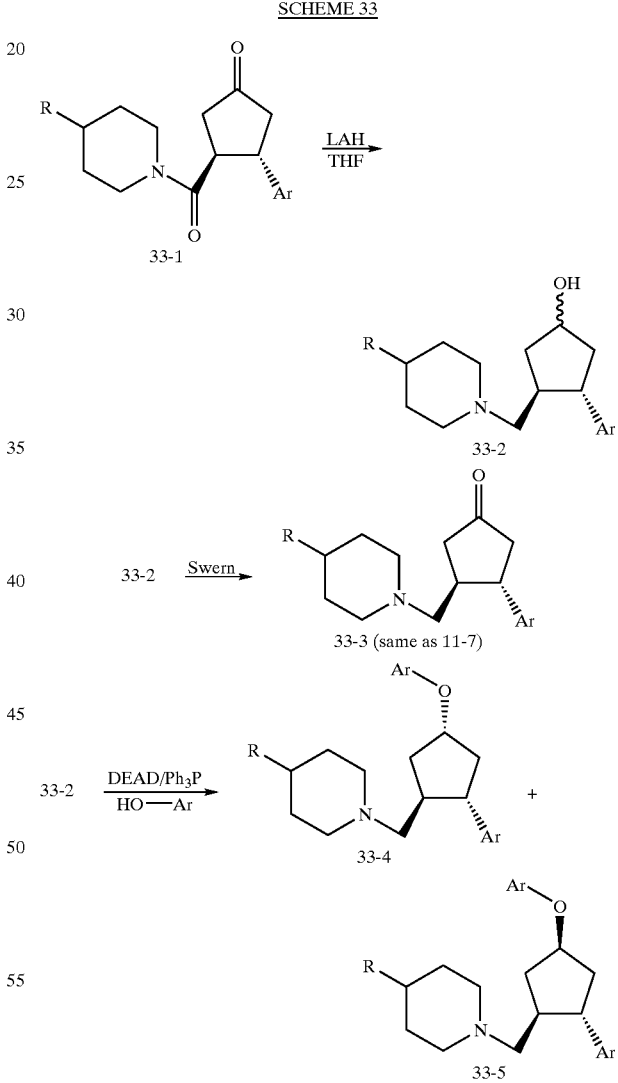

aryl lithium (commercially available or prepared from the aryl iodide or bromide and t-butyl lithium in THF at reduced temperature, such as at −78° C.) or an aryl magnesium iodide or bromide (Grignard reagent) (commercially available or prepared from the aryl iodide or bromide and magnesium in THF or ether) to the aldehyde 32-3 gives a mixture of the four possible C-1 and C-1' isomers 32-4. Reoxidation again using Swern conditions gives the aroyl derivative which may be separable by chromatographic methods to afford the individual C-1 isomers 32-5 and 32-6. Alternatively, 32-4 can be chemically reduced with triethylsilane and borontrifluoride etherate in THF or catalytically under standard conditions with Pd/C or Pearlman's catalyst in methanol to afford the arylmethyl derivatives 32-7 and 32-8 which may be separable by chromatographic methods and which gives an alternative preparation than that shown in Scheme 31.

Another method of preparing compounds within the scope of the instant invention is given in Scheme 32. Hydroboration of 32-1 (see Scheme 11) using borane-THF or borane-Me$_2$S complex in THF followed by a standard oxidative work-up with sodium hydroxide and hydrogen peroxide or trimethylamine-N-oxide affords the hydroxymethyl compound 32-2 as a mixture of C-1 isomers. Oxidation to the aldehyde 32-3 can be done under Swern conditions or with a variety of other reagents (see above). Addition of an Another method of preparing compounds within the scope of the instant invention is given in Scheme 33. Reaction of the ketone/amide 33-1 (see Scheme 31) with LAH in THF under standard conditions gives simultaneous reduction of the amide and ketone to give 33-2. Reoxidation of the alcohol under standard Swern conditions affords 33-3 which can be an alternative preparation of 11-7 in Scheme 11.

Alternatively, reaction of 33-2 with a hydroxyaryl in the presence of triphenylphosphine and DEAD leads to the formation of the ethers 33-4 and 33-5 which may be separable by chromatographic methods.

In some cases the order of carrying out the foregoing reaction schemes may be varied to facilitate the reaction or to avoid unwanted reaction products. The following examples are provided for the purpose of further illustration only and are not intended to be limitations on the disclosed invention.

GENERAL

Concentration of solutions was carried out on a rotary evaporator under reduced pressure. Flash chromatography was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DEEA) saturated aqueous (sat'd), room temperature (rt), hour(s) (h), minute(s) (min).

HPLC CONDITIONS

HPLC A. Retention time using the following conditions: Column: YMC ODS A, 5μ, 4.6×50 mm; Gradient Eluent: 10:90 to 90:10 v/v acetonitrile/water+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5μ 4.6×100 mm column; Gradient Eluent: 10:90 to 90:10 v/v acetonitrile/water+0.5% TFA over 10 min, hold 2 min; Detection: PDA, 200–400 nm; Flow Rate: 2.25 mL/min.

The following are representative Procedures for the preparation of the piperidines used in the following Examples or which can be substituted for the piperidines used in the following Examples and which are not commercially available.

PROCEDURE 1

4-(3-Benzyl-1-ethyl-(1H)-pyrazol-5-yl)piperidine di-Trifluoroacetic Acid Salt

Step A: 1-(1-(t-Butoxycarbonyl)piperidin-4-yl)-4-phenylbutane-1,3-dione

Method A:

n-Butyl lithium (100 mL, 0.16 mole) was added to a stirred solution of diisopropylamine (16.16 g, 22.4 mL, 0.16 mole, distilled) in THF (450 mL) at 0° C. over 45 min under nitrogen. Stirring was continued for 10 min at 0° C. after the addition was complete. After cooling to −78° C., phenylacetone (21.45 g, 21.13 mL, 0.16 mole) in THF (100 mL) was added dropwise over 15 min with stirring. This solution was stirred at −78° C. for 1 h. Meanwhile, a solution of N-Boc isonipecotic acid (18.32 g, 0.080 mole) and carbonyl diimidazole (12.98 g, 0.080 mole) in THF (150 mL) was prepared. After stirring for 15 min, this solution was canulated into the enolate solution dropwise over 15 min. The reaction was stirred at <−70° C. for 1 h and then allowed to warm to rt over 3 h. The reaction was quenched with 1M citric acid (250 mL) and stirred for 16 h. The organic layer was separated and washed with 250 mL each of saturated sodium bicarbonate solution, water and brine. After drying over sodium sulfate, the organic layer was concentrated to give an oil. The residue was purified by FC on silica gel (10% ethyl acetate in 60–80° C. petroleum ether) to give separation of the two isomers. The first higher $R_f$ fractions afforded pure title compound as the minor product (3.5 g) as an oil.

$^1$H NMR (500 MHz, $CDCl_3$): δ 7.34–7.37 (m, 2H), 7.25–7.31 (m, 3H), 5.46 (s, 1H), 4.11–4.17 (m, 2H), 3.63 (s, 2H), 2.70–2.76 (m, 2H), 2.29 (tt, J=11.7 and 3.7 Hz, 1H), 1.75–1.80 (m, 2H), 1.47–1.61 (m, 2H), 1.47 (s, 9H). MS (ESI): m/z 346 (M+1). The lower $R_f$ fractions contained phenylacetone and major product 1-(1-(t-butoxycarbonyl) piperidin-4-yl)-2-phenylbutane-1,3-dione from which the latter crystallized on standing to give 7 g white solid (m.p. 105–106° C.).

$^1$H NMR (360 MHz, $CDCl_3$): δ 15.23 (s, 1H), 7.3–7.45 (m, 3H), 7.15–7.2 (m, 2H), 4–4.1 (m, 2H), 2.35–2.50 (m, 2H), 2.2–2.3 (m, 1H), 1.87 (s, 3H), 1.5–1.75 (m, 4H), 1.43 (s, 9H). MS (ESI): m/z 346 (M+1).

Method B:

Step B1: 1-(t-Butoxycarbonyl)piperidine-4-N-methyl-N-methoxycarboxamide

N-Boc isonipecotic acid (13.56 g, 59.2 mmol), N,O-dimethyl hydroxylamine hydrochloride (8.65 g, 88.7 mmol), and 1-hydroxybenzotriazole hydrate (15.9 g, 118 mmol) were dissolved in DMF (225 mL) in a 500 mL round-bottom flask and diisopropylethylamine (15.3 g, 20.6 mL, 118.3 mmol) was then added with stirring at rt. 1-Ethyl-3-(3-dimethylaminopropyl)carbodiimide (17.01 g, 88.74 mmol) was added in several portions over 10 min with stirring. After 22 h, the reaction mixture was poured into a water and ice mixture (600 mL) and was extracted with ethyl acetate (5×125 mL). The combined organic layers were washed with 1N HCl (2×200 mL), 5% sodium bicarbonate (2×200 mL), water and brine, dried over sodium sulfate and concentrated to give the title compound (15.58 g) as a yellowish oil.

$^1$H NMR (500 MHz, $CDCl_3$): δ 4.11–4.20 (m, 2H), 3.72 (br s, 3H), 3.20 (br s, 3 H), 2.75–2.86 (m, 3H), 1.63–1.76 (m, 4H), 1.47 (s, 9H).

Step B2: 4-Acetyl-1-(t-butoxycarbonyl)piperidine

After dissolving the Weinreb amide from Step B1 in anhydrous ether (400 mL) under nitrogen and cooling the solution in an ice bath, 1.4M methyl magnesium bromide (55 mL) in 3:1 toluene and THF was added with stirring and cooling over 30 min. After stirring at 0° C. for 1 h, the reaction was poured into a mixture of ice water (400 mL) and acetic acid (8 mL, 150 mmol). The layers were separated and the aqueous layer was extracted twice with ether. The combined organic layers were washed with 0.1N HCl (200 mL), 3% sodium bicarbonate (200 mL), water (200 mL) and brine (200 mL), dried over sodium sulfate, and concentrated to give the crude product (14.322 g). FC (20–80% ethyl acetate in hexanes) gave the title compound (9.440 g) as a yellowish oil. $R_f$: 0.27 (25% ethyl acetate in hexanes). Some starting Weinreb amide was also recovered (3.212 g). $R_f$: 0.10 (25% ethyl acetate in hexanes).

$^1$H NMR (500 MHz, $CDCl_3$): δ 4.07–4.14 (m, 2H), 2.75–2.83 (m, 2H), 2.46 (tt, J=11.3 and 3.8 Hz, 1H), 2.17 (s, 3H), 1.82–1.87 (m, 2H), 1.48–1.57 (m, 2 H), 1.46 (s, 9H).

Step B3: 1-(1-(t-Butoxycarbonyl)piperidin-4-yl)-4-phenylbutane-1,3-dione

To a suspension of 60% sodium hydride (1.07 g) in THF (15 mL) at 0° C. was added a solution of 4-acetyl-1-(t-butoxycarbonyl)piperidine from Step B2 (3.03g, 13.3 mmol) and methyl phenylacetate (6.01 g, 39.9 mmol) in THF (6 mL) over 20 min. The reaction was stirred for another 4 h as it was allowed to warm to rt. The mixture was diluted with ether (30 mL) and poured into 1N HCl. The layers were separated and the aqueous layer was extracted three times with ether. The combined organic layers were washed with brine (150 mL), dried over sodium sulfate and concentrated. The crude product was purified by FC (20% ethyl acetate in hexanes) to give the title compound (3.02 g). $R_f$: 0.30 (20% ethyl acetate in hexane). The $^1$H NMR data was the same as that obtained from the product of Method A.

Step B: 4-(1,5-Benzyl-1-ethyl-(1H)-pyrazol-3-yl)-1-(t-butoxycarbonyl)piperidine (Higher $R_f$ isomer) and 4-(3-benzyl-1-ethyl-(1H)-pyrazol-5-yl)-1-(t-butoxycarbonyl) piperidine (Lower $R_f$ isomer)

Method A:

1-(1-(t-Butoxycarbonyl)piperidin-4-yl)-4-phenylbutane-1,3-dione from Step A, from Method A or Method B, Step B3, (0.851 g, 2.46 mmol) in methanol (25 mL) was added over 10 min to a suspension of ethylhydrazine oxalate (0.444 g, 2.96 mmol) in methanol (5 mL) in a 60° C. oil bath. After 15 h, the reaction was concentrated in vacuo and the residue was purified by repeated FC using a gradient of 50–100% ethyl acetate in hexanes to give first 4-(5-benzyl-1-ethyl-(1H)-pyrazol-3-yl)-1-(t-butoxycarbonyl)piperidine (0.148 g total) as the higher $R_f$ product isomer and then the title compound (0.373 g total) as the lower $R_f$.

Higher $R_f$ isomer:

$^1$H NMR (500 MHz, CDCl$_3$): δ 7.2–7.3 (m, 2H), 7.3–7.4 (m, 1H), 7.17 (d, J=7.5 Hz, 2H), 5.77 (s, 1H), 4.0–4.25 (m, 2H), 3.97 (q, J=7.3 Hz, 2H), 3.95 (s, 2H), 2.7–2.9 (m, 2H), 2.76 (tt, J=11.3 and 3.8 Hz, 1H), 1.92 (br d, J=13 Hz, 1H), 1.5–1.65 (m, 2H), 1.47 (s, 9H), 1.29 (t, J=7.3 Hz, 3H).

Lower $R_f$ isomer:

$^1$H NMR (500 MHz, CDCl$_3$): δ 7.25–7.4 (m, 3H), 7.2 (m, 2H), 5.72 (s, 1H), 4.1–4.3 (m, 2H), 4.08 (q, J=7.1 Hz, 2H), 3.95 (s, 2H), 2.7–2.9 (m, 2H), 2.66 (tt, J=11.3 and 3.8 Hz, 1H), 1.82 (br d, J=12.8 Hz, 1H), 1.4–1.6 (m, 2H), 1.48 (s, 9H), 1.47 (t, J=7.1 Hz, 3H).

Method B:

Step B1: 1-(t-Butoxycarbonyl)-4-hydroxymethylpiperidine

A solution of 25.03 g (109.2 mmole) N-Boc isonipecotic acid was dissolved in 200 mL THF and treated with 200 mL 1 M borane-tetrahydrofuran complex in THF, and the mixture was stirred overnight. The mixture was concentrated under vacuum, diluted with 750 mL ethyl acetate, and washed with 150 mL 1 N HCl (6×) and then saturated brine. The organic layer was dried over sodium sulfate and concentrated to give 24.3 of crude product as a white solid. This was used as is in the next step.

$^1$H NMR (500 MHz) δ 4.15 (br d, J=13.7 Hz, 2H), 3.52 (d, J=6.2 Hz, 2H), 2.69~2.75 (m, 2H), 1.71~1.75 (m, 2H), 1.62~1.70 (m, 1H), 1.47 (s, 9H), 1.12~1.21 (m, 2H).

Step B2: 1-(t-Butoxycarbonyl)-4-formylpiperidine

A mixture of 17.62 g (135.6 mmole) oxalyl chloride and 250 mL methylene chloride in a dry ice acetone bath was treated with a solution of 21.19 g (271.2 mmole) DMSO in 150 mL methylene chloride over 20 minutes. After stirring for 20 minutes, a solution of 24.327 g 1-(t-butoxycarbonyl)-4-hydroxymethylpiperidine (from Step B1 above) in 150 mL methylene chloride was added over 1 h. After an additional 15 minutes, 57.17 (565 mmole) triethylamine in 150 mL methylene chloride was added over half an hour. The reaction mixture was allowed to warm up over night in the cooling bath. The reaction mixture was concentrated under vacuum to remove about 400 mL methylene chloride, and the residue was partitioned between 1 L ether and 300 mL water. To this was added 200 mL 1 N NaOH, the layers were separated, and the organic layer was washed with 150 mL 1 N NaOH (2×), water (3×), and saturated brine, dried over sodium sulfate, and concentrated to give 22.562 g crude product. FC (10~60% ethyl acetate in hexanes) gave 20.58 g title compound as slightly yellowish oil.

$R_F$: 0.29 (3:1 v/v hexanes/ethyl acetate).

$^1$H NMR (500 MHz) δ 9.68 (d, J=0.7 Hz, 1H), 3.96~4.02 (m, 2H), 2.92~2.97 (m, 2H), 2.40~2.45 (m, 1H), 1.88~1.94 (m, 2H), 1.53~1.64 (m, 2H), 1.47 (s, 9H).

Step B3: 1-(t-Butoxycarbonyl)-4-(2,2-dibromoethen-1-yl) piperidine

A solution of 48.615 g (146.6 mmole) carbon tetrabromide in 150 mL methylene chloride was added dropwise with stirring to a solution of 76.895 g (293.2 mmole) triphenylphosphine in 150 mL methylene chloride in a 1-L rb flask with ice bath cooling over 1.75 h. After 40 minutes, a solution of 15.631 g (73.29 mmole) 1-(t-butoxycarbonyl)-4-formylpiperidine (from Step B2 above) in 100 mL methylene chloride was added to the resulting brown suspension with stirring and cooling over 40 minutes. After one hour, 200 mL ether and 400 mL hexanes was added. The top suspension was filtered through Celite, and the residue was resuspended in 150 mL methylene chloride and treated with 300 mL ether. The mixture was filtered, and the solid was washed with hexanes until the total filtrate was 2 L. The filtrate was filtered again through Celite and washed with hexanes. The filtrate was washed with 100 mL 5% sodium bicarbonate, 300 mL water (2×), and 150 mL brine. The organic layer was dried over sodium sulfate and concentrated under vacuum to give 53.5 g crude product as a yellowish solid. Flash chromatography (FC) on 250 g silica gel (0~15% ethyl acetate in hexanes) gave 21.595 g title compound as a white solid.

$R_f$: 0.57 (15% ethyl acetate in hexanes).

$^1$H NMR (500 MHz) δ 6.25 (d, J=8.9 Hz, 1H), 4.04~4.12 (m, 2H), 2.75~2.83 (m, 2H), 2.42~2.50 (m, 1H), 1.69~1.75 (m, 2H), 1.47 (s, 9H), 1.29~1.37 (m, 2H).

Step B4: 1-(t-Butoxycarbonyl)-4-(2-tributylstannylethyn-1-yl)piperidine

A mixture of 23.199 g (62.85 mmole) 1-(t-butoxycarbonyl)-4-(2,2-dibromoethen-1-yl)piperidine (prepared as in Step B3 above) and 600 mL anhydrous THF was cooled with dry ice acetone bath under nitrogen. To this mixture was added 88 mL of a 1.6 M butyl lithium solution in hexanes dropwise with stirring and cooling over 50 minutes. After one hour, the flask was transferred into an ice bath. After another hour, a solution of 28.64 g (87.99 mmole) tributyltin chloride in 100 mL THF was added with stirring and cooling over 35 minutes. After three h, the mixture was concentrated under vacuum to remove some THF, and the residue was partitioned between 600 mL ice water and 800 mL ether. The organic layer was washed with 200 mL of water (1×), 2% sodium bicarbonate (1×), water (2×), and saturated brine (1×), dried over sodium sulfate and concentrated under vacuum to give 30.104 g crude product as a green-yellowish liquid. FC on 275 g silica gel using cold 2.5~15% ethyl acetate in hexanes as quickly as possible to give 27.115 g title compound as a colorless liquid.

$R_f$: 0.45 (10% ethyl acetate in hexanes).

$^1$H NMR (500 MHz) δ 3.63~3.67 (m, 2H), 3.25~3.30 (m, 2H), 2.64~2.69 (m, 1H), 1.74~1.79 (m, 2H), 1.54~1.64 (m, 8H), 1.47 (s, 9H), 1.32~1.39 (m, 6H), 0.96~0.99 (m, 6H), 0.92 (t, J=7.3 Hz, 9H).

Step B5: 4-(1-(t-Butoxycarbonyl)piperidin-4-yl)-1-phenylbutan-2-on-3-yne

To a mixture of 1.727 g (3.466 mmole) 1-(t-butoxycarbonyl)-4-(2-tributyl-stannylethyn-1-yl)piperidine (prepared in Step B4 above) in 18 mL 1,2-dichloroethane was added 0.536 g (3.466 mmole) phenylacetyl chloride and 50 mg dichlorobis-(triphenylphosphine)palladium (II). The mixture was refluxed under nitrogen for 2 h, then concentrated under vacuum. Purification of the residue on silica gel (5~35% ethyl acetate in hexanes) gave 0.784 g title compound as a yellow oil.

$R_f$: 0.27 (20% ethyl acetate in hexanes).

$^1$H NMR (500 MHz) δ 7.34~7.38 (m, 2H), 7.28~7.32 (m, 1H), 7.24~7.27 (m, 2H), 3.82 (s, 2H), 3.4')3.54 (m, 2H), 3.17~3.23 (m, 2H), 2.68~2.73 (m, 1H), 1.72~1.77 (m, 2H), 1.51~1.57 (m, 2H), 1.47 (s, 9H).

Tetrakis(triphenylphosphine)palladium gave a similar result.

Step B6: 4-(3-Benzyl-1-ethyl-(1H)-pyrazol-5-yl)-1-(tert-butoxycarbonyl)piperidine Heating 1.204 g (3.677 mmole) 4-(1-(t-butoxycarbonyl)piperidin-4-yl)-1-phenylbutan-2-on-3-yne (prepared in Step B5 above) with 0.662 g (4.413 mmole) ethylhydrazine oxalate and 1.252 g (9.687 mmole) DIEA in 20 mL ethanol over night gave an 8:1 ratio of the title compound and its isomer 4-(5-benzyl-1-ethyl-(1H)-pyrazol-3-yl)-1-(tert-butoxycarbonyl)piperidine. Use of ethylhydrazine free base gave even more favorable ratios of the desired title compound. The desired isomer can be isolated by recrystallization using hexanes or by silica gel chromatography using 5~10% acetonitrile in methylene chloride in addition to the procedure described in Method A above.

Step C: 4-(3-Benzyl-1-ethyl-(1H)-pyrazol-5-yl)piperidine di-TFA Salt

To a solution of 4-(3-benzyl-1-ethyl-(1H)-pyrazol-5-yl)-1-(t-butoxycarbonyl)piperidine from Step B (lower $R_f$ isomer) (0.373 g, 1.01 mmol) and anisole (0.219 mL, 2.02 mmol) in methylene chloride (15 mL) was added trifluoroacetic acid (1.555 mL, 20.2 mmol). The reaction was stirred at rt for 2.5 h and then concentrated. The residue was purified on preparative reverse-phase HPLC using 9.4×250 mm Semi-preparative Zorbax SB-C18 column with 17.5–35% acetonitrile gradient in water having 0.5% (v/v) TFA over 15 min at 6.05 mL per minute to give the title di-TFA salt compound as an oil. When a mixture of isomers from Step B is used, separation is also possible at this step with the above Prep HPLC conditions in which the title isomer elutes prior to 4-(5-benzyl-1-ethyl-(1H)-pyrazol-3-yl)piperidine.

PROCEDURE 2

4-(3-Benzyl-(1H)-pyrazol-5-yl)piperidine di-Trifluoroacetic Acid Salt

Step A: 4-(3-Benzyl-(1H)-pyrazol-5-yl)-1-(t-butoxycarbonyl)piperidine TFA Salt

A solution of 1-(1-(t-butoxycarbonyl)piperidin-4-yl)-4-phenyl-butane-1,3-dione from Procedure 1, Step A (30 mg, 0.087 mmol), hydrazine di-hydrochloride (10.9 mg, 0.1 mmol) and DIPEA (0.045 mL, 0.25 mmol) in methanol (1 mL) was heated at 50° C. for 16 h. The volatiles were then removed under reduced pressure. Purification of the residue was done on preparative reverse-phase HPLC using a 9.4× 250 mm Semi-preparative Zorbax SB-C18 column with 35–50% acetonitrile gradient in water having 0.5% (v/v) TFA over 15 min to give the title compound (45.2 mg) as a gel.

Step B: 4-(-Benzyl-(1H)-pyrazol-5-yl)piperidine di-TFA Salt

To a solution of 4-(3-benzyl-(1H-pyrazol-5-yl))-1-(t-butoxycarbonyl)piperidine TFA salt (from Step A) in methylene chloride (1.5 mL) was added anisole (0.017 mL) and TFA (0.230 mL). After several h at rt, volatiles were removed under reduced pressure. Purification of the residue was done by preparative reverse-phase HPLC using a 9.4× 250 mm Semi-preparative Zorbax SB-C18 column with a 15–25% acetonitrile gradient in water having 0.5% (v/v) TFA over 15 min at 6.0 mL per minute to give the title compound (40.7 mg) as a gel.

PROCEDURE 3

4-(4-(2-Phenyleth-1-yl)-1-ethyl-(1H)-pyrazol-5-yl) piperidine di-TFA Salt

Step A: 4-Phenylbutyl Bromide

To a solution of 4-phenyl-1-butanol (21.75 g) in acetonitrile (300 mL) was added triphenylphosphine dibromide (67.23 g) in portions with stirring over 10 min. After stirring over night under nitrogen, methanol (4 mL) was added and after 1.5 h, the solvent was removed under reduced pressure. Hexanes (200 mL) and ~75 g silica gel were added to the residue and the mixture was filtered and the filter cake was eluted with hexanes. The clear filtrate was concentrated to give 32.8 g of clear colorless liquid. This product was again eluted through silica gel using 1.5 L hexanes to give the title compound (24.7 g) as a colorless liquid.

$^1$H NMR (500 MHz, CDCl$_3$): δ 7.28–7.32 (m, 2H), 7.20–7.23 (m, 3H), 3.44 (t, J=6.8 Hz, 2H), 2.67 (t, J=7.6 Hz, 2H), 1.93–1.89 (m, 2H), 1.77–1.84 (m, 2H).

Step B: (4-Phenylbut-1-yl)triphenylphosphonium Bromide

A solution of 4-phenylbutyl bromide from the Step A (24.7 g) and triphenylphosphine (19.00 g) in toluene (100 mL) was heated at 120–130° C. for 3 days. The reaction was cooled to rt and the solid precipitate was collected by filtration, washed with toluene and air dried. The solid was dissolved in a 2:1 mixture of water and acetonitrile and gave the title compound (30.6 g) as a white solid after lyopholization.

$^1$H NMR (500 MHz, CD$_3$OD): δ 7.84–7.89 (m, 2H), 7.71–7.81 (m, 15H), 7.20–7.23 (m, 1H), 7.11–7.11–7.15 (m, 2H), 3.37–3.43 (m, 2H), 2.66 (t, J=7.5 Hz, 2H), 1.87 (tt, J=7.5 and 7.3 Hz, 2H), 1.63–1.70 (m, 2H).

Step C: 1-Benzyl-4-(4-phenylbutylidene)piperidine

A 0.62M solution of potassium bis(trimethylsilyl)amide in THF (180 mL, 112 mmol) in toluene (250 mL) was added to a mixture of (4-phenylbut-1-yl)triphenylphosphonium bromide from Step B (53 g) in toluene (250 mL) in an ice bath over 15 min with stirring under nitrogen. After stirring for a further 15 min, a solution of 1-benzyl-4-piperidone (16.9 g) in toluene (100 mL) was added over 30 min with stirring. The reaction mixture was allowed to warm to rt over 15 h. The reaction mixture was then poured into cold 1N HCl (400 mL) and the layers were separated. The organic layer was extracted with two more portions of 1N HCl. The combined cloudy HCl solution and an oil layer in between were washed with toluene (200 mL) before the aqueous layer was basified by the addition of potassium hydroxide (30 g). The aqueous layer was extracted with ether (3×150 mL) and the combined organic layers were washed with water and brine, dried over sodium sulfate and concentrated. The crude product was purified by FC (10–15% ethyl acetate in hexanes having 4% (v/v) TEA) to give the title compound (16 g) as a colorless oil. $R_f$: 0.47 (20% ethyl acetate in hexanes having 4% (v/v) TEA).

$^1$H NMR (500 MHz, CDCl$_3$): δ 7.26–7.38 (m, 7H), 7.18–7.21 (m, 3H), 5.18 (t, J=7.4 Hz, 1H), 3.54 (s, 2H), 2.61–2.64 (m, 2H), 2.42–2.49 (m, 4H), 2.22–2.27 (m, 4H), 2.02–2.07 (m, 2H), 1.65–1.71 (m, 2H).

Step D: 1-(1-Benzylpiperidin-4-yl)-4-phenylbutan-1-one

To a solution of 4-(4-phenylbutylidene)-1-benzylpiperidine from Step C (4.37 g) in anhydrous ether (150 mL) under nitrogen with stirring was add 1M borane solution in THF (45 mL). The reaction was stirred for 3 h when water (2 mL) was added dropwise. The mixture was stirred a further 30 min and was then cooled in an ice bath. A solution of chromic anhydride (2.5 g), concentrated sulfuric acid (5.44 mL) and water (125 mL) was added dropwise with vigorous magnetic stirring over 5 min. After another 5 min, the ice bath was removed. After 1.5 h at rt, 0.5N sodium hydroxide and ether (400 mL each) were added and the mixture was stirred until the residue dissolved. The layers were separated and the aqueous layer was extracted twice with ether. The combined ether layers were washed with an aqueous EDTA solution, water and brine (100 mL each), dried over sodium sulfate and concentrated under reduced pressure to give a colorless gel. Flash chromatography on silica gel with 30–50% ethyl acetate in hexanes with 3% (v/v) TEA gave the title compound (1 g) as a colorless gel. $R_f$: 0.43 (30% ethyl acetate in hexanes with 3% (v/v) TEA).

$^1$H NMR (500 MHz, CDCl$_3$): δ 7.25–7.33 (m, 7H), 7.16–7.22 (m, 3H), 3.51 (s, 2H), 2.89–2.93 (m, 2H), 2.63 (t, J=7.6 Hz, 2H), 2.46 (t, J=7.2 Hz, 2H), 2.38 (tt, J=11.5 and 3.9 Hz, 1H), 1.99–2.03 (m, 2H), 1.92 (tt, J=7.2 and 7.6 Hz, 2H), 1.76–1.81 (m, 2H), 1.65–1.72 (m, 2H).

Step E: 1-(1-Benzylpiperidin-4-yl)-2-formyl-4-phenylbutan-1-one

To a solution of potassium t-butoxide (0.673 g) in THF (20 mL) under nitrogen and cooled in an ice bath was added a solution of 1-(1-benzylpiperidin-4-yl)-4-phenylbutan-1-one from Step D (0.71 g) and methyl formate (3.76 mL) in THF (12 mL) over 5 minute. The reaction was stirred for 15 min before being allowed to warm to rt for 2 h. The reaction was poured into water and extracted with ether (4×100 mL), methylene chloride (100 mL), and THF (100 mL). The combined organic layers were washed with water and brine, dried over sodium sulfate and concentrate under reduced pressure. The crude product was purified by FC on silica gel eluting with 5 and 20% methanol in ethyl acetate with 4% TEA to afford the title compound (0.8 g).

$^1$H NMR (500 MHz, CDCl$_3$) showed a 3:1 ratio of enol (δ 8.54 ppm) and aldehyde (δ 9.54 ppm) forms. Other signals from the two forms were only partially resolved. The title compound had a retention time of 9.47 min on a Zorbax SB-C18 column (4.6×75 mm) eluting with 20–100% gradient of acetonitrile in water with 0.1% TFA over 10 min at 1 mL per min.

Step F: 4-(4-(2-Phenyleth-1-yl)-1-ethyl-(1H)-pyrazol-5-yl)-1-benzylpiperidine di-TFA Salt A solution of 1-(1-benzylpiperidin-4-yl)-2-formyl-4-phenyl-1-butanone from Step E (76.5 mg) and ethylhydrazine oxalate (45 mg) in methanol (4 mL) was heated at 45° C. for 15.5 h. The solvent was removed under reduced pressure. The residue was purified by preparative reverse-phase HPLC using a 9.4×250 mm Semi-preparative Zorbax SB-C18 column with 30–50% acetonitrile gradient in water having 0.5% (v/v) TFA over 15 min at 7.1 mL per min to give the title compound (45 mg) as the faster-eluting, minor isomer.

$^1$H NMR (500 MHz, CD$_3$OD): δ 7.46–7.52 (m, 5H), 7.37 (s, 1H), 7.21–7.24 (m, 2H), 7.12–7.15 (m, 3H), 4.32 (s, 2H), 4.17 (q, J=7.2 Hz, 2H), 3.53 (br d, J=12.4 Hz, 2H), 3.06–3.12 (m, 3H), 2.79–2.88 (m, 4H), 2.10–2.20 (m, 2H), 1.78 (br d, J=14.2 Hz, 2H), 1.34 (t, J=7.2 Hz, 3H). The isomeric assignment was confirmed by a NOESY spectrum. HPLC/MS (ESI): m/z 374.3 (M+1), 2.51 min.

Step G: 4-(4-(2-Phenyleth-1-yl)-1-ethyl-(1H)-pyrazol-5-yl) piperidine di-TFA Salt A mixture of ammonium formate (119 mg), 20% Pd(OH)$_2$/C (5 mg) and 4-(4-(2-phenylethyl)-1-ethyl-(1H-pyrazol-5-yl))-1-benzylpiperidine di-TFA salt from Step F in methanol (2 mL) was heated at 60° C. for 1.5 h. The solvent was removed under reduced pressure and the residue was purified by preparative reverse-phase HPLC using a 9.4×250 mm Semi-preparative Zorbax SB-C18 column with 20–35% acetonitrile gradient in water having 0.5% (v/v) TFA over 15 min at 6.25 mL per min to give the title compound as the di-TFA salt (25 mg) as a gel.

$^1$H NMR (500 MHz, CD$_3$OD): δ 7.40 (s, 1 H), 7.22–7.25 (m, 2H), 7.13–7.17 (m, 3H), 4.20 (q, J=7.3 Hz, 2H), 3.42–3.46 (m, 2H), 3.05–3.15 (m, 3H), 2.83–2.90 (m, 4H), 2.04–2.14 (m, 2H), 1.74–1.79 (m, 2H), 1.36 (t, J=7.4 Hz, 3H). The isomer assignment was confirmed by an NOE difference spectrum.

PROCEDURE 4A 4-(3-(4-Fluorobenzyl)-1-ethyl-(1H)-pyrazol-5-yl) piperidine di-TFA

The title compound was prepared using essentially the same procedure as that described in Procedure 1, but substituting methyl 4-fluorophenylacetate for methyl phenylacetate in Step A, Method B, Step B3.

PROCEDURE 4B 4-(3-(3,4-Difluorobenzyl)-1-ethyl-(1H)-pyrazol-5-yl)piperidine di-TFA The title compound was prepared using essentially the same procedure as that described in Procedure 1, but substituting methyl 3,4-difluorophenylacetate for methyl phenylacetate in Step A, Method B.

PROCEDURE 5

4-(3-(Benzofurazan-4-yl)prop-1-yl)piperidine Hydrochloride

Step A: (1-t-Butoxycarbonylpiperidin4-yl)acetaldehyde

A solution of oxalyl chloride (1.23 mL, 14.1 mmol) in methylene chloride (50 mL) was cooled to −78° C. DMSO (2.0 mL, 28.3 mmol), was added slowly via syringe. After 10 min, 4-(2-hydroxyeth-1-yl)-1-t-butoxycarbonylpiperidine (2.7 g, 11.8 mmol) in methylene chloride (15 mL) was added. The cold mixture was stirred for an additional 20 min then TEA (8.2 mL, 59 mmol) was added. The mixture was warmed to rt and stirred for 1.5 h, then diluted with methylene chloride (300 mL). The organic phase was washed with 1M sodium hydroxide, dried over sodium sulfate and concentrated. FC (125 g silica, 2.5/1 hexanes/ethyl acetate) afforded the title compound (2.25 g).

$^1$H NMR (300 MHz, CDCl$_3$): δ 1.1–1.2 (m, 2H), 1.45 (s, 9H), 1.65–1.75 (m, 2H), 1.99–2.13 (m, 1H), 2.38–2.4 (d, 2H), 2.65–2.8 (m, 2H), 4.03–4.15 (m, 2H), 9.78 (s, 1H).

Step B: 4-(Prop-2-en-1-yl)-1-t-butoxycarbonylpiperidine

A solution of methyltriphenylphosphonium bromide (5.3 g, 14.8 mmol) in THF (50 mL) was cooled to 0° C. under nitrogen. Potassium hexamethyl disilazide (27.7 mL, 0.5M toluene solution, 13.9 mmol) was added and the mixture was stirred for 30 min. A solution of (1-t-butoxycarbonylpiperidin-4-yl)acetaldehyde from Step A (2.25 g, 9.9 mmol) in THF (10 mL) was added and the mixture was warmed to rt. After 30 min, the reaction was complete by tlc analysis. The mixture was diluted with ethyl acetate (200 mL) and washed with water and brine (100 mL each). The organic phase was dried over sodium sulfate and concentrated to give an oil which was purified by FC (75 g silica, 10/1 hexane/ethyl acetate) to afford the title compound (1.61 g).

$^1$H NMR (300 MHz, CDCl$_3$): δ 1.03–1.18 (m, 2H), 1.45 (s, 9H), 1.4–1.5 (m, 1H), 1.6–1.7 (m, 2H), 1.99–2.13 (t, 1H), 2.62–2.75 (m, 2H), 4.03–4.15 (m, 2H), 4.98–5.12 (m, 2H), 5.7–5.83 (m, 1H).

Step C: 4-Bromobenzofurazan

To a solution of 2,6-dibromoaniline (10 g, 40 mmol) in glacial acetic acid (160 mL) was added 30% hydrogen peroxide (30 mL). The mixture was left for 48 h at which point crystals had precipitated. The crystals were collected by filtration, washed with acetic acid and water then dried under high vacuum to give 2,6-dibromonitrosobenzene (6.24 g). This material (2.6 g, 10 mmol) was dissolved in DMSO (25 mL) along with sodium azide (650 mg, 10 mmol). The mixture was heated to 100° C. for 1 h then cooled to rt and diluted with ethyl acetate and water. The layers were separated and the organic phase was washed with water and brine, then dried over sodium sulfate and concentrated. FC (75 g silica, 10/1 hexane/ethyl acetate) afforded the title compound (1.7 g).

$^1$H NMR (300 MHz, CDCl$_3$): δ 7.25–7.35 (dd, 1H), 7.6–7.65 (d, 1H), 7.78–7.82 (d, 1H).

Step D: 4-(3-(Benzofurazan-4-yl)prop-1-yl)piperidine Hydrochloride

A solution of 4-(prop-2-en-1-yl)-1-t-butoxycarbonylpiperidine from Step B (330 mg, 1.46 mmol) in dry THF (0.5 mL) was cooled to 0° C. and a solution of 9-BBN (3.2 mL, 0.5 M in THF, 1.61 mmol) was added. The mixture was warmed to rt and stirred for 5 h. Potassium carbonate (405 mg, 2.93 mmol), 1,2-bis (diphenylphosphino)-ferrocenyl palladium dichloride (60 mg, 0.073 mmol) and 4-bromobenzofurazan (from Step C) (292 mg, 1.46 mmol) were added followed by dry DMF (5 mL). The resulting mixture was heated to 55° C. overnight then diluted with ethyl acetate. The solution was washed with water (3×) and brine, then dried over sodium sulfate and concentrated. FC (15 g silica, 5/1 hexane/ethyl acetate) afforded the title Boc derivative. Heating in 1% conc. HCl/methanol at 50° C. for 2 h followed by removal of solvent and drying under vacuum afforded the title compound as the hydrochloride (155 mg).

$^1$H NMR (300 MHz, CD$_3$OD): δ 1.31–1.42 (m, 4H), 1.6–1.75 (m, 1H), 1.84–2.0 (m, 4H), 2.9–3.1 (m, 4H), 3.3–3.4 (m, 2H), 7.25–7.3 (d, 1H), 7.4–7.5 (dd, 1H), 7.7–7.75 (d, 1H).

PROCEDURE 6

4-(3-(Benzofurazan-5-yl)prop-1-yl)piperidine Hydrochloride

Using essentially the same methods as in Procedure 5, but substituting 2,5-dibromoaniline for 2,6-dibromoaniline in Step C, the title compound was prepared.

PROCEDURE 7

4-(3-(4-Cyanophenyl)prop-1-yl)piperidine Hydrochloride

Starting with 4-(prop-2-en-1-yl)-1-t-butoxycarbonylpiperidine from Procedure 5, Step B (475 mg, 2.1 mmol) and using essentially the same methods as in Procedure 5, Step D, but substituting 4-bromobenzonitrile (382 mg, 2.1 mmol), the title compound (337 mg) was obtained as the hydrochloride.

$^1$H NMR (300 MHz, CD$_3$OD). 1.31–1.42 (m, 4H), 1.58–1.75 (m, 5H), 1.9–2.1 (m, 2H), 2.67–2.77 (t, 2H), 2.9–3.0 (m, 2H), 3.3–3.4 (m, 2H), 7.35–7.4 (d, 2H), 7.6–7.63 (d, 2H).

PROCEDURE 8

4-(3-(4-Cyano-3-fluorophenyl)prop-1-yl)piperidine Hydrochloride

Starting with 4-(prop-2-en-1-yl)-1-t-butoxycarbonylpiperidine from Procedure 5, Step B and using essentially the same methods as in Procedure 5, Step D, but substituting 4-bromo-2-fluorobenzonitrile, the title compound was obtained as the hydrochloride.

PROCEDURE 9

4-(3-(4-Fluorophenyl)prop-1-yl)piperidine Hydrochloride

Starting with 4-(prop-2-en-1-yl)-1-t-butoxycarbonylpiperidine (from Procedure 5, Step B) and using essentially the same methods as in Procedure 5, Step D, but substituting 4-bromofluorobenzene, the title compound was obtained as the hydrochloride.

PROCEDURE 10

4-(3-(Quinolin-3-yl)propyl)piperidine di-Hydrochloride Salt

Step A: 1-(t-Butoxycarbonyl)-4-(3-(quinolin-3-yl)propyl) piperidine

A solution of 1-(t-butoxycarbonyl)-4-(prop-2-en-1-yl)piperidine (from Procedure 5, Step B) (260 mg, 1.15 mmol) in THF (3 mL) under argon was treated with 0.5M 9-BBN solution in THF (2.30 mL, 1.15 mmol). The resulting mixture was stirred at rt for 2 h, then treated with sodium methoxide (68 mg, 1.25 mmol). The resulting mixture was stirred until it was homogeneous (15 min) and then was treated with 3-(bromo) quinoline (0.155 mL, 1.15 mmol) and [1,1'-bis(triphenylphosphino)ferrocene) dichloropalladium.methylene chloride (41 mg, 0.05 mmol). The resulting mixture was heated at reflux for 30 min, cooled and quenched with 1N NaOH (20 mL). The quenched reaction was extracted with 2×50 mL of ether; the extracts were dried over magnesium sulfate, combined and concentrated. FC (15 g of silica gel, 4:1 v/v hexanes/ethyl acetate) afforded the title compound (240 ml).

$^1$H NMR (300 MHz, CDCl$_3$): δ 1.00–1.16 (m, 2H), 1.25–1.40 (m, 2H), 1.45 (s, 9H), 1.60–1.80 (m, 5H), 2.62–2.72 (m, 2H), 2.79 (t, J=7.8, 2H), 4.06 (br s, 2H), 7.52 (m, 1H), 7.66 (m, 1H), 7.76 (dd, J=8.0, 1.6, 1H), 7.91 (d, J=1.6, 1H), 8.77 (d, J=2.2, 1H).

Step B: 4-(3-(Quinolin-3-yl)propyl)piperidine di-Hydrochloride Salt

A solution of 1-(t-butoxycarbonyl)-4-(3-(quinolin-3-yl) propyl)piperidine from Step A (240 mg, 0.68 mmol) in 1M HCl solution (8 mL) in methanol was stirred at rt for 48 h. The solution was concentrated and the residue crystallized from ethyl acetate to afford the title compound (182 mg), $^1$H NMR (500 MHz, CD$_3$OD): δ 1.37–1.49 (m, 4H), 1.67–1.74 (m, 2H), 1.85–1.91 (m, 2H), 1.99 (app d, J=13.5 Hz, 2H), 2.99 (app t, J=11.5 Hz, 2H), 3.05 (t, J=8.0 Hz, 2H), 3.38 (app d, J=12.5 Hz, 1H), 7.97 (t, J=7.0 Hz, 1H), 8.13 (dt. J=1.0 and 7.0 Hz, 1H), 8.24 (d, J=8.5 Hz, 1H), 8.31 (d, J=8.0 Hz, 1H), 9.10 (s, 1H), 9.21 (d, J=1.0 Hz, 1H).

PROCEDURE 11

4-(3-(2-Pyridyl)propyl)piperidine di-TFA Salt

Step A: 1-(t-Butoxycarbonyl)-4-(3-(2-pyridyl)propyl) piperidine

The title compound was prepared using a procedure analogous to that described in Procedure 10, Step A, substituting (2-bromo)pyridine for (3-bromo)quinoline. FC (4:1 v/v hexanes/ethyl acetate followed by 3:2 v/v hexanes/ethyl acetate) provided the title compound (135 mg, 48%).

$^1$H NMR (500 MHz, CDCl$_3$): δ 1.05–1.81 (m, 10H), 1.46 (s, 9H), 2.67–2.82 (m, 2H), 3.65 (m, 1H), 4.08–4.16 (m,

2H), 7.14–7.18 (m, 2H), 7.63 (m, 1H), 8.54 (d, J=4.4 Hz, 1H). HPLC/MS (ESI): m/z 304 (M+1).

Step B: 4-(3-(2-Pyridyl)propyl)piperidine di-TFA Salt

To a solution of 1-(t-butoxycarbonyl)-4-(3-(2-pyridyl) propyl)piperidine (from Step A) (128 mg, 0.42 mmol) in methylene chloride (1 mL) was added TFA (1 mL). After stirring for 2 h at rt, the reaction was concentrated to give the title compound (36 mg).

$^1$H NMR (500 MHz, CDCl$_3$): δ 1.22–1.46 (m, 5H), 1.73–1.79 (m, 4H), 2.68 (t, J=11.8 Hz, 2H), 2.78 (t, J=7.8 Hz, 2H), 3.19 (d, J=11.8 Hz, 2H), 5.32 (br s, 1H), 7.09–7.15 (m, 2H), 7.59 (t, J=7.7 Hz, 2H), 8.52 (d, J=4.6 Hz, 1H).

PROCEDURE 12

4-(3-(4-(Trifluoromethyl)pyrimidin-2-yl)propyl) piperidine

Step A: 1-(t-Butoxycarbonyl)-4-(3,3-dibromoprop-2-en-1-yl)piperidine

To a solution of carbon tetrabromide (286 mg, 0.86 mmol) in methylene chloride 34 mL) at −10° C. was added triphenylphosphine (339 mg, 1.29 mmol). After 10 min, a solution of ((1-t-butoxycarbonyl)piperidin-4-yl)acetaldehyde (from Procedure 5, Step A) (98 mg, 0.43 mmol) and TEA (0.060 mL, 0.43 mmol) in methylene chloride (2 mL) was added. After stirring at rt for 2 h, the reaction mixture was concentrated. The residue was purified by FC (9:1 v/v hexanes/ethyl acetate followed by 1:1 v/v hexanes/ethyl acetate) to give the title compound (518 mg).

$^1$H NMR (500 MHz, CDCl$_3$): δ 1.14–1.22 (m, 2H), 1.47 (s, 9H), 1.57–1.60 (m, 1H), 1.67 (br d, J=12.6 Hz, 2H), 2.08 (t, J=7.1 Hz, 2H), 2.70 (t, J=12.7 Hz, 2H), 4.10 (br d, J=12.6 Hz, 2H), 6.42 (t, J=7.4 Hz, 1H).

Step B: 1-(t-Butoxycarbonyl)-4-(prop-2-yn-1-yl)piperidine

To a solution of 118 mg (0.31 mmol) of 1-(t-butoxycarbonyl)-4-(3,3-dibromoprop-2-en-1-yl)piperidine from Step A in THF (4 mL) at −78° C. was added a 2.5M solution of n-butyl lithium (0.370 mL, 0.92 mmol). After stirring at −78° C. for 45 min, the reaction mixture was quenched with sat'd ammonium chloride (4 mL) and diluted with ether (25 mL). After separating the phases, the aqueous layer was extracted with ether. The combined organic phases were washed with brine, dried over magnesium sulfate and concentrated. The residue was purified by FC (4:1 v/v hexanes/ether) to give the title compound (55 mg).

$^1$H NMR (500 MHz, CDCl$_3$): δ 1.18~1.26 (m, 2H), 1.47 (s, 9H), 1.60–1.67 (m, 1H), 1.77 (br d, J=13.2 Hz, 2H), 1.99 (t, J=2.6 Hz, 1H), 2.16 (dd, J=6.6 Hz, 2.5, 2H), 2.68–2.74 (m, 2H), 4.12 (br d, J=13.0 Hz, 2H).

Step C: 1-(t-Butoxycarbonyl)-4-(3-((4-trifluoromethyl) pyrimidin-2-yl)prop-2-yn-1-yl)piperidine To a solution of 1-(t-butoxycarbonyl)-4-(prop-2-yn-1-yl) piperidine from Step B (86 mg, 0.39 mmol) in TEA (4 mL) under argon at 0° C. was added 2-chloro-4-(trifluoromethyl) pyrimidine (0.070 m, 0.58 mmol). After stirring at 0° C. for 5 min, dichlorobis(triphenylphosphine)palladium(II) (27 mg, 0.04 mmol), and copper iodide (4 mg, 0.02 mmol) was added and the reaction vessel was flushed with argon. After 3 h at 60° C., the reaction mixture was cooled to rt and quenched with 1N sodium hydroxide (5 mL) and diluted with ether (25 mL). After separating the phases, the aqueous, layer was extracted again with ether. The combined organic phases were washed with brine, dried over magnesium sulfate and concentrated. The residue was purified by FC (9:1 v/v hexanes/ethyl acetate followed by 2:1 v/v hexanes/ ethyl acetate) to give the title compound (132 mg).

$^1$H NMR (400 MHz, CDCl$_3$): δ 1.26–1.33 (m, 2H), 1.46 (s, 9H), 1.80–1.88 (m, 3H), 2.46 (d, J=6.4 Hz, 2H), 1.99 (br t, J=11.2 Hz, 1H), 4.10–4.40 (m, 2H), 7.54 (d, J=5.0 Hz, 1H), 8.94 (d, J=5.0 Hz, 1H).

Step D: 1-(t-Butoxycarbonyl)-4-(3-((4-trifluoromethyl) pyrimidin-2-yl)prop-1-yl)piperidine To a solution of 1-(t-butoxycarbonyl)-4-(3-((4-trifluoromethyl)pyrimidin-2-yl)prop-2-yn-1-yl)piperidine from Step C (130 mg) in methanol (4 mL) was added 10% palladium on carbon (15 mg). The mixture was hydrogenated using a Parr shaker set at 40 psi. After TLC indicated the absence of the starting material, She reaction was filtered through a 0.45 micron nylon membrane polypropylene filter and concentrated. FC (9:1 v/v hexanes/ethyl acetate followed by 2:1 v/v hexanes/ethyl acetate) of the residue afforded the title compound.

$^1$H NMR (400 MHz, CDCl$_3$): δ 1.04–1.15 (m, 2H), 1.27–1.49 (m, 3H), 1.46 (s, 9H), 1.68 (br d, J=12.7 Hz, 2H), 1.85–1.93 (m, 2H), 2.68 (br t, J=12.1 Hz, 2H), 3.05 (t, J=7.7 Hz, 2H), 4.08 (br d, J=11.5 Hz, 2H), 7.47 (d, J=5.0 Hz, 1H), 8.92 (d, J=5.0 Hz, 1H).

Step E: 4-(3-((4-Trifluoromethyl)pyrimidin-2-yl)prop-1-yl) piperidine

The, title compound was prepared from 1-(t-butoxycarbonyl)-4-(3-((4-trifluoromethyl)pyrimidin-2-yl) prop-1-yl)piperidine (from Step D) (17 mg, 0.046 mmol) using a procedure analogous to that described in Procedure 10, Step B. FC (95:5:0.5 v/v/v methylene chloride/methanol/ NH$_4$OH) afforded the title compound (22 mg).

$^1$H NMR (300 MHz, CDCl$_3$): δ 1.21–3.45 (m, 15H), 7.52 (d, J=5.0 Hz, 1H), 8.95 (d, J=5.0 Hz, 1H).

PROCEDURE 13

4-(N-(Pyrimidin-2-yl)-N-(prop-1-yl)amino) piperidine di-Hydrochloride Salt

Step A: 4-Amino-1-t-butoxycarbonylpiperidine 1-t-butoxycarbonylpiperidin-4-one (20 g, 100 mmol), benzylamine (11 mL, 100 mmol) and sodium triacetoxyborohydride (32 g, 150 mmol) were stirred together in 1,2-dichloroethane (400 mL) for 3 h. The resulting mixture was diluted with ethyl acetate (1 L) and washed with 1M aqueous sodium hydroxide (500 mL) followed by brine (500 mL). The organic phase was dried over sodium sulfate and concentrated to afford 4-N-benzylamino-1-t-butoxycarbonyl piperidine (30.1 g) as a viscous oil. The oil was dissolved in methanol (400 mL) and ammonium formate (39 g, 600 mmol) was added. The vessel was purged with nitrogen and 10% palladium on carbon (6.5 g, 6 mmol) was added. The mixture was refluxed for 1 h and then filtered through celite and concentrated. Drying under vacuum afforded the title compound (20 g).

$^1$H NMR (300 MHz, CDCl$_3$): δ 1.15–1.3 (m, 2H), 1.43 (s, 9H), 1.7–1.9 (m, 4H), 2.65–2.72 (m, 3H), 3.95–4.1 (m, 2H).

Step B: 4-(N-(Pyrimidin-2-yl)amino)-1-t-butoxycarbonylpiperidine

4-Amino-1-t-butoxycarbonylpiperidine from Step A, (1.9 g, 9.5 mmol), 2-chloropyrimidine (1.1 g, 9.5 mmol) and DIPEA (3.3 mL, 19 mmol) were combined in isopropanol (10 mL) and the mixture was refluxed for 24 h. The mixture was cooled, diluted with methylene chloride (100 mL) and washed with water and brine. The organic phase was dried over sodium sulfate and concentrated. FC (60 g silica, 1/1 hexanes/ethyl acetate) afforded the title compound (0.97 g).

$^1$H NMR (300 MHz, CDCl$_3$): δ 1.31–1.45 (m, 2H), 1.44 (s, 9H), 2.0–2.1 (m, 2H), 2.9–3.0 (m, 2H), 3.9–4.1 (m, 3H), 5.0–5.05 (m, 1H), 6.5–6.58, (t, 1H), 8.15–8.2 (d, 2H).

Step C: 4-(N-(Pyrimidin-2-yl)-N-(allyl)amino)-1-t-butoxycarbonyl-piperidine

A solution of 4-(N-(pyrimidin-2-yl)amino)-1-t-butoxycarbonylpiperidine from Step B (528 mg, 1.9 mmol)

in dry THF (5 mL) was cooled to −78° C. and a solution of sodium hexamethyldisilazide (2.8 mL, 1.0 M in THF, 2.8 mmol) was added via syringe. The mixture was stirred cold for 20 min then allyl bromide (0.23 mL, 2.7 mmol) was added. The mixture was then warmed to rt and stirred for 1.5 h at which time TLC showed very little starting material. The solution was poured into sat'd ammonium chloride and methylene chloride. The layers were separated and the organic phase was dried over sodium sulfate and concentrated. FC (25 g silica, 4/1 hexanes/ethyl acetate) afforded the title compound (367 mg).

$^1$H NMR (300 MHz, CDCl$_3$): δ 1.45 (s, 9H), 1.6–1.8 (m, 4H), 2.75–2.85 (m, 2H), 4.1–4.3 (m, 4H), 4.7–4.8 (m, 1H), 5.05–5.17 (m, 2H), 5.92–5.98 (m, 1H), 6.45–6.5 (t, 1H), 8.3–8.35 (d, 2H).

Step D: 4-(N-(Pyrimidin-2-yl)-N-(prop-1-yl)amino) piperidine di-Hydrochloride Salt In a round bottom flask purged with nitrogen 4-(N-(pyrimidin-2-yl)-4-N-(allyl)amino)-1-t-butoxylcarbonylpiperndine from Step C (461 mg, 1.45 mmol) was dissolved in methanol (4 mL) and 10% palladium on carbon (150 mg, 0.14 mmol) was added. The mixture was stirred under 1 atm of hydrogen using a balloon for 1.5 h. The mixture was filtered through celite and concentrated. FC (20 g silica, 3/1 hexanes/ethyl acetate) afforded 4-(N-(pyrimidin-2-yl)-4-N-(prop-1-yl)amino)-1-t-butoxylcarbonylpiperidine.

$^1$H NMR (400 MHz, CDCl$_3$). δ 0.9–1.0 (t, 3H, J=7 Hz), 1.5 (s, 9H), 1.6–1.8 (m, 6H), 2.8–2.9 (m, 2H), 3.33–3.4 (m, 2H), 4.2–4.27 (m, 2H), 4.7–4.8 (m, 1H), 6.42–6.45 (t, 1H),), 8.3–8.35 (d, 2H).

This material was dissolved in 2% conc. HCl/methanol and heated to 50° C. for 2 h. Removal of solvent and drying under vacuum afforded the title compound as a white solid.

PROCEDURE 14

4-(3-(3,4-Difluorophenyl)prop-1-yl)piperidine Hydrochloride Salt

Starting with 4-(prop-2-en-1-yl)-1-t-butoxycarbonylpiperidine from Procedure 5, Step B and using essentially the same methods as in Procedure 5, Step D, but substituting 3,4-difluorobromobenzene, the title compound was obtained as the hydrochloride.

PROCEDURE 15

4-(5-Benzyl-1-(prop-1-yl)-(1H)-pyrazol-3-yl) piperidine di-Hydrochloride Salt (Higher R$_f$ isomer) and 4-(3-Benzyl-1-(prop-1-yl)-(1H)-pyrazol-5-yl) piperidine di-Hydrochloride Salt (Lower R$_f$ isomer)

Using essentially the same methods as in Procedure 1, Step B–C, but substituting propylhydrazine for ethylhydrazine in Step B, the title compounds were prepared.

PROCEDURE 16

4-(3,3-Difluoro-3-phenylprop-1-yl)piperidine
Step A: 1-(Benzyloxycarbonyl)-4-(3-oxo-3-phenylprop-1-en-1-yl)piperidine DIPEA (4.6 mL, 3.4 g, 26 mmol) was added to a solution of 4-(hydroxymethyl)piperidine (2.00 g, 17.4 mmol) dissolved in methylene chloride (20 mL). The solution was cooled in an ice bath and benzyl chloroformate (2.5 mL, 3.0 g, 18 mmol) was added dropwise over 10 min. After warming to rt and stirring for 96 h, the mixture was diluted with ethyl acetate (50 mL) and washed in succession with 25 mL each of saturated aq. sodium bicarbonate, 2N aq. HCl, saturated aq. sodium bicarbonate, and saturated aq. brine. The organic layer was dried (sodium sulfate), decanted, and evaporated to give 4.14 g of 1-(benzyloxycarbonyl)-4-(hydroxymethyl)piperidine.

1,1,1-Triacetoxy-1,1-dihydro-1,2-benzoiodoxol-3(1H)-one (1.92 g, 4.53 mmol) was added to a solution of 1-(benzyloxycarbonyl)-4-(hydroxymethyl)piperidine (1.00 g, 4.01 mmol) in methylene chloride (20 mL) and the mixture was stirred at rt for 45 min. Ether (75 mL) and 1.3 N aq. NaOH (25 mL) were added and stirring was continued for 15 min. The mixture was transferred to a separatory funnel with additional ether (30 mL) and 1.3 N aq. NaOH (20 mL). The organic layer was separated, washed with saturated aq. brine (20 mL), dried (sodium sulfate), decanted, and evaporated to give 846 mg of 1-(benzyloxycarbonyl)-4-piperidine carboxaldehyde as a colorless syrup.

Diethyl (2-oxo-2-phenylethyl)phosphonate (0.96 mL, 1.1 g, 4.4 mmol) was added in one portion to a stirred suspension of sodium hydride (60% oil dispersion, 158 mg, 3.95 mmol) in THF (20 mL). After 15 min. at rt, the clear solution was cooled in an ice bath and 1-(benzyloxycarbonyl)-4-piperidinecarboxaldehyde (840 mg, 3.40 mmol) was added in THF (1.0 mL) with additional THF (2×1.0 mL) for rinsing. Stirring was continued for a total of 2 h, with slow warming to rt. The mixture was then partitioned between ether (120 mL) and 2.5 N aq. NaOH (60 mL). The organic layer was washed with saturated aq. brine (60 mL), dried (sodium sulfate), decanted, and evaporated. The crude product was purified by FC, eluting with 15–20% ethyl acetate in hexane, to give 0.95 g of the title compound as a colorless syrup.

$^1$H NMR (400 MHz, CDCl$_3$): δ 7.82 (d, J=8 Hz, 2H), 7.57 (t, J=8 Hz, 1H), 7.48 (t, J=8 Hz, 2H), 7.39–7.29 (m, 5 H), 6.99 (dd, J=15, 6 Hz, 1H), 6.87 (dd, J=15 and 1 Hz, 1H), 5.15 (s, 2H), 2.97–2.82 (m, 2H), 2.50–2.39 (m, 1H), 1.89–1.77 (m, 2H), 1.54–1.39 (m, 2H). MS (ESI): m/z 367 (M+NH$_3$+H).

Step B: 2-(2-(1-(Benzyloxycarbonyl)piperidin-4-yl)ethyl)-2-phenyl-1,3-dithiolane 1-(Benzyloxycarbonyl)-4-(3-oxo-3-phenylprop-1-en-1-yl)piperidine from Step A (0.95 g, 2.7 mmol) was hydrogenated using 5% Pd/C (10 mg) in 95% ethanol (20 mL) at atmospheric pressure. After 3.5 h, the mixture was filtered and the catalyst was washed with 95% ethanol. Evaporation of the filtrate gave 0.95 g of 1-(benzyloxycarbonyl)-4-(3-oxo-3-phenylprop-1-yl)piperidine as a colorless syrup.

Boron trifluoride-acetic acid complex (BF$_3$.2-CH$_3$CO$_2$H, 0.370 mL, 501 mg, 2.67 mmol) was added to a solution of 1,2-ethanedithiol (0.440 mL, 494 mg, 5.25 mmol) and (1-(benzyloxycarbonyl)-4-(3-oxo-3-phenylprop-1-yl) piperidine (930 mg, 2.65 mmol) in methylene chloride (4.0 mL), at rt. After 6 h, the mixture was diluted with ether 50 mL) and washed with saturated aq. sodium bicarbonate (2×25 mL), 2.5 N aq. NaOH (25 mL), and saturated aq. brine (25 mL). The organic layer was dried (sodium sulfate), decanted, and evaporated. The crude product was purified by FC, eluting with 10% ethyl acetate in hexane, to give 1.05 g of the title compound as a colorless liquid.

$^1$H NMR (400 MHz, CDCl$_3$): δ 7.66 (d, J=8 Hz, 2H), 7.38–7.26 (m, 7H), 7.22 (t, J=8 Hz, 1H), 5.10 (s, 2H), 4.18–4.02 (m, 2H), 3.41–3.32 (m, 2H), 3.29–3.20 (m, 2H), 2.79–2.62 (m, 2H), 2.40–2.32 (m, 2H), 1.65–1.54 (m, 2H), 1.40–1.27 (m, 1H), 1.24–1.16 (m, 2H), 1.10–0.97 (m, 2H); HPLC/MS (ESI): m/z 428 (M+H); HPLC: 4.21 min.

Step C: 1-(t-Butoxycarbonyl)-4-(3,3-difluoro-3-phenylprop-1-yl)piperidine 1,3-Dibromo-5,5-dimethylhydantoin (74 mg, 0.26 mmol) was stirred with methylene chloride (0.50 mL) at rt, and the suspension was then cooled in a dry ice/isopropanol bath. After 5 min., hydrogen fluoride.pyridine (70% HF, 0.18 mL) was added over 1 min. After 5 min., a solution of 2-(2-(1-(benzyloxycarbonyl)piperidin-4-yl)ethyl)-2-phenyl-1,3-dithiolane from Step B (100 mg, 0.234 mmol) in methylene chloride (0.20 mL) was added over 1 min. After 10 min, the reaction mixture was diluted into methylene chloride (25 mL) and washed with water (10 mL) containing sodium bisulfite (0.5 g). The organic layer was washed with saturated aq. sodium bicarbonate (2×10 mL) followed by saturated aq. brine (10 mL), dried (sodium sulfate), decanted, and evaporated to give 98 mg of colorless syrup. This material was combined with 195 mg of crude product from two similar reactions and purified by FC, eluting with 8% ethyl acetate in hexane, to give 247 mg of 1-(benzyloxycarbonyl)-4-(3,3-difluoro-3-phenylprop-1-yl) piperidine ($R_f$: 0.3 using 10% eithyl acetate in hexane) containing some residual impurity.

The partially purified 1-(benzyloxycarbonyl)-4-(3,3-difluoro-3-phenylprop-1-yl)piperidine (247 mg) was hydrogenated at atmospheric pressure in 95% ethanol (4.0 mL) containing 20% $Pd(OH)_2/C$ (60 mg). After 6 h, additional 20% $Pd(OH)_2/C$ (32 mg) was added and the hydrogenation was continued for another 16 h. The mixture was filtered and the catalyst was washed with 95% ethanol. Evaporation of the filtrate gave 164 mg of crude 4-(3,3-difluoro-3-phenylprop-1-yl)piperidine as a colorless syrup.

Di-t-butyl dicarbonate (178 mg, 0.816 mmol) was transferred with methylene chloride (2×0.5 mL) to a solution of crude 4-(3,3-difluoro-3-phenylprop-1-yl)piperidine (164 mg) in methylene chloride (2.0 mL). After stirring at rt for 1 h, the solution was stored at −20° C. for 48 h. The mixture was then diluted into ethyl acetate (25 mL) and washed with saturated aqueous sodium bicarbonate (10 mL) followed by saturated aqueous brine (10 mL). The organic layer was dried (sodium sulfate), decanted, and evaporated. The crude product was purified by FC, eluting with 4–5% ethyl acetate in hexane to give the title compound as 112 mg of colorless syrup. $R_f$: 0.25 (5% ethyl acetate in hexane).

$^1$H NMR (400 MHz, $CDCl_3$): δ 7.50–7.40 (m, 5H), 4.24–3.99 (m, 2H), 2.64 (bt, J=12 Hz, 2H), 2.14 (tm, J=16 Hz, 2H), 1.62 (bd, J=12 Hz, 2H), 1.45 (s, 9H), 1.42–1.33 (m, 3H), 1.13–1.00 (m, 2H).

Step D: 4-(3,3-Difluoro-3-phenylprop-1-yl)piperidine

Trifluoroacetic acid (2.5 mL, 3.7 g, 32 mmol) was added dropwise to a solution of 1-(t-butoxycarbonyl)-4-(3,3-difluoro-3-phenylprop-1-yl)piperidine from Step C (42 mg, 0.12 mmol) in methylene chloride (2.5 mL) at 0° C. After 80 min., the solution was transferred using a double-ended needle to a rapidly stirred solution of sodium bicarbonate (5.0 g, 60 mmol) in water (50 mL). Ether (50 mL) and 2.5 N aq. NaOH (20 mL) were added, followed by solid brine to saturate the aqueous layer. The aqueous layer was separated and extracted with ether (50 mL). The organic layers were washed in succession with saturated aq. brine (20 mL), combined, dried (sodium sulfate), decanted, and evaporated to give the title compound as 27 mg of colorless oil.

$^1$H NMR (400 MHz, $CD_3OD$): δ 7.51–7.40 (m, 5H), 2.98 (dm, J=12 Hz, 2H), 2.53 (td, J=12 and 3 Hz, 2H), 2.24–2.10 (m, 2H), 1.65 (bd, J=12 Hz, 2H), 1.42–1.26 (m, 3H), 1.06 (q, d, J=12 and 4 Hz, 2H). HPLC/MS (ESI): m/z 240 (M+H); HPLC: 2.25 min.

PROCEDURE 17

4-(3,3-Difluoro-3-(4-fluorophenyl)prop-1-yl) piperidine

Step A: 1-(t-Butoxycarbonyl)-4-(hydroxymethyl)piperidine

Di-t-butyl dicarbonate (4.69 g, 21.5 mmol) was transferred in methylene chloride (9 mL) over 10 min. to a solution of 4-(hydroxymethyl)piperidine (2.47 g, 21.4 mmol) in methylene chloride (16 mL). After stirring at rt for 1 h, the solution was diluted with ether (50 mL) and washed with 2 N aq. HCl, saturated aq. sodium bicarbonate, and saturated aq. brine (25 mL of each). The organic layer was dried (sodium sulfate), decanted, and evaporated to give 4.57 g of the title compound as a crystalline solid.

$^1$H NMR (500 MHz, $CD_3OD$): δ 4.08 (d, J=14 Hz, 2H), 3.40 (d, J=6 Hz, 2H), 2.81–2.67 (m, 2H), 1.71 (d, J=13 Hz, 2H), 1.67–1.58 (m, 1H), 1.44 (s, 9H), 1.09 (qd, J=12 and 4 Hz, 2H).

Step B: 1-(t-Butoxycarbonyl)-4-(iodomethyl)piperidine

Metanesulfonyl chloride (4.10 mL, 6.07 g, 52.9 mmol) was added dropwise to a solution of 1-(t-butoxycarbonyl)-4-(hydroxymethyl)piperidine from Step A (10.0 g, 46.4 mmol) and triethylamine (9.80 mL, 7.11 g, 70.3 mmol) in methylene chloride (140 mL) at 5–8° C. After 1 h, the mixture was diluted with ethyl acetate (400 mL) and washed with water (200 mL). The aqueous layer was extracted with ethyl acetate (2×150 mL) and the combined organic layers were washed with 1 N aq. HCl (200 mL), saturated aq. sodium bicarbonate (200 mL), and saturated aq brine (200 mL). The organic layer was dried (sodium sulfate), decanted, and evaporated to give 13.58 g of 1-(t-butoxycarbonyl)piperidin-4-yl methanesulfonate as a pale yellow solid.

A mixture of 1-(t-butoxycarbonyl)piperidin-4-yl methanesulfonate (13.58 g, 46.4 mmol) and sodium iodide (34.68 g, 232 mmol) in acetone (80 mL) was heated to reflux for 3 h. The mixture was partitioned between ether (350 mL) and water (350 mL). The organic layer was washed with saturated aq. brine (250 mL), and the aqueous layers were extracted in succession with ether (250 mL). The combined organic layers were dried (sodium sulfate), decanted, and evaporated to give the title compound (14.8 g) as a pale yellow oil.

$^1$H NMR (500 MHz, $CDCl_3$): δ 4.25–4.00 (m, 2H), 3.12 (d, J=4 Hz, 2H), 2.78–2.52 (m, 2H), 1.85 (d, J=13 Hz, 2H), 1.68–1.56 (m, 1H), 1.48 (s, 9H), 1.15 (qd, J=12 and 4 Hz, 2H).

Step C: ((1-(t-Butoxycarbonyl)piperidin-4-yl)methyl) triphenylphosphonium Iodide A solution of triphenylphosphine (6.63 g, 25.3 mmol) and 1-(t-butoxycarbonyl)-4-(iodomethyl)piperidine from Step B (7.96 g, 24.5 mmol) in acetonitrile (40 mL) was heated to reflux for 72 h. The solution was evaporated to give 13.35 g of white solid. A portion (12.34 g) of this material was dissolved in acetonitrile (25 mL) at 65° C. Ethyl acetate (35 mL) was added and the mixture was allowed to cool slowly to rt and then to −20° C. The supernatant was decanted, and the colorless crystals were washed with ethyl acetate (5×5 mL) and dried under vacuum to give 9.25 g of the title compound.

$^1$H NMR (500 ~1MHz, $CD_3OD$): δ 7.89 (t, J=8 Hz, 3H), 7.86 (dd, J=12 and 8 Hz, 6H), 7.76 (td, J=8 and 4 Hz, 6H), 3.91 (bd, J=13 Hz, 2H), 3.44 (dd, J=14 and 6 Hz, 2H), 2.72–2.58 (m, 2H), 2.08–1.96 (m, 1H), 1.49 (bd, J=12 Hz, 2H), 1.41 (s, 9H), 1.43 (qd, J==13 and 4 Hz, 2H).

Step D: Methyl (4-fluorobenzoyl)formate

Dimethyl oxalate (5.90 g, 50 mmol) was dissolved in THF (50 mL) and ether (50 mL) in a 3-neck round bottom flask fitted with a mechanical stirrer. The solution was stirred vigorously at −65° C. as a 1.0 M THF solution of 4-fluorophenylmagniesium bromide (60 mL, 60 mmol) was added dropwise over 40 min. The mixture was stirred 30 min at −65° C. and allowed to warm to −20° C. over 30 min before being poured into 2N aq. HCl (50 mL) with stirring. The layers were separated and the aq. layer was extracted with ether (3×50 mL). The combined organic layers were washed with saturated aq. brine (2×50 mL), dried (sodium sulfate), decanted, and evaporated. The residue was dissolved in ethyl acetate, dried (sodium sulfate), filtered, and evaporated to give a yellow solid. The crude product was dissolved in warm hexane (25 mL), filtered, and cooled to −20° C. Filtration followed by washing with cold hexane (15 mL) gave 4.95 g of the title compound as light tan crystals.

$^1$H NMR (500 MHz, CDCl$_3$): δ 8.11 (dd, J=9 and 5, Hz, 2H), 7.21 (t,J=9 Hz, 2H), 4.00 (s, 3H).

Step E: Methyl Difluoro(4-fluorophenyl)acetate

Methyl (4-fluorobenzoyl)formate from Step D(4.75 g, 26.1 mmol) was added to (diethylamino)sulfur trifluoride (7.0 mL, 8.5 g, 53 mmol). The mixture was stirred rapidly and an ice bath was used briefly to reduce the temperature to 15° C. After the ice bath was removed, the reaction temperature rose to 48° C. over 10 min and then slowly returned to rt. After a total of 2.75 h, the solution was carefully poured onto crushed ice (30 g) and the mixture was extracted with methylene chloride (2×25 mL). The organic layers were washed in succession with saturated aq. sodium bicarbonate (2×25 mL) and saturated aq. brine (10 mL), combined, dried (sodium sulfate) decanted, and evaporated. The residue was distilled to give the title compound as 4.16 g of light yellow liquid, B.P. 46–48° C. (0.5 mm Hg).

$^1$H NMR (500 MHz, CDCl$_3$): δ 7.63 (dd, J=9, 5 Hz, 2H), 7.16 (d, J=9 Hz, 2H), 3.88 (s, 3H).

Step F: 1-(t-Butoxycarbonyl)-4-(3,3-difluoro-3-(4-fluorophenyl)prop-1-en-1-yl)piperidine A solution of methyl difluoro(4-fluorophenyl)acetate (2.04 g, 10.0 mmol) from Step E in methanol (10.0 mL) was cooled to −60° C. Sodium borohydride (380 mg, 10.0 mmol) was added in 5 portions at 10 to 15 min. intervals. The mixture was cooled to −60 to −55° C. prior to each addition and allowed to warm to −45° C. following each addition. After the last addition, the mixture was stirred 1.25 h at −50 to −45° C. The mixture was cooled to −60° C. and quenched with 1 N aq. HCl (30 mL), with the temperature rising to −20° C. near the end of the addition. After warming to 0° C., the mixture was extracted with ether (3×20 mL). The combined ether layers were washed with water (2×20 mL), dried (sodium sulfate), decanted, and evaporated to give 1.95 g of crude 2,2-difluoro-2-(4-fluorophenyl)-1-methoxyethanol as a pale yellow oil.

A suspension of ((1-(t-butoxycarbonyl)piperidin-4-yl)methyl)triphenylphosphonium iodide (500 mg, 0,92 mmol) from Step C in THF (7.2 mL) was stirred at rt for 30 min. A 0.5 M toluene solution of potassium bis(trimethylsilyl)amide (1.8 mL, 0.90 mmol) was added over 3 min., giving an orange suspension. After 30 min., crude 2,2-difluoro-2-(4-fluorophenyl)-1-methoxyethanol (95 mg, 0.46 mmol) was added in THF (1.0 mL). After an additional 30 min, the mixture was quenched by the addition of saturated aq. NH$_4$Cl (2 mL). The mixture was partitioned between ethyl acetate (50 mL) and water (75 mL), and the aqueous layer was extracted with ethyl acetate (50 mL). The organic layers were washed in succession with saturated aq. brine (25 mL), dried (sodium sulfate), decanted, and evaporated. The crude product was purified by FC, eluting with 10% ether in hexane to give 117 mg of the title compound as a 95:5 mixture of cis and trans isomers, respectively.

$^1$H NMR (500 MHz, CDCl$_3$): δ 7.55 (dd, J=9 and 5 Hz, 2H), 7.13 (t, J=9 Hz, 2H), 5.76 (q, J=12 Hz, 1H), 5.64 (dd, J =12 and 10 Hz, 1H), 4.20–3.95 (m, 2H), 2.80–2.54 (m, 3H), 1.54 (bd, J=12 Hz, 2H), 1.47 (s, 9H), 1.26 (qd, J=12 and 4 Hz, 2H).

Step G: 1-(t-Butoxycarbonyl)-4-(3,3-difluoro-3-(4-fluorophenyl)propyl)piperidine Potassium azodicarboxylate (695 mg, 3.58 mmol) was added to a solution of 1-(t-butoxycarbonyl)-4-(3,3-difluoro-3-(4-fluorophenyl)prop-1-en-1-yl)piperidine from Step F (424 mg, 1.19 mmol) in methanol (3.3 mL). The mixture was stirred at rt as a 9.0 M solution of acetic acid in methanol (0.80 mL, 7.2 mmol) was added over 3 h using a syringe pump. After 30 min., a second portion of potassium azodicarboxylate (695 mg, 3.58 mmol) was added followed by the addition of 9.0 M acetic acid in methanol (0.80 mL, 7.2 mmol) over 3 h. After 20 min, a third portion of potassium azodicarboxylate (695 mg, 3.58 mmol) was added followed by the addition of 9.0 M acetic acid in methanol (0.80 mL, 7.2 mmol) over 3 h. After stirring for 20 h at rt, the mixture was diluted with ethyl acetate (80 mL), and washed with 2 N aq. HCl (40 mL), saturated aq. sodium bicarbonate (40 mL), and saturated aq. brine (40 mL). The organic layer was dried (sodium sulfate), decanted, and evaporated to give 417 mg of a mixture containing the title compound and 20–25% of unreduced 1-(t-butoxycarbonyl)-4-(3,3-difluoro-3-(4-fluorophenyl)prop-1-en-1-yl)piperidine.

A portion (365 mg) of the crude mixture containing residual olefin was hydrogenated at atmospheric pressure for 16 h using iridium black (30 mg) in a mixture of t-butanol (24 mL) and ethyl acetate (2.4 mL). The mixture was filtered, the catalyst was wished with methanol, and the filtrate was evaporated to give 371 mg of the title compound as a pale yellow syrup. R$_f$: 0.2 (5% ethyl acetate in hexane).

$^1$H NMR (500 MHz, CDCl$_3$): δ 7.46 (dd, J=9 and 5 Hz, 2H), 7.12 (t, J=9 Hz, 2H), 4.18–4.00 (m, 2H), 2.73–2.61 (m, 2H), 2.14 (tm, J=16 Hz, 2H), 1.64 (bd,J=12 Hz, 2H), 1.46 (s, 9H), 1.46–1.33 (m, 3H), 1.08 (qd, J=12 and 4 Hz, 2H).

Step H: 4-(3,3-Difluoro-3-(4-fluorophenyl)prop-1-yl)piperidine 1-(t-Butoxycarbonyl)-4-(3,3-difluoro-3-(4-fluorophenyl)prop-1-yl)piperidine from Step G (122 mg, 0.34 mmol) was dried by evaporation of a toluene solution at reduced pressure. The residue was dissolved in chloroform (7.6 mL) and iodotrimethylsilane (0.100 mL, 141 mg, 0.70 mmol) was added. After stirring 30 min at rt, the solution was poured into a mixture of saturated aqueous sodium bicarbonate (15 mL) and 2.5 N aq. NaOH (5 mL), and extracted with ether (50 mL). The organic layer was washed with saturated aq. brine (15 mL), dried (sodium sulfate), decanted, and evaporated to give the title compound as 88 mg of colorless oil.

$^1$H NMR (500 MHz, CD$_3$OD): δ 7.51 (dd, J=9 and 5 Hz, 2H), 7.17 (t, J=9 Hz, 2H), 2.98 (dm, J=12 MHz, 2H), 2.52 (td, J=12,3 Hz, 2H), 2.17 (tm, J=16 Hz 2H), 1.65 (bd, J=13 Hz, 2H), 1.42–1.26 (m, 3H), 1.07 (qd, J=12 and 4 Hz, 2H). HPLC/MS (ESI): m/z 258 (M+H); HPLC: 2.64 min.

PROCEDURE 18

4-(2-((4-Fluorophenyl)sulfonyl)eth-1-yl)piperidine Trifluoroacetic Acid Salt

Step A: 4-(2-Hydroxyeth-1-yl)piperidine Acetic Acid Salt

Combined 4-(2-hydroxyeth-1-yl)pyridine (25 g, 0.2 mol) and platinum oxide (1 g, 4.4 mmol) in 400 mL acetic acid. Placed under 45 psi hydrogen at 60° C. for 24 h. Decanted, then filtered through Celite and removed the solvent to afford 38 g (100%) of the crude product, which was used without further purification.

Step B: 4-(2-Hydroxyeth-1-yl)-1-tert-butoxycarbonylpiperidine

Dissolved sodium bicarbonate (134 g, 1.6 mol) and 4-(2-hydroxyeth-1-yl)piperidine acetic acid salt (38 g, 0.2 mol, from Step A) in 500 mL of 50% tetrahydrofuran in water. Added di-tert-butyl dicarbonate (35 g, 0.2 mol) and stirred at rt overnight. Diluted with ethyl acetate and extracted the aq. layer with 2×300 mL of ethyl acetate. Washed the combined organic layers with 2×300 mL of 1 N HCl and brine. Dried over magnesium sulfate and concentrated to afford 37.4 g (81%) of the title compound.

ESI-MS: 230 (M+H); HPLC A: 2.76 min.

Step C: 4-(2-Iodoeth-1-yl)-1-tert-butoxycarbonylpiperidine

Combined 4-(2-hydroxyeth-1-yl)-1-tert-butoxylcarbonylpiperidine (37.4 g, 0.16 mol, from Step B), triphenylphosphine (55 g, 0.21 mol) and imidazole (14 g, 0.21 mol) in 800 mL of 33% acetonitrile in ether. Cooled to 0° C. and added iodine (56 g, 0.22 mol) portionwise. The iodine is de-colored until the endpoint of the reaction. Diluted with 1 L of ether. Washed organic layer with 2×500 mL each of sat'd. aq. $Na_2S_2O_3$, sat. aq. $CuSO_4$ and brine. Dried over magnesium sulfate, filtered and concentrated. Triphenylphosphine oxide precipitates. Added ether and filtered the slurry through a plug of silica gel. Purified a portion of the crude material by flash chromatography (5% ethyl acetate in hexane eluent) to afford the title compound.

$^1$H-NMR (400 MHz, $CDCl_3$): δ 4.10 (br s, 2H), 3.23 (t, 2H, J=7.2 Hz), 2.72 (br t, 2H, 12.3 Hz), 1.79 (q, 2H, J=7 Hz), 1.67 (br d, 2H, 14 Hz), 1.61 (m, 1H), 1.47 (s, 9H), 1.14 (qd, 2H, J=4.3, 12 Hz); ESI-MS: 340 (M+H); HPLC A: 3.74 min.

Step D: 4-(2-(4-Fluorophenylthio)eth-1-yl)-1-tert-butoxycarbonylpiperidine

To a slurry of sodium hydride (47 mg, 60% in mineral oil, 1.2 mmol) in tetrahydrofuran at 0° C. was added 4-fluorothiophenol (0.1 mL, 0.94 mmol). The reaction mixture was warmed to rt. for 20 min, followed by addition of 4-(2-iodoeth-1-yl)-1-tert-butoxycarbonylpiperidine (265 mg, 0.78 mmol, from Step C). The reaction was then heated to reflux for 10 min, cooled and diluted with ether. The organic layer was washed with 1 N NaOH, dried over magnesium sulfate and concentrated to provide 252 mg (95%) of the title compound. ESI-MS: 340.0 (M+H); HPLC A: 4.07 min.

Step E: 4-(2-(4-Fluorophenylsulfonyl)eth-1-yl)piperidine Trifluoroacetic Acid Salt Added a solution of oxone (1.14 g, 1.86 mmol) in water to a solution of 4-(2-(4-fluorophenylthio)eth-1-yl)-1-tert-butoxycarbonylpiperidine (252 mg, 0.74 mmol, from Step D) in methanol at 0° C. Warmed to rt. After 90 min., added an additional 0.5 g of oxone. After 3 h, the reaction mixture was diluted with methylene chloride and washed with 1 N NaOH containing sodium bisulfite. The aq. layer was extracted twice with methylene chloride, and the combined organic layers were dried over magnesium sulfate. The solution was concentrated and dissolved in 5% trifluoroacetic acid in methylene chloride for 1 h. The solvent was evaporated to afford 297 mg (100%) of the title compound.

ESI-MS: 239.8 (M+H); HPLC A: 2.54 min.

PROCEDURE 19

4-((5-Benzyl)pyrid-3-yl)piperidine di-TFA Salt

Step A: N-tert-Butoxycarbonyl-1,2,5,6-tetrahydropyridine-4-trifluoromethane Sulfonate.

A dry flask under nitrogen was charged with a solution of sodium hexamethyldisilazide (11 mL, 1.0 M in THF) and was cooled to −78° C. A solution of N-tert-butoxycarbonyl-4-piperidone (2.0 g, 10 mmol) in 10 mL THF was added dropwise via cannula. After 30 min. a solution of 2-(N,N-bis(trifluoromethanesulfonyl) amino-5-chloropyridine (4.7 g, 12 mmol) in 15 mL THF was added. The mixture was warmed to room temperature, quenched with sat'd ammonium chloride and extracted with ethyl acetate. The ethyl acetate layer was separated and washed with sat'd brine then dried over sodium sulfate and concentrated. Flash chromatography (100 g silica, 10/1 Hexane/ethyl acetate) afforded 1.9 g (58%) of the title compound.

$^1$H NMR (400 MHz, $CDCl_3$). δ 1.5 (s, 9H), 2.4–2.48 (m, 2H), 3.62–3.68 (t, 2H), 4.05–4.07 (m, 2H), 5.77–5.8 (bs, 1H).

Step B: N-tert-Butoxycarbonyl-4-trimethylstannyl-1,2,5,6-tetrahydropyridine

A dry flask under nitrogen was charged with 20 mL THF, lithium chloride (1.6 g, 37.3 mmol), tetrakistriphenylphosphine palladium(0), (331 mg, 0.28 mmol) and hexamethyldistannane (1.2 mL, 5.7 mmol). N-tert-butoxycarbonyl-1,2,5,6-tetrahydropyridine-4-trifluoromethane sulfonate (1.9 g, 5.7 mmol) was added and the mixture was stirred overnight at 60° C. The mixture was diluted with water and extracted with ethyl acetate (3×150 mL). The combined organic layers were dried over sodium sulfate and concentrated. Flash chromatography (100 g silica, 20/1 Hexane/ethyl acetate) afforded 1.56 g (79%) of the title compound.

$^1$H NMR (300 MHz, $CDCl_3$). δ 0.5 (s, 9H), 1.5 (s, 9H), 2.25–2.35 (m, 2H), 3.62–3.68 (t, 2H), 3.95–3.97 (m, 2H), 5.77–5.8 (bs, 1H).

Step C: 3-Bromo-5-benzylpyridine

A dry flask under nitrogen was charged with zinc chloride (16 mL, 0.5 M in THF, 8 mmol), and a solution of phenylmagnesium chloride (4 mL, 2.0 M in THF, 8 mmol). The mixture was heated to 50° C. for 3h then cooled to room temperature and transferred via cannula to a solution of 3,5-dibromopyridine (1.26 g, 5.3 mmol), copper iodide (61 mg, 0.32 mmol), and bis(diphenylphosphino)ferrocene palladium dichloride (218 mg, 0.27 mmol) in 15 mL THF. The resulting mixture was heated to 50° C. overnight. Sat'd ammonium chloride was added and the mixture was extracted with ethyl acetate. The organic portion was dried over sodium sulfate and concentrated. Flash chromatography (8/1 hexane/ethyl acetate) afforded 433 mg (33%) of the title compound. $^1$H NMR (400 MHz, $CDCl_3$). δ 4.02 (s, 2H), 7.18–7.4 (m, 8H), 7.65 (s, 1H).

Step D: 4-((5-Benzyl)pyrid-3-yl)piperidine di-TFA

A flask was purged with nitrogen and charged with DMF, 3-bromo-5-benzylpyridine (618 mg, 2.5 mmol, from Step C), tetrakis triphenylphosphine palladium (58 mg, 0.05 mmol), and N-tert-butoxycarbonyl-4-trimethylstannyl-1,2,5,6-tetrahydropyridine (1.04 g, 3 mmol). The mixture was heated to 100° C. and stirred for 10 h. An additional portion of tetrakis triphenylphosphine palladium (40 mg, 0.03 mmol) was added and stirring was continued for 14 h. The solution was cooled and diluted with ethyl acetate then washed with water, dried over sodium sulfate and concentrated. Flash chromatography (2.5/1 hexane/ethyl acetate) afforded 590 mg (67%) of the coupling product. The product was dissolved in 4 mL methanol and 50 mg 10% Pd/C was added. The mixture was stirred under 1 atm of hydrogen for 3h. The catalyst was filtered off and the residue was dissolved in 1/1 TFA/methylene chloride. Removal of the solvent and drying under vacuum afforded the title compound as its TFA salt.

$^1$H NMR (500 MHz, $CDCl_3$). δ 1.55–1.64 (m, 2H), 1.75–1.8 (d, 2H), 2.57–2.62 (m, 1H), 2.68–2.73 (t, 2H), 3.15–3.2 (d, 2H), 7.14–7.15 (d, 2H), 7.19–7.21 (m, 1H), 7.26–7.32 (m, 3H), 8.30–8.31 (d, 2H).

PROCEDURE 20

4-(2-(Benzyl)-(2H)-tetrazol-5-yl)piperidine
Step A: 1-(t-Butoxycarbonyl)-4-cyanopiperidine Isonipecotamide (10.0 g, 78.0 mmol) was added in portions to 25 mL of POCl$_3$ at 0° C. The cooling was removed and the mixture was allowed to reach rt. The mixture was heated at reflux for 2 h, then cooled to rt. The mixture was poured onto 100 g of ice. The pH of the aqueous mixture was adjusted to 11 with solid KOH and extracted with 4×200 mL of methylene chloride. The extracts were combined, dried over magnesium sulfate and concentrated to afford 8.0 g of crude (4-cyano)piperidine.

The crude (4-cyano)piperidine was dissolved in 50 mL of methanol and treated with 17.0 g (78.0 mmol) of di-t-butyl dicarbonate and the resulting mixture was stirred at rt for 1 h. The mixture was concentrated. Flash chromatography on 250 g of silica gel using 1:1 v/v hexanes/ether afforded 13.4 g (80%) of the title compound:

$^1$H NMR (300 MHz) δ 1.46 (s, 9H), 1.76–1.96 (4H), 2.78–2.82 (m, 1H), 3.31–3.37 (m, 2H), 3.63–3.69 (m, 2H).

Step B: 1-(t-Butoxycarbonyl)-4-(1H-tetrazol-5-yl)piperidine

A mixture of 2.10 g (10.0 mmol) of 1-(t-butoxycarbonyl)-4-cyanopiperidine (from Step A), 1.95 g (30.0 mmol) of sodium azide and 1.60 g (30.0 mmol) of ammonium chloride in 20 mL of DMF was stirred at 100° C. for 20 h. The mixture was cooled and partitioned between 200 mL of methylene chloride and 200 mL of 1.0 N HCl and the layers were separated. The organic layer was washed with 200 mL of water, dried over magnesium sulfate and concentrated. Flash chromatography on 50 g of silica gel using 4:1 v/v methylene chloride/ethyl acetate+1% acetic acid, then 2:1 v/v methylene chloride/ethyl acetate+1% acetic acid as the eluent afforded 1.51 g (60%) of the title compound:

$^1$H NMR (500 MHz) δ 1.49 (s, 9H), 1.83–1.89 (m, 2H), 2.13–2.15 (m, 2H), 2.96–3.04 (m, 2H), 3.13–3.36 (m, 1H), 4.14–4.22 (m, 2H).

Step C: 1-(t-Butoxycarbonyl)-4-((1-benzyl)-(1H)-tetrazol-5-yl)piperidine and 1-(t-Butoxycarbonyl)-4-((2-benzyl)-(2H)-tetrazol-5-yl)piperidine A solution of 438 mg (1.7 mmol) of 1-(t-butoxycarbonyl)-4-(1H-tetrazol-5-yl)piperidine (from Step B) in 2 mL of DMF at 0° C. was treated with 83 mg (0.50 mmol) of sodium hydride (60% in mineral oil) and 0.41 mL (3.4 mmol) of benzyl bromide. The resulting mixture was warmed to rt and stirred for 2.5 h. The mixture was partitioned between 50 mL of ether and 50 mL of water and the layers were separated. The organic layer was washed with 50 mL sat'd brine, dried over magnesium sulfate and concentrated. Flash chromatography using 2:1 v/v methylene chloride/ether, then 1:2 v/v methylene chloride/ether afforded 85 mg (15%) of 1-(t-butoxycarbonyl)-4-(2-(benzyl)-(2H)tetrazol-5-yl) piperidine. Elution with 2:1 v/v ethyl acetate/methylene chloride afforded 95 mg (17%) of 1-(t-butoxycarbonyl)-4-(1-(benzyl)-(1H)-tetrazol-5-yl)piperidine.

For 1-(t-butoxycarbonyl)-4-(2-(benzyl)-(2H)-tetrazol-5-yl)piperidine: $^1$H NMR (500 MHz) δ 1.47 (s, 9H), 1.76–1.84 (2H), 2.02–2.05 (2H), 2.91–2.95 (2H), 3.07–3.12 (m, 1H), 4.00–4.20 (2H), 5.71 (s, 2H), 7.35–7.40 (5H).

For 1-(t-butoxycarbonyl)-4-(1-(benzyl)-(1H)-tetrazol-5-yl)piperidine: $^1$H NMR (500 MHz) δ 1.45 (s, 9H), 1.59–1.61 (2H), 1.76–1.84 (2H), 2.70–2.80 (2H), 2.85–2.89 (m, 1H), 4.00–4.20 (2H), 5.55 (s, 2H), 7.17–7.19 (2H), 7.36–7.39 (3H).

Step D: 4-(2-(Benzyl)-(2H)-tetrazol-5-yl)piperidine

A solution of 85 mg (0.25 mmol) of 1-(t-butoxycarbonyl)-4-((2-benzyl)tetrazol-5-yl)piperidine (from Step C) in 2 mL of 1:1 v/v methylene chloride/TFA was stirred at rt for 2 h. The solution was concentrated. Flash chromatography on silica gel using 19:1:0.1 v/v/v methylene chloride/methanol/NH$_4$OH as the Eluant afforded 57 mg (94%) of the title compound.

PROCEDURE 21

4-(1-(4-Methyl sulfonylbenzyl)-3-ethyl-(1H)-pyrazol-4-yl)piperidine di-TFA Salt Step A: N-tert-Butoxycarbonyl-4-piperid-4-ylacetaldehyde A solution of oxalyl chloride (2.4 mL, 27.5 mmol) in 125 mL methylene chloride was cooled to −78° C. and DMSO (3.3 mL, 47.1 mmol) was added slowly. After 10 min a solution of 2-(N-tert-butoxycarbonylpiperidin-4-yl)ethanol (4.5 g, 19.6 mmol) in 10 mL methylene chloride was added. The mixture was stirred for 20 min then triethylamine (13.6 mL, 98.1 mmol) was added and the mixture was warmed to room temperature. After 30 min the mixture was diluted with ethyl acetate and washed with water (3×). The organic portion was dried over sodium sulfate and concentrated. Flash chromatography (3/1 hexane/ethyl acetate) afforded 3.7 g (83%) of the desired aldehyde.

$^1$H NMR (400 MHz, CDCl$_3$). δ 1.13–1.43 (m, 2H), 1.48 (s, 9H), 1.68–1.77 (m, 2H), 2.04–2.11 (m, 1H), 2.38–2.41 (d, 2H), 2.71–2.8 (m, 2H), 4.04–4.14 (m, 2H), 9.8 (s, 1H).

Step B: 3-Ethyl-4-(N-t-butoxycarbonylpiperidin-4-yl)-(1H)-pyrazole

A solution of N-tert-butoxycarbonylpiperidin-4-ylacetaldehyde (4.5 g, 19.8 mmol, from Step A), and morpholine (1.7 mL, 19.8 mmol) in 100 mL benzene was refluxed using a dean-stark apparatus. After refluxing over night the mixture was concentrated to provide the enamine. The crude enamine was dissolved in 40 mL methylene chloride and the solution was cooled to 10° C. Propionyl chloride (1.7 mL, 19.8 mmol) and then triethylamine (1.4 mL, 9.9 mmol) were added. The mixture was gradually warmed to room temperature and stirred for 40 h then concentrated. The residue was dissolved in 60 mL of ethanol and hydrazine (6.2 mL, 198 mmol) was added. The solution was refluxed for 5 h. The solvent was removed and ethyl acetate was added. The organic was washed with water and sat'd sodium chloride then dried over magnesium sulfate and concentrated. Flash chromatography (0.5% methanol/methylene chloride->2% methanol/methylene chloride) afforded 2.1 g (38%) of the title compound.

$^1$H NMR (400 MHz, CDCl$_3$). δ 1.25–1.31 (t, 3H), 1.44–1.57 (m, 1H), 1.46 (s, 9H), 1.78–1.83 (s, 2H), 2.53–2.6 (m, 1H), 2.62–2.7 (q, 2H), 2.77–2.82 (m, 2H), 4.12–4.23 (m, 2H), 7.32 (s, 1H).

Step C: 4-(1-(4-Methylsulfonylbenzyl)-3-ethyl-(1H)-pyrazol-4-yl)-N-t-butoxylcarbonylpiperidine A dry flask was charged with 5 mL DMF and sodium hydride (224 mg, 60% dispersion in mineral oil, 5.6 mmol). A solution of 3-ethyl-4-(N-t-butoxycarbonylpiperidin-4-yl)-(1H)-pyrazole (1.3 g, 4.7 mmol, from Step B) in 5 mL DMF was added. The mixture was stirred for th at room temperature and a solution of (4-methylsulfonyl)benzyl chloride (1.05 g, 5.2 mmol) in 5 mL DMF was added. After 3 h the solvent was removed and the product was purified by preparative HPLC (35% acetonitrile/water->85% acetonitrile/water, C-18 stationary phase) to give 0.5 g of product as a mixture of isomeric N-alkylation products. The isomers were separated by preparative HPLC using a chiral stationary phase (Chiracel-OJ, 1/1 hexane/ethanol) to provide 210 mg (10%) of the desired isomer along with 70 mg (3%) of the undesired isomer. The substitution pattern of both isomers was determined by NOE difference.

¹H NMR (400 MHz, CDCl₃, desired isomer). δ 1.25–1.31 (t, 3H), 1.38–1.47 (m, 1H), 1.46 (s, 9H), 1.8~1.85 (m, 2H), 2.5–2.6 (m, 1H), 2.6–2.66 (q, 2H), 2.75–2.82 (m, 2H), 3.03 (s, 3H), 4.13–4.22 (m, 2H), 5.32 (s, 2H), 7.13 (s, 1H), 7.28–7.31 (d, 2H), 7.89–7.91 (d, 2H).

Step D: 4-(1-(4-Methylsulfonylbenzyl)-3-ethyl-(1H)-pyrazol-4-yl)piperidine di-TFA Salt 4-((1-(4-Methylsulfonylbenzyl)-3-ethyl)-(1H)-pyrazol-4-yl)-N-t-butoxylcarbonylpiperidine from Step C was treated with TFA for 1 h and evaporated to afford the title, compound as the TFA salt.

PROCEDURE 22

4-(2-Benzylthiazol-5-yl)piperidine di-HCl Salt
(Method A)

Step A: 1-t-Butyloxycarbonyl-4-(nitromethylcarbonyl)piperidine

To a solution of 1-t-butyloxycarbonylpiperidine-4-carboxylic acid (22.9 g, 100 mmol) in 200 mL of anhydrous THF was added carbonyl diimidazole (20.0 g, 125 mmol) under nitrogen. Effervescence was observed and the reaction mixture was stirred 1 h at ambient temperature. Freshly distilled nitromethane (7.4 mL, 135 mmol) followed by DBU (21.0 mL, 140 mmol) were added. The resulting reaction mixture was stirred for 1 day at room temperature. After dilution with ethyl acetate, the mixture was washed with 2N HCl and brine. The organic phase was dried over anhydrous magnesium sulfate. Evaporation of the solvent followed by the purification of the residue on silica gel using 1:1 mixture of ethyl acetate-hexane with 1% acetic acid as an eluent gave 25 g of the nitroketone as a semi solid. After removal of last traces of acetic acid by azeotroping with toluene.

¹H NMR (CDCl₃) 1.48 (9H, s); 1.65, 1.90, 2.65, 2.80, 4.15 (all multiplets); 5.36 (2H, s).

Step B: 1-t-Butyloxycarbonyl-4-(1-hydroxy-2-nitro)ethyl)piperidine

Sodium borohydride (1.52 g, 40 mmol) was added portionwise to a suspension of 1-t-butyloxycarbonyl-4-(nitromethylcarbonyl)piperidine (10.5 g, 40 mmol) from Step A in methanol (80 mL) at 0° C. After 6.5 h, the solvent was removed in vacuo. The residue was diluted with ethyl acetate and stirred with 2N HCl and the layers were separated. The organic phase was washed with brine and dried over magnesium sulfate. Solvent removal gave 9.1 g of the desired product as amorphous solid.

¹H NMR (CDCl₃) 1.45 (9H, s); 4.45 (2H, m); 1.3, 1.65, 1.85, 2.7, 4.2 (multiplets).

Step C: 1-t-Butyloxycarbonyl-4-(1-hydroxy-2-amino)ethylpiperidine

To a stirred suspension of 1-t-butyloxycarbonyl-4-(1-hydroxy-2-nitro)ethyl)piperidine (9.0 g, 33 mmol) from Step B in anhydrous methanol (100 mL), 10% Pd-C (2.0 g) followed by ammonium formate (12.6 g, 200 mmol) were cautiously added. The reaction mixture was stirred 1.5 days at ambient temperature. The catalyst was filtered through a pad of celite and washed with methanol. The filtrate was concentrated after adding 42 mL of triethylamine to free the product from any formic acid salts. The residue was purified on silica gel using 10:10:1 mixture of ethyl acetate, hexane and NH₄OH as solvent to yield 6.9 g of the desired amino alcohol as white solid after azeotroping with toluene.

¹H NMR (CDCl₃): 1.5 (9H, s); 3.6 (2H, s) 1.2, 1.75, 2.6, 3.24, 3.4, 4.15 (all multiplets).

Step D: 1-t-Butyloxycarbonyl-4-(1-hydroxy-2-phenylacetylamino)ethylpiperidine

Phenylacetyl chloride (0.44 mL, 3.3 mmol) was added dropwise to a mixture of 1-t-butyloxycarbonyl-4-(1-hydroxy-2-amino)ethylpiperidine (0.732 g, 3 mmol) from Step C and triethylamine (0,465 mL, 3.3 mmol) in methylene chloride (15 mL) at ice bath temperature and the bath was removed. After stirring for 3 h at room temperature, the reaction mixture was diluted with ethyl acetate and washed with saturated sodium bicarbonate and brine. The organic phase was dried over anhydrous magnesium sulfate. Solvent removal gave a crude product which was used in the next step without further purification.

¹H NMR (CDCl₃) 1.45 (9H, s); 3.42 (2H, s); 1.2, 1.75, 2.6, 3.2, 3.42, 4.12 (all multiplets).

Step E: 1-t-Butyloxycarbonyl-4-(2-phenylacetamido)acetylpiperidine

To a stirred solution of 1-t-butyloxycarbonyl-4-(1-hydroxy-2-phenylacetylamino)ethylpiperidine from Step D in acetone at ice bath temperature 8 N Jones reagent was added until the orange color of the reagent persisted. After stirring for 0.5 h, 0.2 mL of isopropanol was added and the stirring was continued for 0.5 h. Solvent was removed in vacuo and the residue was partitioned between water and ethyl acetate. The organic phase was washed with brine and dried over anhydrous magnesium sulfate. Solvent removal gave an oil which was purified on silica gel using 1: ethyl acetate-hexane as solvent to yield 606 mg of the desired ketone as oil.

¹H NMR (CDCl₃): 1.46 (9H, s); 3.62 (2H, s); 4.18 (2H, d, J=2); 1.45, 1.8, 2.5, 2.78, 4.1, 7.35, 7.4 (all multiplets).

Step F: 1-t-Butyloxycarbonyl-4-(2-benzylthiazol-5-yl)piperidine

A mixture of 1-t-butyloxycarbonyl-4-(2-phenylacetamido)acetylpiperidine (595 mg, 1.653 mmol) from Step E and Lawesson's reagent (607 mg, 1.66 mmol) in 5 mL of toluene was heated to 120° C. for 3.5 h. After cooling, 3:1 mixture of ethyl acetate and methylene chloride and saturated sodium bicarbonate solution were added and the mixture was stirred for 0.5 h. The organic phase was separated and washed with brine. Solvent removal gave a crude product which was purified on silica gel using 2:3 mixture of ethyl acetate-hexane as solvent to give 330 mg of the desired product.

¹H NMR (CDCl₃): 1.45 (9H, s); 4.4 (2H, s); 7.46 (1H. s); 1.58, 1.95, 2.85, 2.95, 4.2 (all multiplets).

Step G: 4-(2-Benzylthiazol-5-yl)piperidine di-Hydrochloride

Acetyl chloride (0.3 mL) was added dropwise to a solution 1-t-butyloxycarbonyl-4-(2-benzylthiazol-5-yl)piperidine from Step F in methanol (2 mL) at ice bath temperature. The reaction mixture was stirred 3.5 h as it warmed to room temperature. Solvent removal in vacuo gave the desire amine as glassy solid.

¹H NMR (CD₃OD): 4.58 (2H, s); 8.02 (1H, s); 1.94, 2.24, 3.15, 3.35, 3.45 (all multiplets).

PROCEDURE 23

4-(2-Benzylthiazol-5-yl)piperidine di-HCl Salt
(Method B)

Step A: 1-t-Butyloxycarbonyl-4-(2-hydroxyethyl)piperidine

A mixture of 4-(2-hydroxyethyl)piperidine(5.0 g, 40 mmol), di-t-butyl dicarbonate (10.9 g, 50 mmol), and triethylamine (7 mL, 50 mmol) in 100 mL of anhydrous methylene chloride was stirred overnight at room temperature. Volatiles were removed in vacuo and the resulting oil was purified on a silica gel column using 20% ethyl acetate in hexane as eluent to give 7.9 g of the desired product as a colorless oil.

Step B: 1-t-Butyloxycarbonyl-4-formylylmethylpiperidine

Oxalyl chloride (2.2 mL, 25 mmol) was added to 75 mL of anhydrous methylene chloride at −78° C. DMSO (3.5 mL, 50 mmol) was then added dropwise over 5 min, and the resulting mixture was stirred for 15 min. 1-t-Butyloxycarbonyl-4-(2-hydroxyethyl)piperidine (2.29 g, 10 mmol, Step A) was dissolved in 5 mL of anhydrous methylene chloride and added over 10 min to the above mixture. After stirring 30 min, DIEA (17.4 mL, 100 mmol) was added over 10 min. The mixture was then warmed to 0° C. and maintained at that temperature for 1 h. After quenching with water, the reaction mixture was diluted with 75 mL of methylene chloride and the layers were separated. The organic phase was washed with 3×50 mL of water and dried over anhydrous magnesium sulfate. Solvent removal gave an oil, which was purified on silica gel using 20% ethyl acetate in hexane to give 2.05 g of the desired aldehyde which hardened overnight into an oily solid.

NMR: δ 2.15 (2H, d, J=3); 9.8 (1H, s); 1.2, 1.5, 1.7, 2.75, 4.1 (all multiplets).

Step C: 1-t-Butyloxycarbonyl-4-(α-bromo-formylmethyl)piperidine

A mixture of 1-t-butyloxycarbonyl-4-formylylmethylpiperidine (0.57 g, 2.25 mmol, step B), 3,3-dibromo-Meldrum's acid (0.75 g, 2.5 mmol) in 10 mL of anhydrous ether was stirred for 2 days at room temperature under nitrogen. The reaction mixture was diluted with ethyl acetate and washed with sat'd. sodium bicarbonate solution. The organic phase was dried over anhydrous magnesium sulfate. Solvent removal and purification on silica gel using 20% ethyl acetate in hexane as solvent gave 59% of the pure bromo aldehyde as a colorless oil.

$^1$H NMR: δ (CDCl3): 4.04 (1H, dd; J=1.5; 2); 9.46 (1H, d; J=1.5) 1.35, 1.7, 1.95, 2.1, 2.75, 4.2 (all multiplets).

Step D: 1-t-Butyloxycarbonyl-4-(2-benzylthiazol-5-yl)piperidine

A mixture of 1-t-butyloxycarbonyl-4-(α-bromo-formylmethyl)piperidine (612 mg, 2 mmol), benzyl thioamide (500 mg, 2.55 mmol) in 10 mL of anhydrous toluene was heated to reflux for 6 h. Solvent was then removed and the residue was purified on silica gel using 25% ethyl acetate in hexane as solvent to give 350 mg of the desired thiazole as an oil.

$^1$H NMR (CDCl$_3$): 1.45 (9H, s); 4.4 (2H, s); 7.46 (1H, s); 1.58, 1.95, 2.85, 2.95, 4.2 (all multiplets).

Step E: 4-(2-Benzylthiazol-5-yl)piperidine di-Hydrochloride

The title compound was prepared by removal of the protecting group of 1-t-butyloxycarbonyl-4-(2-benzylthiazol-5-yl)piperidine as described in Example 22, Step G.

PROCEDURE 24

4-(2-Benzyl-4-methylthiazol-5-yl)piperidine

The title thiazole was prepared according to the method of Procedure 22 by substituting nitroethane for nitromethane in Step A.

PROCEDURE 25

4-(2-Benzyl-4-ethylthiazol-5-yl)piperidine

The title compound was obtained by the procedure of Procedure 22 by substituting nitropropane for nitromethane in Step A.

PROCEDURE 26

4-(2-(2-Pyridylmethyl)thiazol-5-yl)piperidine di-HCl Salt

Step A: 1-t-Butyloxycarbonyl-4-((1-hydroxy)-2-(2-pyridylmethyl)carbonylamino)ethylpiperidine To 0.361 g (2.08 mmol) of 2-pyridyleacetic acid hydrochloride in 8 mL of methylene chloride, 0.337 g (2.5 mmol) of 1-hydroxybenzotriazole, 0.478 g (2.5 mmol) of EDC and 0.57 mL (5.2 mmol) of N-methylmorpholine were added. After 10 min 0.508 g (2.08 mmol) of 1-t-butyloxycarbonyl-4-(2-amino-1-hydroxy)ethylpiperidine from Procedure 22, Step C was added and the solution was stirred overnight. The reaction was quenched with saturated sodium bicarbonate and extracted with methylene chloride. The combined methylene chloride layer was washed with brine, dried and concentrated. The residue was chromatographed on a flash column using a gradient of 5–10% methanol in ethyl acetate containing 1% triethylamine to isolate 0.68 g of the desired product.

$^1$H NMR (CDCl$_3$): δ 1.24 (m, 3H), 1.45 (s, 9H), 1.58 (m, 1H), 1.82 (m, 1H), 2.6 (br, 2H), 3.21 (m, 1H), 3.49 (m, 2H), 3.75 (s, 2H), 4.12 (br, 2H), 7.22 (m, 1H), 7.29 (d, 1H), 7.69 (m, 1H), 8.52 (m, 1H).

Step B: 1-t-Butyloxycarbonyl-4-(2-(2-pyridylmethyl)carbonylamino)acetylpiperidine To a solution of 0.22 mL (3.2 mmol) of DMSO in 1 mL of methylene chloride cooled in a dry ice-acetone bath, 0.14 mL (1.6 mmol) of oxalyl chloride was added. After 0.5 h, 0.145 g of 1-t-butyloxycarbonyl-4-((1-hydroxy)-2-(2-pyridylmethyl)carbonylamino)ethylpiperidine (Step A) in 1 mL of methylene chloride was added. After 1 h, 0.89 mL (6.38 mmol) of triethylamine was added, the cold bath was removed and the reaction was stirred for 1.5 h. The solution was partitioned between water and methylene chloride. The organic layer was washed with brine, dried and concentrated. The residue was purified on a prep TLC plate using 5% methanol—ethyl acetate as an eluent to furnish 67 mg of the desired product.

$^1$H NMR (CDCl$_3$): δ 1.45 (s, 9H), 1.5–2.0 (m, 4H), 2.53 9m, 1H), 2.77 (br, 2H), 3.79 (s, 2H), 4.1 (br, 2H), 4.22 (d, 2H), 7.2–8.0 (m, 3H), 8.61 (d, 1H).

Step C: 1-t-Butyloxycarbonyl-4-(2-(2-pyridylmethyl)thiazol-5-yl)piperidine

The title compound was prepared by reacting 1-t-butyloxycarbonyl-4-(2-(2-pyridylmethyl)carbonylamino)acetylpiperidine (Step B) with Lawesson's reagent as described in Procedure 22, Step F.

$^1$H NMR (CDCl$_3$): δ 1.47 (s, 9H), 1.6 (m, 2H), 1.99 (m, 2H), 2.82 (br, 2H), 2.94 (m, 1H), 4.17 (br, 2H), 4.48 (s, 2H), 7.2–7.8 (m, 4H), 8.6 (br, 1H).

Step D: 4-(2-(2-Pyridylmethyl)thiazole-5-yl)piperidine di-HCl Salt

Removal of the t-butyloxycarbonyl protecting group as described in Procedure 22, Step G furnished the title compound.

PROCEDURE 27

4-(Imidazo[1,2-a]pyridin-3-yl)piperidine di-TFA Salt

Step A: 1-(t-Butoxycarbonyl)4-(imidazo[1,2-a]pyridin-3-yl)piperidine

To a solution of 1.15 g of 1-(t-butoxycarbonyl)-4-(1-bromo-2-oxoethyl)piperidine (from Procedure 23, Step C) in 15 mL ethanol was added 388 mg of 2-aminopyridine. After refluxing for 18 h, the solvent was evaporated. The mixture was partitioned between ethyl acetate and saturated sodium bicarbonate solution. Aqueous layer was extracted with ethyl acetate (3×). The combined organic phase was washed with brine, dried over magnesium sulfate and concentrated. The residue was purified by flash chromatography with 50% ethyl acetate in hexanes, followed by 100% ethyl acetate to give 401 mg of the title compound as a solid.

¹H NMR (500 MHz, CDCl₃) δ 1.48 (s, 9H), 1.70 (m, 2H), 2.06 (d, J=13 Hz, 2H), 2.93–3.02 (m, 3H), 4.26 (br, 2H), 6.87 (t, J=6.8 Hz, 1H), 7.21 (m, 1H), 7.44 (s, 1H), 7.69 (d, J=9.2 Hz, 1H), 7.99 (d, J=6.9 Hz, 1H).

Step B: 4-Imidazo[1,2-a]pyridin-3-yl)piperidine di-TFA Salt

To 100 mg of 1-(t-butoxycarbonyl)-4-(imidazo[1,2-a]pyridin-3-yl)piperidine from Step A was added 2 mL TFA. The reaction was stirred at rt for 1 h. The mixture was concentrated under reduced pressure to afford 180 mg of a viscous oil.

PROCEDURE 28

4-(7-t-Butylimidazo[1,2-a]pyridin-3-yl)piperidine, TFA Salt

Step A: 2-Amino-4-t-butylpyridine

To 790 mg of sodium amide were added 20 mL of N,N-dimethylaniline and 2.74 g of 4-t-butyl pyridine at rt. The mixture was stirred at 150° C. for 6 h. During this period, 3 more portions of sodium amide (790 mg each) were added. The reaction was cooled down to rt. The mixture was partitioned between ethyl acetate and water. Aqueous layer was extracted with ethyl acetate (3×). The combined organic phase was washed with brine, dried over magnesium sulfate and concentrated. The residue was purified by flash chromatography with 50% ethyl acetate in hexanes followed by 100% ethyl acetate to give 1.68 g of the title compound as a solid:

¹H NMR (500 MHz, CDCl₃) δ 1.21 (s, 9H), 6.44 (t, 1H), 6.6.62 (dd, J=5.5 Hz and, 1H), 7.94 (d, J=5.5 Hz, 1H).

Step B: 1-(t-Butoxycarbonyl)-4-(7-t-butylimidazo[1,2-a]pyridin-3-yl)piperidine

The title compound was prepared from 470 mg of 1-(t-butoxycarbonyl)-4-(1-bromo-2-oxoethyl)piperidine (from Procedure 23, Step C) and 277 mg of 2-amino-4-t-butyl pyridine (from Step A) in 12 mL ethanol using a procedure analogous to that described in Example 235, Step A to provide 130 mg of the title compound as a solid.

Step C: 4-(7-t-Butylimidazo[1,2-a]pyridin-3-yl)piperidine, TFA Salt

The title compound was prepared from 35 mg of 1-(t-butoxycarbonyl)-4-((7-t-butyl)imidazo[1,2-a]pyridin-3-yl)piperidine (from Step B) in 2 mL of TFA, using a procedure analogous to that described in Procedure 27, Step B to provide 60 mg of the title compound as a viscous oil.

PROCEDURE 29

4-(2-Ethyl-5,6,7,8-tetrahydroimidazo[1,2-a]pyridin-3-yl)piperidine, Acetic Acid Salt Step A: 2-Ethyl-imidazo[1,2-a]pyridine The title compound was prepared from 2-aminopyridine and 1-bromo-2-butanone, employing procedures analogous to those described in Procedure 27 Step A.

¹H NMR (500 MHz, CDCl₃): δ 1.34 (t, J=7.3 Hz, 3H), 2.82 (q, J=7.6 Hz, 2H), 6.70 (t, J=6.6 Hz, 1H), 7.10 (m, 1H), 7.32 (s, 3H), 7.51 (d, J=8.9 Hz, 1H), 8.03 (dd, J=6.6, 0.9 Hz, 1H).

Step B: 3-Bromo-2-ethyl-imidazo[1,2-a]pyridine

To a solution of 2-ethyl-imidazo[1,2-a]pyridine (2.17 g, 14.9 mmol) in ethanol (25 mL) was added bromine (2.0 g, 12.5 mmol) in water (5 mL) dropwise at rt. After stirring it at rt for 4 h, ethanol was evaporated under reduced pressure. The residue was basified with aqueous sodium bicarbonate and extracted with methylene chloride (3×). The organic phase was washed with brine and dried over anhydrous magnesium sulfate. Concentration followed by flash chromatography eluting with 20% ethyl acetate in hexanes, followed by 50% ethyl acetate in hexanes afforded the title compound (1.88 g) as a viscous oil.

¹H NMR (500 MHz, CDCl₃): δ 1.36 (t, J=7.5 Hz, 3H), 2.83 (q, J=7.6 Hz, 2H), 6.88 (t, J=6.8 Hz, 1H), 7.20 (m, 1H), 7.55 (dd, J=8.9, 0.9 Hz, 1H), 8.05 (dd, J=6.9, 1.2 Hz, 1H).

Step C: 2-Ethyl-3-(4-pyridyl)-imidazo[1,2-a]pyridine

To a solution of 3-bromo-2-ethyl-imidazo[1,2-a]pyridine (1.4 g, 6.28 mmol), 4-tributyistannylpyridine (2.31 g, 6.28 mmol) and Pd (II) (Ph₃P)₂Cl₂ (442 mg, 0.63 mmol) in toluene (5 mL) was added lithium chloride (26.7 mg, 0.63). After refluxing for 18 h, the mixture was partitioned between ethyl acetate and aqueous sodium bicarbonate. The aqueous layer was extracted with ethyl acetate (3×). Combined organic phase was washed with brine and dried over anhydrous magnesium sulfate. Concentration followed by flash chromatography eluting with 100% ethyl acetate, then 10% methanol in methylene chloride afforded the title compound (543 mg) as a viscous oil.

¹H NMR (500 MHz, CDCl₃): δ 1.36 (t, J=7.5 Hz, 3H), 2.84 (q, J=7.5 Hz, 2H), 6.68 (dt, J=6.8, 1.1 Hz, 1H), 7.21 (m, 1H), 7.39 (dd, J=5.9, 1.6 Hz, 2H), 7.61 (dd, J=8.9, 1.0 Hz, 1H), 8.75 (d, J=5.9 Hz, 2H).

Step D: 4-(2-Ethyl-5,6,7,8-tetrahydroimidazo[1,2-a]pyridin-3-yl)piperidine, Acetic Acid Salt A solution of 2-ethyl-3-(4-pyridyl)-imidazo[1,2-a]pyridine (700 mg, 3.13 mmol) in ethanol (12 mL) and acetic acid (4 mL) was hydrogenated using Platinum (IV) oxide (40 mg) under 40 psi of H₂ gas in a Parr shaker at rt for 18 h. The mixture was Filtered through celite and concentrated to give the title compound (1.47 g) as a viscous oil.

PROCEDURE 30

4-(2-Benzyloxazol-5-yl)piperidine

Step A: 1-Benzoylisonipecotic Acid

To a solution of 10 g of isonipecotic acid in 100 mL of water was added 31 mL of 5 N NaOH at 0° C. The reaction was warmed to room temperature and stirred for 0.5 h. The reaction was again cooled to 0° C. and 11.97 g of benzoyl chloride was added. The reaction was then warmed to room temperature and stirred for 1.5 h. Concentrated HCl was then added until a precipitate formed. The mixture was extracted with 3×150 mL of ethyl acetate and the combined organic layers were dried over magnesium sulfate. The solvent was evaporated under reduced pressure and the residue was dissolved in methylene chloride. Ether was then slowly added to precipitate the product which was filtered to give 8 g of the title compound.

¹H NMR (500 MHz) 1.83 (m, 3H), 2.10 (m, 1H), 2.65 (m, 1H), 3.12 (m, 2H), 3.79 (m, 1H), 4.53 (m, 1H), 7.38 (m, 5H).

Step B: 4-Hydroxymethyl-1-benzoylpiperidine

To a solution of 2 g of 1-benzoylisonipecotic acid (Step A) in 50 mL THF at 0° C. were added 1.47 g of triethylamine and 1.99 g of isobutyl chloroformate. The reaction was stirred for 1 h at 0° C. To a solution of 1.10 g of sodium borohydride in 30 mL DMF at 0° C. was slowly added the above THF mixture. The reaction was again stirred for 1 H at 0° C. Water (80 mL) was slowly added to the reaction and the mixture was extracted 5×80 mL ethyl acetate and the combined organic layers were dried over magnesium sulfate. The solvent was then evaporated under reduced pressure. The residue was purified by flash chromatography with 1:1 hexane: ethyl acetate followed by hexane: ethyl acetate: methanol, 50:50:5 to give 1.865 g of the title compound.

ESI-MS 219.9 (M+H); HPLC A: 2.34 min. (65148-258)

Step C: 1-Benzoylpiperidine-4-carboxaldehyde

To 1.99 g of dimethyl sulfoxide in 45 mL methylene chloride at −78° C. was added 2.16 g of oxalyl chloride.

After 10 min, 1.865 g of 4-hydroxymethyl-N-benzoylpiperidine (Step B) in 15 mL of methylene chloride was added at −78° C. and stirred for 30 min. DIEA (5.49 mL) was added and this mixture was stirred for an additional 30 min. at −78° C. and then warmed to room temperature and stirred another 30 min. The reaction was quenched with 50 mL water and extracted with 3×50 mL methylene chloride. The combined organic layers were dried over magnesium sulfate and evaporated under reduced pressure. The residue was chromatographed with 2:1 hexane:ethyl acetate followed by 1:1 hexane:ethyl acetate to give 1.445 g of the title compound.

$^1$H NMR (500 MHz) 1.72 (m, 2H), 1.90 (m, 1H), 2.14 (m, 1H), 2.58 (m, 1H), 3.21 (m, 2H), 3.68 (m, 1H), 4.41 (m, 1H), 7.39 (m, 5H), 9.72 (m, 1H).

Step D: 4-(1-Hydroxy-prop-2-enyl)-1-benzoylpiperidine

To a solution of 500 mg of 1-benzoylpiperidine-4-carboxaldehyde (Step C) in 10 mL THF at −78° C., was added 2.99 mmol of vinyl magnesium bromide. The solution was warmed to 0° C. and stirred for 1 h. The reaction was quenched with 15 mL of aq. ammonium chloride and extracted with 3×20 mL ether and the combined organic layers were dried over magnesium sulfate. The solvent was evaporated under reduced pressure and the residue was purified by flash chromatography with 2:1 hexane:ethyl acetate followed by 1:1 hexane:ethyl acetate followed by hexane:ethyl acetate:methanol, 50:50:5 to give 411 mg of the title compound.

$^1$H NMR (500 MHz) 1.31 (m, 2H), 1.74 (m, 5H), 2.69 (m, 1H), 2.92 (m, 1H), 4.80 (m, 1H), 3.68 (m, 1H), 5.22 (dd, 2H), 5.84 (m, 1H), 7.43 (m, 5H).

Step E: 4-(1-Phenylacetyoxy-prop-2-enyl)-1-benzoylpiperidine

To 264 mg of 4-(1-hydroxy-prop-2-enyl)-1-benzoylpiperidine (Step D) in 5 mL DMF was added 220 mg of phenyl acetic acid, 292 mg of 1-hydroxybenzotriazole, 414 mg of EDC, and 419 mg of DIEA. The reaction was stirred at room temperature overnight. The solution was diluted with 50 mL of ether and washed with 2×40 mL water. The aqueous layers were then extracted with 2×50 mL ether and the combined organic layers were dried over magnesium sulfate. The solvent was evaporated under reduced pressure and the residue was purified by flash chromatography with 4:1 hexane:ethyl acetate followed by 2:1 hexane:ethyl acetate to give 123 ml of the title compound.

ESI-MS 364.1 (M+H).

Step F: 1-Benzoyl-4-(2-benzyloxazol-5-yl)piperidine

Ozone was bubbled through a solution of 120 mg of 4-(1-phenylacetyoxy-prop-2-enyl)-1-benzoylpiperidine (Step E) in 8 mL methylene chloride at −78° C. until the reaction turned blue. To this solution 205 mg of methyl sulfide was added and the reaction was stirred at room temperature overnight. The solvent was evaporated under reduced pressure to give 121 mg of the residue. This residue was dissolved in 3 mL of acetic acid and 76 mg of ammonium acetate was added. The reaction was stirred at 110° C. for 2.5 h, 20 mL of water was added and the mixture was extracted with 3×20 mL methylene chloride. The combined organic layers were dried over magnesium sulfate. The solvent was evaporated under reduced pressure and the residue was purified by flash chromatography with 2:1 hexane:ethyl acetate followed by 1:1 hexane:ethyl acetate followed by hexane:ethyl acetate:methanol, 50:50:5 to give 40 mg of the title compound.

ESI-MS 347.0 (M+H); HPLC A: 3.68 min.

Step G: 4-(2-Benzyloxazol-5-yl)piperidine

To 40 mg of 1-benzoyl-4-(2-benzyloxazol-5-yl)piperidine (step F) in 4.5 mL methanol and 0.5 mL water was added 260 mg of potassium hydroxide. The reaction was stirred at 80° C. overnight, 20 mL of water was added and the mixture was extracted with 3×20 mL ethyl acetate. The combined organic layers were dried over magnesium sulfate. The solvent was evaporated under reduced pressure to give 22 mg of the title Compound.

ESI-MS 242.9 (M+H); HPLC A: 2.29 min.

PROCEDURE 31

4-(2-Benzyl-1,3-imidazol-5-yl)piperidine

Step A: 4-Bromoacetyl-1-(t-butoxycarbonyl)piperidine

To a freshly prepared solution of LDA (from diisopropylamine (0.61 g, 6.0 mmol) and n-butyl lithium (2.2 mL, 2.5 M sol'n. In hexane) in 10 mL THF at −78° C. was added, solution of 4-acetyl-1-(t-butoxycarbonyl)piperidine (1.0 g, 4.7 mmol) in 2.0 mL THF and the resultant mixture was stirred for 20 min. A mixture of trimethylsilyl chloride and triethylamine(1.37 mL, 10.8 mmol and 2.16 mL, 15.5 mmol) was added and the reaction mixture was gradually warmed to rt and stirred for an additional 1 h. All the volatile were removed and the crude silyl enol ether was dissolved in 10 mL of THF and the mixture was cooled to 0° C. To this mixture was added in succession propylene oxide (1.0 mL) and NBS (1.0 g) and the mixture was stirred for 15 min, quenched with a saturated sodium bicarbonate followed by extraction with mthylene chloride. The methylene chloride layer was washed with brine, dried, evaporated and purified by silica column chromatography. Elution with methylene chloride and ether (19:1) gave the title compound (1.11 g) as a yellow solid.

$^1$HNMR (500MHz, CDCl$_3$): δ 4.16 (s, 2H), 4.12 (m, 2H), 2.79–2.84 (m, 3H), 1.47 (s, 3H).

Step B: 4-(2-(2,6-Dichlorobenzyl)-1,3-imidazol-5-yl)-1-(t-butoxycarbonyl)piperidine A mixture of the bromo compound (0.4 g, 1.36 mmol) from Step A and 2,6-dichlorophenylacetamidine (0.55 g, 2.7 mmol) in 30 mL of chloroform was refluxed for 4 h. The reaction mixture was filtered. The filtrate was evaporated and purified by silica column chromatography. Elution with hexane:ethyl acetate:methanol 49:49:2 gave (0.28 g) of the title compound.

$^1$HNMR (500 MHz, CDCl$_3$): δ 7.35–7.15 (m, 3H), 6.55 (s, 1H), 4.45 (s, 2H), 4.14 (br, 2H), 2.81–2.69 (m, 3H), 1.46 (s, 3H).

Step C: 4-((2-Benzyl)-1,3-imidazol-5-yl)-1-(t-butoxycarbonyl)piperidine

A mixture of 4-(2-(2,6-dichlorobenzyl)-1,3-imidazol-5-yl)-1-(t-butoxycarbonyl)piperidine (0.51 g, 1.24 mmol) from Step B, Pd/C (0.13 g) and ammonium formate (1.5 g, 24.8 mmol) in 8 mL of methanol was refluxed for 30 min. The reaction mixture was filtered and the filtrate was evaporated. The residue was partitioned between methylene chloride and water (200 mL). The methylene chloride layer was washed with brine, dried, evaporated and purified by silica column chromatography. Elution with 3% methanol-methylene chloride gave (0.35 g) of the title compound.

$^1$HNMR (500 MHz, CDCl$_3$): δ 7.34–7.22 (m, 5H), 6.58 (s, 1H), 4.18 (br, 2H), 4.08 (s, 2H), 2.71 (br, 2H), 2.68 (m, 1H), 1.47 (s, 3H).

Step D: 4-(2-Benzyl-1,3-imidazol-5-yl)piperidine Hydrochloride

To 4-((2-benzyl)-1,3-imidazol-5-yl)-1-(t-butoxycarbonyl)piperidine (0.16 g) from Step C in 2 mL of ethyl acetate at 0° C. was added a 2 mL saturated solution of HCl in ethyl acetate. The reaction mixture was stirred for 30 min. Evaporation of ethyl acetate followed by trituration of the resultant oil gave (0.15 g) of the title compound.

¹HNMR (500 MHz, CD₃OD): δ 7.40–7.29 (m, 6H), 4.32 (s, 2H), 3.49 (m, 2H), 3.31–3.01 (m, 3H), 2.24 (m, 2H), 1.92 (m, 2H).

PROCEDURE 32

4-((2-Benzyl-4-ethyl)-1,3-imidazol-5-yl)piperidine

Step A: 4-((2-Benzyl-4-iodo)-1,3-imidazol-5-yl)-1-(t-butoxycarbonyl)piperidine

To a mixture of 4-((2-benzyl)-1,3-imidazol-5-yl)-1-(t-butoxycarbonyl)piperidine (0.15 g, 0.43 mmol). Iodine (0.16 g, 0.65 mmol) and potassium iodide (0.22 g, 1.3 mmol) in 4 mL THF: water (1:1) was added a solution of sodium hydroxide (0.5 mL) and stirred at rt for 30 min. After confirming the completion of reaction by TLC, the reaction was quenched with a saturated solution of sodium thiosulfate and the pH was adjusted to 7–8. The resultant mixture was extracted with ethyl acetate. The ethyl acetate layer was washed with brine, dried, evaporated and purified by silica column chromatography. Elution with 1% methanol-methylene chloride gave (0.17 g) of the title compound.

¹HNMR (500 MHz, CDCl₃): δ 7.32–7.22 (m, 5H), 4.13 (br, 2H), 4.06 (s, 2H), 2.74 (m, 3H), 1.47 (s, 3H).

Step B: 4-((2-Benzyl-4-ethenyl)-1,3-imidazol-5-yl)-1-(t-butoxycarbonyl)piperidine A mixture of 4-((2-benzyl-4-iodo)-1,3-imidazol-5-yl)-1-(t-butoxycarbonyl)piperidine (0.17 g, 0.36 mmol) from Step A, tri-n-butyl vinyltin (0.17 g, 0.54 mmol) and tetrakistriphenylphosphinyl palladium (0.020 g) in 4 mL toluene was stirred at 100–110° C. until the completion of reaction by TLC. Evaporation of the volatiles followed by purification by silica column and elution with 1% methanol-methylene chloride gave (0.061 g) of the title compound.

¹HNMR (500 MHz, CDCl₃): δ 7.36–7.26 (m, 5H), 6.61–6.55 (m, 1H), 5.10 (m, 2H), 4.33 (br, 2H), 4.13 (s, 2H), 1.47 (s, 3H).

Step C: 4-((2-Benzyl-4-ethyl)-1,3-imidazol-2-yl)-1-(t-butoxycarbonyl)piperidine

A mixture of 4-((2-benzyl-4-ethenyl)-1,3-imidazol-5-yl)-1-(t-butoxycarbonyl)piperidine (0.073 g) from Step B in 3.0 mL methanol was hydrogenated over Pd/C (5 mg) at rt. Evaporation of the volatiles followed by purification by preparative silica chromatography and elution with 1% methanol-methylene chloride gave (0.043 g) of the title compound.

¹HNMR (500 MHz, CDCl₃): δ 7.31–7.20 (m, 5H), 4.19 (br, 2H), 4.01 (s, 2H), 2.74–2.66 9m, 3H), 2.51 (q, 2H), 1.46 (s, 3H), 1.15 (t, 3H).

Step D: 4-((2-Benzyl-4-ethyl)-1,3-imidazol-2-yl)piperidine di-Hydrochloride

To 4-((2-benzyl-4-ethyl)-1,3-imidazol-2-yl)-1-(t-butoxycarbonyl)piperidine (0.043 g) from Step C in 1.0 mL ethyl acetate at 0° C. was added a 2.0 mL saturated solution of HCl in ethyl acetate. The reaction mixture was stirred for 30 min. Evaporation of ethyl acetate followed by trituration of the resultant oil gave (0.038 g) of the title compound.

PROCEDURE 33

4-(2-Ethyl-4,5,6,7-tetrahydro-(2H)-indazol-3-yl)-1-piperidine

Step A: (1-Benzylpiperidin-4-yl)-(cyclohexanon-2-yl) ketone

To a suspension of 1.60 g 60% sodium hydride in 10 mL dry THF was added a solution of 1.963 g (20 mmole) cyclohexanone and 9.893 g (40 mmole) of 1-benzylpiperidine-4-carboxylic acid ethyl ester in 30 mL THF. This mixture was heated to reflux over night. Work-up followed by silica gel FC (15~50% ethyl acetate in hexanes with 1% triethylamine) provided 4.4 g product containing about 5.7:1 molar ratio of starting 1-benzylpiperidine-4-carboxylic acid ethyl ester and title compound.

ESI-MS 300.3 (M+H), HPLC A: 2.90 and 3.57 min. (for tautomeric forms).

Step B: 4-(2-Ethyl-4,5,6,7-tetrahydro-(2H)-indazol-3-yl)-1-benzylpiperidine

The title compound was prepared from the semi-crude (1-benzylpiperidin-4-yl)-(cyclohexanon-2-yl)ketone from step A and 34% aqueous ethylhydrazine in 4:1 acetonitrile and water at room temperature. This provided 8:1 ratio of isomeric ethyl pyrazoles in favor of the title compound. (Note: Use of ethyl hydrazine oxalate in the presence of DIEA gave about 2:1 ratio of the same isomers.) The 1-benzylpiperidine-4-carboxylic acid ethyl ester present in the starting β-diketone was removed after saponification of the crude product with sodium hydroxide in water ethanol mixture followed by extractive work-up. The desired ethyl isomer is the higher R$_f$ isomer. It was isolated on silica gel chromatography (60~100% ethyl acetate in hexanes and 5~20% methanol in ethyl acetate, both with 1% triethylamine).

¹H NMR (500 MHz) δ 7.33~7.36 (m, 4H), 7.26~7.30 (m, 1H), 4.07 (q, 7.2 Hz, 2H), 3.57 (s, 2H), 3.00~3.03 (m, 2H), 2.64~2.66 (m, 2H), 2.60~2.63 (m, 2H), 2.57~2.63 (m, 1H), 1.96~2.08 (m, 4H), 1.69~1.81 (m, 6H), 1.39 (t, 7.2 Hz, 3H). The identity of the title compound was confirmed by NOE difference spectroscopy.

Step C: 4-(2-Ethyl-4,5,6,7-tetrahydro-(2H)-indazol-3-yl) piperidine

A mixture of 0.273 g 4-(2-ethyl-4,5,6,7-tetrahydro-(2H)-indazol-3-yl)-1-benzylpiperidine from Step B above, 0.789 g ammonium formate, and 35 mg 20% Pd(OH)₂ in 6 mL, methanol was heated at 65° C. for 1 h. Basic aqueous work-up with ether extraction provided 0.192 g title compound as a colorless solid (97%).

¹H NMR (500 MHz) δ 4.08 (q, 7.2 Hz, 2H), 3.19 (br d, 11.9 Hz, 2H), 2.71~12.77 (m, 1H), 2.68~2.74 (m, 2H), 2.64~2.66 (m, 2H), 2.60~2.62 (m, 2H), 1.82~1.91 (m, 2H), 1.71~1.80 (m, 6H), 1.40 (t, 7.2 Hz, 3H). The identity of the title compound was confirmed again by NOE difference spectroscopy.

PROCEDURE 34

4-(4,5,6,7-Tetrahydro-(2H)-indazol-3-yl)-1-piperidine

Step A: 4-4,5,6,7-Tetrahydro-(2H)-indazol-3-yl)-1-benzyl Piperidine, Trifluoroacetic Acid Salt The title compound was prepared using a procedure similar to that in Procedure 33, Step B with hydrazine instead of ethyl hydrazine. It was further purified on HPLC.

¹H NMR (500 MHz, CD₃OD) δ 7.47~7.55 (m, 5H), 4.35 (s, 2H), 3.61 (br d, 12.3 Hz, 2H), 3.13~3.21 (m, 3H), 2.71~2.73 (m, 2H), 2.56~2.58 (m, 2H), 2.17 (br d, 13.3 Hz, 2H), 2.04~2.12 (m, 2H), 1.79~1.89 (m, 4H). ESI-MS 296.3 (M+H), HPLC A: 2.33 min.

Step B: 4-(4,5,6,7-Tetrahydro-(2H)-indazol-3-yl)piperidine

The title compound was prepared using a procedure similar to that in Procedure 33, Step) C as a white solid.

¹H NMR (500 MHz) δ 3.20 (br d, 12.4 Hz, 2H), 2.72~2.797 (m, 3H), 2.64~2.66 (m, 2H), 2.49~2.52 (m, 2H), 1.87~1.90 (m, 2H), 1.70~1.84 (m, 6H). ESI-MS 206.2 (M+H), HPLC A: 0.80 min.

PROCEDURE 35

3,3-Difluoro-3-(2-pyridyl)propyl)piperidine
Step A: Ethyl oxo(2-Pyridyl)acetate A solution of n-butyl lithium (100 mL, 1.6 M, 160 mmol) in hexanes was added over 2 min. to a stirred solution of 2-bromopyridine (15.0 mL, 24.9 g, 157 mmol) in 500 mL of ether cooled in a dry ice/isopropanol bath, causing a temporary rise in temperature to −47° C. After 25 min., the solution was transferred rapidly to a stirred 0° C. solution of diethyl oxalate (75 mL, 81 g, 550 mmol) in 1000 mL of ether. After 2 h at 0° C., the mixture was washed with saturated aq. sodium bicarbonate (900 mL), water (900 mL), and saturated aq. brine (450 mL). The organic layer was dried (magnesium sulfate), filtered, and evaporated. Distillation gave the title compound as 11.68 g of yellow liquid, B.p. 96–108° C. (0.3 mm Hg pressure). For the title compound:

$^1$H NMR (500 MHz, CDCl$_3$) δ 8.78 (d, J=5, 1H), 8.13 (d, J=8, 1H), 7.93 (td, J=8, 2, 1H), 7.56 (ddd, J=8, 5, 1, 1H), 4.51 (q, J=7, 2H), 1.44 (t, J=7, 3H).

Step B: Ethyl Difluoro(2-pyridyl)acetate

Ethyl oxo(2-pyridyl)acetate (11.59 g, 64.7 mmol, from Procedure 35, Step A) was added to a flask containing (diethylamino)sulfur trifluoride (18.0 mL, 22.0 g, 136 mmol) and the solution was heated to 45 ° C. overnight. An additional portion of (diethylamino)sulfur trifluoride (24.9 g, 154 mmol) was added and the solution was heated to 55° C. for 2 days. After cooling to rt; the solution was added carefully to a stirred mixture of ethyl acetate (600 mL), ice (500 g), water (500 mL), and sodium bicarbonate (100 g). After the resulting reaction had subsided, the layers were separated and the organic layer was washed with 250 mL each of saturated aq. sodium bicarbonate, water, and saturated aq. brine. The organic layer was dried (sodium sulfate), decanted, and evaporated. Distillation gave 8.45 g of yellow liquid, B.p. 50–63° C. (0.1 mm Hg), containing a residual impurity. Further purification by flash column chromatography on silica gel, eluting with 80:20 v/v to 75:25 v/v hexanes/ethyl acetate, gave the title compound as 6.54 g of yellow oil. For the title compound:

$^1$H NMR (500 MHz, CDCl$_3$) δ 8.68 (d, J=5, 1H), 7.88 (td, J=8, 2, 1H), 7.76 (d, J=8, 1H), 7.44 (dd, J=8, 5, 1H), 4.40 (q, J=7, 2H), 1.35 (t, J=7, 3H).

Step C: 1-(t-Butoxycarbonyl)-4-(3,3-difluoro-3-(2-pyridyl)prop-1-en-1-yl)piperidine Ethyl difluoro(2-pyridyl)acetate (1.00 g, 4.97 mmol, from Procedure 35, Step B) was dissolved in CH$_3$OH (15 mL) in a 3-neck round bottom flask fitted with a mechanical stirrer, and the resulting solution was cooled in a dry ice/isopropanol bath. Sodium borohydride (114 mg, 3.0 mmol) was added in 2 portions 15 min. A part. After an additional 55 min., the cold reaction was quenched by the addition of saturated aq. ammonium chloride (6.5 mL) over 12 min. After 10 min., the cooling bath was removed and the mixture was stirred for 35 min. before being diluted with saturated aq. brine (100 mL) and extracted with ethyl acetate (4×75 mL). The combined organic layers were dried (sodium sulfate), decanted, and evaporated to give 1.02 g of crude 2,2-difluoro-2-(2-pyridyl)-1-methoxyethanol as an amber oil.

A suspension of ((1-(t-butoxycarbonyl)piperidin-4-yl)methyl)triphenylphosphonium iodide (5.29 g, 9.00 mmol, from Procedure 17, Step C) in THF (70 mL) was stirred at rt for 40 min. A toluene solution of potassium bis(trimethylsilyl)amide (18 mL, 0.5 M, 9.0 mmol) was added, giving an orange suspension. After 40 min., crude 2,2-difluoro-2-(2-pyridyl)-1-methoxyethanol (940 mg, 4.97 mmol) was added in THF (20 mL). After an additional 50 min., the mixture was quenched by the addition of saturated aq. NH$_4$Cl (10 mL). The mixture was partitioned between ethyl acetate (100 mL) and water (100 mL), and the aqueous layer was extracted with ethyl acetate (3×100 mL). The organic layers were washed in succession with saturated aq. brine (100 mL), dried (sodium sulfate), decanted, and evaporated. Purification by flash column chromatography on silica gel, eluting with 90:10 v/v to 80:20 v/v hexanes/ethyl acetate, gave 1.18 mg of the title compound (approximately 95:5 cis/trans mixture) as an oil which solidified upon standing. For the title compound:

$^1$H NMR (500 MHz, CDCl$_3$) δ 8.68 (d, J=5, 1H), 7.84 (td, J=8, 2, 1H), 7.70 (d, J=8, 1H), 7.39 (dd, J=8, 5, 1H), 5.93 (td, J=14, 11, 1H), 5.70 (ddt, J=11, 10, 2, 1H), 4.17–3.99 (bs, 2H), 2.80–2.62 (m, 3H), 1.58 (d, J=12, 2H), 1.46 (s, 9H), 1.26 (qd, J=12, 4, 2H). ESI-MS 339 (M+H); HPLC A: 4.28 min.

Step D: 1-(t-Butoxycarbonyl)-4-(3,3-difluoro-3-(2-pyridyl)propyl)piperidine

Potassium azodicarboxylate (246 mg, 1.27 mmol) was added to a stirred solution of 1-(t-butoxycarbonyl)-4-(3,3-difluoro-3-(2-pyridyl)prop-1-enyl)piperidine (143 mg, 0.42 mmol, from Procedure 35, Step C) in methanol (1.4 mL) at rt. A solution (0.58 mL) of 75:25 v/v CH$_3$OH/AcOH was added in three portions at 30-min. intervals. After two h, an additional portion of potassium azodicarboxylate (246 mg, 1.27 mmol) was added, followed by a solution (0.58 mL) of 75:25 v/v CH$_3$OH/AcOH added in three portions at 30-min. intervals. After another two h, a third portion of potassium azodicarboxylate (246 mg, 1.27 mmol) was added, followed by a solution (0.58 mL) of 75:25 v/v CH$_3$OH/AcOH added in the same manner as before. After stirring overnight, the mixture was diluted with ethyl acetate (50 mL) and washed with saturated aq. sodium bicarbonate (30 mL) followed by saturated aq. brine (30 mL). The organic layer was dried (sodium sulfate), decanted, and evaporated to give the crude product containing approximately 30% starting olefin. This material was combined with crude product similarly obtained from 1-(t-butoxycarbonyl)-4-(3,3-difluoro-3-(2-pyridyl)prop-1-enyl)piperidine (20 mg, 0.059 mmol) and purified by preparative HPLC on a 20×250 mm Chiracel OD column, eluting with 98:2 v/v hexanes/isopropanol, to give 105 mg of the title compound:

$^1$H NMR (500 MHz, CDCl$_3$) δ 8.68 (d, J=5, 1H), 7.82 (td, J=8, 2, 1H), 7.64 (d, J=8, 1H), 7.38 (dd, J=8, 5, 1H), 4.17–4.00 (bs, 2H), 2.75–2.62 (m, 2H), 2.42–2.30 (m, 2H), 1.67 (d, J=12, 2H), 1.46 (s. 9H), 1.45–1.38 (m, 3H), 1.15–1.04 (m, 2H). ESI-MS 241 (M+H–100); HPLC A: 4.36 min.

Step E: 4-(3,3-Difluoro-3-(2-pyridyl)propyl)piperidine

The title compound was prepared using procedures analogous to those described in Procedure 17, Step H, substituting 1-(t-butoxycarbonyl)-4-(3,3-difluoro-3-(2-pyridyl)propyl)piperidine (from Procedure 35, Step D) for 1-(t-butoxycarbonyl)-4-(3,3-difluoro-3-(4-fluorophenyl)propyl)piperidine. For the title compound:

$^1$H NMR (500 MHz, CD$_3$OD) δ 8.62 (d, J=5, 1H), 7.95 (td, J=8, 2, 1H), 7.68 (d, J=8, 1H), 7.50 (dd, J=8, 5, 1H), 2.99 (d, J=12, 2H), 2.53 (td, J=12, 3, 2H), 2.37–2.26 (m, 2H), 1.67 (d, J=12, 2H), 1.42–1.28 (m, 3H), 1.08 (dq, J=12, 4, 2H); ESI-MS 241 (M+H); HPLC A: 2.21 min.

PROCEDURE 36

4-(3,3-Difluoro-3-(6-methylpyridazin-3-yl)propyl)piperidine

Step A: 3-Bromo-6-methylpyridazine

A solution (3.0 mL) containing 30% HBr in acetic acid was added to 3-(trifluoromethanesulfonyloxy)-6-methylpyridazine (prepared as described by M. Rohr, et al., *Heterocycles*, 1996, 43, 1459–64) and the mixture was heated in a 100° C. oil bath for 2.5 h. The mixture was cooled in an ice bath, adjusted to pH≧9 (as determined using pH paper) by the careful addition of 20% aqueous NaOH, and extracted with ether (3×20 mL). The organic layers were dried (sodium sulfate), decanted, and evaporated to give title compound as 359 mg of pale tan crystals. For the title compound:

$^1$H NMR (500 MHz, CDCl$_3$) δ 7.56 (d, J=9, 1H), 7.22 (d, J=9, 1H), 2.70 (s, 3H).

Step B: Ethyl Difluoro(6-methylpyridazin-3-yl)acetate

This procedure is derived from the general method of T. Taguchi, et al. (*Tetrahedron Lett.*, 1986, 27, 6103–6106). Ethyl difluoroiodoacetate (0.355 mL, 651 mg, 2.60 mmol) was added to a rapidly stirred suspension of copper powder (333 mg, 5.24 mmol) in DMSO (6.5 mL) at rt. After 50 min., 3-bromo-6-methylpyridazine (300 mg, 1.73 mmol) was added in DMSO (1.0 mL). After 20 h, the mixture was transferred to a separatory funnel containing water (25 mL) and saturated aq. NH$_4$Cl (25 mL), and extracted with ethyl acetate (2×50 mL). The organic extracts were washed with saturated aq. brine, dried (sodium sulfate), decanted, and evaporated. Purification by flash column chromatography on silica gel, eluting with 70:30 v/v hexanes/ethyl acetate, gave 363 mg of the title compound as an amber liquid. For the title compound:

$^1$H NMR (500 MHz, CDCl$_3$) δ 7.79 (d, J=9, 1H), 7.53 (d, J=9, 1H), 4.43 (q, J=7, 2H), 2.82 (s, 3H), 1.38 (t, J=7, 3H).

Steps C–E: 4-(3,3-Difluoro-3-(6-methylpyridazin-3-yl)propyl)piperidine

The title compound was prepared using procedures analogous to those described in Procedure 35, Steps C–E, substituting ethyl difluoro(6-methylpyridazin-3-yl)acetate (from Procedure 36 Step B) for ethyl difluoro(2-pyridyl)acetate in Step C. For the title compound:

$^1$H NMR (500 MHz, CD$_3$OD) δ 7.86 (d, J=9, 1H), 7.74 (d, J=9, 1H), 2.99 (dm, J=12, 2H), 2.74 (s, 3H), 2.54 (td, J=12, 3, 2H), 2.51–2.40 (m, 2H), 1.69 (bd, J=12, 2H), 1.47–1.34 (m, 3H), 1.10 (qd, J=12, 4, 2H).

PROCEDURE 37

4-(3,3-Difluoro-3-(5-(trifluoromethyl)pyrid-2-yl)propyl)piperidine

The title compound was prepared using procedures analogous to those described in Procedure 36, substituting 2-bromo-5-(trifluoromethyl)pyridine for 3-bromo-6-methylpyridazine in Step B. For the title compound:

$^1$H NMR (500 MHz, CD$_3$OD) δ 8.96 (s, 1H), 8.28 (dd, J=8, 2, 1H), 7.88 (d, J=8, 1H), 2.99 (bd, J=12, 2H), 2.53 (td, J=12, 2, 2H), 2.43–2.31 (m, 2H), 1.68 (bd, J=13, 2H), 1.44–1.28 (m, 3H), 1.09 (qd, J=12, 3, 2H); ESI-MS 309 (M+H); HPLC A: 2.32 min.

PROCEDURE 38

4-(3,3-Difluoro-3-(3-pyridyl)propyl)piperidine

Step A: Dimethyl (2-oxo-2-(3-Pyridyl)ethyl)phosphonate

A solution of n-butyl lithium in hexanes (9.0 mL, 1.6 M, 14 mmol) was added over 10 min. to a solution of dimethyl methylphosphonate (1.50 mL, 1.72 g, 13.8 mmol) in THF (60 mL) cooled in a dry ice/isopropanol bath. After 30 min., a solution of methyl nicotinate (757 mg, 5.52 mmol) in THF (6 mL) was added over 2 min. The solution was stirred in the cooling bath for 45 min. before being allowed to warm to 0° C. over 1 h. The reaction was quenched with saturated aq. NHCl (50 mL) and then partitioned between saturated aq. brine (50 mL) and methylene chloride (200 mL). The aq. layer was extracted with methylene chloride (2×100 mL). The combined organic layers were dried (sodium sulfate) decanted, and evaporated. Purification by flash column chromatography on silica gel, eluting with ethyl acetate followed by 97:3 v/v methylene chloride/CH$_3$OH, gave material containing some residual impurity. Further purification by flash column chromatography on silica gel, eluting with 50:50:5 v/v/v to 50:50:10 v/v/v toluene/ethyl acetate/CH$_3$OH gave 1.15 g of the title compound. For the title compound: $^1$H NMR (500 MHz, CDCl$_3$) δ 9.26–9.20 (bs, 1H), 8.83 (d, J=4, 1H), 8.34 (dt, J=8, 2, 1H), 7.70 (dd, J=8, 4, 1H), 3.82 (d, J=11, 6H), 3.67 (d, J=24, 2H).

Step B: 1-(t-Butoxycarbonyl)-4-(3-oxo-3-(3-pyridyl)prop-1-enyl)piperidine 1,1,1-Triacetoxy-1,1-dihydro-1,2-benzoiodoxol-3(1H)-one (750 mg, 1.77 mmol) was added to a solution of 1-(t-butoxycarbonyl)-4-(hydroxymethyl)piperidine (339 mg, 1.57 mmol, from Procedure 17, Step A) in methylene chloride (10 mL) and the mixture was stirred at rt. After 45 min., and additional portion of 1,1,1-triacetoxy-1,1-dihydro-1,2-benzoiodoxol-3(1H)-one (150 mg, 0.35 mmol) was added. After an additional 30 min., ether (30 mL) and 1.3 N NaOH (10 mL) were added and stirring was continued for 20 min. The mixture was transferred to a separatory funnel with additional ether (30 mL) and 1.3 N NaOH (15 mL). The organic layer was separated, washed with water (20 mL), dried (sodium sulfate) decanted, and evaporated to give 291 mg of 1-(t-butoxycarbonyl)-4-piperidinecarboxaldehyde as a colorless oil.

A solution of dimethyl (2-oxo-2-(3-pyridyl)ethyl)phosphonate (150 mg, 0.65 mmol, from Procedure 38, Step A) in THF (1.8 mL) was added to a stirred suspension of sodium hydride (60% oil dispersion, 15 mg of sodium hydride, 0.63 mmol) in THF (3.0 mL). The resulting suspension was warmed in a 45° C. oil bath for 30 min. After the mixture had cooled to rt, 1-(t-butoxycarbonyl)-4-piperidinecarboxaldehyde (112 mg, 0.53 mmol) was added in THF (1.5 mL). After stirring overnight at rt, the mixture was diluted with ether (20 mL) and washed with 2.5 N NaOH (20 mL) followed by saturated aq. brine (20 mL). The aq. layers were extracted in succession with ether (20 mL), and the combined organic layers were dried (sodium sulfate), decanted, and evaporated. Purification by flash column chromatography on silica gel, eluting with 80:20 v/v to 60:40 v/v hexanes/ethyl acetate, gave 135 mg of the title compound (trans isomer) as a yellow syrup. For the title compound: $^1$H NMR (500 MHz, CDCl$_3$) δ 9.17–9.13 (bs, 1H), 8.81 (bd, J=4, 1H), 8.27 (d, J=8, 1H), 7.49 (dd, J=8, 4, 1H), 7.07 (dd, J=15, 7, 1H), 6.85 (dd, J=15, 1, 1H), 4.25–4.13 (bs, 2H), 2.87–2.78 (m, 2H), 2.51–2.41 (m, 1H), 1.83 (d, J=12, 2H), 1.49 (s, 9H), 1.45 (qd, J=12, 4, 2H). ESI-MS 261 (M+H−56), 217 (M+H−100); HPLC A: 1.73 min.

Step C: 1-(t-Butoxycarbonyl)-4-(3-oxo-3-(3-pyridyl)propyl)piperidine 1-(t-Butoxycarbonyl)-4-(3-oxo-3-(3-pyridyl)prop-1-enyl)piperidine (940 mg, 2.97 mmol, from Procedure 38, Step B) was hydrogenated using 5% Pd/C in 95% ethanol at atmospheric pressure. Purification by flash column chromatography on silica gel, eluting with 90:10 v/v to 50:50 v/v hexanes/ethyl acetate gave 884 mg of the title compound as a colorless syrup. For the title compound:

$^1$H NMR (500 MHz, CDCl$_3$) δ 9.23–9.15 (bs, 1H), 8.81 (bd, J=4, 1H), 8.28 (dt, J=8, 1, 1H), 7.48 (dd, J=8, 4, 1H), 4.19–4.04 (bs, 2H), 3.04 (t, J=8, 2H), 2.70 (bt, J=11, 2H), 1.78–1.70 (m, 4H), 1.56–1.45 (m, 1H), 1.47 (s, 9H), 1.17 (qd, J=12, 4, 2H). ESI-MS 263 (M+H−56), 219 (M+H−100); HPLC A: 1.78 min.

Step D: 1-(t-Butoxycarbonyl)-4-(3,3-difluoro-3-(3-pyridyl) propyl)piperidine

A solution of 1-(t-butoxycarbonyl)-4-(3-oxo-3-(3-pyridyl)propyl)piperidine (810 mg, 2.54 mmol, from Procedure 38, Step C) in (diethylamino)sulfur trifluoride (3.30 mL, 3.66 g, 23 mmol) was stirred in a teflon tube at 40° C. for 2 days. The reaction was diluted with methylene chloride (20 mL) and the resulting solution was added in portions to a stirred mixture of water (150 mL), ice (150 g) and sodium bicarbonate (29.3 g). After the resulting reaction had subsided, the mixture was extracted with ethyl acetate (2×200 mL). The organic layers were washed in succession with saturated aq. brine (100 mL), dried (sodium sulfate), decanted, and evaporated. Flash column chromatography on silica gel, eluting with 80:20 v/v to 50:50 v/v toluene/ether, gave material containing some residual impurity. Further purification by preparative HPLC on a 20×250 mm Chiracel OD column, eluting with 80:20 v/v hexanes/isopropanol, gave 395 mg of the title compound:

$^1$H NMR (500 MHz, CD$_3$OD) δ 8.69 (s, 1H), 8.64 (d, J=5, 1H), 7.97 (d, J=8, 1H), 7.54 (dd, J=8, 5, 1H), 4.04 (d, J=13, 2H), 2.78–2.62 (bs, 2H), 2.31–2.20 (m, 2H), 1.68 (d, J=12, 2H), 1.50–1.40 (m, 1H), 1.43 (s, 9H), 1.40–1.34 (m, 2H), 1.02 (qd, J=12, 4, 2H). ESI-MS 285 (M+H−56), 241 (M+H−100); HPLC A: 2.10 min.

Step E: 4-(3,3-Difluoro-3-(3-pyridyl)propyl)piperidine

The title compound was prepared using procedures analogous to those described in Procedure 17, Step H, substituting 1-(t-butoxycarbonyl)-4-(3,3-difluoro-3-(3-pyridyl)propyl) piperidine (from Procedure 38, Step D) for 1-(t-butoxycarbonyl)-4-(3,3-difluoro-3-(4-fluorophenyl)propyl) piperidine. For the title compound:

$^1$H NMR (500 NHz, CD$_3$OD) δ 8.68 (s, 1H), 8.64 (d, J=4, 1H), 7.97 (d, J=8, 1H), 7.54 (dd, J=8, 4, 1H), 2.98 (bd, J=12, 2H), 2.52 (td, J=12, 3, 2H), 2.30–2.18 (m, 2H), 1.66 (bd, J=13, 2H), 1.44–1.30 (m, 3H), 1.08 (qd, J=12, 3, 2H); ESI-MS 241 (M+H).

PROCEDURE 39

4-(3,3-Difluoro-3-(1-methylpyrazol-4-yl)propyl) piperidine

The title compound was prepared using procedures analogous to those described in Procedure 38, substituting ethyl 1-methyl-4-pyrazolecarboxylate, obtained by methylation of ethyl 4-pyrazolecarboxylate with iodomethane and K$_2$CO$_3$ in CH$_3$CN at rt, for methyl nicotinate in Step A. For the title compound:

$^1$H NMR (500 MHz, CD$_3$OD) δ 7.78 (s, 1H), 7.54 (s, 1H), 3.89 (s, 3H), 3.00 (dt, J=12, 3, 2H), 2.55 (td, J=12, 3, 2H), 2.22–2.10 (m, 2H), 1.69 (bd, J=12, 2H), 1.45–1.34 (m, 3H), 1.10 (qd, J=12, 4, 2H). ESI-MS:244 (M+H, 60%), 224 (M−19, 100%); HPLC A: 0.98 min.

PROCEDURE 40

4-(7-Chloroimidazo[1,2-a]pyridin-3-yl)piperidine, TFA Salt

The title compound was prepared from 350 mg of 1-(t-butoxycarbonyl)-4-(1-bromo-2-oxoethyl)piperidine (from Procedure, Step C) and 162 mg of 2-amino-4-chloropyridine (prepared using procedures analogous to those described by R. J. Sundberg et al, *Org. Preparations & Procedures Int.* 1997, 29, (1), 117–122) in 10 mL ethanol using a procedure analogous to that described in Procedure 27, Step A–B to provide 240 mg of the BOC intermediate as a solid prior to the final de-BOC to give the title TFA salt.

PROCEDURE 41

4-(7-n-Propylimidazo[1,2-a]pyridin-3-yl)piperidine, TFA Salt

The title compound was prepared according to the general procedures of Procedure 27 and 28, employing 2-amino-4-n-propylpyridine (prepared using a procedure analogous to that described in Procedure 28, Step A) in place of 2-aminopyridine in Procedure 27, Step A.

PROCEDURE 42

4-(6-Fluoroimidazo[1,2-a]pyridin-3-yl)piperidine, TFA Salt

The title compound was prepared from 1-(t-butoxycarbonyl)-4-(1-bromo-2-oxoethyl)piperidine (from Procedure 23, Step B) and 2-amino-5-fluoropyridine (prepared using procedures analogous to those described by D. C. Baker et al, *Synthesis.* 1989, 905) using a procedures similar to that described in Procedure 27, Step A–C. For the BOC intermediate:

$^1$H NMR (500 MHz, CDCl$_3$): δ 1.51 (s, 9H), 1.60–1.80 (m, 2H), 2.07 (br d, 2H), 2.85–3.00 (m, 3H), 4.20–4.40 (br, 2H), 7.11 (m, 1H), 7.47 (s, 3H), 7.60 (m, 1H), 7.89 (m, 1H).

PROCEDURE 43

4-(6-Fluoro-7-methylimidazo[1,2-a]pyridin-3-yl) piperidine

The title compound was prepared using procedures analogous to those described in Procedure 27, Step A–C, except 2-amino-5-fluoro-4-methylpyridine (prepared using procedures analogous to those described by D. C. Baker et al, *Synthesis.* 1989, 905) was employed in place of 2-amino-5-fluoropyridine in Step A.

PROCEDURE 44

4-(2-Ethylindazol-3-yl)piperidine, TFA Salt

Step A: 2-Ethylindazole

To a solution of indazole (6.2 g, 52.5 mmol) in DMF (30 mL) was added sodium hydride (60% dispersion in mineral oil, 3.0 g, 75.0 mmol) at 0° C. After stirring at 0° C. for 20 min., ethyl iodide (5 mL, 62.5 mmol) was added dropwise at 0° C. The mixture was stirred at rt for 1 h, and then partitioned between ethyl acetate and water. The aqueous layer was extracted with ethyl acetate (3×). The combined organic phases were washed with brine, and dried over anhydrous magnesium sulfate. TLC indicated that a 2:1 mixture of two isomers was formed. The mixture was purified by flash chromatography (hexanes:ethyl acetate= 4:1, then 1:1) to give 2.34 g of the title compound as a viscous oil (slow moving isomer).

Step B: 2-Ethyl-3-bromoindazole

To a solution of 2-ethylindazole (2.32 g, 15.87 mmol) in ethanol (20 mL) was added bromine (2.54 g, 15.87 mmol) in ethanol (1 mL)/water (1 mL) at 0° C. After stirring at 0° C. for 10 min. and at rt for 1 h, the reaction was quenched with aq. sodium bicarbonate. The mixture was partitioned between ethyl acetate and aq. sodium bicarbonate. The aqueous layer was extracted with ethyl acetate (3×). The combined organic phase was washed with brine, and dried over anhydrous magnesium sulfate. Purification by flash chromatography (hexanes:ethyl acetate=1:1, then 100% ethyl acetate) gave 2.34 g of the title compound as a viscous oil.

Step C: 1-(t-Butoxycarbonyl)-4-hydroxy-4-(2-ethyl-indazol-3-yl)piperidine

To a solution of 2-ethyl-3-bromoindazole (3.4 g, 15.18 mmol) in THF (30 mL) was added t-BuLi (1.7 M in pentane, 10.72 mL, 18.22 mmol) dropwise at −78° C. After stirring at −78° C. for 20 min., was added tert-butyl 4-oxo-1-piperidinecarboxylate (3.03 g, 15.18 mmol) in THF (10 mL) dropwise at −78° C. The mixture was stirred at −78° C. for 10 min. and at rt for 18 h. After the reaction was quenched with aq. $NH_4Cl$, the mixture was partitioned between ethyl acetate and water. The aqueous layer was extracted with ethyl acetate (3×). The combined organic phases were washed with brine, and dried over anhydrous magnesium sulfate. Concentration followed by purification by flash chromatography (hexanes ethyl acetate=4:1, then 1:1) to give 1.18 g of the title compound as a foamy solid.

Step D: 1-(t-Butoxycarbonyl)-4-(2-ethyl-indazol-3-yl)-[1,2,3,6]tetrahydropyridine To a solution of 1-(t-butoxycarbonyl)-4-hydroxy-4-(2-ethyl-indazol-3-yl)piperidine (651 mg, 1.89 mmol) in toluene (5 mL) was added (methoxycarbonylsulfamoyl)-triethylammonium hydroxide inner salt (540 mg, 2.27 mmol). After heating up to 70° C. for 10 min., was added additional 5 mL of toluene. The mixture was stirred at 70° C. for additional 2 h. The mixture was partitioned between ethyl acetate and aq. sodium bicarbonate. Aqueous layer was extracted with ethyl acetate (3×). The combined organic phases were washed with brine, and dried over anhydrous magnesium sulfate. Concentration followed by purification by flash chromatography (hexanes:ethyl acetate=4:1, then 1:1) gave 514 mg of the title compound as a viscous oil.

Step E: 1-(t-Butoxycarbonyl)-4-(2-ethyl-[5,6,7,8]tetrahydroindazol-3-yl)piperidine A solution of 1-(t-butoxycarbonyl)-4-(2-ethyl-indazol-3-yl)-[1,2,3,6]tetrahydropyridine (500 mg, 1.53 mmol) in methanol (5 mL) was hydrogenated using, $Pd(OH)_2$ (100 mg) under atmospheric $H_2$ for 4.5 h. After the addition of Platinum (IV) oxide (100 mg) hydrogenation was continued for additional 4 h. The mixture was filtered through celite and concentrated to give the title compound (461 mg) as a viscous oil. ESI-MS 333 (M+1); HPLC A: 2.45 min.

Step F: 1-(t-Butoxycarbonyl)-4-(2-ethylindazol-3-yl)piperidine

To a solution of 1-(t-butoxycarbonyl)-4-(2-ethyl-[5,6,7,8]tetrahydroindazol-3-yl)piperidine (80 mg, 0.24 mmol) in toluene (3 mL) was added DDQ (115 mg, 0.51 mmol) at rt. After refluxing for 4 h, the mixture was partitioned between ethyl acetate and water. The aqueous layer was extracted with ethyl acetate (3×). The combined organic phases were washed with brine, and dried over anhydrous magnesium sulfate. Concentration gave 25 mg of the title compound as a viscous oil.

ESI-MS 274 (M+1-t-Bu); HPLC A: 3.09 min.

Step G: 4-(2-Ethylindazol-3-yl)piperidine, TFA Salt

Using essentially the same method as Procedure 27, Step B, the title compound was obtained as the TFA salt.

PROCEDURE 45

4-(1,3-Diethyl-4-methyl-(1H)-pyrazol-5-yl)piperidine di-HCl Salt

Step A: 1-(t-Butoxycarbonyl)-4-(N-methyl-N-methoxycarboxamido)piperidine

A solution of 1-(t-butoxycarbonyl)isonipecotic acid (13.74 g, 0.06 mol), TEA (14.7 mL, 0.105 mol), 4-DMAP (1.83 g, 0.015 mol), N-ethyl-N'-(3-dimethylaminopropyl) carbodiimide×HCl (11.50 g, 0.06 mol) and O,N-dimethylhydroxylamine×HCl (6.27 g, 0.09 mol) in methylene chloride (250 mL) was stirred at rt for 60 h. The mixture eras partitioned between 1 L of ether and 500 mL of water and the layers were separated. The organic layer was washed with 500 mL of 1.0 N HCl, 500 mL of 1.0 N NaOH, 500 mL of sat'd sodium chloride, dried over magnesium sulfate and concentrated to afford 14.34 g (88%) of the title compound:
$^1H$ NMR (500 MHz) δ 1.46 (s, 9H), 1.65–1.80 (4H), 2.76–2.86 (3H), 3.19 (s, 3H), 3.71 (s, 3H), 4.15 (2H).

Step B: 1-(t-Butoxycarbonyl)-4-formylpiperidine

A solution of 1-(t-butoxycarbonyl)-4-(N-methyl-N-methoxycarboxamido)piperidine (4.80 g, 17.6 mmol) (from Step A) in methylene chloride (100 mL) at −78° C. was treated with 1.0 M DIBALH solution in methylene chloride (25 mL) and stirred cold for 30 min. The reaction was quenched with 1.0 N HCl (250 mL) and warmed to rt. The quenched mixture was extracted with 300 mL of ether; the extract was washed with 150 mL of 1.0 N NaOH, 150 mL of sat'd sodium chloride, dried over magnesium sulfate and concentrated. Flash chromatography on 125 g of silica gel using 1:1 v/v hexanes/ether as the eluant afforded 3.60 g (95%) of the title compound:
$^1H$ NMR (500 MHz) δ 1.46 (s, 9H), 1.52–1.59 (m, 2H), 1.85–1.91 (m, 2H), 2.38–2.43 (m, 1H), 2.93 (app t, J=11.0, 2H), 3.95–4.05 (m, 2H), 9.66 (s, 1H).

Step C: 1-(t-Butoxycarbonyl)-4-(1-(RS)-hydroxy-2-(RS)-methyl-3-oxopent-1-yl)piperidine A solution of diisopropylamine (0.63 mL, 4.5 mmol) in THF (16 mL) at 0° C. was treated with 1.6 M n-butyllithium in sol'n in hexanes (2.8 mL). The resulting solution was stirred at 0° C. for 10 min, then cooled to −78° C. 3-Pentanone (0.41 mL, 4.1 mmol) was added and the resulting mixture was stirred cold for 1 h. A solution of 1-(t-butoxycarbonyl)-4-formylpiperidine (435 mg, 2.05 mmol) (from Step B) in THF (3 mL) was then added. After 15 min, the reaction was quenched with sat'd ammonium chloride (25 mL) and extracted with ether (100 mL). The extract was dried over magnesium sulfate and concentrated. MPLC (Biotage) on a 40S silica cartridge using 4:1 v/v, then 3:2 v/v hexanes/ethyl acetate as the eluent afforded 517 mg (85%) of the title compound.

Step D: 1-(t-Butoxycarbonyl)-4-(1,3-dioxo-2-(RS)-methylpent-1-yl)piperidine

A solution of oxalyl chloride (0.34 mL, 3.9 mmol) in methylene chloride (12 mL) at −78° C. was treated with DMSO (0.43 mL, 6.0 mmol) and the resulting mixture was stirred cold for 10 min. A solution of 1-(t-butoxycarbonyl)-4-(1-(RS)-hydroxy-2-(RS)-methyl-3-oxopent-1-yl)piperidine (514 mg, 1.7 mmol) (from Step C) was added and the resulting solution was stirred cold for 1 h. N,N-Diisopropylethylamine (2.4 mL, 13.7 mmol) was added and the resulting mixture was warmed to 0° C. The reaction was quenched with 1.0 N HCl (25 mL) and extracted with ether (100 mL). The extract was dried over magnesium sulfate and concentrated. MPLC (Biotage) on a 40S silica cartridge using 2:1 v/v hexanes/ethyl acetate as the eluent afforded 435 mg (85%) of the title compound.

Step E: 1-(t-Butoxycarbonyl)-4-(1,3-diethyl-4-methyl-(1H)-pyrazol-5-yl)piperidine A solution of 1-(t-butoxycarbonyl)-4-(1,3-dioxo-2-(RS)-methylpent-1-yl)piperidine (435 mg, 1.5 mmol) (from Step D) in 2:1 v/v acetonitrile/water (12 mL) was treated with ethylhydrazine (34% sol'n in water, 0.28 mL, 1.6 mmol) and the resulting mixture was stirred at rt for 20 h. The reaction mixture was partitioned between 75 mL of ether and 25 mL of sat'd sodium chloride and the layers were separated. The organic layer was dried over magnesium sulfate and concentrated. MPLC (Biotage) on a 40S silica cartridge using 4:1 v/v, then 1:1 v/v hexanes/ethyl acetate as the eluent afforded 348 mg (74%) of the title compound:

$^1$H NMR (500 MHz) δ 1.21 (t, J=7.5, 3H), 1.36 (t, J=7.5, 3H), 1.49 (s, 9H), 1.68–1.72 (m, 2H), 1.86–1.91 (m, 2H), 2.54 (q, J=1.5, 2H), 2.72–2.79 (3H), 4.08 (q, J=7.5, 2H), 4.20–4.30 (m, 2H).

Step F: 4-(1,3-Diethyl-4-methyl-(1H)-pyrazol-5-yl)piperidine di-HCl Salt

A solution of 1-(t-butoxycarbonyl)-4-(1,3-diethyl-4-methyl-(1H)-pyrazol-5-yl)piperidine (348 mg) (from Step E) in 2.5 N HCl in methanol was stirred at rt for 16 h. The solution was concentrated and the resulting solid was suspended in ethyl acetate, filtered and dried to afford 293 mg (92%) of the title compound.

PROCEDURE 46

Using essentially the same methods as described in Procedure 45 and substituting the appropriate starting material and/or hydrazine reagent, a variety of other 4-(1,3,4-trialkyl)-(1H)-pyrazol-5-yl)piperidines can be prepared, usually as the di-hydrochloride salts, and utilized in the following Examples as required.

PROCEDURE 47

Using essentially the same methods as described in Procedures 1 and 2 and substituting the appropriate starting material and/or hydrazine reagent, the following representative 4-(3-(substituted)-1-(H or alkyl)-(1H)-pyrazol-5-yl)piperidines can be prepared, usually as the di-hydrochloride salts, and utilized in the following Examples as required.

4-(3-(Benzyl)-1-(methyl)-(1H)-pyrazol-5-yl)piperidine
4-(3-(Benzyl)-1-(n-propyl)-(1H)-pyrazol-5-yl)piperidine
4-(3-(Benzyl)-1-(isopropyl)-(1H)-pyrazol-5-yl)piperidine
4-(3-(2-Fluorobenzyl)-1-(ethyl)-(1H)-pyrazol-5-yl)piperidine
4-(3-(3-Fluorobenzyl)-1-(ethyl)-(1H)-pyrazol-5-yl)piperidine
4-(3-(4-Fluorobenzyl)-1-(ethyl)-(1H)-pyrazol-5-yl)piperidine
4-(3-(4-Fluorobenzyl)-(1H)-pyrazol-5-yl)piperidine
4-(3-(4-Fluorobenzyl)-1-(methyl)-(1H)-pyrazol-5-yl)piperidine
4-(3-(4-Fluorobenzyl)-1-(n-propyl)-(1H)-pyrazol-5-yl)piperidine
4-(3-(3,4-Difluorobenzyl)-1-(ethyl)-(1H)-pyrazol-5-yl)piperidine
4-(3-(3,4-Difluorobenzyl)-1-(methyl)-(1H)-pyrazol-5-yl)piperidine
4-(3-(3,4-Difluorobenzyl)-(1H)-pyrazol-5-yl)piperidine
4-(3-(3,5-Difluorobenzyl)-1-(ethyl)-(1H)-pyrazol-5-yl)piperidine
4-(3-(2,4-Difluorobenzyl)-1-(ethyl)-(1H)-pyrazol-5-yl)piperidine
4-(3-(3-Chlorobenzyl)-1-(ethyl)-(1H)-pyrazol-5-yl)piperidine
4-(3-(4-Chlorobenzyl)-1-(ethyl)-(1H)-pyrazol-5-yl)piperidine
4-(3-(3,4-Dichlorobenzyl)-1-(ethyl)-(1H)-pyrazol-5-yl)piperidine
4-(3-(3-Cyanobenzyl)-1-(ethyl)-(1H)-pyrazol-5-yl)piperidine
4-(3-(4-Cyanobenzyl)-1-(ethyl)-(1H)-pyrazol-5-yl)piperidine
4-(3-(3-Methylsulfonylbenzyl)-1-(ethyl)-(1H)-pyrazol-5-yl)piperidine
4-(3-(4-Methylsulfonylbenzyl)-1-(ethyl)-(1H)-pyrazol-5-yl)piperidine
4-(3-(3-Methoxybenzyl)-1-(ethyl)-(1H)-pyrazol-5-yl)piperidine
4-(3-(4-Methoxybenzyl)-1-(ethyl)-(1H)-pyrazol-5-yl)piperidine
4-(3-(4-Methoxybenzyl)-1-(methyl)-(1H)-pyrazol-5-yl)piperidine
4-(3-(4-Methoxybenzyl)-(1H)-pyrazol-5-yl)piperidine
4-(3-(3-Ethoxybenzyl)-1-(ethyl)-(1H)-pyrazol-5-yl)piperidine
4-(3-(4-Ethoxybenzyl)-1-(ethyl)-(1H)-pyrazol-5-yl)piperidine
4-(3-(4-Ethoxybenzyl)-(1H)-pyrazol-5-yl)piperidine
4-(3-(3-Isopropoxybenzyl)-1-(ethyl)-(1H)-pyrazol-5-yl)piperidine
4-(3-(4-Isopropoxybenzyl)-1-(ethyl)-(1H)-pyrazol-5-yl)piperidine
4-(3-(4-Cyclopropoxybenzyl)-1-(ethyl)-(1H)-pyrazol-5-yl)piperidine
4-(3-(4-Butoxybenzyl)-1-(ethyl)-(1H)-pyrazol-5-yl)piperidine
4-(3-(4-t-Butoxybenzyl)-1-(ethyl)-(1H)-pyrazol-5-yl)piperidine
4-(3-(4-Cyclobutoxybenzyl)-1-(ethyl)-(1H)-pyrazol-5-yl)piperidine
4-(3-(4-Difluoromethoxybenzyl)-1-(ethyl)-(1H)-pyrazol-5-yl)piperidine
4-(3-(4-Trifluoromethoxybenzyl)-1-(ethyl)-(1H)-pyrazol-5-yl)piperidine
4-(3-(4-(2,2,2-Trifluoroethoxy)benzyl)-1-(ethyl)-(1H)-pyrazol-5-yl)piperindine
4-(3-(3,4-Methylenedioxybenzyl)-1-(ethyl)-(1H)-pyrazol-5-yl)piperidine
4-(3-(3,4-Dimethoxybenzyl)-1-(ethyl)-(1H)-pyrazol-5-yl)piperidine
4-(3-(3,4-Diethoxybenzyl)-1-(ethyl)-(1H)-pyrazol-5-yl)piperidine
4-(3-(3-Fluoro-4-methoxybenzyl)-1-(ethyl)-(1H)-pyrazol-5-yl)piperidine
4-(3-(4-Fluoro-3-methoxybenzyl)-1-(ethyl)-(1H)-pyrazol-5-yl)piperidine
4-(3-(3-Fluoro-4-ethoxybenzyl)-1-(ethyl)-(1H)-pyrazol-5-yl)piperidine
4-(3-(4-Fluoro-3-ethoxybenzyl)-1-(ethyl)-(1H)-pyrazol-5-yl)piperidine
4-(3-(3-Cyano-4-methoxybenzyl)-1-(ethyl)-(1H)-pyrazol-5-yl)piperidine
4-(3-(4-Cyano-3-methoxybenzyl)-1-(ethyl)-(1H)-pyrazol-5-yl)piperidine 4-(3-(3-Cyano-4-ethoxybenzyl)-1-(ethyl)-(1H)-pyrazol-5-yl)piperidine
4-(3-(4-Cyano-3-ethoxybenzyl)-1-(ethyl)-(1H)-pyrazol-5-yl)piperidine
4-(3-(Benzofuran-6-yl)-1-(ethyl)-(1H)-pyrazol-5-yl)piperidine
4-(3-(Benzofuran-5-yl)-1-(ethyl)-(1H)-pyrazol-5-yl)piperidine
4-(3-(2,3-Dihydrobenzofuran-6-yl)-1-(ethyl)-(11H)-pyrazol-5-yl)piperidine
4-(3-(4-Benzyloxybenzyl)-1-(ethyl)-(1H)-pyrazol-5-yl)piperidine
4-(3-(4-Hydroxybenzyl)-1-(ethyl)-(1H)-pyrazol-5-yl)piperidine
4-(3-(3-Methylbenzyl)-1-(ethyl)-(1H)-pyrazol-5-yl)piperidine
4-(3-(4-Methylbenzyl)-1-(ethyl)-(1H)-pyrazol-5-yl)piperidine
4-(3-(3-Ethylbenzyl)-1-(ethyl)-(1H)-pyrazol-5-yl)piperidine
4-(3-(4-Ethylbenzyl)-1-(ethyl)-(1H)-pyrazol-5-yl)piperidine
4-(3-(4-Ethylbenzyl)-1-(methyl)-(1H)-pyrazol-5-yl)piperidine
4-(3-(4-Ethylbenzyl)-(1H)-pyrazol-5-yl)piperidine
4-(3-(4-Isopropylbenzyl)-1-(ethyl)-(1H)-pyrazol-5-yl)piperidine
4-(3-(4-t-Butylbenzyl)-1-(ethyl)-(1H)-pyrazol-5-yl)piperidine
4-(3-(4-Trifluoromethylbenzyl)-1-(ethyl)-(1H)-pyrazol-5-yl)piperidine
4-(3-(3-Phenylbenzyl)-1-(ethyl)-(1H)-pyrazol-5-yl)piperidine
4-(3-(4-Phenylbenzyl)-1-(ethyl)-(1H)-pyrazol-5-yl)piperidine
4-(3-(1-Naphthyl)-1-(ethyl)-(1H)-pyrazol-5-yl)piperidine
4-(3-(2-Naphthyl)-1-(ethyl)-(1H)-pyrazol-5-yl)piperidine
4-(3-(4-Acetylbenzyl)-1-(ethyl)-(1H)-pyrazol-5-yl)piperidine
4-(3-(4-(1-Methyl-1-hydroxyethylbenzyl)-1-(ethyl)-(1H)-pyrazol-5-yl)piperidine
4-(3-(3-Trifluoromethylbenzyl)-1-(ethyl)-(1H)-pyrazol-5-yl)piperidine
4-(3-(4-Trifluoromethylbenzyl)-1-(ethyl)-(1H)-pyrazol-5-yl)piperidine
4-(3-(Pyridin-3-yl)-1-(ethyl)-(1H)-pyrazol-5-yl)piperidine
4-(3-(Pyridin-3-yl)-(1H)-pyrazol-5-yl)piperidine
4-(3-(Cyclohexylmethyl)-1-(ethyl)-(1H)-pyrazol-5-yl)piperidine
4-(3-(4-Methylcyclohexylmethyl)-1-(ethyl)-(1H)-pyrazol-5-yl)piperidine
4-(3-(Cycloheptylmethyl)-1-(ethyl)-(1H)-pyrazol-5-yl)piperidine
4-(3-(Pyran-4-ylmethyl)-1-(ethyl)-(1H)-pyrazol-5-yl)piperidine
4-(3-(Thiopyran-4-ylmethyl)-1-(ethyl)-(1H)-pyrazol-5-yl)piperidine, S,S-dioxide

PROCEDURE 48

Using essentially the same methods as described in Procedures 22–26 and substituting the appropriate starting material and/or reagent, the following representative 4-(2-(substituted)-4-(H or alkyl)thiazol-5-yl)piperidines can be prepared, usually as the di-hydrochloride salts, and utilized in the following Examples as required.

4-(2-(Benzyl)-4-(ethyl)thiazol-5-yl)piperidine
4-(2-(Benzyl)-4-(methyl)thiazol-5-yl)piperidine
4-(2-(Benzyl)thiazol-5-yl)piperidine
4-(2-(2-Fluorobenzyl)-4-(ethyl)thiazol-5-yl)piperidine
4-(2-(2-Fluorobenzyl)-4-(methyl)thiazol-5-yl)piperidine
4-(2-(2-Fluorobenzyl)thiazol-5-yl)piperidine
4-(2-(3-Fluorobenzyl)-4-(ethyl)thiazol-5-yl)piperidine
4-(2-(3-Fluorobenzyl)-4-(methyl)thiazol-5-yl)piperidine
4-(2-(3-Fluorobenzyl)thiazol-5-yl)piperidine
4-(2-(4-Fluorobenzyl)-4-(ethyl)thiazol-5-yl)piperidine
4-(2-(4-Fluorobenzyl)-4-(methyl)thiazol-5-yl)piperidine
4-(2-(4-Fluorobenzyl)thiazol-5-yl)piperidine
4-(2-(2-Chlorobenzyl)-4-(ethyl)thiazol-5-yl)piperidine
4-(2-(2-Chlorobenzyl)-4-(methyl)thiazol-5-yl)piperidine
4-(2-(2-Chlorobenzyl)thiazol-5-yl)piperidine
4-(2-(3-Chlorobenzyl)-4-(ethyl)thiazol-5-yl)p)peridine
4-(2-(3-Chlorobenzyl)-4-(methyl)thiazol-5-yl)piperidine
4-(2-(3-Chlorobenzyl)thiazol-5-yl)piperidine
4-(2-(4-Chlorobenzyl)-4-(ethyl)thiazol-5-yl)piperidine
4-(2-(4-Chlorobenzyl)-4-(methyl)thiazol-5-yl)piperidine
4-(2-(4-Chlorobenzyl)thiazol-5-yl)piperidine
4-(2-(3-Cyanobenzyl)-4-(ethyl)thiazol-5-yl)piperidine
4-(2-(3-Cyanobenzyl)-4-(methyl)thiazol-5-yl)piperidine
4-(2-(3-Cyanobenzyl)thiazol-5-yl)piperidine
4-(2-(4-Cyanobenzyl)-4-(ethyl)thiazol-5-yl)piperidine
4-(2-(4-Cyanobenzyl)-4-(methyl)thiazol-5-yl)piperidine
4-(2-(4-Cyanobenzyl)thiazol-5-yl)piperidine
4-(2-(3,4-Difluorobenzyl)-4-(ethyl)thiazol-5-yl)piperidine
4-(2-(3,4-Difluorobenzyl)-4-(methyl)thiazol-5-yl)piperidine
4-(2-(3,4-Difluorobenzyl)thiazol-5-yl)piperidine
4-(2-(3,5-Difluorobenzyl)-4-(ethyl)thiazol-5-yl)piperidine
4-(2-(3,5-Difluorobenzyl)-4-(methyl)thiazol-5-yl)piperidine
4-(2-(3,5-Difluorobenzyl)thiazol-5-yl)piperidine
4-(2-(2,4-Difluorobenzyl)-4-(ethyl)thiazol-5-yl)piperidine
4-(2-(2,4-Difluorobenzyl)-4-(methyl)thiazol-5-yl)piperidine
4-(2-(2,4-Difluorobenzyl)thiazol-5-yl)piperidine
4-(2-(3,4-Dichlorobenzyl)-4-(ethyl)thiazol-5-yl)piperidine
4-(2-(3,4-Dichlorobenzyl)-4-(methyl)thiazol-5-yl)piperidine
4-(2-(3,4-Dichlorobenzyl)thiazol-5-yl)piperidine
4-(2-(3,5-Dichlorobenzyl)-4-(ethyl)thiazol-5-yl)piperidine
4-(2-(3,5-Dichlorobenzyl)-4-(methyl)thiazol-5-yl)piperidine
4-(2-(3,5-Dichlorobenzyl)thiazol-5-yl)piperidine
4-(2-(2,4-Dichlorobenzyl)-4-(ethyl)thiazol-5-yl)piperidine
4-(2-(2,4-Dichlorobenzyl)-4-(methyl)thiazol-5-yl)piperidine 4-(2-(2,4-Dichlorobenzyl)thiazol-5-yl)piperidine
4-(2-(3-Methylbenzyl)-4-(ethyl)thiazol-5-yl)piperidine
4-(2-(3-Methylbenzyl)-4-(methyl)thiazol-5-yl)piperidine
4-(2-(3-Methylbenzyl)thiazol-5-yl)piperidine
4-(2-(4-Methylbenzyl)-4-(ethyl)thiazol-5-yl)piperidine
4-(2-(4-Methylbenzyl)-4-(methyl)thiazol-5-yl)piperidine
4-(2-(4-Methylbenzyl)thiazol-5-yl)piperidine
4-(2-(3-Ethylbenzyl)-4-(ethyl)thiazol-5-yl)piperidine
4-(2-(3-Ethylbenzyl)-4-(methyl)thiazol-5-yl)piperidine
4-(2-(3-Ethylbenzyl)thiazol-5-yl)piperidine
4-(2-(4-Ethylbenzyl)-4-(ethyl)thiazol-5-yl)piperidine
4-(2-(4-Ethylbenzyl)-4-(methyl)thiazol-5-yl)piperidine
4-(2-(4-Ethylbenzyl)thiazol-5-yl)piperidine
4-(2-(4-Isopropylbenzyl)-4-(ethyl)thiazol-5-yl)piperidine
4-(2-(4-Isopropylbenzyl)-4-(methyl)thiazol-5-yl)piperidine
4-(2-(4-Isopropylbenzyl)thiazol-5-yl)piperidine
4-(2-(4-t-Butylbenzyl)-4-(ethyl)thiazol-5-yl)piperidine
4-(2-(4-t-Butylbenzyl)-4-(methyl)thiazol-5-yl)piperidine
4-(2-(4-t-Butylbenzyl)thiazol-5-yl)piperidine
4-(2-(3-Trifluoromethylbenzyl)-4-(ethyl)thiazol-5-yl)piperidine
4-(2-(3-Trifluoromethylbenzyl)-4-(methyl)thiazol-5-yl)piperidine
4-(2-(3-Trifluoromethylbenzyl)thiazol-5-yl)piperidine
4-(2-(4-Trifluoromethylbenzyl)-4-(ethyl)thiazol-5-yl)piperidine
4-(2-(4-Trifluoromethylbenzyl)-4-(methyl)thiazol-5-yl)piperidine
4-(2-(4-Trifluoromethylbenzyl)thiazol-5-yl)piperidine
4-(2-(3-Methoxybenzyl)-4-(ethyl)thiazol-5-yl)piperidine
4-(2-(3-Methoxybenzyl)-4-(methyl)thiazol-5-yl)piperidine
4-(2-(3-Methoxybenzyl)thiazol-5-yl)piperidine
4-(2-(4-Methoxybenzyl)-4-(ethyl)thiazol-5-yl)piperidine
4-(2-(4-Methoxybenzyl)-4-(methyl)thiazol-5-yl)piperidine
4-(2-(4-Methoxybenzyl)thiazol-5-yl)piperidine
4-(2-(3-Ethoxybenzyl)-4-(ethyl)thiazol-5-yl)piperidine
4-(2-(3-Ethoxybenzyl)-4-(methyl)thiazol-5-yl)piperidine
4-(2-(3-Ethoxybenzyl)thiazol-5-yl)piperidine
4-(2-(4-Ethoxybenzyl)-4-(ethyl)thiazol-5-yl)piperidine
4-(2-(4-Ethoxybenzyl)-4-(methyl)thiazol-5-yl)piperidine
4-(2-(4-Ethoxybenzyl)thiazol-5-yl)piperidine
4-(2-(3-Trifluoromethoxybenzyl)-4-(ethyl)thiazol-5-yl)piperidine
4-(2-(3-Trifluoromethoxybenzyl)-4-(methyl)thiazol-5-yl)piperidine
4-(2-(3-Trifluoromethoxybenzyl)thiazol-5-yl)piperidine
4-(2-(4-Trifluoromethoxybenzyl)-4-(ethyl)thiazol-5-yl)piperidine
4-(2-(4-Trifluoromethoxybenzyl)-4-(methyl)thiazol-5-yl)piperidine
4-(2-(4-Trifluoromethoxybenzyl)thiazol-5-yl)piperidine
4-(2-(4-Methylsulfonylbenzyl)-4-(ethyl)thiazol-5-yl)piperidine
4-(2-(4-Methylsulfonylbenzyl)thiazol-5-yl)piperidine
4-(2-(4-Nitrobenzyl)-4-(ethyl)thiazol-5-yl)piperidine
4-(2-(4-Nitrobenzyl)-4-(methyl)thiazol-5-yl)piperidine
4-(2-(4-Nitrobenzyl)thiazol-5-yl)piperidine

EXAMPLE 1

1-(SR)-Benzyloxy-3-(SR)-((4-(phenyl)piperidin-1-yl)methyl)-4-(SR)-phenylcyclopentane Hydrochloride Salt Step A: (+−)-cis- and trans-4-oxo-2-Phenylcyclopentanoic Acid A mixture of the title compounds (11.1 g) was prepared as described by von A. W. Frahm, *Liebigs Ann. Chem.*, 1969, 728, 21 from methyl trans-cinnamate (16.2 g, 0.1 mol) and trimethyl 1,1,2-ethane tricarboxylate (20.4 g, 0.1 mol). After refluxing the intermediate triester (17.7 g) in acetic acid/aq HCl for 5 days, the crude mixture of the cis and trans products was used directly in the next step without separation of the isomers.

Step B: Methyl (+−)-cis- and trans-4-oxo-2-Phenylcyclopentanoate

To the crude acid products from Step A (6.6 g, 32 mmol) in methanol (60 mL) and methylene chloride (180 mL) was added dropwise 2M trimethylsilyldiazomethane in hexanes (18 mL) after which the yellow color persisted. After an additional 20 min, the excess trimethylsilyldiazomethane was quenched with acetic acid and the reaction was concentrated in vacuo. The crude mixture was purified by FC using a gradient of 5 to 15% ethyl acetate in hexanes to give the higher $R_f$ trans product (2.05 g) and then the lower cis product (3.71 g). The assignments were based on the NMR of each which were the same as reported in the literature.

Step C: Methyl 1-(SR)-4-(RS)-Hydroxy-2-(SR)-phenylcyclopentanoate (Higher Isomer) and Methyl 1-(SR)-4-(SR)-Hydroxy-2-(SR)-phenylcyclopentanoate (Lower Isomer)

To a solution of methyl (+−)-trans-4-oxo-2-phenylcyclopentanoate (1.3 g, 6.0 mmol) from Step B in methanol (50 mL) was added portionwise over 5 min sodium borohydride (0.23 g, 6.0 mmol). After 1 h, the reaction was complete by TLC and was quenched by addition to dilute aq. HCl. This was extracted twice with ether and the organic layers were each washed with brine, dried over sodium sulfate and concentrated in vacuo. The residue was purified by FC using a gradient of 20 to 30% ethyl acetate in hexanes to give pure higher $R_f$ title product (0.3 g), mixed fractions (0,41 g), and then clean lower title product (0.6 g).

Higher isomer: NMR (CDCl$_3$) δ: 1.6 (br s, 1H), 1.79 (dddd, J=1.3, 4.3, 9.1, 13.7 Hz, 1H), 2.0–2.2 (m, 2 H), 2.55 (ddd, J=6.0, 9.3, 13.7 Hz, 1H), 3.15 (br q, J=9 Hz, 1H), 3.38 (q, J=9 Hz, 1H), 3.58 (s, 3 H), 4.50 (m, 1H), 7.1–7.3 (m, 5 H).

Lower isomer: NMR (CDCl$_3$) δ: 1.58 (br s, 1H), 1.92 (ddd, J=5.0, 11.3, 13.5 Hz, 1H), 2.04 (ddt, J=2.2, 5.3, 15 Hz, 1H), 2.23 (ddt, J=1.7, 7.5, 13.5 Hz, 1H), 2.39 (ddd, J=5.2, 10, 14.4 Hz, 1H), 2.94 (ddd, J=5.3, 8.3, 10 Hz, 1H), 3.65 (s, 3H), 3.67 (m, 1H), 4.49 (m, 1H), 7.15–7.35 (m, 5H).

Step D: Methyl 1-(SR)-4-(SR)-Benzyloxy-2-(SR)-phenylcyclopentanoate

To a solution of methyl 1-(SR)-4-(SR)-hydroxy-2-(SR)-phenylcyclopentanoate (Lower isomer from Step C) (550 mg, 2.5 mmol) and benzyl bromide (2.2 g, 12.5 mmol) in DMF (5 mL) was added portionwise sodium hydride (60% in mineral oil) (250 mg, 6.25 mmol) over 20 min. After 30 min, the reaction was quenched into aq. HCl and was extracted twice with ether. The organic layers were each washed with brine, dried over sodium sulfate and concentrated in vacuo. The residue was purified by FC using a gradient of 5 to 10% ethyl acetate in hexanes to give the title product (0.375 g). Elution with 20 to 50% ethyl acetate in hexanes afforded recovered starting material (120 mg).

NMR (CDCl$_3$) δ: 1.90 (ddd, 1H), 2.20 (dddd, 1H), 2.31 (ddt, 1H), 2.43 (ddd, 1H), 2.85 (q, 1H), 3.60 (s, 3H), 3.69 (dt, 1H), 4.17 (m, 1H), 4.50 (Abq, 2H), 7.15–7.4 (m, 10H).

Step E: 1-(SR)-Benzyloxy-3-(SR)-hydroxymethyl-4-(SR)-phenylcyclopentane

To a solution of methyl 1-(SR)-4-(SR)-benzyloxy-2-(SR)-phenylcyclopentanoate (370 mg, 1.2 mmol) (from Step D) in THF (10 mL) under nitrogen was added lithium borohydride (55 mg, 2.4 mmol). The reaction was stirred at RT for 16 h and then at 50° C. for 4 h when TLC indicated that the reaction was complete. The reaction was quenched into dilute aq. HCl and was extracted twice with ether. The organic layers were each washed with brine, dried cover sodium sulfate and concentrated in vacuo. The residue was purified by FC using a gradient of 20 to 40% ethyl acetate in hexanes to give the title product (0.34 g).

NMR (CDCl$_3$) δ: 1.7–1.9 (m, 2H+br OH), 2.2–2.4 (m, 3H), 3.16 (ddd, 1H), 3.62 (dABq, 2H), 4.17 (m, 1H), 4.51 (ABq, 2H), 7.15–7.45 (m, 10 H).

Step F: 1-(SR)-4-(SR)-Benzyloxy-2-(SR)-phenylcyclopentanecarboxaldehyde

To a solution of oxalyl chloride (0.27 mL, 3.0 mmol) in methylene chloride (5 mL) at −70° C. was added dropwise DMSO (0.47 mL, 6.0 mmol). After 15 min, a solution of 1-(SR)-benzyloxy-3-(SR)-hydroxymethyl-4-(SR)-phenylcyclopentane (340 mg, 1.2 mmol) (from Step E) in methylene chloride (5 mL) was added. The reaction was stirred at −70° C. for 2 h and then DIPEA (2.2 mL, 12 mmol) was added. After a further 10 min, the mixture was allowed to warm to RT for 1 h and was then diluted with methylene chloride and poured into dilute aq. HCl and the layers were separated. The aq. layer was reextracted with a second and the organic layers were each washed with brine, dried over sodium sulfate, combined and concentrated in vacuo. The residue was purified by FC using a gradient of 10 to 15% ethyl acetate in hexanes to give the title product (0.335 g) as an oil.

NMR (CDCl$_3$) δ: 1.89 (ddd, 1H), 2.2–2.35 (m, 2H), 2.38 (ddt, 1H), 2.83 (m, 1H), 3.66 (ddd, 1H), 4.20 (m, 1H), 4.48 (Abq, 2H), 7.15–7.4 (m, 10 H), 9.67 (d, 1H).

Step G: 1-(SR)-Benzyloxy-3-(SR)-((4-(phenyl)piperidin-1-yl)methyl)-4-(SR)-phenylcyclopentane Hydrochloride Salt To a solution of 1-(SR)-4-(SR)-benzyloxy-2-(SR)-phenylcyclopentanecarboxaldehyde (20 mg, 0.072 mmol) from Step F in 1,2-dichloroethane (1 mL) was added 4-(phenyl)piperidine hydrochloride (30 mg, 0.14 mmol) and DIPEA (0.020 mL, 0.14 mmol). After 10 min, sodium triacetoxyborohydride (23 mg, 0.11 mmol) was added and the reaction was stirred at RT for 16 h. The reaction was quenched with aq. sodium carbonate and extracted 3 times with methylene chloride. The organic layers were each washed with brine, dried over sodium sulfate, combined and concentrated in vacuo. The residue was purified by Prep TLC eluting with 2% methanol in methylene chloride to give the title product. The hydrochloride salt was prepared by taking up the free amine in ether, addition of excess 1M hydrogen chloride in ether and evaporation to afford the title compound (30 mg) as a white solid.

NMR (CDCl$_3$) (free amine) δ: 1.6–1.8 (m, 6H), 1.8–1.95 (m, 2H), 1.95–2.1 (m, 1H), 2.15–2.3 (m, 2H), 2.3–2.5 (m, 3H), 2.8–2.9 (m, 1H), 2.9–3.0 (m, 2H), 4.16 (m, 1H), 4.51 (Abq, 2H), 7.1–7.4 (m, 10H). MS (NH$_3$/Cl): m/z 426 (M+1)

EXAMPLE 2

1-(SR)-Benzyloxy-3-(SR)-((spiro(2,3-dihydro-benzothiophene-3,4'-piperidin-1'-yl))methyl)-4-(SR)-phenylcyclopentane Hydrochloride Salt Using essentially the same procedure as Example 1, Step G but using spiro(2,3-dihydro-benzothiophene-3,4'-piperidine hydrochloride, the title compound was prepared.

NMR (CDCl$_3$) (free amine) δ: 1.5–1.65 (m, 1H), 1.65–2.1 (m, 8H), 2.15–2.3 (m, 2H), 2.3–2.5 (m, 2H), 2.6–2.75 (m, 1H), 2.75–2.9 (m, 1H), 2.9–3.0 (br q, 1H), 3.18 (m, 2H), 4.16 (m, 1H), 4.51 (Abq, 2H), 7.1–7.4 (m, 10H). MS (NH$_3$/Cl): m/z 470 (M+1).

EXAMPLE 3

1-(SR)-Benzyloxy-3-(SR)-((spiro(2,3-dihydro-1-oxo-benzothiophene-3,4'-piperidin-1'-yl))methyl)-4-(SR)-phenylcyclopentane Hydrochloride Salt A solution of 1-(SR)-benzyloxy-3-(SR)-((spiro(2,3-dihydro-benzothiophene-3,4'-piperidin-1'-yl))methyl)-4-(SR)-phenylcyclopientane (20 mg, 0.042 mmol) from Example 2 in methanol (1 mL) was cooled in an ice bath and oxone (27 mg) in water (1 mL) was added. After 10 min, the reaction was quenched with aqueous sodium sulfite and was extracted twice with ethyl acetate. The organic layers were each washed with brine, dried, combined and concentrated. The residue was purified by Prep TLC (2% methanol in methylene chloride) to give the title compound (20 mg).

MS (NH$_3$/Cl): m/z 486 (M+1).

EXAMPLE 4

1-(SR)-Benzyloxy-3-(SR)-((spiro(2,3-dihydro-1,1-dioxo-benzothiophene-3,4'-piperidin-1'-yl))methyl)-4-(SR)-phenylcyclopentane Hydrochloride Salt A solution of 1-(SR)-benzyloxy-3-(SR)-((spiro(2,3-dihydro-benzothiophene-3,4'-piperidin-1'-yl))methyl)-4-(SR)-phenylcyclopentane (20 mg, 0.042 mmol) from Example 2 in methanol (1 mL) was cooled in an ice bath and oxone (54 mg) in water (1 mL) was added. After 3 h, the reaction was quenched with aqueous sodium sulfite and was extracted twice with ethyl acetate. The organic layers were each washed with brine, dried, combined and concentrated. The residue was purified by Prep TLC (2% methanol in methylene chloride) to give the title compound (18 mg).

MS (NH$_3$/Cl): m/z 502 (M+1).

EXAMPLES 5–7

Using essentially the same procedures as in Example 1–3 but using aldehyde derived from the higher R$_f$ alcohol intermediate from Example 1, Step C, the following 3 title compounds were prepared.

EXAMPLE 5

1-(RS)-Benzyloxy-3-(SR)-((4-(phenyl)piperidin-1-yl)methyl)-4-(SR)-phenylcyclopentane Hydrochloride Salt MS (NH$_3$/Cl): m/z 426 (M+1)

EXAMPLE 6

1-(RS)-Benzyloxy-3-(SR)-((spiro(2,3-dihydro-benzothiophene-3,4'-piperidin-1'-yl))methyl)-4-(SR)-phenylcyclopentane Hydrochloride Salt MS (NH$_3$/Cl): m/z 470 (M+1)

EXAMPLE 7

1-(RS)-Benzyloxy-3-(SR)-((spiro(2,3-dihydro-1-oxo-benzothiophene-3,4'-piperidin-1'-yl))methyl)-4-(SR)-phenylcyclopentane Hydrochloride Salt MS (NH$_3$/Cl): m/z 486 (M+1).

EXAMPLE 8

1-(SR)-((RS)-(1-Phenyl-1-ethoxy))-3-(SR)-((4-phenylpiperidin-1-yl)methyl)-4-(SR)-phenylcyclopentane Hydrochloride Salt or 1-(SR)-((SR)-(1-Phenyl-1-ethoxy))-3-(SR)-((4-phenylpiperidin-1-yl)methyl)-4-(SR)-phenylcyclopentane Hydrochloride Salt (The absolute assignment was not made.)

Step A: (O)-((R)-1-phenyl-1-ethyl))trichloroacetimidate

Sodium hydride (60% in mineral oil, 50 mg, 1.2 mmol) was suspended in dry ether (10 mL) under nitrogen and after stirring for 10 min, (R)-1-phenylethanol (1.5 g, 12.3 mmol) was added. The suspension was stirred for 10 min and then warmed to reflux for 1.5 min, however the suspension did not clarify. Trichloroacetonitrile (1.4 mL, 13.5 mmol) was added directly to the above mixture (rather than usual inverse addition) at which time the reaction was clear. After 3 h at RT, TLC (20% ethyl acetate in hexanes) indicated still mostly starting alcohol. Additional sodium hydride (50 mg) was added and the mixture was heated to 40° C. for 3 h and then stirred at RT for 3 days. Even though TLC indicated a mixture of product and starting material, the reaction was concentrated and the residue was purified by FC (10% ethyl acetate in hexanes) to afford the title product (1.9 g) as an oil.

NMR (CDCl$_3$) δ: 1.66 (d, 3H), 5.98 (q, 1H), 7.2–7.4 (m, 5H), 8.30 (s, 1H).

Step B: Methyl 1-(SR)-4-(SR)-((RS and SR)-1-Phenyl-1-ethoxy)-2-(SR)-phenylcyclopentanoate To a solution of methyl 1-(SR)-4-(SR)-hydroxy-2-(SR)-phenylcyclopeantanoate (lower isomer from Example 1, Step C) (200 mg, 0.91 mmol) in methylene chloride (2 mL) at 0° C. under nitrogen was added (O-((R)-1-phenyl-1-ethyl))trichloroacetimidate (485 mg, 1.82 mmol) (Step A) in cyclohexane (2 mL) followed by a catalytic amount of TfOH in methylene chloride. The reaction was stirred at 0° C. for 1 h and was then diluted with methylene chloride and quenched into water. The layers were separated and the aq. layer was extracted with methylene chloride. The organic layers were each washed with brine, dried over sodium sulfate, combined and concentrated in vacuo. The residue was purified by FC using a gradient of 0 to 5% ethyl acetate in hexanes to give the title product (0.12 g) as an oil. There was no evidence for separation of isomers. NMR indicated a 1:1 mixture.

NMR (CDCl$_3$) δ: 1.43 (2d, 3H), 1.75–1.9 (m, 1H), 1.95–2.1 and 2.15–2.25 (2m, 1H), 2.25–2.4 (m, 2H), 2.7–2.9 (2 app. q, 1H), 3.59 and 3.64 (2s, 3H), 3.6–3.8 (m, 1H), 3.98 (m, 1H), 4,49 (app. p, 1H), 7.15–7.4 (m, 10H).

Step C: 1-((SR)-((RS)-1-Phenyl-1-ethoxy))-3-(SR)-hydroxymethyl-4-(SR)-phenylcyclopentane and 1-((SR)-((SR)-1-Phenyl-1-ethoxy))-3-(SR)-hydroxymethyl-4-(SR)-phenylcyclopentane (The absolute assignments were not made.)

Using essentially the same procedure as Example 1, Step E, the 1:1 mixture of methyl 1-(SR)-4-(SR)-((RS and SR)-1-phenyl-1-ethoxy)-2-(SR)-phenylcyclopentanoate (120 mg, 0.37 mmol) from Step B was converted to the title compounds which were separated by FC (5 to 10% ethyl acetate in hexanes) to give 2 racemic products (60 mg each).

Higher R$_f$: NMR (CDCl$_3$) δ: 1.44 (d, 3H), 1.6–1.8 (m, 2H), 2.1–2.25 (m, 2H), 2.25–2.4 (m, 1H), 3.15–3.3 (m, 1H), 3.55–3.7 (br dABq, 2H), 3.96 (m, 1H), 5.53 (q, 1H), 7.1–7.4 (m, 10H).

Lower R$_f$: NMR (CDCl$_3$) δ: 1.42 (d, 3H), 1.6–1.85 (m, 2H), 2.05–2.15 (m, 1H), 2.15–2.3 (m, 2H), 3.1–3.2 (dt, 1H), 3.62 (dABq, 2H), 3.99 (m, 1H), 4.51 (q, 1H), 7.1–7.4 (M, 10H).

Step D: 1-(SR)-4-((SR)-((RS)-1-Phenyl-1-ethoxy))-4-(SR)-phenylcyclopentane carboxaldehyde and 1-(SR)-4-((SR)-((SR)-1-Phenyl-1-ethoxy))-4-(SR)-phenylcyclopentane Carboxaldehyde Using essentially the same procedure as Example 1, Step F, each of the 1-((SR)-((RS)-1-phenyl-1-ethoxy))-3-(SR)-hydroxymethy-4-(SR)-phenylcyclopentane and 1-((SR)-((SR)-1-phenyl-1-ethoxy))-3-(SR)-hydroxymethyl-4-(SR)-phenylcyclopentane isomers (60 mg, 0.20 mmol) from Step C were converted to their respective title compounds which were purified by FC (10% ethyl acetate in hexanes) to give the respective higher and lower racemic aldehyde products (25 and 35 mg).

Step E: 1-(SR)-((RS)-(1-Phenyl-1-ethoxy))-3-(SR)-((4-phenylpiperidin-1-yl)methyl)-4-(SR)-phenylcyclopentane Hydrochloride Salt or 1-(SR)-((SR)-(1-Phenyl-1-ethoxy))-3-(SR)-((4-phenylpiperidin-1-yl)methyl)-4-(SR)-phenylcyclopentane Hydrochloride Salt Using essentially the same procedure as Example 1, Step G, the higher of the 1-(SR)-4-((SR)-((RS)-1-phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde isomers (11 mg, 0.037 mmol) from Step D was reacted with 4-phenylpiperidine to afford one of the title products (15 mg).

Higher R$_f$: MS (NH$_3$/Cl): m/z 440 (M+1).

EXAMPLE 9

1-(SR)-((RS)-(1-Phenyl-1-ethoxy))-3-(SR)-((4-phenylpiperidin-1-yl)methyl)-4-(SR)-phenylcyclopentane Hydrochloride Salt or 1-(SR)-((SR)-(1-Phenyl-1-ethoxy))-3-(SR)-((4-phenylpiperidin-1-yl)methyl)-4-(SR)-phenylcyclopentane Hydrochloride Salt (The Absolute Assignment was not Made.)

Using essentially the same procedure as Example 1, Step G, the lower of the 1-(SR)-4-((SR)-((RS)-1-phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde isomers (6 mg, 0.019 mmol) from Example 8, Step D was also r(acted with 4-phenylpiperidine to afford one of the title products (8 mg).

Lower R$_f$: MS (NH$_3$/Cl): m/z 440 (M+1).

EXAMPLE 10

1-(RS)-((RS)-(1-Phenyl-1-ethoxy))-3-(SR)-((4-phenylpiperidin-1-yl)methyl)-4-(SR)-phenylcyclopentane Hydrochloride Salt and 1-(RS)-((SR)-(1-phenyl-1-ethoxy))-3-(SR)-((4-phenylpiperidin-1-yl)methyl)-4-(SR)-phenylcyclopentane Hydrochloride Salt (The Isomers were not Separable and the Absolute Assignments were not Made.)

Using essentially the same procedure as Example 1, Step G, a mixture of 1-(SR)-4-((RS)-((RS)-1-phenyl-1-ethoxy))-4-(SR)-phenylclyclopentane carboxaldehyde and 1-(SR)-4-((RS)-((SR)-1-phenyl-1-ethoxy))-4-(SR)-phenylcyclopentane carboxaldehyde isomers (15 mg, 0.051 mmol) (prepared as in Example 8, Step B–D but starting with the higher alcohol isomer from Example 1, Step C) was reacted with 4-phenylpiperidine to afford a mixture of the title products (20 mg).

MS (NH$_3$/Cl): m/z 440 (M+1).

EXAMPLE 11

1-(RS)-(N-(Methyl)-N-(phenylsulfonyl)amino)-3-(SR)-((4-phenylpiperidin-1-yl)methyl)-4-(SR)-phenylcyclopentane Hydrochloride Salt Step A: Methyl 1-(SR)-4-((RS and SR)-(N-Methyl)amino)-2-(SR)-phenylcyclopentanoate To a solution of methyl (+−)-trans-4-oxo-2-phenylcyclopentanoate (0.30 g, 1.4 mmol) from Example 1, Step B in 1,2-dichloroethane (5 mL) was added methylamine hydrochloride (185 mg, 2.8 mmol) and DIPEA (0.50 mL, 2.8 mmol). After 10 min, sodium triacetoxyborohydride (600 mg, 2.8 mmol) was added. The reaction was stirred at RT for 2 h before being quenched with dilute aq. sodium carbonate solution and extracted twice with methylene chloride. The organic layers were washed with brine, dried over sodium sulfate, combined and concentrated. The crude solution of the title C-4 isomers was used directly in subsequent reactions.

Step B: Methyl 1-(SR)-4-(RS and SR)-(N-(Methyl)-N-(phenylsulfonyl)amino)-2-(SR)-phenylcyclopentanoate To ½ of the crude methyl 1-(SR)-4-((RS and SR)-(N-methyl)amino)-2-(SR)-phenylcyclopentanoate mixture (assumed 0.7 mmol) from Step A in methylene chloride (3 mL) was added benzenesulfonyl chloride (250 mg, 1.4 mmol) and DIPEA (0.365 mL, 2.2 mmol). The reaction was stirred at RT for 16 h and was then quenched with dilute aq. HCl and extracted twice with methylene chloride. The organic layers were washed with brine, dried over sodium sulfate, combined and concentrated. The residue was purified by FC (20–40% ethyl acetate in hexanes) to afford a 1:2 mixture of the title isomers (215 mg).

NMR (CDCl$_3$) δ: 1.7–2.2 (m, 4H), 2.7–2.9 (m, 1H), 2.78 and 2.82 (2s (1:2), 3H), 3.24 and 3.32 (ddd and q (1:2), 1H), 3.54 and 3.56 (2s (2:1), 3H), 4.63 and 4.74 (2m (1:2), 1H), 7.1–7.3 (m, 5H), 7.45–7.6 (m, 3H), 7.79 (2d, 2H). MS (NH$_3$/ESI): m/z 374 (M+1), 391 (100%, M+1+17).

Step C: 1-(RS)-(N-(Methyl)-N-(phenylsulfonyl)amino)-3-(SR)-(hydroxymethyl)-4-(SR)-phenylcyclopentane (Higher R$_f$ isomer) and 1-(SR)-(N-(Methyl)-N-(Phenylsulfonyl)amino)-3-(SR)-(hydroxymethyl)-4-(SR)-phenylcyclopentane (Lower R$_f$ isomer)

To a solution of methyl 1-(SR)-4-(RS and SR)-(N-(methyl)-N-(phenylsulfonyl)amino)-2-(SR)-phenylcyclopentanoate (200 mg, 0.54 mmol) from Step B in THF (10 mL) under nitrogen was added 2M lithium borohydride in THF (0.27 mL, 0.54 mmol). The reaction was stirred at RT for 16 h and then an additional aliquot of 2M lithium borohydride was added. After 4 h at 60° C., TLC indicated that the reaction was complete. The reaction was quenched into dilute aq. HCl and was extracted twice with ether. The organic layers were each washed with brine, dried over sodium sulfate and concentrated in vacuo. The residue was purified by FC using a gradient of 25 to 40%, ethyl acetate in hexanes to give separation of the title products (66 mg and 120 mg).

Higher: NMR (CDCl$_3$) δ: 1.44 (br s, 1H), 1.65–1.85 (m, 3H), 1.9–2.0 (m, 1H), 2.1–2.2 (m, 1H), 2.66 (ddd, 1H), 2.81 (s, 3H), 3.46 (dABq, 2H), 4.53 (m, 1H), 7.1–7.2 (m, 3H), 7.2–7.3 (m, 2H), 7.45–7.55 (m, 3H), 7.80 (m, 2H).

Lower: NMR (CDCl$_3$) δ: 1.38 (br s, 1H), 1.55 (q, 1H), 1.8–1.9 (m, 2H), 1.9–2.1 (m, 2H), 2.85–2.95 (s and m, 4H), 3.48 (dAbq, 2H), 4.71 (m, 1H), 7.1–7.2 (m, 3H), 7.2–7.3 (m, 2H), 7.45–7.55 (m, 3H), 7.79 (m, 2H).

Step D: 1-(RS)-(N-(Methyl)-N-(phenylsulfonyl)amino)-3-(SR)-(formyl)-4-(SR)phenylcyclopentane (Higher R$_f$ isomer)

To a solution of oxalyl chloride (0.045 mL, 0.50 mmol) in methylene chloride (2 mL) at −70° C. was added dropwise DMSO (0.045 mL, 1.0 mmol). After 15 min, a solution of 1-(RS)-(N-(methyl)-N-(phenylsulfonyl)amino)-3-(SR)-(hydroxymethyl)-4-(SR)-phenylcyclopentane (Higher R$_f$ isomer from Step C) (65 mg, 0.2 mmol) in methylene chloride (2 mL) was added. The reaction was stirred at −70° C. for 1.5 h and then DIPEA (0.35 mL, 2.0 mmol) was added. After a further 10 min, the mixture was allowed to warm to RT for 1 h and was then diluted with methylene chloride and poured into dilute aq. HCl and the layers were separated. The aq. layer was reextracted with a second portion of methylene chloride and the organic layers were each washed with brine, dried over sodium sulfate, combined and concentrated in vacuo. The residue was purified by FC using a gradient of 20 to 30% ethyl acetate in hexanes to give the title product (57 mg) as an oil.

NMR (CDCl$_3$) δ: 1.75–1.85 (m, 2H), 2.05–2.2 (m, 2H), 2.81 (s, 3H), 2.8–2.95 (m, 1H), 3.2–3.3 (m, 1H), 4.4–4.5 (m, 1H), 7.1–7.35 (m, 5H), 7.45–7.6 (m, 3H), 7.81 (m, 2H).

Step E: 1-((RS)-(N-(Methyl)-N-(phenylsulfonyl)amino)-3-(SR)-(4-phenylpiperidin-1-yl)methyl)-4-(SR)-phenylcyclopentane Hydrochloride Salt To a solution of 1-(RS)-(N-(methyl)-N-(phenylsulfonyl)amino)-3-(SR)-(formyl)-4-(SR)-phenylcyclopentane (from Step D, derived from Higher R$_f$ isomer in Step C) (10 mg, 0.029 mmol) (from Step F) in 1,2-dichloroethane (1 mL) was added 4-phenylpiperidine hydrochloride (12 mg, 0.058 mmol) and DIPEA (0.010 mL, 0.058 mmol). After 15 min, sodium triacetoxyborohydride (19 mg, 0.087 mmol) was added and the reaction was stirred at RT for 4–16 h. The reaction was evaporated under nitrogen, quenched with aq. sodium carbonate and extracted 3 times with ethyl acetate. The organic layers were each washed with brine, dried over sodium sulfate, combined and concentrated in vacuo. The residue was purified by Prep TLC eluting with 2–5% methanol in methylene chloride to give the title product as the free amine. The hydrochloride salt was prepared by taking up the free amine in ether, addition of excess 1M hydrogen chloride in ether and evaporation to dryness to afford the title compound usually as a white solid (10 mg).

NMR (CDCl$_3$) (free amine) δ: 1.5–1.8 (m, 7H), 1.8–2.0 (m, 4H), 2.1–2.3 (m, 3H), 2.3–2.45 (1H), 2.5–2.7 (m, 1H), 2.7–2.9 (m, 2H), 2.78 and 2.81 (2s, 3H), 4.51 and 4.67 (2p, 1H), 7.1–7.2 (m, 6H), 7.2–7.3 (m, 4H), 7.4–7.6 (m, 3H), 7.8 (m, 2H). MS (NH$_3$/ESI): m/z 489 (M+1).

EXAMPLE 12

1-(SR)-(N-(Methyl)-N-(phenylsulfonyl)amino)-3-(SR)-((4-phenylpiperidin-1-yl)methyl)-4-(SR)-phenylcyclopentane Hydrochloride Salt Using essentially the same procedures as in Example 11, Step D–E but substituting the lower R$_f$ product from Example 11, Step C, the title compound was prepared.

MS (NH$_3$/ESI): m/z 489 (M+1).

EXAMPLE 13

1-(RS)-(N-(Methyl)-N-(phenylcarbonyl)amino)-3-(SR)-((4-phenylpiperidin-1-yl)methyl)-4-(SR)-phenylcyclopentane Hydrochloride Salt Using essentially the same procedures as in Example 11, Steps B–E but substituting benzoyl chloride in Step B, the title compound was prepared.

MS (NH$_3$/ESI): m/z 453 (M+1).

EXAMPLE 14

1-(SR)-(N-(Methyl)-N-(phenylcarbonyl)amino)-3-(SR)-((4-phenylpiperidin-1-yl)methyl)-4-(SR)-phenylcyclopentane Hydrochloride Salt Using essentially the same procedures as in Example 11, Steps B–E but substituting the lower R$_f$ product from Example 11, Step C and benzoyl chloride in Step B, the title compound was prepared.

MS (NH$_3$/ESI): m/z 453 (M+1).

EXAMPLE 15

1-(RS)-(N-(Methyl)-N-(phenylcarbonyl)amino)-3-(SR)-((3-phenylpiperidin-1-yl)methyl)-4-(SR)-phenylcyclopentane Hydrochloride Salt Using essentially the same procedures as in Example 11, Steps B–E but substituting benzoyl chloride in Step B and 3-phenylpiperidine in Step E, the title compound was prepared.

MS (NH$_3$/ESI): m/z 453 (M+1).

EXAMPLE 16

1-(RS)-(N-(Methyl)-N-(phenylcarbonyl)amino)-3-(SR)-((4-benzylpiperidin-1-yl)methyl)-4-(SR)-phenylcyclopentane Hydrochloride Salt Using essentially the same procedures as in Example 11, Steps B–E but substituting benzoyl chloride in Step B and 3-benzylpiperidine in Step E, the title compound was prepared.

MS (NH$_3$/ESI): m/z 467 (M+1).

EXAMPLE 17

1-(RS)-(N-(Methyl)-N-(phenylcarbonyl)amino)-3-(SR)-((4-(3-phenylprop-1-yl)piperidin-1-yl)methyl)-4-(SR)-phenylcyclopentane Hydrochloride Salt Using essentially the same procedures as in Example 11, Steps B–E but substituting benzoyl chloride in Step B and 4-(3-phenylprop-1-yl)piperidine in Step E, the title compound was prepared.

MS (NH$_3$/ESI): m/z 495 (M+1).

EXAMPLE 18

1-(RS)-(N-(Methyl)-N-(phenylcarbonyl)amino)-3-(SR)-((4-(hydroxy)-4-(3-phenylprop-1-yl)piperidin-1-yl)methyl)-4-(SR)-phenylcyclopentane Hydrochloride Salt Using essentially the same procedures as in Example 11, Steps B–E but substituting benzoyl chloride in Step B and 4-hydroxy-4-(3-phenylprop-1-yl)piperidine in Step E, the title compound was; prepared.

MS (NH$_3$/ESI): m/z 511 (M+1).

EXAMPLE 19

1-(SR)-(N-(Methyl)-N-(phenylcarbonyl)amino)-3-(SR)-((4-(3-phenylprop-1-yl)piperidin-1-yl)methyl)-4-(SR)-phenylcyclopentane Hydrochloride Salt Using essentially the same procedures as in Example 11, Steps B–E but substituting the lower R$_f$ product from Example 11, Step C, benzoyl chloride in Step B and 4-(3-phenylprop-1-yl)piperidine in Step E, the title compound could be prepared.

EXAMPLE 20

1-(SR)-(Benzyloxycarbonylamino)-3-(SR)-((4-(3-phenylprop-1-yl)piperidin-1-yl)methyl)-4-(SR)-phenylcyclopentane Step A: Methyl (+−)-trans-4-methylene-2-phenylcyclopentanoate A mixture of methyl trans-cinnamate (5.0 g, 31 mmol), tetrakis(triphenylphosphine) palladium(0) (2.6 g, 2.3 mmol), 1,2-bis(diphenylphosphino)ethane (0.70 g, 1.8 mmol) and 2-((trimethylsilyl)methyl)-2-propen-1-yl acetate (6.90 g, 37 mmol) in THF (60 mL) under argon was heated to reflux for 4 h. An additional aliquot of 2-((trimethylsilyl)methyl)-2-propen-1-yl acetate (3.40 g was added and the reaction was continued for another 16 h. The volatiles were then removed in vacuo and the residue was purified by FC (10% ethyl acetate in hexanes) to afford the title compound (6.2 g).

NMR (CDCl$_3$) δ: 2.52 (m, 1H), 2.68 (m, 1H), 2.75–2.9 (m, 2H), 2.95 (ddd, 1H), 3.45 (ddd, 1H), 3.57 (s, 3H), 4.92 (m, 2H), 7.15–7.3 (m, 5H).

Step B: (+−)-trans-1-Hydroxymethyl-4-methylene-2-phenylcyclopentane

To a solution of methyl (+−)-trans-4-methylene-2-phenylcyclopentanoate (26.0 g, 128 mmol) prepared as in Step A in THF (600 mL) under nitrogen and cooled to −10° C. was added dropwise over 15 min 1M lithium aluminum hydride (LAH) in THF (193 mL). After 1 h, the bath was removed and the reaction was stirred at RT for 16 h. The reaction was cooled in an ice/methanol bath and the excess LAH was quenched by dropwise addition of acetone. The reaction was then poured into dilute aq. HCl. The mixture was extracted twice with ether and the organic layers were washed with brine, dried over sodium sulfate, combined and concentrated. The residue was purified by FC (20–30% ethyl acetate in hexanes) to afford the title product (23.8 g).

Step C: (+−)-trans-1-Hydroxymethyl-4-oxo-2-phonylcyclopentane

Into a solution of (+−)-trans-1-hydroxymethyl-4-methylene-2-phenylcyclopentane from Step B (22.7 g, 121 mmol) in methanol (300 mL) cooled in a dry ice/acetone bath was bubbled ozone until the blue color persisted. The excess ozone was removed with a stream of nitrogen and then dimethylsulfide (25 mL) was added. After 30 min, the bath was removed and the reaction was allowed to warm to RT over 16 h. The volatiles were removed in vacuo and the residue was purified by FC (15–30% ethyl acetate in hexanes) to give the title compound (22.1 g).

NMR (CDCl$_3$) δ: 2.2–2.5 (m, 4H), 2.71 (dd, 1H), 3.28 (m, 1H), 3.55 (dABq, 2H), 7.23 (m, 3H), 7.34 (m, 2H).

Step D: 1-(SR)-Benzylamino-3-(SR)-hydroxymethyl-4-(SR)-phenylcyclopentane and 1-(RS)-benzylamino-3-(SR)-hydroxymethyl-4-(SR)-phenylcyclopentane To a solution of (+−)-trans-1-hydroxymethyl-4-oxo-2-phenylcyclopentane from Step C (9.8 g, 52 mmol) in 1,2-dichloroethane (200 mL) was added benzylamine (11.3 mL, 103 mmol) and acetic acid (6.2 mL, 103 mmol). After 10 min, sodium triacetoxyborobydride (33 g, 155 mmol) was added in portions and the reaction was, stirred at RT for 3 hr. The reaction was quenched into dilute aq. sodium carbonate and the mixture was extracted twice with ethyl acetate. The organic layers were washed with brine, dried over sodium sulfate, combined and concentrated. The residue was purified by FC (1–5% methanol in ether) to obtain the title products (13.1 g) as a mixture of C-1 isomers.

Step E: 1-(SR)-Benzyloxycarbonylamino-3-(SR)-hydroxymethyl-4-(SR)-phenylcyclopentane (Higher R$_f$ isomer) and 1-(RS)-Benzyloxycarbonylamino-3-(SR)-hydroxymethyl-4-(SR)-phenylcyclopentane (Lower R$_f$ isomer)

To a solution of 1-(SR)-benzylamino-3-(SR)-hydroxymethyl-4-(SR)-phenylcyclopentane and 1-(RS)-benzylamino-3-(SR)-hydroxymethyl-4-(SR)-phenylcyclopentane (13 g, 46 mmol) from Step D was added 20% palladium hydroxide (2.5 g, 50% by wt water), ammonium formate (60 g, 930 mmol) and an additional 200 mL of methanol. The reaction was heated at 60° C. for 6 h. The reaction was filtered and concentrated. The residue was taken up in water and extracted twice with methylene chloride to remove any remaining benzylamine intermediate. The aqueous layer was made basic with 2N sodium hydroxide and extracted twice with methylene chloride. The organic layers were washed with brine, dried over sodium sulfate, combined and concentrated to afford 8.1 g of crude amino-alcohol.

The above product (8.1 g, 42 mmol) was taken up in methylene chloride (200 mL), cooled in an ice bath and DIPEA (22 mL, 126 mmol) and benzyl chloroformate (6.33 mL, 44 mmol) were added. After 2.5 h at RT, the reaction was poured into dilute aq. HCl and extracted twice with methylene chloride. The organic layers were washed with brine, dried over sodium sulfate, combined and concentrated. The residue was purified by Prep LC (30–75% ethyl acetate in hexanes) to afford the title compounds (4.0 g higher, 6.6 g lower).

Step F: 1-(SR)-Benzyloxycarbonylamino-3-(SR)-formyl-4-(SR)-phenylcyclopentane (Higher $R_f$ isomer) and 1-(SS)-Benzyloxycarbonylamino-3-(SR)-formyl-4-(SR)-phenylcyclopentane (Lower $R_f$ isomer)

To a solution of oxalyl chloride (0.350 mL, 3.85 mmol) in methylene chloride (10 mL) at –70° C. was added dropwise DMSO (0.550 mL, 7.65 mmol). After 15 min, a solution of 1-(SR)-benzyloxycaibonylamino-3-(SR)-hydroxymethyl-4-(SR)-phenylcyclopentane (Higher $R_f$ isomer from Step E) (500 mg, 1.53 mmol) in methylene chloride (10 mL) was added. The reaction was stirred at –70° C. for 1 h and then DIPEA (2.7 mL, 15 mmol) in methylene chloride (5 mL) was added dropwise over 5 min. After a further 10 min, the mixture was allowed to warm to RT for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20–30% ethyl acetate in hexanes) to give the title product (465 mg) as an oil.

NMR (CDCl$_3$) δ: 1.9–2.0 (m, 1H, 2b-H), 2.05–2.15 (m, 2H, both 5-H's), 2.3–2.45 (m, 1H, 2a-H), 3.06 (q, 1H, 3-H), 3.47 (q, 1H, 4-H), 4.32 (br m, 1H, 1-H), 4.94 (br s, 1H, NH), 5.08 (s, 2H, CH$_2$O), 7.1–7.4 (m, 10H), 9.74 (s, 1H, COH). The assignment of cis stereochemistry between C-1 and C-3 and trans between C-1 and C-4 were confirmed bit 2-D NOESY NMR.

Using essentially the same procedure as above, material derived from the lower isomer from Step E (500 mg, 1.5 mmol) was also converted to the lower $R_f$ title compound (457 mg).

NMR (CDCl$_3$) δ: 1.71 (q, 1H, 5a-H), 1.8–1.95 (m, 1H, 2a-H), 2.48 (p, 1H, 2b-H), 2.5–2.6 (m, 1H, 5b-H), 3.0–3.1 (m, 1H, 3-H), 3.3–3.4 (m, 1H, 4-H), 4.0–4.2 (m, 1H, 1-H), 4.82 (br s, 1H, NH), 5.08 (s, 2H, OCH$_2$), 7.2–7.4 (m, 10H), 9.63 (d, 1H, COH). The assignment of trans stereochemistry between C-1 and C-3 and cis between C-1 and C-4 were confirm ed by 2-D NOESY NMR.

Step G: 1(SR)-(Benzyloxycarbonylamino)-3-(SR)-((4-(3-phenylprop-1-yl)piperidin-1-yl)methyl)-4-(SR)-phenylcyclopentane (Higher $R_f$ isomer)

To a solution of 1-((SR)-(benzyloxycarbonylamino)-3-(SR)-(formyl)-4-(SR)-phenylcyclopentane (from Step F, derived from Higher $R_f$ isomer in Step D) (450 mg, 0.1.4 mmol) in 1,2-dichloroethane (10 mL) was added 4-(3-phenylprop-1-yl)piperidine (424 mg, 2.1 mmol) and acetic acid (0.125 mL, 2.1 mmol). After 15 min, sodium triacetoxyborohydride (890 mg, 4.2 mmol) was added in portions over 30 min and the reaction was stirred at RT for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC (30–40% ethyl acetate in hexanes) to give the title product (698 mg) as the free amine.

MS (NH$_3$/ESI): m/z 511 (M +1).

EXAMPLE 21

1-(SR)-(Benzyloxycarbonylamino)-3-(SR)-((4-(3-(4-fluorophenyl)prop-1-yl)piperidin-1-yl)methyl)-4-(SR)-phenylcyclopentane (Higher $R_f$ isomer)

Using essentially the same procedure as Example 20, Step G, material derived from the higher isomer from Step E–F could also converted to the title compound.

EXAMPLE 22

1-(SR)-(Phenylcarbonylamino)-3-(SR)-((4-(3-(phenylprop-1-yl)piperidin-1-yl)methyl)-4-(SR)-phenylcyclopentane (Higher $R_f$ isomer)

Step A: 1-(SR)-(Amino)-3-(SR)-((4-(3-phenylprop-1-yl)piperidin-1-yl)methyl)-4-(SR)-phenylcyclopentane (Higher $R_f$ isomer)

A solution of 1-(SR)-(benzyloxycarbonylamino)-3-(SR)-((4-(3-phenylprop-1-yl)piperidin-1-yl)methyl)-4-(SR)-phenylcyclopeantane (Higher $R_f$ isomer from Example 20, Step G) (500 mg, 1.0 mmol) in methanol (10 mL) was hydrogenated over 10% palladium on carbon at 40 psi for 2 h. The catalyst was filtered off and the reaction was concentrated to give the title compound (350 mg) as an oil.

Step B: 1-(SR)-(Phenylcarbonylamino)-3-(SR)-((4-(3-(phenylprop-1-yl)piperidin-1-yl)methyl)-4-(SR)-phenylcyclopentane (Higher $R_f$ isomer)

To a solution of 1-(SR)-(amino)-3-(SR)-((4-(3-phenylprop-1-yl)piperidin-1-yl)methyl)-4-(SR)-phenylcyclopentane (Higher $R_f$ isomer from Step A) (25 mg, 0.067 mmol) in methylene chloride (2 mL) was added DIPEA (0.025 mL, 0.13 mmol) and benzoyl chloride (0.014 mL, 0.10 mmol). The reaction was stirred at RT for 2 h and methanol (0.25 mL) was added. After 15 min, the reaction was diluted with ethyl acetate and aq. sodium carbonate. The layers were separated and the aqueous layer was reextracted twice with eithyl acetate. The organic layers were each washed with brine, dried over sodium sulfate, combined and concentrated. The residue was purified by Prep TLC (50% ethyl acetate in hexanes) to give the title compound (30 mg).

MS (NH$_3$/ESI): m/z 481 (M+1).

EXAMPLE 23

1-(RS)-(Benzyloxycarbonylamino)-3-(SR)-((4-(3-phenylprop-1-yl)piperidin-1-yl)methyl)-4-(SR)-phenylcyclopentane (Lower $R_f$ isomer)

Using essentially the same procedure as Example 20, Step G, material derived from the lower isomer from Example 20, Step E–F (450 mg, 1.4 mmol) was also converted to the title compound (600 mg).

MS (NH$_3$/ESI): m/z 511 (M+1).

EXAMPLE 24

1-(RS)-(Benzyloxycarbonylamino)-3-(SR)-((4-(3-(4-fluorophenyl)prop-1-yl)piperidin-1-yl)methyl)-4-(SR)-phenylcyclopentane (Lower $R_f$ isomer)

Using essentially the same procedure as Example 20, Step G, material derived from the lower isomer from Example 20, Step E–F could also converted to the title compound.

EXAMPLE 25

1-(RS)-(Benzyloxycarbonylamino)-3-(SR)-((4-(3-phenylprop-1-yl)piperidin-1-yl)methyl)-4-(SR)-phenylcyclopentane (Lower $R_f$ isomer)

Using essentially the same procedure as Example 22, material derived from the lower isomer from Example 20, Step E–G was also converted to the title compound (30 mg).

MS (NH$_3$/ESI): m/z 481 (M+1).

EXAMPLE 26

1-(R)-(N-(Metltyl)-N-(t-butoxycarbonyl)amino)-3-(S)-((4-(3-(4-fluorophenyl)prop-1-yl)piperidin-1-yl)methyl)-4-(S)-phenylcyclopeantane Step A: (+−)-trans-4-Methylene-2-phenylcyclopentanoic acid To a solution of methyl (+−)-trans-4-methylene-2-phenylcyclopentanoate prepared as in Example 20, Step A (28.4 g, 131 mmol) in methanol (400 mL) was added 5N sodium hydroxide (131 mL, 656 mmol). The reaction was heated at 65° C. for 1 h then cooled and concentrated. The residue was taken up diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+)-trans-4-Methylene-2-phenylcyclopentanoic Acid, (S)-(−)-a-Methylbenzylamine salt and (−)-trans-4-methylene-2-phenylcyclopentanoic Acid, (R)-(+)-a-methylbenzylamine Salt The crude (+−)-trans-4-methylene-2-phenylcyclopentanoic acid from Step A (assumed 131 mmol) was taken up in 2-propanol (400 mL), warmed to 80° C. and treated with (S)-(−)-a-methylbenzylamine (8.45 mL, 66 mmol). The mixture was stirred while allowed to cool to RT over 16 h and was then cooled to −10° C. for 1 h. The salt was filtered, washed with a small amount of ether to remove 2-propanol and air dried to give 6.442 g of salt. This was recrystallized from 2-propanol to give the title salt (4.713 g), $[\alpha]_D$=+56 (MeOH, c=0.20).

The combined mother liquors from above were concentrated and the residue taken up in water, acidified with 2M hydrochloric acid and extracted twice with methylene chloride. The organic layers were each washed with brine, dried over sodium sulfate, combined and concentrated in vacuo. The residue was taken up in 2-propanol (400 mL), warmed to 80° C. and treated with (R)-(+)-a-methylbenzylamine (9.1 mL, 70 mmol). The mixture was stirred while allowed to cool to RT over 16 h and was then cooled to −10° C. for 1 h. The salt was filtered, washed with a small amount of ether to remove 2-propanol and air dried to give 8.22 g of salt. This was recrystallized from 2-propanol to give the title salt (6.31 g), $[\alpha]_D$=−55 (MeOH, c=0.21).

Step C: (+and −)-trans-4-Methylene-2-phenylcyclopentanoic Acid

Method A:

The (+)-trans-4-methylene-2-phenylcyclopentanoic acid, (S)-(−)-a-methylbenzylamine salt from Step B (4.7 g) was suspended in methylene chloride and water and acidified with 2M hydrochloric acid and extracted twice with methylene chloride. The organic layers were each washed with brine, dried over sodium sulfate, combined and concentrated in vacuo to give the title (+) acid (3.1 g), $[\alpha]_D$=+101 (MeOH, c=0.135).

Similarly, the (−)-trans-4-methylene-2-phenylcyclopentanoic acid, (R)-(+)-a-methylbenzylamine salt (6.3 g) was converted to the free (−)-title acid (4.23 g), $[\alpha]_D$=−103 (MeOH, c=0.23).

Method B:

Step B1: 1-(S)-(((S)-(−)-4-Benzyl-2-oxazolidin-1-yl)carbonyl)-3-methylene-2-(S)-phenylcyclopentane (higher $R_f$) and 1-(R)-(((S)-(−)-4-Benzyl-2-oxazolidin-1-yl)carbonyl)-3-methylene-2-(R)-phenylcyclopentane (lower $R_f$)

A solution of (+−)-trans-4-methylene-2-phenylcyclopentanoic acid (47.5 g, 235 mmol) in ether (1L) and TEA (36 mL, 260 mmol) was cooled to −10° C. Trimethylacetyl chloride (31.8 mL, 260 mmol) was then added slowly and after stirring at −10° C. for 10 min, the reaction was allowed to warm to 10° C. over 1 h. The reaction was then recooled to −60° C.

To the above solution at −60° C. was added via a canula a solution of (S)-(−)-4-benzyl-2-oxazolidinone (45.8 g, 260 mmol) in THF (500 mL) which had been treated at −50° C. with 2.5 M n-butyl lithium (103 mL, 257 mmol) and aged at −50° C. for 45 min. The reaction was allowed to warm to rt over 16 h. The reaction was diluted with either (1L) and quenched with sat'd aqueous ammonium chloride (1L). The layers were separated and the aqueous layer was reextracted with a second portion of ether. The organic layers were each washed twice with 2N hydrochloric acid, twice with 1N sodium hydroxide and brine, dried over sodium sulfate, combined and concentrated. The residue was purified by chromatography (20% ethyl acetate in hexanes) to give the two diastereomeric products, higher $R_f$ (18.4 g) and lower $R_f$ (17.7 g).

Step B2: (+)-trans-4-Methylene-2-phenylcyclopentanoic Acid

A solution of 1-(S)-(((S)-(−)-4-benzyl-2-oxazolidin-1-yl)carbonyl)-3-methylene-2-(S)-phenylcyclopentane (higher $R_f$ product from Step B1) (20.9 g, 58 mmol) in a 3:1 mixture of THF: water (1L) was cooled to 5° C. Hydrogen peroxide (30%, 39.5 mL, 350 mmol) and lithium hydroxide (4.85 g, 106 mmol) were added and the reaction was stirred for 3.5 h. The excess peroxide was quenched by dropwise addition of sodium sulfite (60 g) in water (1L) over 1.5 h while maintaining the temperature below 5° C. After stirring for 2 additional hours, most of the THF was removed in vacuo and the aqueous layer was washed 3 times with methylene chloride. The aqueous layer was acidified to pH=2 with conc. HCl and reextracted twice with methylene chloride. The organic layers were washed with brine, dried and concentrated to give the (+) title product, $[\alpha]_D$=+100.5 (MeOH, c=0.207).

Step D: (+and −)-trans-1-Hydroxymethyl-4-methylene-2-phenylcyclopentane

A solution of (+)-trans-4-methylene-2-phenylcyclopentanoic acid from Step C (4.15 g, 20.5 mmol) in THF (100 mL) under nitrogen was cooled to −7° C. and 1M LAH in THF (31 mL, 31 mmol) was added dropwise over 15. The reaction was allowed to warm to RT over 16 h. The excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title (+) product (3.93 g), $[\alpha]_D$=+50 (MeOH, c=0.20).

Similarly, the (−)-trans-4-methylene-2-phenylcyclopentanoic acid from Step C (4.23 g) was converted to the title (−) alcohol (3.75 g), $[\alpha]_D$=−51 (MeOH, c=0.2).

Step E: (+and −)-trans-1-Trimethylsilyloxymethyl-4-oxo-2-phenylcyclopentane

Using essentially the same procedure as in Example 20, Step D but substituting the chiral (+)-trans-1-hydroxymethyl-4-methylene-2-phenylcyclopentane from Step D (3.93 g, 21 mmol), the title (+) compound (5.6 g) was prepared, $[\alpha]_D$=+42.3 (MeOH, c=0.18).

Similarly, (−)-trans-1-hydroxymethyl-4-methylene-2-phenylcyclopeantane from Step D (3.75 g) was converted to the title (−) alcohol (5.5 g), $[\alpha]_D$=−44.4 (MeOH, c=0.18).

Step F: (+and −)-trans-1-Hydroxymethyl-4-oxo-2-phenylcyclopentane

A solution of (+)-trans-1-trimethylsilyloxymethyl-4-methylene-2-phenylcyclopentane from Step E (4.6 g, 15 mmol) in methanol (100 mL) was cooled to −70° C. in a dry-ice acetone bath and ozone was bubbled through until a blue color persisted which was discharged with a stream of nitrogen. Dimethylsulfide (10 mL) was added and water 15 min, the reaction was allowed to warm to RT offer 16 h. Since by TLC (20% ethyl acetate in hexanes) indicated that there was significant loss of the silyl as well as dimethylketal formation, the methanol was mostly remove in vacuo.

The residue was diluted with water and treated with sulfuric acid (6 mL) and stirred for 2 h. The mixture was extracted twice with ethyl acetate and the organic layers were washed with brine (containing some sodium bicarbonate), dried over sodium sulfate, combined and concentrated. The residue was purified by FC (15–30% ethyl acetate in hexanes) to give the (+) title ketone/alcohol (2.87 g).

Similarly, (−)-trans-1-trimethylsilyloxymethyl-4-methylene-2-phenylcyclopentane from Step E (4.48 g) was converted to the title (−) ketone/alcohol (2.86 g).

Step G: 1-(R)-(N-(Methyl)-N-t-butylcarbonylamino)-3-(S)-(hydroxymethyl)-4-(S)-phenylcyclopentane (Higher $R_f$ isomer) and 1-(S)-(N-(Methyl)-N-t-butylcarbonylamino)-3-(S)-(hydroxymethyl)-4-(S)-phenylcyclopentane (Lower $R_f$ isomer)

Using essentially the same procedures as in Example 11, Steps A and B but starting with chiral (+)-trans-1-hydroxymethyl-4-oxo-2-phenylcyclopentane from Step F (1.19 g, 6.26 mmol) and using di-t-butyl dicarbonate in place of phenylsulfonyl chloride, the two chiral title C-1 isomeric products (260 mg higher, 215 mg lower, plus mix fractions) were obtained after FC (20% ethyl acetate in hexanes) and were the same as the racemic products from Example 15.

Step H: 1-([R)-(N-(Methyl)-N-(t-butoxycarbonyl)amino)-3-(S)-((4-(3-(4-fluorophenyl)prop-1-yl)piperidin-1-yl)methyl)-4-(S)-phenylcyclopentane Using essentially the same procedure as in Example 20, Steps F and G but starting with 1-(R)-(N-(Methyl)-N-t-butylcarbonylamino)-3-(S)-(hydroxymethyl)-4-(S)-phenylcyclopentane (Higher $R_f$ isomer) from Step G and using 4-(3-(4-fluorophenyl)prop-1-yl)piperidine hydrochloride (from Procedure 9), the title compound can be obtained.

EXAMPLE 27

1-(S)-(N-(Methyl)-N-(t-butoxycarbonyl) amino)-3-(R)-((4-(3-(4-fluorophenyl)prop-1-yl)piperidin-1-yl)methyl)-4-(R)-phenylcyclopentane Step A: 1-(S)-(N-(Methyl)-N-t-butylcarbonylamino)-3-(R)-(hydroxymethyl)-4-(R)-phenylcyclopentane (Higher $R_f$ isomer) and 1-(R)-(N-(Methyl)-N-t-butylcarbonylamino)-3-(R)-(hydroxymethyl)-4-(R)-phenylcyclopentane (Lower $R_f$ isomer) Similar to Example 26, Step G, (−)-trans-1-hydroxymethyl-4-oxo-2-phenylcyclopentane from Example 26, Step F (1.16 g, 6.1 mmol) was converted to the chiral title C-1 epimers (330 mg higher, 180 mg lower, plus mixed fractions).

Step B: 1-(S)-(N-(Methyl)-N-(t-butoxycarbonyl)amino)-3-(R)-((4-(3-(4-fluorophenyl)prop-1-yl)piperidin-1-yl)methyl)-4-(R)-phenylcyclopentane Similarly to Example 26, Step H, 1-(S)-(N-(methyl)-N-t-butylcarbonylaimino)-3-(R)-(hydroxymethyl)-4-(R)-phenylcyclopentane (Higher $R_f$ isomer from Example 27, Step A) can be converted to the chiral title enantiomer.

EXAMPLE 28

1-(S)-(N-(Methyl)-N-(t-butoxycarbonyl)amino)-3-(S)-((4-(3-(4-fluorophenyl)prop-1-yl)piperidin-1-yl)methyl)-4-(S)-phenylcyclopentane Using essentially the same procedures as in Example 26, Step G and H, the lower $R_f$ C-1 epimer from Example 26, Step G can be converted to the title compound.

EXAMPLE 29

1-(R)-(N-(Methyl)-N-(t-butoxycarbonyl)amino)-3-(R)-((4- (3-(4-fluorophenyl)prop-1-yl)piperidin-1-yl)methyl)-4-(R)-phenylcyclopentane Using essentially the same procedures as in Example 26, Step G and H, the lower $R_f$ C-1 epimer from Example 27, Step A can be converted to the title compound.

EXAMPLE 30

1-(S)-((t-Butoxcarbonyl)amino)-3-(S)-((4-(3-(4-fluorophenyl)prop-1-yl)piperidin-1-yl)methyl)-4-(S)-phenylcyclopentane Using essentially the same procedure as Example 20, Step E–H, starting with (+)-trans-1-hydroxymethyl-4-oxo-2-phenylcyclopentane from Example 26, Step F (1.19 g, 6.3 mmol) and using the higher $R_f$ Boc/alcohol epimer, the title compound can be prepared.

EXAMPLE 31

1-(R)-((t-Butoxycarbonyl)amino)-3-(S)-((4-(3-(4-fluorophenyl)prop-1-yl)piperidin-1-yl)methyl)-4-(S)-phenylcyclopentane Using essentially the same procedure as Example 20, Step E–H, (+)-trans-1-hydroxymethyl-4-oxo-2-phenylcyclopentane from Example 26, Step F (1.19 g, 6.3 mmol) and using the lower $R_f$ Boc/alcohol epimer, the title compound can be prepared.

EXAMPLE 32

1-(R)-(N-(Methyl)-N-(methylsulfonyl)amino)-3-(S)-((4-(3-(4-fluorophenyl)prop-1-yl)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(3-(4-fluorophenyl)prop-1-yl)piperidin-1-yl)methyl)-4-(S)-phenylcyclopentane from Example 26, Step H in Step A and methylsulfonyl chloride in Step B, the title compound can be prepared.

EXAMPLE 33

1-(S)-(N-(Methyl)-N-(methylsulfonyl) amino)-3-(S)-((4-(3-(4-fluorophenyl)prop-1-yl)piperidin-1-yl)methyl)-4-(S)-phenylcyclopentane Using essentially the same procedure as in Example 16, Step A and B but substituting 1-(S)-(N-(methyl)-N-(t- butoxycarbonyl)amino)-3-(S)-((4-(3-(4-fluorophenyl)prop-1-yl)piperidin-1-yl)methyl)-4-(S)-phenylcyclopentane from Example 28 in Step A and methylsulfonyl chloride in Step B, the title compound can be prepared.

EXAMPLE 34

1-(S)-((Methylsulfonyl)amino)-3-(S)-((4-(3-(4-fluorophenyl)prop-1-yl)piperidin-1-yl)methyl)-4-(S)-phenylcyclopentane Using essentially the same procedure as in Example 16, Step A and B but substituting 1-(S)-(N-(t-butoxycarbonyl)amino)-3-(S)-((4-(3-(4-fluorophenyl)prop-1-yl)piperidin-1-yl)methyl)-4-(S)-phenylcyclopentane from Example 30 in Step A and methylsulfonyl chloride in Step B, the title compound can be prepared.

EXAMPLE 35

1-(R)-((Methylsulfonyl)amino)-3-(S)-((4-(3-(4-fluorophenyl)prop-1-yl)piperidin-1-yl)methyl)-4-(S)-phenylcyclopentane Using essentially the same procedure as in Example 16, Step A and B but substituting 1-(R)-(N-(t-butoxycarbonyl)amino)-3-(S)-((4-(3-(4-fluorophenyl)prop-1-yl)piperidin-1-yl)methyl)-4-(S)-phenylcyclopentane from Example 31 in Step A arid methylsulfonyl chloride in Step B, the title compound can be prepared.

EXAMPLE 36

Using essentially the same procedures as in Examples 32–35, but substituting the appropriate benzoyl or sulfonyl chloride, the following compounds can be prepared.

- 1-(R)-(N-(Methyl)-N-(phenylsulfonyl)amino)-3-(S)-((4-(3-(4-fluorophenyl)prop-1-yl)piperidin-1-yl)methyl)-4-(S)-phenylcyclopentane
- 1-(S)-(N-(Methyl)-N-(phenylsulfonyl)amino)-3-(S)-((4-(3-(4-fluorophenyl)prop-1-yl)piperidin-1-yl)methyl)-4-(S)-phenylcyclopentane
- 1-(S)-((Phenylsulfonyl)amino)-3-(S)-((4-(3-(4-fluorophenyl)prop-1-yl)piperidin-1-yl)methyl)-4-(S)-phenylcyclopentane
- 1-(R)-((Phenylsulfonyl)amino)-3-(S)-((4-(3-(4-fluorophenyl)prop-1-yl)piperidin-1-yl)methyl)-4-(S)-phenylcyclopentane
- 1-(R)-(N-(Methyl)-N-(phenylcarbonyl)amino)-3-(S)-((4-(3-(4-fluorophenyl)prop-1-yl)piperidin-1-yl)methyl)-4-(S)-phenylcyclopentane
- 1-(S)-(N-(Methyl)-N-(phenylcarbonyl)amino)-3-(S)-((4-(3-(4-fluorophenyl)prop-1-yl)piperidin-1-yl)methyl)-4-(S)-phenylcyclopentane
- 1-(S)-((Phenylcarbonyl)amino)-3-(S)-((4-(3-(4-fluorophenyl)prop-1-yl)piperidin-1-yl)methyl)-4-(S)-phenylcyclopentane
- 1-(R)-((Phenylcarbonyl)amino)-3-(S)-((4-(3-(4-fluorophenyl)prop-1-yl)piperidin-1-yl)methyl)-4-(S)-phenylcyclopentane

EXAMPLE 37

Using essentially the same procedures as in Examples 32–35, but substituting the appropriate benzoyl or sulfonyl chloride and substituting 1-(R or S)-(N-(t-butoxycarbonyl)amino)-3-(S)-((4-((N-propyl)-(N-pyrimidin-2-yl)amino)piperidin-1-yl)methyl)-4-(S)-phenylcyclopentane, which can be prepared as in Examples 26, 28, 30 and 31, the following compounds can be prepared.

- 1-(R)-(N-(Methyl)-N-(phenylsulfonyl)amino)-3-(S)-((4-((N-propyl)-(N-pyrimidin-2-yl)amino)piperidin-1-yl)methyl)-4-(S)-phenylcyclopeantane
- 1-(S)-(N-(Methyl)-N-(phenylsulfonyl)amino)-3-(S)-((4-((N-propyl)-(N-pyrimidin-2-yl)amino)piperidin-1-yl)methyl)-4-(S)-phenylcyclopentane
- 1-(S)-((Phenylsulfonyl)amino)-3-(S)-((4-((N-propyl)-(N-pyrimidin-2-yl)amino)piperidin-1-yl)methyl)-4-(S)-phenylcyclopentane
- 1-(R)-((Phenylsulfonyl)amino)-3-(S)-((4-((N-propyl)-(N-pyrimidin-2-yl)amino)piperidin-1-yl)methyl)-4-(S)-phenylcyclopentane
- 1-(R)-(N-(Methyl)-N-(phenylcarbonyl)amino)-3-(S)-((4-((N-propyl)-(N-pyrimidin-2-yl)amino) piperidin-1-yl)methyl)-4-(S)-phenylcyclopentane
- 1-(S)-(N-(Methyl)-N-(phenylcarbonyl)amino)-3-(S)-((4-((N-propyl)-(N-pyrimidin-2-yl)amino)piperidin-1-yl)methyl)-4-(S)-phenylcyclopentane
- 1-(S)-((Phenylcarbonyl)amino)-3-(S)-((4-((N-propyl)-(N-pyrimidin-2-yl)amino)piperidin-1-yl)methyl)-4-(S)-phenylcyclopentane
- 1-(R)-((Phenylcarbonyl)amino)-3-(S)-((4-((N-propyl)-(N-pyrimidin-2-yl)amino)piperidin-1-yl)methyl)-4-(S)-phenylcyclopentane

EXAMPLE 38

Using essentially the same procedures as in Examples 32–35, but substituting the appropriate benzoyl or sulfonyl chloride and substituting 1-(R or S)-(N-(t-butoxycarbonyl)amino)-3-(S)-(4-(5-benzyl-2-ethylpyrazol-3-yl)piperidin-1-yl)methyl)-4-(S)-phenylcyclopentane, which can be prepared as in Examples 26, 28, 30 and 31, the Following compounds can be prepared.

- 1-(R)-(N-(Methyl)-N-(phenylsulfonyl)amino)-3-(S)-(4-(5-benzyl-2-ethylpyrazol-3-yl)piperidin-1-yl)methyl)-4-(S)-phenylcyclopentane
- 1-(S)-(N-(Methyl)-N-(phenylsulfonyl)amino)-3-(S)-(4-(5-benzyl-2-ethylpyrazol-3-yl)piperidin-1-yl)methyl)-4-(S)-phenylcyclopentane
- 1-(S)-((Phenylsulfonyl)amino)-3-(S)-(4-(5-benzyl-2-ethylpyrazol-3-yl)piperidin-1-yl)methyl)-4-(S)-phenylcyclopentane
- 1-(R)-((Phenylsulfonyl)amino)-3-(S)-(4-(5-benzyl-2-ethylpyrazol-3-yl)piperidin-1-yl)methyl)-4-(S)-phenylcyclopentane
- 1-(R)-(N-(Methyl)-N-(phenylcarbonyl)amino)-3-(S)-(4-(5-benzyl-2-ethylpyrazol-3-yl)piperidin-1-yl)methyl)-4-(S)-phenylcyclopentane
- 1-(S)-(N-(Methyl)-N-(phenylcarbonyl)amino)-3-(S)-(4-(5-benzyl-2-ethylpyrazol-3-yl)piperidin-1-yl)methyl)-4-(S)-phenylcyclopentane
- 1-(S)-((Phenylcarbonyl)amino)-3-(S)-(4-(5-benzyl-2-ethylpyrazol-3- yl)piperidin-1-yl)methyl)-4-(S)-phenylcyclopentane
- 1-(R)-((Phenylcarbonyl)amino)-3-(S)-(4-(5-benzyl-2-ethylpyrazol-3-yl)piperidin-1-yl)methyl)-4-(S)-phenylcyclopentane

EXAMPLE 39

1-(RS and SR)-(N-(Benzenesulfonyl)-N-(benzyl)amino)-3-(SR)-((4-hydroxy-4-(3-phenylprop-1-yl)piperidin-1-yl)methyl)-4-(SR)-phenylcyclopentane Hydrochloride Salt The following example illustrates the use of a 4-sulfamylbenzoyl AM resin (Novabiochem, cat #01-64-

0121) to prepare the title compound and is based on the procedures of G. W. Kenner, et al., *J. Chem. Soc., Chem. Comm.*, 1971, 636.

Step A: Loading of the Resin With (+−)-trans-4-oxo-2-phenylcyclopentanoic Acid

To a solution of (+−)-trans-4-oxo-2-phenylcyclopentanoic acid (2.35 g, 11.5 mmol) from Example 42, Step A and DMAP (70 mg, 0.57 mmol) in 1:1 methylene chloride: THF (23 mL) was added DIC (0.90 mL, 5.7 mmol). The reaction was aged at rt for 10 min and was then added to the resin (1.0 g, 1.15 mmol/g) which had been pre-treated with 1:1 methylene chloride:THF to swell the beads. DIPEA (1.0 mL, 5.7 mmol) was added and the reaction was gently mixed at rt for 3 h. The resin was filtered, washed with solvent and retreated with another aliquot of acid for 3 h. The resin was washed again and air dried before use in the next step.

Step B: Reductive Amination With Aniline.

A solution of benzylamine (0.054 mL, 0.57 mmol) and acetic acid (0.033 mL, 0.57 mmol) in methylene chloride (1 mL) was added to the resin (50 mg, 0.057 mmol) from Step A. Sodium triacetoxyborohydride (0.122 g, 0.57 mmol) was added and the reaction was gently mixed at rt for 16 h. The resin was then washed with solvent and used in the next step.

Step C: Sulfonylation with Benzenesulfonyl Chloride.

A solution of benzene sulfonyl chloride (0.051 mL, 0.4 mmol) in methylene chloride (1 mL) was added to the resin (50 mg, 0.057 mmol) from Step B. DIPEA (0.105 mL, 0.6 mmol) in methylene chloride (1 mL) was added and the reaction was gently mixed at rt for 16 h. The resin was then washed with solvent and used in the next step.

Step D: Activation and Cleavage From the Resin with an Amine. 1-(RS and SR)-(N-(Benzenesulfonyl)-N-(benzyl) amino)-3-(SR)-((4-hydroxy-4-(3-phenylprop-1-yl) piperidin-1-yl),carbonyl)-4-(SR)-phenylcyclopentane TFA Salt The resin from Step C (50 mg, 0.057 mmol) was treated twice with 1:1 2.0 M trimethylsilyldiazomethane in hexanes: THF (1 mL) for 2 h. The resin was washed with THF and then treated with 4-hydroxy-4-(3-phenylprop-1-yl) piperidine (25 mg, 0.11 mmol) in THF (1 mL) at rt for 16 h. The resin was filtered off, the solution was evaporated under nitrogen and the residue was taken up in 70% acetonitrile in water. The sample was purified on a Gilson Combinatorial Chromatography system using a 9.4 mm×25 cm Zorbax SB-C18 column with a 0.1% TFA acetonitrile/water gradient. The fractions were collected based on the UV absorption and analyzed by mass spec to identify the product fractions. These were combined and evaporated to afford the title compound (4.1 mg).

MS (NH$_3$/ESI): m/z 666 (M+1).

Step E: Reduction of the Amide with Borane-dimethyl Sulfide. 1-(RS and SR)-(N-(Benzenesulfonyl)-N-(benzyl) amino)-3-(SR)-((4-hydroxy-4-(3-phenylprop-1-yl) piperidin-1-yl)methyl)-4-(SR)-phenylcyclopentane Hydrochloride Salt A solution of 0.5 M borane-dimethyl sulfide in dioxane (0.25 mL) was added to the product of Step D and the reaction was heated at 50° C. for 3 h. The volatiles were removed in vacuo and the residue was taken up in a 1% HCl in methanol solution (1 mL). After 16 h at 50° C., HPLC/MS indicated that the reaction was complete and clean of impurities. The volatiles were removed in vacuo to give the title compound.

MS (NH$_3$/ESI): m/z 652 (M+1).

EXAMPLE 40

Using essentially the same procedure as in Example 39, but substituting methylamine in Step B and the appropriate substituted sulfonyl chloride in Step C, the following compounds 41A-K were prepared. The final products and penultimate amides were purified by HPLC and analyzed by HPLC/MS for purity and the correct molecular weights.

EXAMPLE 40A 1-(RS and SR)-(N-(Benzenesulfonyl)-N-(methyl) amino)-3-(SR)-((4-hydroxy-4-(3-phenylprop-1-yl) piperidin-1-yl)methyl)-4-(SR)-phenylcyclopentane

EXAMPLE 40B 1-(RS and SR)-(N-(1-Naphthylsulfonyl)-N-(methyl) amino)-3-(SR)-((4-hydroxy-4-(3-phenylprop-1-yl) piperidin-1-yl)methyl)-4-(SR)-phenylcyclopentane

EXAMPLE 40C 1-(RS and SR)-(N-(2-Naphthylsulfonyl)-N-(methyl) amino)-3-(SR)-((4-hydroxy-4-(3-phenylprop-1-yl) piperidin-1-yl)methyl)-4-(SR)-phenylcyclopentane

EXAMPLE 40D 1-(RS and SR) (N-(3-Chlorobenzenesulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 40E 1-(RS and SR)-(N-(4-Chlorobenzenesulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 40F 1-(RS and SR)-(N-(2-Chlorobenzenesulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 40G 1-(RS and SR)-(N-(2-(1-Naphthyl)ethylsulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 40H 1-(RS and SR)-(N-(4-t-Butylbenzenesulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 40I 1-(RS and SR)-(N-(4-Trifluoromethoxybenzenesulfonyl)-N-(methyl) amino)-3-(SR)-((4-hydroxy-4-(3-phenylprop-1-yl) piperidin-1-yl)methyl)-4-(SR)-phenylcyclopentane

EXAMPLE 40J 1-(RS and SR)-(N-(Methanesulfonyl)-N-(methyl) amino)-3-(SR)-((4-hydroxy-4-(3-phenylprop-1-yl) piperidin-1-yl)methyl)-4-(SR)-phenylcyclopentane

EXAMPLE 40K 1-(RS and SR)-(N-(3,4-Dichlorobenzenesulfonyl)-N-(methyl)amino)-3-(SR)-((4-hydroxy-4-(3-phenylprop-1-yl)piperidin-1-yl)methyl)-4-(SR)-phenylcyclopentane

EXAMPLE 41

Using essentially the same procedure as in Example 39, but substituting methylamine in Step B, the appropriate substituted sulfonyl chloride in Step C, and 4-phenylpiperidine in Step D, the following compounds 41A–K were prepared. The final products and penultimate amides were purified by HPLC and analyzed by HPLC/MS for purity and the correct molecular weights.

EXAMPLE 41A 1-(RS and SR)-(N-(Benzenesulfonyl)-N-(methyl) amino)-3-(SR)-((4-phenylpiperidin-1-yl)methyl)-4-(SR)-phenylcyclopentane

EXAMPLE 41B 1-(RS and SR)-(N-(1-Naphthylsulfonyl)-N-(methyl) amino)-3-(SR)-((4-phenylpiperidin-1-yl)methyl)-4-(SR)-phenylcyclopentane

EXAMPLE 41C 1-(RS and SR)-(N-(2-Naphthylsulfonyl)-N-(methyl) amino)-3-(SR)-((4-phenylpiperidin-1-yl)methyl)-4-(SR)-phenylcyclopentane

EXAMPLE 41D 1-(RS and SR)-(N-(3-Chlorobenzenesulfonyl)-N-(methyl)amino)-3-(SR)-((4-phenylpiperidin-1-yl) methyl)-4-(SR)-phenylcyclopentane

EXAMPLE 41E 1-(RS and SR)-(N-(4-Chlorobenzenesulfonyl)-N-(methyl)amino)-3-(SR)-((4-phenylpiperidin-1-yl) methyl)-4-(SR)-phenylcyclopentane

EXAMPLE 41F 1-(RS and SR)-(N-(2-Chlorobenzenesulfonyl)-N-(methyl)amino)-3-(SR)-((4-phenylpiperidin-1-yl) methyl)-4-(SR)-phenylcyclopentane

EXAMPLE 41G 1-(RS and SR)-(N-(2-(1-Naphthyl)ethylsulfonyl)-N-(methyl)amino)-3-(SR)-((4-phenylpiperidin-1-yl) methyl)-4-(SR)-phenylcyclopentane

EXAMPLE 41H 1-(RS and SR)-(N-(4-t-Butylbenzenesulfonyl)-N-(methyl)amino)-3-(SR)-((4-phenylpiperidin-1-yl) methyl)-4-(SR)-phenylcyclopentane

EXAMPLE 41I 1-(RS and SR)-(N-(4-Trifluoromethoxybenzenesulfonyl)-N-(methyl) amino)-3-(SR)-((4-phenylpiperidin-1-yl)methyl)-4-(SR)-phenylcyclopentane

EXAMPLE 41J 1-(RS and SR)-(N-(Methanesulfonyl)-N-(methyl) amino)-3-(SR)-((4-phenylpiperidin-1-yl)methyl)-4-(SR)-phenylcyclopentane

EXAMPLE 41K 1-(RS and SR)-(N-(3,4-Dichlorobenzenesulfonyl)-N-(methyl)amino)-3-(SR)-((4-phenylpiperidin-1-yl) methyl)-4-(SR)-phenylcyclopentane

EXAMPLE 42

1-(RS and SR)-(N-(Methyl)-N-(cyclohexyl)amino)-3-(SR)-((4-hydroxy-4-(3-phenylprop-1-yl)piperidin-1-yl)methyl)-4-(SR)-phenylcyclopentane TFA Salt
Step A: (+−)-trans4-oxo-2-Phenylcyclopentanoic Acid A solution of 1-(SR)-3-methylene-4-(SR)-phenylcyclopentanoic acid (84.8 g, 0.42 mol) from Example 20, Step B in methanol (2.5 L) was cooled to −70° C. in a dry-ice acetone bath. Ozone was bubbled through the solution until the blue color persisted. Excess ozone was removed with a stream of nitrogen and dimethyl sulfide (125 mL, 1.68 mol) was added. The mixture was then allowed to warm to rt over 16 h. Most of the methanol was removed in vacuo and the residue was taken up in ethyl acetate and washed twice with water and brine, dried over sodium sulfate and concentrated. The residue was triturated with hexanes and the solid was filtered and dried to afford the title compound (61.4 g).

Step B: 3-(SR)-((4-Hydroxy-4-(3-phenylprop-1-yl) piperidin-1-yl)(carbonyl)-4-(SR)-phenylcyclopentan-1-one To a solution of (+−)-trans-4-oxo-2-phenylcyclopentanoic acid (0.20 g, 0.1 mmol) and 4-hydroxy-4-(3-phenylprop-1-yl)piperidine (0.30 g, 0.12 mmol) in methylene chloride (12 mL) was added EDC (0.225 g, 0.12 mmol), DIPEA (0.205 mL, 0.12 mmol) and a cat. amount of DMAP. The reaction was stirred a rt for 2 h and was then diluted with methylene chloride and washed with 1N HCl, 1N NaOH and brine, dried over sodium sulfate and evaporated to dryness. The sample was essentially clean product by HPLC/MS.

Step C: 1-(RS and SR)-(N-(Methyl)-N-(cyclohexyl)amino)-3-(SR)-((4-hydroxy-4-(3-phenylprop-1-yl)piperidin-1-yl) carbonyl)-4-(SR)-phenylcyclopentane To a solution of 3-(SR)-((4-hydroxy-4-(3-phenylprop-1-yl)piperidin-1-yl)carbonyl)-4-(SR)-phenylcyclopentan-1-one (0.030 g, 0.067 mmol) from Step B and N-methylaminocyclohexane (0.076 mL, 0.67 mmol) in 1,2-dichloroethane (3 mL) was added acetic acid (0.038 mL, 0.67 mmol) and sodium triacetoxyborohydride (0.142 g, 0.67 mmol). The reaction was stirred at rt for 16 h and then diluted with methylene chloride and quenched with 1N NaOH. The mixture was washed with 1N NaOH, 1N HCl and brine, dried over sodium sulfate and evaporated to dryness. The sample was purified by HPLC and the fractions containing the title compound by HPLC/MS were combined and evaporated.

Step D: 1-(RS and SR)-(N-(Methyl)-N-(cyclohexyl)amino)-3-(SR)-((4-hydroxy-4-(3-phenylprop-1-yl)piperidin-1-yl) methyl)-4-(SR)-phenylcyclopentane TFA Salt A solution of 1-(RS and SR)-(N-(methyl)-N-(cyclohexyl) amino)-3-(SR)-((4-hydroxy-4-(3-phenylprop-1-yl) piperidin-1-yl)carbonyl)-4-(SR)-phenylcyclopentane obtained in Step C and 2M borane-dimethyl sulfide in THF (0.027 mL, 0.054 mmol) in dioxane (0.6 mL) was heated at 50° C. for 3 h. The volatiles were removed under a stream of nitrogen and the residue was taken up in 1% HCl in methanol (1 mL) and heated at 50° C. for 16 h. The volatiles were removed in vacuo to dryness. The residue was purified by HPLC during which the 2 diastereomers at C-1 were separated. The fractions containing the title compounds by HPLC/MS were combined and evaporated.

EXAMPLE 43

Using essentially the same procedure as in Example 42, but substituting a primary cycloalkylamine or substituted cycloalkylamine in Step C, the following C-1 amino compounds 43A–G can be prepared. The final products and penultimate amides were each purified by HPLC and analyzed by HPLC/MS for purity and the correct molecular weights. In these cases, the C-1 diastereomers were not separated.

EXAMPLE 43A 1-(RS and SR)-(Cyclohexylamino)-3-(SR)-((4-hydroxy-4-(3-phenylprop-1-yl)piperidin-1-yl)methyl)-4-(SR)-phenylcyclopentane

EXAMPLE 43B 1-(RS and SR)-(2-(Cyclohexyl)cyclohexylamino)-3-(SR)-((4-hydroxy-4-(3-phenylprop-1-yl)piperidin-1-yl)methyl)-4-(SR)-phenylcyclopentane

EXAMPLE 43C 1-(RS and SR)-(3,3,5-Trimethylcyclohexylamino)-3-(SR)-((4-hydroxy-4-(3-phenylprop-1-yl)piperidin-1-yl)methyl)-4-(SR)-phenylcyclopentane

EXAMPLE 43D 1-(RS and SR)-(4-t-Butylcyclohexylamino)-3-(SR)-((4-hydroxy-4-(3-phenylprop-1-yl)piperidin-1-yl)methyl)-4-(SR)-phenylcyclopentane

EXAMPLE 43E 1-(RS and SR)-(Cyclopentylamino)-3-(SR)-((4-hydroxy-4-(3-phenylprop-1-yl)piperidin-1-yl)methyl)-4-(SR)-phenylcyclopentane

EXAMPLE 43F 1-(RS and SR)-(Cyclopropylamino)-3-(SR)-((4-hydroxy-4-(3-phenylprop-1-yl)piperidin-1-yl)methyl)-4-(SR)-phenylcyclopentane

EXAMPLE 43G 1-(RS and SR)-(Cycloheptylamino)-3-(SR)-((4-hydroxy-4-(3-phenylprop-1-yl)piperidin-1-yl)methyl)-4-(SR)-phenylcyclopentane

EXAMPLE 44

1-(RS and SR)-(N-(Acetyl)-N-(cyclohexyl)amino)-3-(SR)-((4-hydroxy-4-(3-phenylprop-1-yl)piperidin-1-yl)methyl)-4-(SR)-phenylcyclopentane To a solution of 1-(RS and SR)-(cyclohexylamino)-3-(SR)-((4-hydroxy-4-(3-phenylprop-1-yl)piperidin-1-yl)methyl)-4-(SR)-phenylcyclopentane (prepared as in Example 43A) in methylene chloride (2 mL) was added acetic anhydride (0.17 mL, 1.67 mmol) and pyridine (0.17 mL, 2 mmol). The reaction was stirred at rt for 16 h. It was then diluted with methylene chloride and quenched with 1N NaOH. The mixture was washed with 1N NaOH and brine, dried over sodium sulfate and evaporated to dryness. The sample was purified by HPLC and the fractions containing the title compound by HPLC/MS were combined and evaporated.

EXAMPLE 45

Using essentially the same procedures as in Example 42 and 44, but substituting a cycloalkylamine or substituted cycloalkylamine in Example 42, Step C and acetic anhydride, Methanesulfonyl chloride or methyl chloroformate in Example 44, the following compounds 45A–I can be prepared. In the carbamate cases, the acylation reaction with methyl chloroformate could also be done prior to the borane-dimethyl sulfide reduction step. The final products and penultimate amides were each purified by HPLC and analyzed by HPLC/MS for purity and the correct molecular weights. In these cases, the C-1 diastereormers may not be separable under the above conditions.

EXAMPLE 45A 1-(RS and SR)-(N-(Methoxycarbonyl)-N-(cyclohexyl)amino)-3-(SR)-((4-hydroxy-4-(3-phenylprop-1-yl)piperidin-1-yl)methyl)-4-(SR)-phenylcyclopentane

EXAMPLE 45B 1-(RS and SR)-(N-(Methanesulfonyl)-N-(cyclohexyl)amino)-3-(SR)-((4-hydroxy-4-(3-phenylprop-1-yl)piperidin-1-yl)methyl)-4-(SR)-phenylcyclopeantane

EXAMPLE 45C 1-(RS and SR)-(N-(Acetyl)-N-(2-cyclohexylcyclohexyl)amino)-3-(SR)-((4-hydroxy-4-(3-phenylprop-1-yl)piperidin-1-yl)methyl)-4-(SR)-phenylcyclopentane

EXAMPLE 45D 1-(RS and SR)-(N-(Methoxycarbonyl)-N-(2-cyclohexylcyclohexyl)amino)-3-(SR)-((4-hydroxy-4-(3-phenylprop-1-yl)piperidin-1l-yl)methyl)-4-(SR)-phenylcyclopentane

EXAMPLE 45E 1-(RS and SR)-(N-(Acetyl)-N-(4-t-butylcyclohexyl)amino)-3-(SR)-((4-hydroxy-4-(3-phenylprop-1-yl)piperidin-1-yl)methyl)-4-(SR)-phenylcyclopentane

EXAMPLE 45F 1-(RS and SR)-(N-(Methanesulfonyl)-N-(4-phenylcyclohexyl)amino)-3-(SR)-((4-hydroxy-4-(3-phenylprop-1-yl)piperidin-1-yl)methyl)-4-(SR)-phenylcyclopentane

EXAMPLE 45G 1-(RS and SR)-(N-(Methanesulfonyl)-N-(cyclopropyl)amino)-3-(SR)-((4-hydroxy-4-(3-phenylprop-1-yl)piperidin-1-yl)methyl)-4-(SR)-phenylcyclopentane

EXAMPLE 45H 1-(RS and SR)-(N-(Methoxycarbonyl)-N-(cycloheptyl)amino)-3-(SR)-((4-hydroxy-4-(3-phenylprop-1-yl)piperidin-1-yl)methyl)-4-(SR)-phenylcyclopentane

EXAMPLE 45I 1-(RS and SR)-(N-(Methanesulfonyl)-N-(cyclopentyl)amino)-3-(SR)-((4-hydroxy-4-(3-phenylprop-1-yl)piperidin-1-yl)methyl)-4-(SR)-phenylcyclopentane

EXAMPLE 46

Using essentially the same procedure as in Example 42, but substituting a secondary cyclic amine in Step C, the following compounds 46A–C can be prepared after automated HPLC purification.

EXAMPLE 46A 1-(RS and SR)-(Decahydroquinolin-1-yl)-3-(SR)-
((4-(3-phenylprop-1-yl)piperidin-1-yl)methyl)-4-
(SR)-phenylcyclopentane

EXAMPLE 46B 1-(RS and SR)-(Duodecahydrocarbazol-1-yl)-3-
(SR)-((4-(3-phenylprop-1-yl)piperidin-1-yl)methyl)-
4-(SR)-phenylcyclopentane

EXAMPLE 46C 1-(RS and SR)-(1-Aza-2-methyl-6-hydroxy-[4.4.0]-
bicyclodecan-1-yl)-3-(SR)-((4-(3-phenylprop-1-yl)
piperidin-1-yl)methyl)-4-(SR)-phenylcyclopentane

EXAMPLE 47

1-(RS)-(N-(Benzoyl)-N-(methyl)amino)-3-(SR)-((4-
(3-phenylprop-1-yl)piperidin-1-yl)methyl)-4-(SR)-
phenylcyclopentane TFA Salt Step A: Methyl 1-(SR)-4-((RS and SR)-(N-methyl)amino)-2-(SR)-phenylcyclopentanoate Methyl (+−)-trans-4-oxo-2-phenylcyclopentanoate (6.4 g, 29.3 mmol) from Example 1, Step B, (or ozonolysis of methyl (+−)-trans-4-meyhylene-2-phenylcyclopentane from Example 20, Step A as in Example 42, Step A) methylamine (2M in tetrahydrofuran, 16.4 mL, 32.8 mmol) and acetic acid (1.87 mL, 32.7 mmol) were combined in 1,2-dichloroethane (150 mL). Sodium triacetoxyborohydride (6.95 g, 32.8 mmol) was added in one portion to the vigorously stirred solution. After 18 hours at ambient temperature, the suspension was diluted with dichloroethane (100 mL) and vigorously stirred as the pH was adjusted to pH10–11 with 1N NaOH. The layers were separated and the organic layers were washed twice with brine, dried over sodium sulfate and concentrated to afford the crude title compound (5.8 g) which was essentially the same as Example 11, Step A.

Step B: Methyl 1-(SR)-4-(RS and SR)-(N-(methyl)-N-(benzoyl)amino)-2-(SR)-phenylcyclopentanoate Methyl 1-(SR)-4-((RS and SR)-(N-methyl)amino)-2-(SR)-phenylcyclopentanoate (5.8g, 24.9 mmol) from Step A was dissolved in dichloromethane (100 mL). Benzoyl chloride (3.5 mL, 30.1 mmol) and N,N-diisopropylethylamine (10.4 mL, 59.7 mmol) were added sequentially. After 3 hours, the organic layers were washed sequentially with 1N NaOH, 1N HCl and brine, then dried over sodium sulfate and concentrated to afford the crude title compound (4.4 g) which was essentially the same as Example 11, Step B.

Step C: 1-(RS)-(N-(Methyl)-N-(benzoyl)amino)-3-(SR)-(hydroxymethyl)-4-(SR)-phenylcyclopentane (Higher $R_f$ isomer) and 1-(SR)-(N-(Methyl)-N-(benzoyl)amino)-3-(SR)-(hydroxymethyl)-4-(SR)-phenylcyclopentane (Lower $R_f$ isomer)

Methyl 1-(SR)-4-(RS and SR)-(N-(methyl)-N-(benzoyl) amino)-2-(SR)-phenylcyclopentanoate (4.4 g, 13.0 mmol) from Step B was dissolved in tetrahydrofuran (15 mL) and chilled to −10° C. Lithium borohydride (2M in THF, 13 mL, 26 mmol) was added slowly via syringe and the bath was removed. After 24 hours, the reaction was quenched by the cautious addition of 1N HCl. The organic layers were partitioned between ethyl ether and water and the layers were separated. The organic layers were washed sequentially with 1N NaOH and brine, then dried over sodium sulfate and concentrated. The diastereomers were separated using a Biotage Flash 40 chromatography apparatus. A gradient of 50% ethyl acetate in hexanes increasing to 60% ethyl acetate was used to elute the compounds. The higher $R_f$ diastereomer weighed 1.26 g and the lower diastereomer weighed 2.0 g. The remaining steps of this Example were performed using the higher separated diastereomer) which was the same as Example 11, Step C.

Step D: 1-(RS)-(N-(Methyl)-N-(benzoyl)amino)-3-(SR)-(formyl)-4-(SR)-phenylcyclopentane (Higher $R_f$ isomer)

Oxalyl chloride (0.884 mL, 10.2 mmol) was dissolved in dichloromethane (30 mL) and chilled to −78°. Dimethylsulfoxide (1.44 mL, 10.3 mmol) was added slowly and the solution was aged 15 minutes. A solution of 1-(RS)-(N-(methyl)-N-(benzoyl)amino)-3-(SR)-(hydroxymethyl)4-(SR)-phenylcyclopentane (1.26 g, 4.1 mmol), the higher $R_f$ isomer from Step C, in methylene chloride (3 mL) was added slowly and the solution was aged for one hour. N,N-diisopropylethylamine (7.09 mL, 40.7 mmol) was added to the solution. After aging 10 minutes at −78°, the bath was removed and the solution was warmed to ambient temperature over one hour. The organic layers were washed sequentially with 1N HCl, water and brine, then dried over sodium sulfate and concentrated to afford the crude title compound which was essentially the same as Example 11, Step D.

Step E: 1-(RS)-(N-(Methyl)-N-(benzoyl)amino)-3-(SR)-((4-(3-phenylprop-1-yl)piperidin-1-yl)methyl)-4-(SR)-phenylcyclopentane Hydrochloride Salt To a 13×100 mm threaded vial can be added 4-(3-phenylprop-1-yl)piperidine-TFA salt (0.093 mmol). A solution of 1-(RS)-(N-(methyl)-N-(benzoyl)amino)-3-(SR)-(formyl)-4-(SR)-phenylcyclopentane (19 mg, 0.062 mmol) from Step D (derived from the higher $R_f$ isomer in Step C) and acetic acid (0.006 mL, 0.1 mmol) in 1,2-dichloroethane (1 mL) can then be added to the vial. Sequentially, N,N-diisopropylethylamine (0.022 mL, 0.126 mmol) and a solution of sodium triacetoxyborohydride (26 mg, 0.123 mmol) in 1,2-dichloroethane (2 mL) are then added. The vial is sealed with a septum cap, gently shaken and stored at ambient temperature. After 18 hours, solvent is removed by a stream of warm nitrogen and the residue is redissolved in 80% acetonitrile in water. The sample can be purified on a Gilson Combinatorial Chromatography system using a 9.4 mm×25 cm Zorbax SB-C18 column. Fractions are collected based on the UV absorption and analyzed by mass spec to identify the title compound fractions. These are combined and evaporated.

EXAMPLE 48

1-(SS)-(N-(Benzoyl)-N-(methyl)amino)-3-(SR)-((4-
(3-phenylprop-1-yl)piperidin-1-yl)methyl)-4-(SR)-
phenylcyclopentane TFA Salt Using essentially the same procedures as in Example 7, but substituting the lower $R_f$ isomer from Step C, the title compound can be prepared.

EXAMPLE 49

Using essentially the same procedures as in Examples 47 and/or 48, but substituting a 4-substituted piperidine from Procedures 1–15 in Example 47, Step E and/or a substituted benzoyl or sulfonyl chloride in Example 47, Step B, a variety of 1-(RS and/or SS)-(N-(substituted-benzoyl)-N-(methyl)amino)-3-(SR)-((4-(substituted)piperidin-1-yl)

methyl)-4-(SR)-phenylcyclopentane and 1-(RS and/or SS)-(N-(substituted-phenylsulfonyl)-N-(methyl)amino)-3-(SR)-((4-(substituted)piperidin-1-yl)methyl)-4-(SR)-phenylcyclopentane final compounds can be prepared.

EXAMPLE 50

1-((E)-Benzylidene)-3-(SR)-(4-(phenyl)piperidin-1-yl)carbonyl)-4-(SR)-phenylcyclopentane and 1-((Z)-benzylidene)-3-(SR)-(4-(phenyl)piperidin-1-yl)carbonyl)-4-(SR)-phenylcyclopentane Step A: 3-(SR)-(4-(Phenyl)piperidin-1-yl)carbonyl)-4-(SR)-phenylcyclopentan-1-one To a solution of (+−)-trans-4-oxo-2-phenylcyclopentanoic acid (3.7 g, 18.1 mmol) (from Example 42, Step A) in methylene chloride (20 mL) was added EDAC (4.5 g, 23.6 mmol). The reaction was stirred a rt for 20 min before 4-(phenyl)piperidine (3.8 g, 23.6 mmol) was added. The reaction was stirred for 16 h at rt. The mixture was then diluted with methylene chloride and washed with 1N HCl, sat'd sodium bicarbonate and brine, dried over magnesium sulfate and evaporated to dryness. The residue was purified by FC (5:4:1 hexanes: t-butyl methyl ether: acetonitrile) to give the title compound (4.51 g).
$^1$H-NMR (500 MHz CDCl$_3$): δ 0.34/1.30/1.44–1.89 (m, 4H), 2.50–2.66 (m, 4 H), 2.82–3.01 (m, 3H), 3.45–3.56 (m, 1H), 3.69–3.81 (m, 2H), 4.80 (m, 1H), 6.98 (m, 2H), 7.15 (m, 1H), 7.22 (m, 1H), 7.28–7.32 (m, 3H), 7.35–7.41 (m, 3H). $^{13}$C-NMR (CDCl$_3$): δ 170.29, 214.81. MS (ESI): m/e 348 (M+1).

Step B: 1-((E)-Benzylidene)-3-(SR)-(4-(phenyl)piperidin-1-yl)carbonyl)-4-(SR)-phenylcyclopentane and 1-((Z)-Benzylidene)-3-(SR)-(4-(phenyl)piperidin-1yl)carbonyl)-4-(SR)-phenylcyclopentane To a solution of benzyltriphenylphosphonium bromide (1.25 g, 2.88 mmol) in THF (10 mL) under nitrogen was added dropwise 1.0M sodium hexamethyldisilazide until the color persisted, then an additional 2.9 mL (2.9 mmol) was added. The solution was cooled to −20° C. and 3-(SR)-(4-(phenyl)piperidin-1-yl)carbonyl)-4-(SR)-phenylcyclopentan-1-one (500 mg, 1.43 mmol) (from Step A.) in THF (5 mL) was added dropwise. The reaction was then warmed to 40° C. for 20 h, then to 67° C. for 12 h afterwhich it was cooled to rt, diluted with ethyl acetate and quenched with 1M HCl and water. The layers were separated and the organic layer was washed with brine, dried over magnesium sulfate and concentrated in vacuo. The residue was purified by FC (20% ethyl acetate in hexanes) to afford the two title products as clean higher R$_f$(80 mg), mixture (60 mg) and lower R$_f$ (35 mg) (R$_f$=0.4 and 0.3 in 35% ethyl acetate in hexanes). The E and Z isomers were not assigned. Higher isomer:
$^1$H NMR (CDCl$_3$): δ 0.44/1.30 (m, 1H), 1.45–1.88 (m, 3H), 2.52–2.67 (m, 2H), 2.89–3.18 (m, 5H), 2.40 (m, 1H), 3.59 (m, 1H), 3.82 (m, 1H), 4.82 (m, 1H), 6.46 (br, 1H), 6.99 (m, 1H), 7.16–7.40 (m, 14H). $^{13}$C NMR (CDCl$_3$): δ 32.51, 32.78, 33.20, 33.98, 36.23, 36.46, 42.36, 42.44, 42.56, 42.58, 42.77, 45.62, 46.35, 48.49, 49.24, 49.38, 121.88, 171.78. MS (ESI): m/e 422 (M$^+$+1).
Lower isomer:
$^1$H NMR (CDCl$_3$): δ 0.47/1.29 (m, 1H), 1.47–1.89 (m, 3H), 2.53–3.17 (m, 6H), 3.26–3.35 (m, 2H), 3.64/3.73 (m, 1H), 3.90 (m, 1H), 4.82 (m, 1H), 6.44 (m, 1H), 6.98 (m, 1H), 7.19–7.37 (m, 14H). $^{13}$C NMR (CDCl$_3$): δ 32.71, 32.98, 33.34, 34.30, 39.11, 39.31, 40.57, 42.61, 42.75, 42.93, 45.86, 46.50, 47.92, 49.81, 51.08, 121.97, 122.0, 171.67, 171.83. MS (ESI): m/e 422 (M$^+$+1).

EXAMPLE 51

1-((E)-Benzylidene)-3-(SR)-(4-(phenyl)piperidin-1-yl)methyl)-4-(SR)-phenylcyclopentane and/or 1-((Z)-Benzylidene)-3-(SR)-(4-(phenyl)piperidin-1-yl)methyl)-4-(SR)-phenylcyclopentane To a solution of 1-((E or Z)-benzylidene)-3-(SR)-(4-(phenyl)piperidin-1-yl)carbonyl)-4-(SR)-phenylcyclopentane (higher R$_f$ product from Example 50, Step B) (80 mg, 0.19 mmol) in THF (1 mL) under nitrogen was added 1M LAH in THF (1.9 mL, 1.9 mmol). The reaction was stirred at rt for 2 h and was then quenched with aq. potassium hydroxide (1 mL), filtered and evaporated. The residue was purified by FC (25:4:1 hexanes: t-butyl methyl ether: acetonitrile) to afford clean either E or Z title compound (30 mg).
$^1$H-NMR (500 MHz, CDCl$_3$): δ 1.74–1.84 (m, 3H), 1.95 (m, 1H), 2.09 (m, 1H), 2.4–2.59 (m, 5H), 2.79–3.07 (m, 6H), 3.21 (m, 1H), 6.47 (brs, 1H), 7.25–7.46 (m, 15H). $^{13}$C-NMR (CDCl$_3$): δ 33.34, 33.41, 37.28, 42.65, 44.68, 45.22, 49.47, 53.83, 55.44, 63.21, 121.46, 138.41, 144.08, 144.40, 146.55. MS (ESI): m/e 408 (M$^+$+1).

Similarly, the lower R$_f$ product from Example 50, Step B (35 mg, 0.082 mmol) was reduced with 1M LAH (0.82 mL, 0.82 mmol) to afford clean either Z or E title compound (15 mg).
$^1$H-NMR (500 MHz, CDCl$_3$): δ 1.74–1.83 (m, 3H), 1.94 (m, 1H), 2.08 (m, 1H), 2.34–2.52 (m, 5H), 2.72 (m, 2H), 2.91 (m, 2H), 3.05 (m, 2H), 3.19 (m, 1H), 6.45 (brs, 1H), 7.28–7.47 (m, 15H). $^{13}$C-NMR (CDCl$_3$): δ 33.35, 33.42, 37.32, 42.68, 44.68, 45.26, 49.51, 53.86, 55.46, 63.23, 121.46, 138.44, 144.11, 144.45, 146.58. MS (ESI): m/e 408 (M$^+$+1).

Similarly, the mixed fractions from Example 50, Step B (60 mg, 0.14 mmol) was reduced with 1M LAH (1.4 mL, 1.4 mmol) to afford a mixture of title compounds (15 mg).

EXAMPLE 52

1-(RS and SR)-Benzyl-3-(SR)-(4-(phenyl)piperidin-1-yl)methyl)-4-(SR)-phenylcyclopentane To a solution of a mixture of 1-((E)-benzylidene)-3-(SR)-(4-(phenyl)piperidin-1-yl)methyl)-4-(SR)-phenylcyclopentane and 1-((Z)-benzylidene)-3-(SR)-(4-(phenyl)piperidin-1-yl)methyl)-4-(SR)-phenylcyclopentane (52 mg, 0.13 mmol) (prepared as in Example 51 without separation of the isomers) in methanol (4 mL) was added 10% Pd/C (20 mg) and the mixture was hydrogenated at 6.50 psi for 24 h. The reaction was filtered and the filtrate was concentrated. The residue was purified by FC (10% ethyl acetate in hexanes) to give the title compounds as a mixture of C-1 isomers (38 mg).
$^1$H NMR (CDCl$_3$, stereoisomers): δ 1.62/1.32 (m, 1 H), 1.73–3.10 (m, 19H), 7.31–7.44 (m, 15H). $^{13}$C NMR (CDCl$_3$): δ 33.23, 33.44, 37.72,39.94, 40.51, 40.56, 40.92, 42.38, 42.64, 42.78, 43.30, 43.65, 46.19, 49.81, 51.49, 53.99, 54.07, 54.92, 55.28, 63.77, 64.37, 141.67, 145.37, 146.30, 146.56. MS (ESI) m/e 410 (M$^+$+1).

EXAMPLE 53

1-(RS or SR)-Benzylamino-3-(SR)-(4-(phenyl)piperidin-1-yl)methyl)-4-(SR)-phenylcyclopentane and/or 1-(SR or RS)-Benzylamino-(SR)-(4-(phenyl)piperidin-1-yl)methyl)-4-(SR)-phenylcyclopeantane Step A: 1-(RS or SR)-Hydroxy-3-(SR)-(4-(phenyl)piperidin-1-yl)methyl)-4-(SR)-phenylcyclopentane and 1-(SR or RS)-Hydroxy-(SR)-(4-(phenyl)piperidin-1-yl)methyl)-4-(SR)-phenylcyclopentane To a solution of 3-(SR)-(4-(phenyl)piperidin-1-yl)carbonyl)-4-(SR)-phenylcyclopentan-1-one (1.71 g, 4.9 mmol) in THF (14 mL) it 0° C. was added dropwise 1.0M LAH in THF (14.76 mL, 14.76 mmol). The reaction was allowed to warm to rt and was stirred for 16 h. The excess LAH was quenched with water (2 mL), 15% potassium hydroxide (2 mL) and another aliquot of water (2 mL). After stirring for 30 min, the mixture was filtered and the filtrate was concentrated. The residue was purified by FC (5% methanol in methylene chloride) to give clean faster $R_f$ isomer (850 mg) and a mixture of C-1 isomers (400 mg). The stereochemistry at C-1 was not assigned.

$^1$H-NMR (500 MHz, CDCl$_3$): δ 1.72–1.95 (m, 7H), 2.20–2.58 (m, 7H), 3.08 (m, 2H), 3.18 (m, 1H), 4.48 (m, 1H), 7.23–7.38 (m, 10H). $^{13}$C-NMR (CDCl$_3$): δ 33.23, 33.26, 40.45, 42.09, 45.37, 45.51, 47.19, 55.80, 56.57, 62.07, 72.53. MS (ESI): m/e 336 (M$^+$+1).

Step B: 3-(SR)-(4-(Phenyl)piperidin-1-yl)methyl)-4-(SR)-phenylcyclopentan-1-one

To) a solution of oxalyl chloride (454 mg, 3.6 mmol) in methylene chloride (10 mL) at –70° C. was added DMSO (560 mg, 7.2 mmol) in methylene chloride (5 mL). The reaction was stirred for 10 min and then a solution of 1-(RS or SR)-hydroxy-3-(SR)-(4-(phenyl)piperidin-1-yl)methyl)-4-(SR)-phenylcyclopentane (600 mg, 1.8 mmol) (higher isomer from Step A) in methylene chloride (6 mL) was added. After 30 min, TEA (1.8 g, 17.9 mmol) was added and the reaction was allowed to warm to rt over 45 min. The mixture was quenched with water and sodium bicarbonate and was extracted twice with methylene chloride. The organic layers were each washed with brine, dried over sodium sulfate, combined and concentrated. The residue was purified by FC (25% ethyl acetate in hexanes) to give the title compound (441 mg), $R_f$=0.42 (50% ethyl acetate in hexanes).

$^1$H NMR (CDCl$_3$): δ 1.68 1.83 (m, 4H), 1.99 (m, 1H), 2.12 (m, 1H), 2.21 (m, 1H), 2.40–2.51 (m, 4H), 2.65 (m, 1H), 2.77 (m, 2H), 2.91 (m, 1H), 2.98 (m, 1H), 3.12 (m, 1H), 7.23–7.42 (m, 10H). $^{13}$C NMR (CDCl$_3$): δ 32.08, 32.14, 40.74, 41.24, 43.34, 45.79, 45.91, 52.63, 54.11, 61.08, 215.85. MS (ESI): m/e 334 (M$^+$+1).

Step C: 1-(RS or SR)-Benzylamino-3-(SR)-(4-(phenyl)piperidin-1-yl)methyl)-4-(SR)-phenylcyclopentane and/or 1-(SR or RS)-Benzylamino-(SR)-(4-(phenyl)piperidin-1-yl)methyl)-4-(SR)-phenylcyclopentane To a solution of 3-(SR)-(4-(phenyl)piperidin-1-yl)methyl)-4-(SR)-phenylcyclopentan-1-one (80 mg, 0.24 mmol) (from Step B) and benzylamine (257 mg, 2.4 mmol) in 1,2-dichloroethane (3 mL) after 10 min was added sodium triacetoxyborohydride (100 mg, 0.48 mmol). The reaction was stirred at rt for 30 min, then at 42° C. for 16h. Sodium cyanoborohydride (30 mg, 0.48 mmol) was added and the reaction was stirred a further 2 h at 42° C. The mixture was quenched with water and sodium bicarbonate and was extracted twice with ethyl acetate. The organic layers were each washed with brine, dried over sodium sulfate, combined and concentrated. The residue was purified by FC (2:1 acetone:methylene chloride) to give separation of clean higher $R_f$ title compound (13 mg), $R_f$=0.57 (4:1 acetone:methylene chloride), mixed fractions (29 mg), and then clean lower $R_f$ title compound (21 mg), $R_f$=0.44 (4:1 acetone:methylene chloride). The stereochemistry at C-1 was not assigned.

Higher isomer:
$^1$H NMR (CDCl$_3$): δ 1.63–1.80 (m, 5H), 1.89 (m, 2H), 2.00 (m, 2H), 2.35 (m, 2H), 2.40–2.54 (m, 3H), 2.69 (m, 1H), 2.84 (m, 1H), 3.00 (m, 1 H), 3.35 (m, 1H), 3.86 (brs, 2H), 7.21–7.40 (m, 15H). $^{13}$C NMR (CDCl$_3$): δ 33.25, 33.41, 38.94, 42.64, 43.06, 43.45, 50.30, 52.66, 53.85, 55.19, 57.34, 63.86. MS (ESI): m/e 425 (M$^+$+1).

Lower isomer:
$^1$H NMR (CDCl$_3$): δ 1.33–1.45 (m, 2H), 1.69–2.10 (m, 8H), 2.30–2.55 (m, 4H), 2.89–3.02 (m, 3H), 3.47 (m, 1H), 3.86 (m, 2H), 7.24–7.40 (m, 15H). $^{13}$C NMR (CDCl$_3$): δ 33.20, 33.39, 40.16, 42.09, 42.57, 44.62, 48.96, 52.40, 53.92, 55.32, 57.42, 63.51. MS (ESI): m/e 425 (M$^+$+1).

EXAMPLE 54

1-(RS or SR)-Phenoxy-3-(SR)-(4-(phenyl)piperidin-1-yl)methyl)-4-(SR)-phenylcyclopentane To a solution of 1-(RS or SR)-hydroxy-3-(SR)-(4-(phenyl)piperidin-1-yl)methyl)-4-(SR)-phenylcyclopentane (100 mg, 0.30 mmol) (higher $R_f$ isomer from Example 53, Step A), phenol (280 mg, 3.0 mmol) and triphenylphosphine (156 mg, 0.60 mmol) in THF (5 mL) under nitrogen was added dropwise DEAD (99 mg, 0.57 mmol) over 20 min. The reaction was stirred at rt for 16 h. The mixture was quenched with water and sodium bicarbonate and was extracted twice with ethyl acetate. The organic layers were each washed with brine, dried over sodium sulfate, combined and concentrated. The residue was purified by FC (12.5% t-butyl methyl ether in hexanes) to give a single isomer of the title compound (13 mg), $R_f$=0.28 (25% t-butyl methyl ether in hexanes). The stereochemistry was not assigned.

MS (EI) m/e 411 (M$^+$).

EXAMPLE 55

1-(RS and SR)-Phenoxy-3-(SR)-(4-(phenyl) piperidin-1-yl)methyl)-4-(SR)-phenylcyclopentane Using essentially the same procedure as in Example 54, but using the mixture of C-1 isomers from Example 53, Step A, a mixture of tile title compounds can be obtained.

$^1$H NMR (CDCl$_3$, 500 MHz): δ 1.70–1.85 (m, 4H), 1.93 (m, 1H), 2.15 (m, 1H), 2.40–2.52 (m, 4H), 2.67–2.84 (m, 3H), 2.92 (m, 1H), 3.07 (m, 1H), 4.95 (m, 1H), 7.03–7.43 (m, 15H). $^{13}$C NMR (CDCl$_3$): δ 33.25, 33.35, 39.42, 42.24, 42.56, 43.72, 50.01, 53.78, 55.35, 62.94, 77.34, 115.40, 120.29, 125.89, 126.04, 126.73, 127.67, 128.23, 128.26, 129.35, 144.40, 146.47, 157.85. MS (EI) m/e 411 (M$^+$).

EXAMPLE 56

1-(RS and SR)-3,4-Dichlorophenoxy-3-(SR)-(4-(phenyl)piperidin-1-yl)methyl)-4-(SR)-phenylcyclopentane Using essentially the same procedure as in Example 54, but using the mixture of C-1 isomers from Example 53, Step A and substituting 3,4-dichlorophenol for phenol, a mixture of the title compounds was obtained.

$^1$H NMR (CDCl$_3$, 500 MHz): δ 1.70–2.05 (m, 6H), 2.37 (m, 5H), 2.57 (m, 1H), 2.71 (m, 2H), 2.84 (m, 1H), 2.98 (m, 1H), 4.81 (m, 1H), 6.79 (dd, 1H. J$_1$=3.0 Hz, J$_2$=8.5 Hz), 7.03 (d, 1H, J=3.0 Hz), 7.19–7.35 (m, 11H). $^{13}$C NMR (CDCl$_3$): δ 33.28, 39.35, 42.08, 42.58, 43.68, 50.01, 53.77, 55.56, 62.76, 78.37. MS (EI): m/e 479, 481, 483 (M$^+$/$^{35}$Cl/$^{37}$Cl-isotope pattern), 480, 482, 484 (M$^+$+1/$^{35}$Cl/$^{37}$Cl-isotope pattern).

EXAMPLE 57

1-(RS and SR)-1-Naphthyloxy-3-(SR)-(4-(phenyl) piperidin-1-yl)methyl)-4-(SR)-phenylcyclopentane Using essentially the same procedure as in Example 54, but using the mixture of C-1 isomers from Example 53, Step A and substituting 1-naphthol for phenol, a mixture of the title compounds was obtained.

¹H NMR (CDCl₃, 500 MHz): δ 1.67–2.45 (m, 11H), 2.55 (m, 1H), 2.80 (m, 2H), 2.89 (m, 1H), 3.02 (m, 1H), 5.07 (m, 1H), 6.84 (d, 1H, J=7.5Hz), 7.19–7.54 (m, 14H), 7.83 (m, 1H), 8.39 (m, 1H). ¹³C NMR (CDCl₃): δ 33.15, 33.23, 39.60, 42.28, 42.51, 43.86, 50.08, 53.77, 55.41, 62.88, 77.92, 105.94, 144.28, 146.39, 153.54. MS (EI): m/e 461 (M⁺), 462 (M⁺+1).

EXAMPLE 58

1-(RS and SR)-Benzoyl-3-(SR)-(4-(phenyl) piperidin-1-yl)methyl)-4-(SR)-phenylcyclopentane Step A: (+−)-trans-4-Methylene-2-phenylcyclopentane Carboxaldehyde To a solution of oxalyl chloride (2.78 mL, 32 mmol) in methylene chloride (30 mL) at −70° C. was added DMSO (4.5 mL, 64 mmol) in methylene chloride (20 mL). The reaction was stirred for 10 min and then a solution of (+−)-trans-1-hydroxymethyl-4-methylene-2-phenylcyclopentane (3.0 g, 16 mmol) (from Example 20, Step B) in methylene chloride (70 mL) was added. After 60 min, TEA (11.1 mL, 80 mmol) was added and the reaction was allowed to warm to rt over 60 min. The mixture was quenched with water and sodium bicarbonate and was extracted twice with methylene chloride. The organic layers were each washed with 1N HCl, 5% sodium bicarbonate and brine, dried over magnesium sulfate, combined and concentrated to give the crude title compound (2.97 g) which was used in Step B.

¹H-NMR (50 MHz, CDCl₃): δ 2.60 (m, 1H), 2.74 (m, 2H), 2.86 (m, 1H), 3.07 (m, 1H), 3.44 (m, 1 H), 5.00 (br s, 1H), 7.25–7.34 (m, 5 H), 9.66 (br s, 1H). MS (EI): m/e 186 (M⁺).

Step B: 1-Methylene-3-(SR)-(4-(phenyl)piperidin-1-yl) methyl)-4-(SR)-phenylcyclopentane To a solution of (+−)-trans-4-methylene-2-phenylcyclopentane carboxaldehyde (2,97 g, 16 mmol) (from Step A) and 4-phenylpiperidine (3.1 g, 19.2 mmol) in 1,2-dichloroethane (50 mL) after 10 min was added sodium triacetoxyborohydride (5.1 g, 24 mmol). The reaction was stirred at rt for 45 min, then the mixture was quenched with water and sodium bicarbonate and was extracted twice with methylene chloride. The organic layers were each washed with brine, dried over magnesium sulfate, combined and concentrated. The residue was purified by FC (20% ethyl acetate in hexanes) to give the title compound (4.45 g).

¹H-NMR (500 MHz, CDCl₃): δ 1.71–1.78 (m, 5H), 1.91 (m, 1H), 2.04 (m, 1H), 2.22–2.54 (m, 6H), 2.80–2.91 (m, 3H), 3.00 (m, 1 H), 4.94 (br s, 2H), 7.21–7.35 (m, 10H). ¹³C NMR (CDCl₃): δ 633.29, 33.39,39.03, 42.04, 42.59, 44.75, 50.51, 25 53.77, 55.33, 63.01, 105.48, 125.92, 126.06, 126.74, 127.32, 128.23, 128.28, 144.36, 146.43, 150.69. MS (ESI): m/e 332 (M⁺+1).

Step C: 1-(RS and SR)-Hydroxymethyl-3-(SR)-(4-(phenyl) piperidin-1-yl)methyl)-4-(SR)-phenylcyclopentane To 1-methylene-3-(SR)-(4-(phenyl)piperidin-1-yl) methyl)-4-(SR)-phenylcyclopentane (2.0 g, 6.0 mmol) (from Step B) was added 1M borane-methyl sulfide in THF (20 mL, 20 mmol). The reaction was stirred at 40° C. for 2 h and was then cooled to 0° C. and carefully quenched with 15% sodium hydroxide (10 mL) and 30% hydrogen peroxide (10 mL). After 2 h at rt, the mixture was diluted with water and extracted twice with ethyl acetate. The organic layers were each washed with brine, dried over magnesium sulfate, combined and concentrated. The residue was purified by FC (50% ethyl acetate in hexanes) to give the title compounds (0.80 g).

¹H NMR (CDCl₃, 500 MHz): δ 0.95 (m, 1H), 1.27 (m, 1H), 1.53–2.06 (m, 6H), 2.24 (m, 1H), 2.36 (m, 1H), 2.45–2.53 (m, 2H), 2.59–2.66 (m, 2H), 2.78–2.89 (m, 2H), 3.00–3.14 (m, 3H), 3.57–3.70 (m, 2H), 6.91 (m, 1H), 7.21–7.38 (m, 10H). ¹³C NMR (CDCl₃): δ 25.50, 25.66, 27.73, 27.76, 36.61, 36.99, 37.95, 38.09, 39.91, 39.99, 40.26, 42.25, 43.82, 50.80, 52.50, 55.89, 56.15, 57.80, 58.28, 59.94, 60.02, 66.90, 67.02. MS (ESI): m/e 350 (M⁺1).

Step D: 1-(RS and SR)-Formyl-3-(SR)-(4-(phenyl) piperidin-1-yl)methyl)-4-(SR)-phenylcyclopentane Using essentially the same procedure as in Step A, 1-(RS and SR)-hydroxymethyl-3-(SR)-(4-(phenyl)piperidin-1-yl) methyl)-4-(SR)-phenylcyclopentane (100 mg, 0.286 mmol) (from Step C) was oxidized to the crude title compounds (100 mg) which were used in Step E.

Step E: 1-(RS and SR)-((1-(RS and SR)-Hydroxy)benzyl)-3-(SR)-(4-(phenyl)piperidin-1-yl)methyl)-4-(SR)-phenylcyclopentane To a solution of iodobenzene (0.37 mL, 2.86 mmol) in THF (5 mL) at −78° C. under nitrogen was added 1.7M t-butyl lithium. After 30 min, a solution of 1-(RS and SR)-formyl-3-(SR)-(4-(phenyl)piperidin-1-yl)methyl)-4-(SR)-phenylcyclopentane (100 g, 0.286 mmol) (from Step C) in THF (2 mL) was added by syringe. The reaction was warmed to 0° C. over 30 min and then quenched with sat'd ammonium chloride (10 mL). The mixture was extracted twice with ethyl acetate. The organic layers were each washed with brine, dried over magnesium sulfate, combined and concentrated to give the crude title compounds (122 mg).

Step F: 1-(RS and SR)-Benzoyl-3-(SR)-(4-(phenyl) piperidin-1-yl)methyl)-4-(SR)-phenylcyclopentane Using essentially the same procedure as Step A, 1-(RS and SR)-((1-(RS and SR)-hydroxy)benzyl)-3-(SR)-(4-(phenyl)piperidin-1-yl)methyl)-4-(SR)-phenylcyclopentane (122 mg, 0.263 mmol), (from Step E) was oxidized to the crude title compounds (116 mg). This mixture was purified by FC (5% t-butyl methyl ether in hexanes) to give the title compounds as a mixture of C-1 isomers (139 mg).

¹H NMR (CDCl₃, stereoisomers major/minor): δ 0.91/ 1.00 (m, 1H), 1.30 (m, 1H), 1.59–1.82 (m, 2H), 2.08–3.31 (m, 13H), 4.03/4.11 (m, 1H), 6.80/6.94 (d, 1H), 7.24–7.60 (m, 13H), 8.04 (d, 1H). ¹³C NMR (CDCl₃): δ 24.88, 27.03, 27.20, 36.71, 36.94, 36.99, 37.25, 40.28, 42.40, 43.30, 44.14, 44.22, 51.09, 51.46, 52.55, 52.67, 53.53, 54.47, 56.20, 57.1:3, 201.64, 201.81. MS (ESI) m/e 424 (M⁺+1).

EXAMPLE 59

1-(RS and SR)-(1-Naphthoyl)-3-(SR)-(4-(phenyl) piperidin-1-yl)methyl)-4-(SR)-phenylcyclopentane Using essentially the same procedures as in Example 58, Steps E and F, but substituting 1-bromonaphthalene for iodobenzene in Step E, the title compounds were prepared as a mixture of C-1 isomers.

¹H NMR (CDCl₃, stereoisomers major/minor): δ 0.97 (m, 1H), 1.33 (m, 1H), 1.60–1.80 (m, 2H), 2.16 (m, 1H), 2.34–3.31 (m, 12H), 4.06/4.16 (m, 1H), 6.81/6.93 (d, 1H), 7.26–7.66 (m, 14H), 7.91 (m, 1H), 8.00/8.63 (dd, 1H). ¹³C NMR (CDCl₃): δ 24.92, 27.04, 27.22, 36.90, 37.25, 37.38, 37.44, 40.30, 40.32, 42.42, 43.39, 47.77, 47.95, 51.22, 51.60, 52.64, 52.67, 53.62, 54.46, 56.25, 57.09, 206.22, 206.42. MS (ESI) m/e 474 (M⁺+1).

EXAMPLE 60

1-(RS and SR)-((3,4-Dichlorobenzoyl)-3-(SR)-(4-(phenyl)piperidin-1-yl)methyl)-4-(SR)-phenylcyclopentane Using essentially the same procedures as in Example 58, Steps E and F, but substituting 3,4-dichlorobromobenzene and magnesium in ether (to prepare the Grignard reagent) for iodobenzene and t-butyl lithium in Step E, the title compounds were prepared as a mixture of C-1 isomers.

$^1$H NMR (CDCl$_3$, stereoisomers major/minor): δ 0.85/ 0.96 (m, 1 H), 1.30 (m, 1H), 1.70 (m, 2H), 2.1–3.64 (m, 13H), 3.91/4.00 (m, 1 H), 6.77/6.90 (d, 1H), 7.22–7.43 (m, 9 H), 7.58 (m, 1H), 7.82 (m, 1H), 8.08 (m, 1H). $^{13}$C NMR (CDCl$_3$): δ 199.70, 199.80. MS (ESI): m/e 491, 493, 495 (M$^+$/$^{35}$Cl/$^{37}$Cl-isotope pattern), 492, 494, 496 (M$^+$+1/$^{35}$Cl/ $^{37}$Cl-isotope pattern).

EXAMPLE 61

1-(RS and SR)-(1-Naphthylmethyl)-3-(SR)-(4-(phenyl)piperidin-1-yl)methyl)-4-(SR)-phenylcyclopentane To a solution of 1-(RS and SR)-((1-(RS and SR)-hydroxy)-(1-naphthyl))-3-(SR)-(4-(phenyl)piperidin-1-yl) methyl)-4-(SR)-phenylcyclopentane (190 mg, 0.38 mmol) (from Example 59, Step E) in methylene chloride (2 mL) was added triethylsilane (1 mL) and borontrifluoride etherate (0.50 mL). The reaction was stirred at rt for 2 h and was then quenched with sat'd sodium bicarbonate. The mixture was extracted twice with ethyl acetate. The organic layers were each washed with brine, dried over magnesium sulfate, combined and concentrated. The residue was purified by FC (5% t-butyl methyl ether in hexanes) to give a mixture of the title compounds (119 mg).

$^1$H NMR (CDCl$_3$): δ 1.01 (m, 1H), 1.31 (m, 1H), 1.52–3.52 (m, 18H), 6.86 (m, 1H), 7.22–7.56 (m, 13H), 7.73 (m, 1H), 7.87 (m, 1H), 8.10 (m, 1H). MS (ESI) m/e 460 (M$^+$+1).

EXAMPLE 62

1-(RS or SR)-(1-Naphthoyl)-3-(SR)-(4-(phenyl) piperidin-1-yl)methyl)-4-(SR)-(3-thienyl) cyclopentane and 1-(SR or RS)-(1-Naphthoyl)-3-(SR)-(4-(phenyl)piperidin-1-yl)methyl)-4-(SR)-(3-thienyl)cyclopentane Step A: Methyl 3-(3-Thienyl)acrylate A suspension of potassium t-butoxide (61.5 g, 0.55 mol) in THF (800 mL) was cooled in an ice bath and trimethylphospbonoacetate (98 mL, 0.60 mol) in THF (100 mL) was slowly added. After 45 min, thiophene 3-carboxaldehyde (50 mL, 0.55 mol) in THF (100 mL) was slowly added while stirred in the ice bath. The mi,suture was allowed to warm to rt and stirred for 16 h. The reaction was quenched with 5% sulfuric acid (300 mL) and extracted twice with ether. The organic layers were each washed with brine, dried over magnesium sulfate, combined and concentrated. The residue was purified by FC (10% ethyl acetate in hexanes) and then crystallized from hexanes to give the title compound (71.3 g).

$^1$H-NMR (500 MHz, CDCl$_3$): δ 3.77 (s, 3H), 6.25 (d, 1H, J=15.5 Hz), 7.26 (m, 1H), 7.30 (m, 1H), 7.46 (m, 1H), 7.66 (d, 1H, J=15.5 Hz). $^{13}$C NMR (CDCl$_3$): δ 51.43, 117.27, 124.98, 126.80, 127.98, 137.34, 138.13, 167.42

Step B: Methyl(+–)-trans-4-Methylene-2-(3-thienyl) cyclopentanoate

A mixture of methyl 3-(3-thienyl)acrylate (10.0 g, 59.5 mmol), tetrakis(triphenylphosphine) palladium(0) (5.15 g, 5.6 mmol), 1,2-bis(diphenylphosphino)ethane (1.35 g, 3.4 mmol) and 2-((trimethylsilyl)methyl)-2-propen-1-yl acetate (20 g, 107 mmol) in THF (125 mL) under argon was heated to reflux for 24 h. The volatiles were then removed in vacuo and the residue was purified by FC (5% ethyl acetate in hexanes) to afford the title compound (11.4 g).

MS (CI) m/e 222 (M$^+$).

Step C: (+–)-trans-1-Hydroxymethyl-4-methylene-2-(3-thienyl)cyclopentane

To a solution of methyl (+–)-trans-4-methylene-2-(3-thienyl)cyclopentanoate (6.0 g, 27 mmol) prepared as in Step B in THF (70 mL) under nitrogen and cooled to −10° C. was added dropwise over 15 min 1M lithium aluminum hydride (LAH) in THF (54 mL). After 1 h, the bath was removed and the reaction was stirred at rt for 3 h. The reaction was cooled in an ice/methanol bath and the excess LAH was quenched by dropwise addition of water/1N potassium hydroxide/water and the salts were removed by filtration through celite. The filtrate was then poured into dilute aq. HCl. The mixture was extracted twice with ether and the organic layers were washed with brine, dried over sodium sulfate, combined and concentrated to afford the crude title product (4.09 g).

$^1$H-NMR (500 MHz, CDCl$_3$): δ 2.21–2.30 (m, 2H), 2.42–2.53 (m, 2 H), 2.68 (m, 1H), 2.77 (m, 1H), 3.03 (m, 1H), 3.49 and 3.65 (ABX, 2H, J$_{AB}$=11.0 Hz, J$_{AX}$=6.5 Hz, J$_{BX}$=4.5 Hz), 4.92 (br s, 1H). $^{13}$C NMR (CDCl$_3$): δ 36.0, 41.49, 42.91, 49.11, 64.69, 105.90, 119.72, 125.63, 126.61, 114.84, 149.78. MS (ESI) m/e 1915 (M$^+$+1).

Step D: 1-(RS or SR)-(1-Naphthoyl)-3-(SR)-(4-(phenyl) piperidin-1-yl)methyl)-4-(SR)-(3-thienyl)cyclopentane and 1-(SR or RS)-(1-naphthoyl)-3-(SR)-(4-(phenyl)piperidin-1-yl)methyl)-4-(SR)-(3-thienyl)cyclopentane Using essentially the same procedures as in Example 58 and 59, (+–)-trans-1-hydroxymethyl-4-methylene-2-(3-thienyl)cyclopeantane from Step C was converted to a 1:1 mixture of the title compounds which were separable by FC (10:4:1 hexanes:t-butyl methyl ether:acetonitrile). The stereochemistry at C-1 was not assigned.

Higher isomer:

$^1$H NMR (CDCl$_3$): δ 1.69–2.10 (m, 8H), 2.39–2.50 (m, 5H), 2.59 (m, 1H), 2.92 (m, 1H), 3.01–3.10 (m, 3 H), 4.05 (m, 1H), 7.05 (m, 2H), 7.19–7.22 (m, 3H), 7.28–7.32 (m, 3H), 7.51–7.64 (m, 3H), 7.86 (m, 1 H), 7.91 (d, 1H J=8.0 Hz), 8.00 (d, 1H, J=8.0 Hz), 8.52 (d, 1H, J=8.5 Hz). $^{13}$C NMR (CDCl$_3$): δ 33.20, 33.32, 36.06, 37.23, 42.46, 45.14, 45.25, 48.04, 53.82, 55.:39, 63.00, 206.42. MS (ESI) m/e 480 (M$^+$+1).

Lower isomer:

$^1$H NMR (CDCl$_3$): δ 1.75 (m, 4H), 1.91 (m, 2H), 2.07 (m, 1H), 2.26 (m, 1H), 2.33–2.53 (m, 6H), 2.88–2.98 (m, 2H), 3.04 (m, 1H), 3.97 (m, 1H), 7.09–7.13 (m, 2H), 7.19–7.23 (m, 3H), 7.28–7.32 (m, 3H), 7.52–7.62 (m, 3H), 7.86 (dd, 1H), 7.91 (dd, 1H), 8.00 (d, 1H, J=8.0 Hz), 8.50 (d, 1H, J=8.5 Hz). $^{13}$C NMR (CDCl$_3$): δ 33.29, 35.10, 38.34, 42.57, 43.81, 46.65, 48.44, 53.64; 55.46, 63.9;6, 206.60. MS (ESI) m/e 480 (M$^+$+1).

EXAMPLE 63

1-(RS or SR)-(3,4-Dichlorobenzoyl)-3-(SR)-(4-(phenyl)piperidin-1-yl)methyl)-4-(SR)-(3-thienyl) cyclopentane and 1-(SR or RS)-(3,4-Dichlorobenzoyl)-3-(SR)-(4-(phenyl)piperidin-1-yl) methyl)-4-(SR)-(3-thienyl)cyclopentane Using essentially the same procedures as in Example 58 and 60, (+–)-trans-1-hydroxymethyl-4-methylene-2-(3-thienyl)cyclopentane from Example 62, Step C was converted to a 1:1 mixture of the title compounds which were separable by FC (10:4:1 hexane: t-butyl methyl ether: acetonitrile). The stereochemistry at C-1 was not assigned.

Higher isomer:

$^1$H NMR (CDCl$_3$): δ 1.72–1.84 (m, 5H), 1.96 (m, 1H), 2.07 (m, 2H), 2.34–2.54 (m, 6H), 2.92–3.06 (m, 3H), 3.90

(m, 1H), 7.06 (m, 2H), 7.20–7.25 (m, 3H), 7.30–7.33 (m, 3H), 7.58 (d, 1H, J=8.5 Hz), 7.83 (dd, 1H, J$_1$=1.5 Hz, J$_2$=8.5 Hz), 8.09 (d, 1H, J=1.5 Hz). $^{13}$C NMR (CDCl$_3$): δ 33.24, 33.36, 35.85, 37.20, 42.52, 44.45, 45.13, 45.25, 53.88, 55.53, 62.95, 199.70. MS (ESI): m/e 498, 500, 502 (M$^+$+1/ $^{35}$Cl/$^{37}$Cl-isotope pattern).

Lower isomer:
$^1$H NMR (CDCl$_3$): δ 1.72–1.80 (m, 4H), 1.94 (m, 2H), 2.10 (m, 1H), 2.19 (m, 1H), 2.33–2.48 (m, 6H), 2.91–3.06 (m, 3H), 3.84 (m, 1H), 7.08 (m, 2H), 7.20–7.23 (m, 3H), 7.29–7.32 (m, 3H), 7.58 (d, 1H, J=8.5 Hz), 7.84 (dd, 1H, J$_1$=2.0 Hz, J$_2$=8.5 Hz), 8.09 (d, 1H, J=2.0 Hz). $^{13}$C NMR (CDCl$_3$): δ 33.12, 33.14, 35.16, 37.78, 42.46, 43.75, 44.56, 46.65, 53.46, 55.153, 62.98, 199.67. MS (ESI): m/e 498, 500, 502 (M$^+$+1/$^{35}$Cl/$^{37}$Cl-isotope pattern).

EXAMPLE 64

1-(RS or SR)-(Benzoyl)-3-(SR)-(4-(phenyl) piperidin-1-yl)methyl)-4-(SR)-(3-thienyl) cyclopentane and 1-(SR or RS)-(Benzoyl)-3-(SR)- (4-(phenyl)piperidin-1-yl)methyl)-4-(SR)-(3-thienyl) cyclopentane Using essentially the same procedures as in Example 58, (+−)-trans-1-hydroxymethyl-4-methylene-2-(3-thienyl) cyclopentane from Example 62, Step C was converted to a 1:1 mixture of the title compounds which were separable by FC (20% ethyl acetate in hexanes). The stereochemistry at C-1 was not assigned.

Higher isomer:
$^1$H NMR (CDCl$_3$): δ 1.79 (m, 4H), 1.95 (m, 2H), 2.10 (m, 1H), 2.25 (m, 1H), 2.40–2.48 (m, 6H), 2.92–3.07 (m, 3H), 3.96 (m, 1H), 7.11 (m, 2H), 7.21–7.34 (m, 6H), 7.52 (m, 2H), 7.60 (m 1H), 8.06 (d, 1H, J=8 Hz).
$^{13}$C NMR (CDCl$_3$): δ 33.12, 33.25, 35.80, 37.28, 42.36, 44.22, 45.02, 45.11, 53.74, 55.28, 62.90, 119.55, 125.29, 125.78, 126.58, 128.09, 128.30, 128.32, 132.61, 136.23, 144.83, 146.22, 202.12. MS (ESI) m/e 430 (M$^+$+1).

Lower isomer:
$^1$H NMR (CDCl;$_3$): δ 1.79 (m, 4H), 1.95 (m, 2H), 2.10 (m, 1H), 2.25 (m, 1H), 2.40–2.48 (m, 6H), 2.92–3.07 (m, 3H), 3.96 (m, 1H), 7.11 (m, 2H), 7.21–7.34 (m, 6H), 7.52 (m, 2H), 7.60 (m 1H), 8.06 (d, 1H, J=8 Hz). $^{13}$C NMR (CDCl$_3$): δ 33.22, 33.25, 35.25, 38.02, 42.48, 43.82, 44.45, 46.67, 53.54, 55.44, 63.21, 119.91, 125.33, 125.88, 126.69, 128.19, 128.38, 128.45, 132.76, 136.46, 144.55, 146.33, 202.14. MS (ESI) m/e 430 (M$^+$+1).

EXAMPLE 65

1-(RS or SR)-(Benzyl)-3-(SR)-(4-(phenyl)piperidin-1-yl)methyl)-4-(SR)-(3-thienyl)cyclopentane and 1-(SR or RS)-(Benzyl)-3-(SR)-(4-(phenyl)piperidin-1-yl)methyl)-4-(SR)-(3-thienyl)cyclopentane Using essentially the same procedures as in Example 58 and 61, (+−)-trans-1-hydroxymethyl-4-methylene-2-(3-thienyl)cyclopentane from Example 62, Step C was converted to a 1:1 mixture of the title compounds which were separable by FC (20% ethyl acetate in hexanes). The stereochemistry at C-1 was not assigned.

$^{13}$C NMR (CDCl$_3$) d 33.22, 33.32, 33.35, 37.47, 39.59, 39.94, 40.09, 40.21, 42.26, 42.54, 42.57, 43.15, 44.47, 45.38, 46.15, 54.02, 55.01, 55.17, 64.04, 64.50. MS (ESI) m/e 416 (M$^+$+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as reasonable.

What is claimed is:
1. A compound of the formula I:

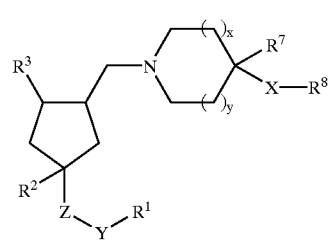

wherein:
X is selected from: —(C$_{0-6}$ alkyl)—Q—(C$_{0-6}$ alkyl)-, —(C$_{0-6}$ alkyl)-C$_{3-8}$ cycloalkyl-(C$_{0-6}$ alkyl)-, C$_{2-10}$ alkznyl, and C$_{2-10}$ alkynyl,
  where the alkyl is unsubstituted or substituted with 1–7 substituents where the substituents are independently selected from:
  (a) halo,
  (b) hydroxy,
  (c) —O—C$_{1-3}$ alkyl, and
  (d) trilluoromethyl,
  and where Q is selected from:
  a single bond, —O—, —SO$_2$—, —NR$^{10}$—, —NR$^{10}$—SO$_2$—, —SO$_2$—NR$^{10}$—, —S—, and —SO—,
  and where R$^{10}$ is independently selected from: hydrogen, C$_{1-6}$ alkyl, benzyl, phenyl, (CO)C$_{1-36}$ alkyl, —SO$_2$—C$_{1-6}$ alkyl, and C$_{1-6}$ alkyl-C$_{3-6}$ cycloalkyl,
  which is unsubstituted or substituted with 1–3 substituents where the substituents are independently selected from: halo, C$_{1-3}$ alkyl, C$_{1-3}$ alkoxy and trifluoromethyl;

Y is selected from:
  a single bond, —(CO)—, —(CO)O—, —O(CO)—, —SO$_2$—, —C$_{1-10}$ alkyl-, —(CO)NR$^9$—, —NR$^9$(CO)—, —(CS)NR$^9$—, and —NR$^9$(CS)—;
  where R$^9$ is independently selected from: hydrogen, C$_{1-10}$ alkyl, C$_{3-8}$ cycloalkyl, C$_{1-6}$ alkyl-C$_{3-6}$ cycloalkyl, C$_{2-10}$ alkenyl, C$_{2-10}$ alkynyl, benzyl or phenyl, which is unsubstituted or substituted with 1–3 substituents where the substituents are independently selected from: halo, C$_{1-6}$ alkyl, C$_{1-3}$ alkoxy, C$_{3-8}$ cycloalkyl, phenyl and trifluoromethyl;

Z is selected from:
  a single bond, —NR$^9$—, —O—, and —C$_{1-10}$ alkyl-;
R$^1$ is selected from:
  phenyl, naphthyl, tetrazolyl, C$_{1-10}$ alkyl, C$_{3-6}$ cycloalkyl, C$_{1-6}$ alkyl-C$_{3-6}$ cycloalkyl, C$_{2-10}$ alkenyl, C$_{2-10}$ alkynyl, or C$_{1-4}$ alkyl-phenyl, which is unsubstituted or substituted with 1–3 substituents where the substituents are independently selected from: halo, C$_{1-3}$ alkyl, C$_{1-3}$ alkoxy, triiluoromethoxy and trifluoromethyl,
R$^2$ is selected from:
  (1) hydrogen, and
  (2) hydroxy,
    or R$^2$ and Z may be joined together to form a double bond;
R$^3$ is selected from the group consisting of:
  phenyl and thienyl,
  which is unsubstituted or substituted with 1–7 substituents where the substituents are independently selected from:
    (a) halo,
    (b) trifluoromethyl,
    (c) hydroxy,
    (d) C$_{1-3}$ alkyl,
    (e) —O—C$_{1-3}$ alkyl,
    (f) —CO$_2$R$^9$,
    (g) —NR$^9$R$^{10}$, and
    (h) —CONR$^9$R$^{10}$;
R$^7$ is selected from:
  (1) hydrogen,
  (2) C$_{1-6}$ alkyl, which is unsubstituted or substituted with 1–4 substituents where the substituents are independently selected from: hydroxy, cyano, and halo,
  (3) hydroxy,
  (4) halo, and
  (5) phenyl,
    or R$^7$ and R$^8$ may be linked together through X and the carbon atom to which they are attached to form a 5-membered ring selected from the group consisting of:

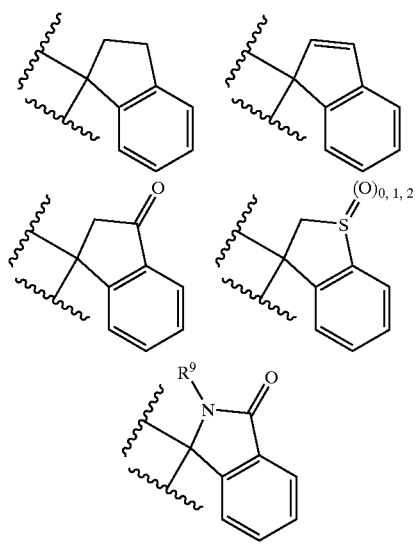

R$^8$ is selected from:
  hydrogen, C$_{3-8}$ cycloalkyl, phenyl, naphthyl, biphenyl, imidazopyridyl, imidazolyl, oxazolyl, pyrazolyl, pyridyl, thiazolyl, tetrahydroindazolyl, tetrahydroimidazopyridyl, and tetrahydropyrazolopyridyl;
  which is unsubstituted or substituted with 1–7 of R$^{12}$ where R$^{12}$ is independently selected from:
    (a) halo,
    (b) cyano,
    (c) hydroxy,
    (d) C$_{1-6}$ alkyl, which is unsubstituted or substituted with 1–5 of R$^{13}$ where R$^{13}$ is independently selected from: halo, cyano, hydroxy, C$_{1-6}$ alkoxy, —CO$_2$H, —CO$_2$(C$_{1-6}$ alkyl), trifluoromethyl, and —NR$^9$R$^{10}$,
    (e) —O—C$_{1-6}$ alkyl, which is unsubstituted or substituted with 1–5 of R$^{13}$,
    (f) —CF$_3$,
    (g) —CHF$_2$,
    (h) —CH$_2$F,
    (i) —NO$_2$,
    (j) C$_{0-6}$ alkyl-phenyl or C$_{0-6}$ alkyl-pyridyl, which is unsubstituted or substituted with 1–7 substituents where the substituents are independently selected from:
      (i) halo,
      (ii), hydroxy,
      (iii) C$_{1-6}$ alkyl,
      (iv) —O—C$_{1-6}$ alkyl,
      (v) —CF$_3$,
      (vi) —OCF$_3$,
      (vii) —NO$_2$,
      (viii) —CN,
      (ix) —SO$_2$—C$_{1-6}$ alkyl,
      (x) —CO$_2$R$^9$,
      (xi) —NR$^9$R$^{10}$,
      (xii) —CONR$^9$R$^{10}$,
      (xiii) —SO$_2$—NR$^9$R$^{10}$, and
      (xiv) —NR$^9$—SO$_2$—R$^{10}$;
    (k) —CO$_2$R$^9$,
    (l) tetrazolyl,
    (m) —NR$^9$R$^{10}$,
    (n) —NR$^9$—COR$^{10}$,
    (o) —NR$^9$—CO$_2$R$^{10}$,
    (p) —CO—NR$^9$R$^{10}$,
    (q) —OCO—NR$^9$R$^{10}$,
    (r) —NR$^9$CO—NR$^9$R$^{10}$,
    (s) —S(O)$_m$—R$^9$, wherein m is an integer selected from 0, 1 and 2,
    (t) —S(O)$_2$—NR$^9$R$^{10}$,
    (u) —NR$^9$S(O)$_2$—R$^{10}$, and
    (v) —NR$^9$S(O)$_2$—NR$^9$R$^{10}$;
  x is an integer selected from 0, 1 and 2, and y is an integer selected from 0, 1 and 2, with the proviso that the sum of x and y is 2;
and pharmaceutically acceptable salts thereof and individual diastereomers thereof.

2. A compound of claim 1, wherein Y is selected from a single bond, —(CO)—, —(CS)NR$^9$—, —(CO)O—, —SO$_2$—, and —(CO)NR$^9$—, and where R$^9$ is independently selected from hydrogen and C$_{1-6}$ alkyl;
  Z is selected from a single bond, —O—, and —NR$^9$—; and
  R$^1$ is selected from:
    phenyl, tetrazolyl, C$_{1-10}$ alkyl, C$_{3-6}$ cycloalkyl, C$_{1-6}$ alkyl-C$_{3-6}$ cycloalkyl, C$_{2-10}$ alkenyl, C$_{2-10}$ alkynyl, or C$_{1-4}$ alkyl-phenyl, which is unsubstituted or substituted with 1–3 substituents where the substituents are independently selected from: halo, C$_{1-3}$ alkyl, C$_{1-3}$ alkoxy, trifluoromethoxy and trifluoromethyl;

and pharmaceutically acceptable salts thereof and individual diastereomers thereof.

3. A compound of claim 1, wherein X is —($C_{0-2}$ alkyl)—Q—($C_{0-2}$ alkyl)-, where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl,
  where Q is selected from a single bond, —O—, —$SO_2$—, —$NR^{10}$—, —S—, and —SO—,
  where $R^{10}$ is independently selected from hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cycloalkyl, which is unsubstituted or substituted with 1–3 substituents where the substituents are independently selected from halo, $C_{1-3}$ alkyl, $C_{1-3}$ alkoxy and trifluoromethyl;
and pharmaceutically acceptable salts thereof and individual diastereomers thereof.

4. A compound of claim 3, wherein X is —($C_{0-2}$ alkyl)—Q—($C_{0-2}$ alkyl)-, where the alkyl is unsubstituted or substituted with fluoro;
  where Q is selected from a single bond, —$SO_2$—, —SO—, and —$NR^{10}$—;
  where $R^{10}$ is independently selected from: hydrogen, $C_{1-3}$ alkyl, $C_{2-3}$ alkenyl, and $C_{2-3}$ alkynyl;
and pharmaceutically acceptable salts thereof and individual diastereomers thereof.

5. A compound of claim 4, wherein X is selected from
(1) a single bond,
(2) —$CH_2CH_2$—,
(3) —$CH_2CH_2CH_2$—,
(4) —$CH_2CH_2$—$CF_2$—,
(5) —$CH_2CH_2$—$SO_2$—, and
(6) —$CH_2CH_2$—SO—;
and pharmaceutically acceptable salts thereof and individual diastereomers thereof.

6. A compound of claim 1, wherein Y is selected from a single bond, —(CO)—, —(CS)$NR^9$—, —(CO)O—, —$SO_2$—, and —(CO)$NR^9$—, and where $R^9$ is independently selected from hydrogen and $C_{1-6}$ alkyl;
and pharmaceutically acceptable salts thereof and individual diastereomers thereof.

7. A compound of claim 1, wherein Z is selected from a single bond, —O—, and —$NR^9$—, where $R^9$ is independently selected from hydrogen, $C_{1-6}$ alkyl, $C_{3-8}$ cycloalkyl, phenyl, and $C_{1-6}$ alkyl-phenyl, which is unsubstituted or substituted with 1–3 substituents where the substituents are independently selected from: halo, $C_{1-3}$ alkyl, $C_{1-3}$ alkoxy, phenyl and trifluoromethyl;
and pharmaceutically acceptable salts thereof and individual diastereomers thereof.

8. A compound of claim 1, wherein $R^1$ is selected from $C_{1-10}$ alkyl, cyclohexyl, $C_{0-2}$ alkyl-phenyl, tetrazolyl, and $CH_2$-cyclohexyl, which is unsubstituted or substituted with 1–3 substituents where the substituents are independently selected from: halo, $C_{1-3}$ alkyl, $C_{1-3}$ alkoxy, trifluoromethoxy and trifluoromethyl;
and pharmaceutically acceptable salts thereof and individual diastereomers thereof.

9. A compound of claim 1, wherein $R^2$ is hydrogen;
and pharmaceutically acceptable salts thereof and individual diastereomers thereof.

10. A compound of claim 1, wherein $R^3$ is selected from the group consisting of phenyl and thienyl, which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl;
and pharmaceutically acceptable salts thereof and individual diastereomers thereof.

11. A compound of claim 10, wherein $R^3$ is unsubstituted phenyl, (3-fluoro)phenyl or 3-thienyl;
and pharmaceutically acceptable salts thereof and individual diastereomers thereof.

12. A compound of claim 1, wherein $R^7$ is hydrogen;
and pharmaceuticailly acceptable salts thereof and individual diastereomers thereof.

13. A compound of claim 1, wherein $R^8$ is selected from: phenyl, imidazopyridyl, inidazolyl, oxazolyl, pyrazolyl, pyridyl, thiazolyl, tetrahydroindazolyl, tetrahydroimidazopyridyl, and tetrahydropyrazolopyridyl;
  which is unsubstituted or substituted with 1–5 substituents where the substituents are independently selected from:
    (a) halo,
    (b) cyano,
    (c) —$NO_2$,
    (d) —$CF_3$,
    (e) —$CHF_2$,
    (f) —$CH_2F$,
    (h) $C_{1-6}$ alkyl,
    (i) $C_{1-3}$ alkyl-phenyl or $C_{1-3}$ alkyl-pyridyl, which is unsubstituted or substituted with 1–4 substituents where the substituents are independently selected from:
      (i) halo,
      (ii) $C_{1-6}$ alkyl,
      (iii) —O—$C_{1-6}$ alkyl,
      (iv) —$CF_3$,
      (vi) —$OCF_3$,
      (vii) —CN, and
    (j) —O—$C_{1-6}$ alkyl;
and pharmaceutically acceptable salts thereof and individual diastereomers thereof.

14. A compound of claim 13, wherein $R^8$ is selected from 5-(3-benzyl)pyrazolyl, 5-(1-methyl-3-benzyl)pyrazolyl, 5-(1-ethyl-3-benzyl)-pyrazolyl, 5-(2-benzyl)thiazolyl, 5-(2-benzyl-4-methyl)thiazolyl, and 5-(2-benzyl-4-ethyl)thiazolyl);
and pharmaceutically acceptable salts thereof and individual diastereomers thereof.

15. A compound of claim 1, which is selected from the group consisting of:

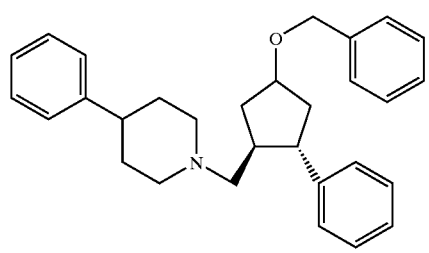

167
-continued
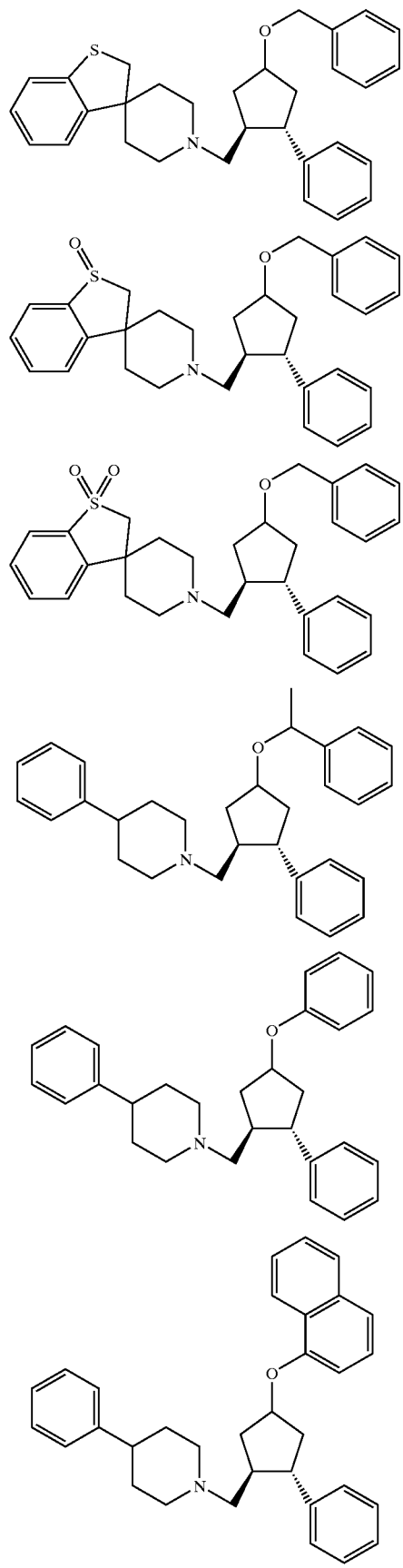
168
-continued
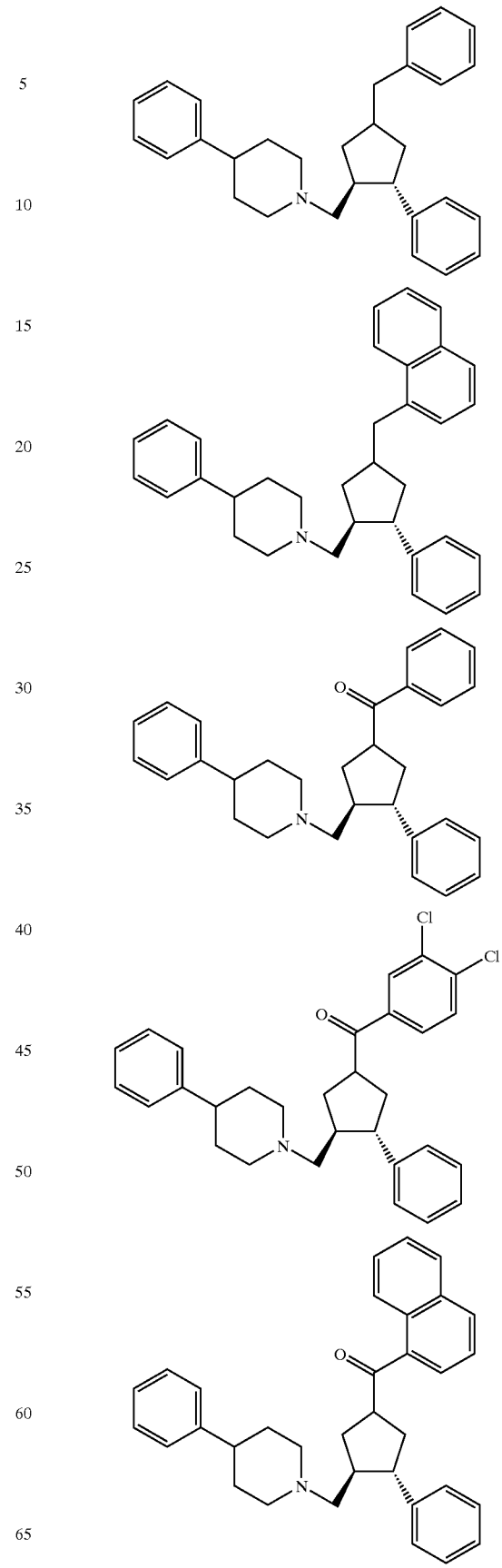

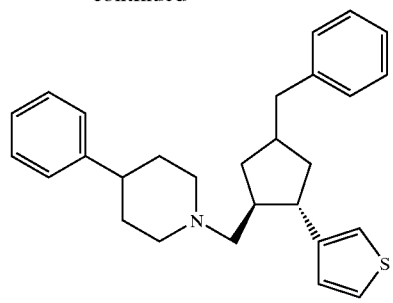
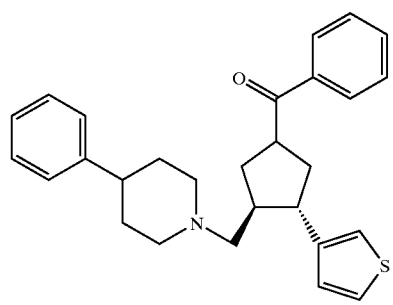
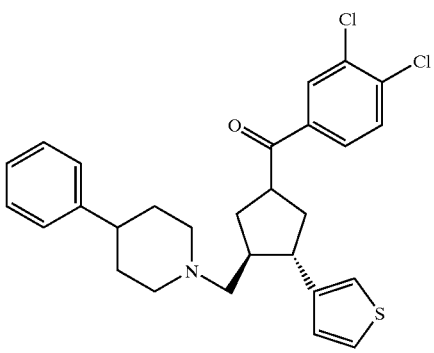
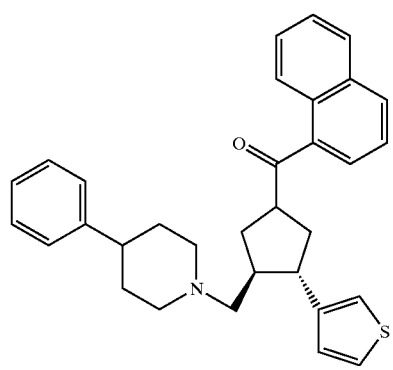
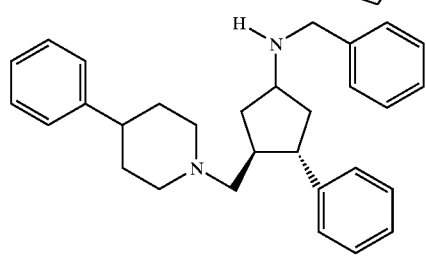
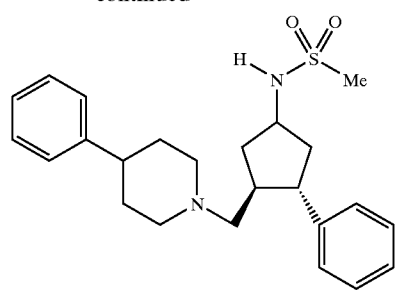
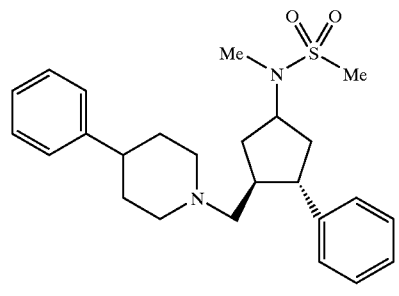
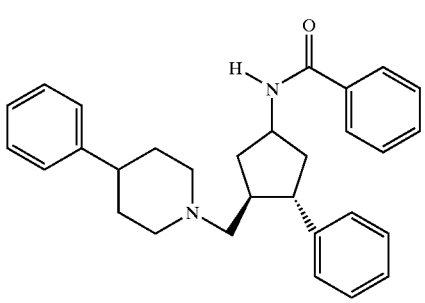
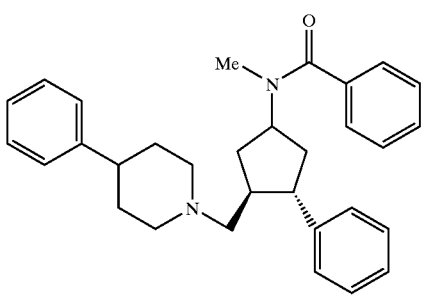
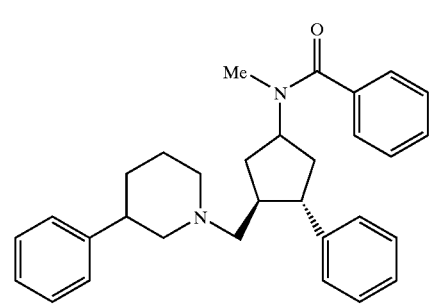

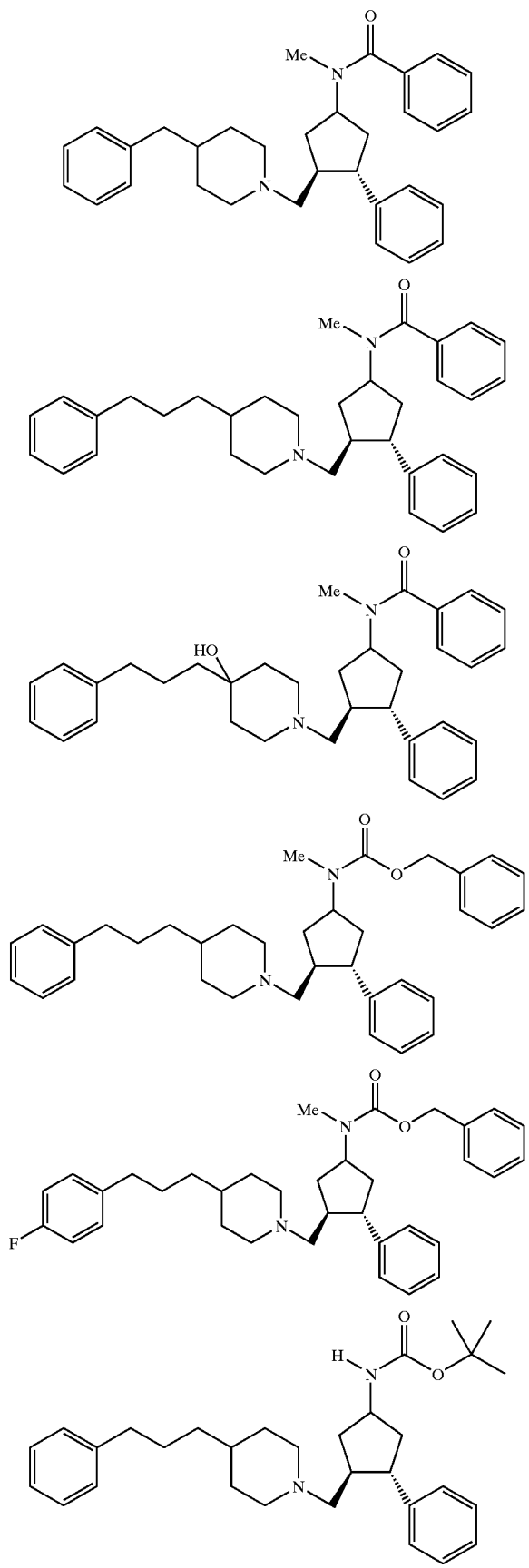
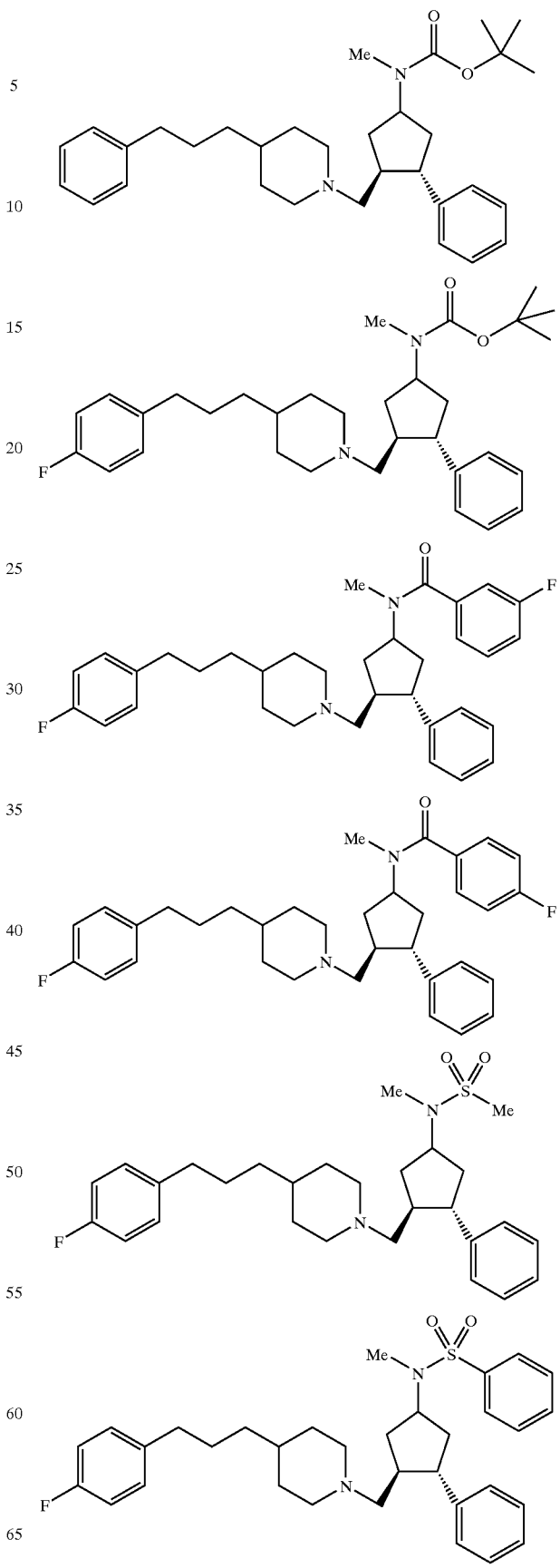

173
-continued
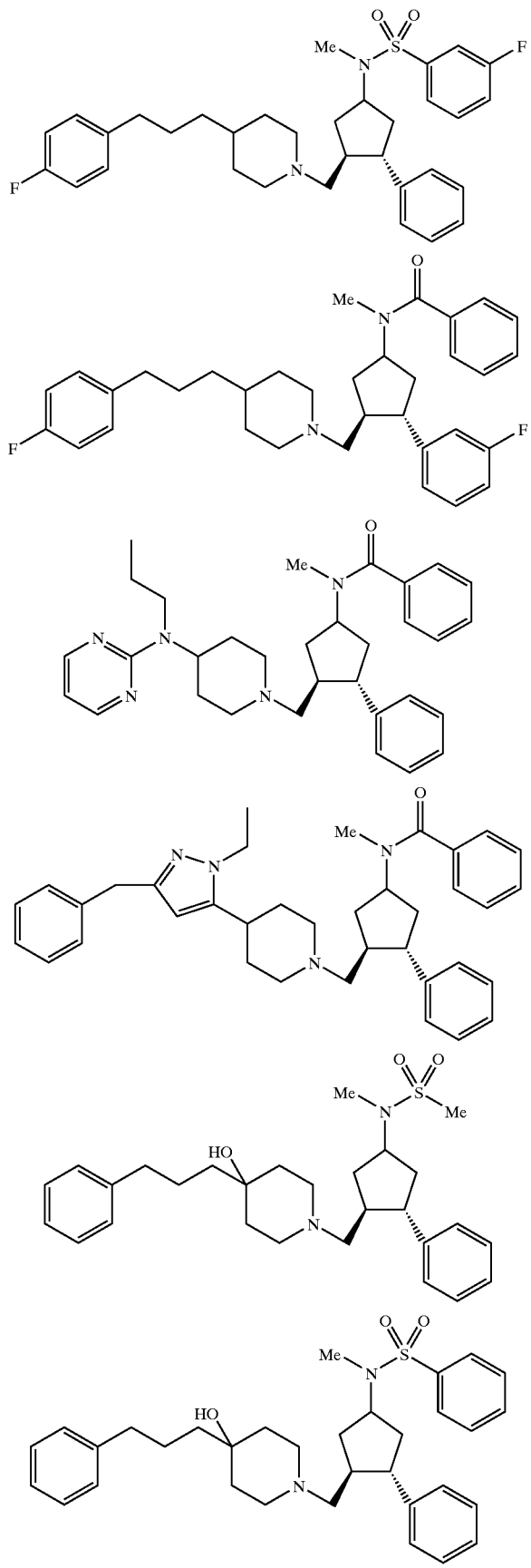
174
-continued
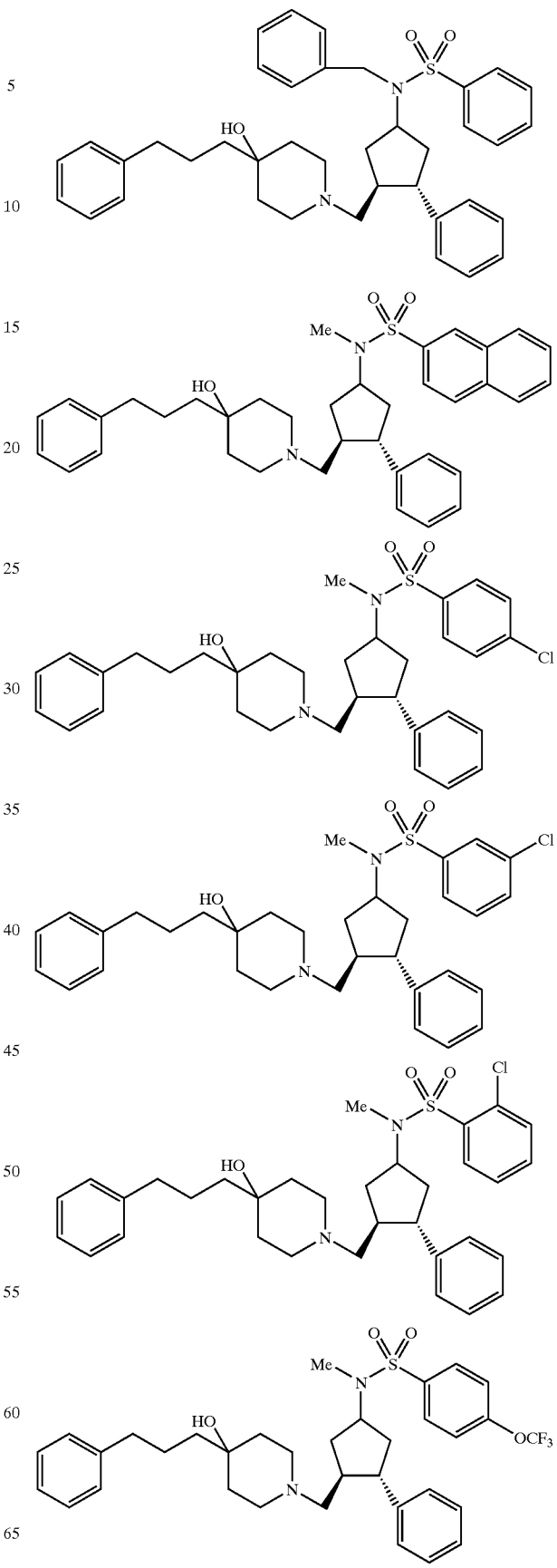

175
-continued
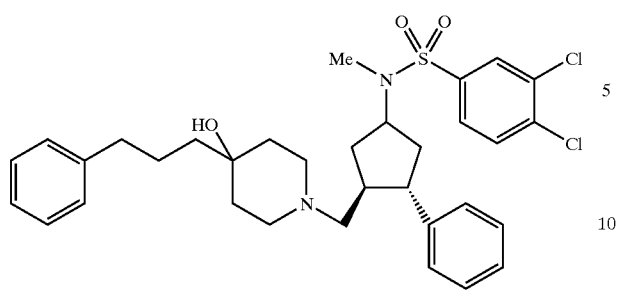
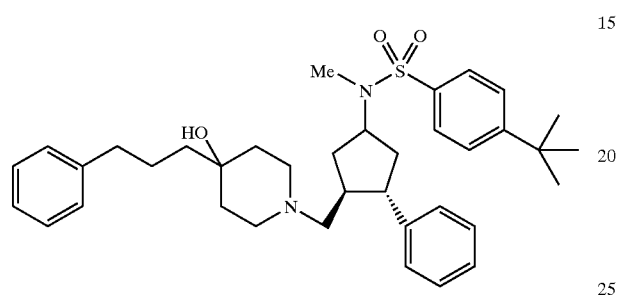
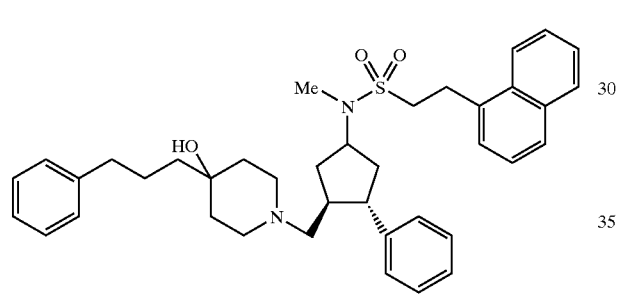
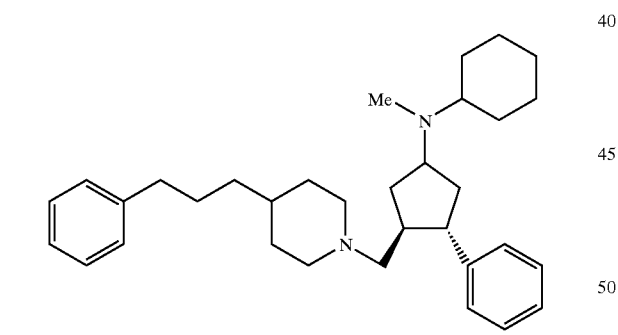
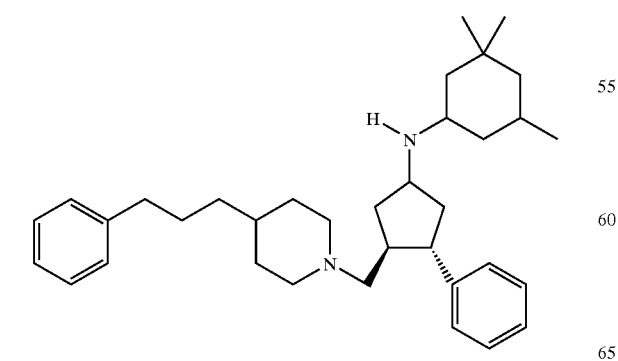
176
-continued
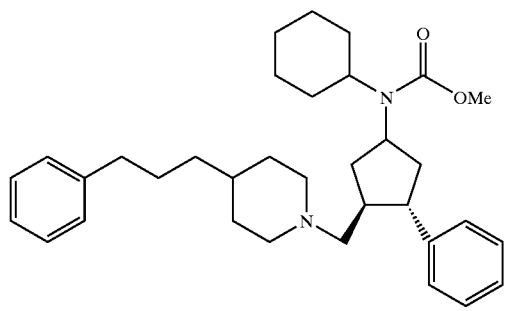
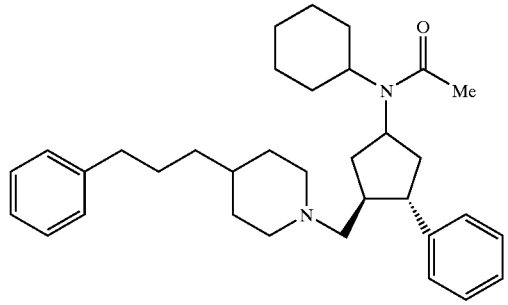
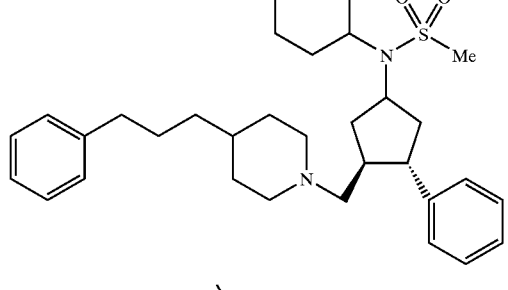
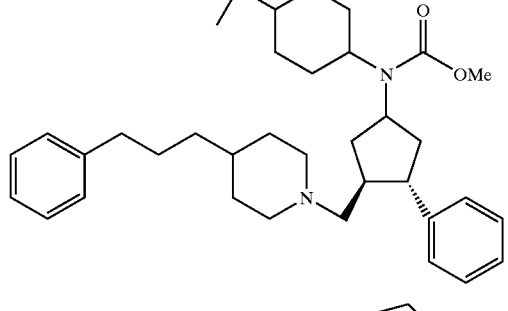
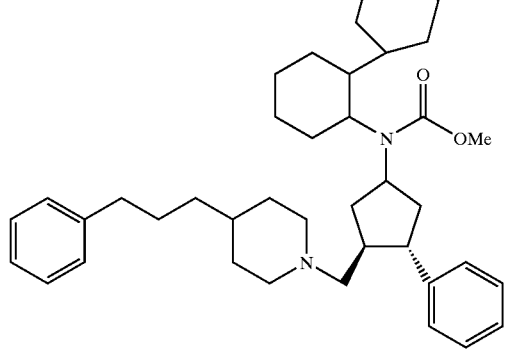

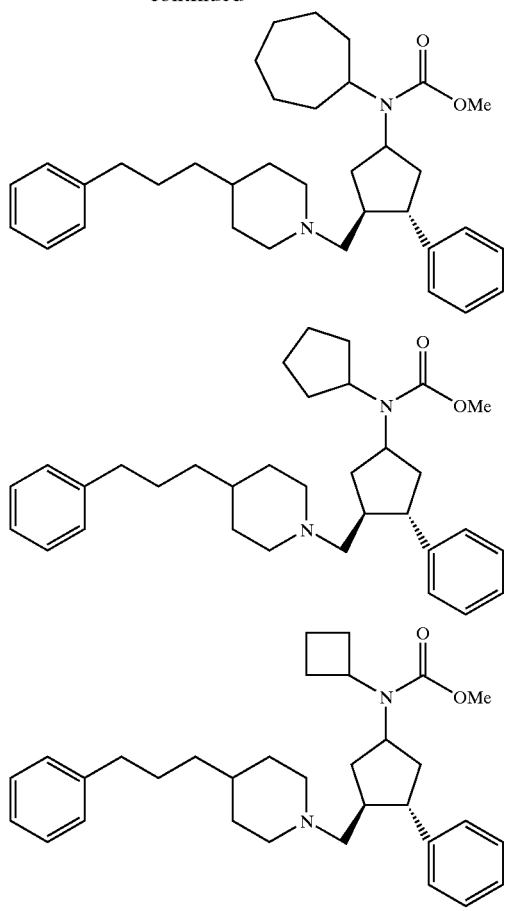

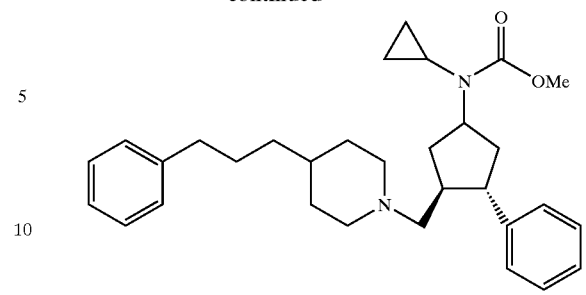

and pharmaceutically acceptable salts thereof and individual diastereomers thereof.

16. A compound of claim 1, wherein x is an integer which is 1 and y is an integer which is 1;
and pharmaceutically acceptable salts thereof and individual diastereomers thereof.

17. A pharmaceutical composition which comprises an inert carrier and a compound of claim 1.

18. A method for modulation of CCR-3 or CCR-5 chemokine receptor activity in a mammal which comprises the administration of an effective amount of the compound of claim 1 or a pharmaceutically acceptable salt or an individual diastereomer thereof.

19. A method for preventing infection by HIV, treating infection by HIV, delaying the onset of AIDS, or treating AIDS comprising administration to a patient of an effective amount of the compound of claim 1 or a pharmaceutically acceptable salt or an individual diastereomner thereof.

20. A method for the treatment of asthma or rheumatoid arthritis which comprises the administration of an effective amount of the compound of claim 1 or a pharmaceutically acceptable salt or an individual diastereomer thereof.

* * * * *